(12) United States Patent
Morikawa et al.

(10) Patent No.: US 7,985,744 B2
(45) Date of Patent: Jul. 26, 2011

(54) VITAMIN D DERIVATIVES

(75) Inventors: Kazumi Morikawa, Shizuoka (JP); Masayuki Ohmori, Shizuoka (JP); Kazuki Shimizu, Shizuoka (JP); Akira Kawase, Shizuoka (JP); Takashi Emura, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 400 days.

(21) Appl. No.: 10/311,538

(22) PCT Filed: Jun. 14, 2001

(86) PCT No.: PCT/JP01/05062
§ 371 (c)(1),
(2), (4) Date: Jul. 21, 2003

(87) PCT Pub. No.: WO01/96293
PCT Pub. Date: Dec. 20, 2001

(65) Prior Publication Data
US 2004/0019023 A1    Jan. 29, 2004

(30) Foreign Application Priority Data

Jun. 15, 2000  (JP) .................. 2000-179251
Nov. 17, 2000  (JP) .................. 2000-351412
Dec. 8, 2000   (JP) .................. 2000-375024

(51) Int. Cl.
*A61K 31/59*   (2006.01)
*C07C 401/00*  (2006.01)

(52) U.S. Cl. ....................... 514/167; 552/653

(58) Field of Classification Search .......... 514/167; 552/653, 553
See application file for complete search history.

(56) References Cited

U.S. PATENT DOCUMENTS

| | | | | |
|---|---|---|---|---|
| 5,756,733 A * | 5/1998 | Hesse et al. | .................. | 544/164 |
| 5,824,811 A | 10/1998 | Kubodera et al. | | |
| 6,100,294 A * | 8/2000 | Reddy | .................. | 514/451 |
| 6,184,398 B1 * | 2/2001 | Kawase | .................. | 552/653 |
| 6,326,503 B1 * | 12/2001 | Kawase | .................. | 552/623 |
| 6,433,200 B1 * | 8/2002 | Kawase | .................. | 552/636 |
| 6,555,699 B2 * | 4/2003 | Kawase | .................. | 552/653 |
| 7,074,777 B2 * | 7/2006 | Kawase et al. | .................. | 514/167 |
| 2010/0217020 A1 * | 8/2010 | Ogasawara et al. | .................. | 549/540 |
| 2010/0261917 A1 * | 10/2010 | Kawase et al. | .................. | 552/610 |

FOREIGN PATENT DOCUMENTS

| | | |
|---|---|---|
| EP | 0 619 304 A1 | 10/1994 |
| EP | 0 755 922 A1 | 1/1997 |
| EP | 0 947 504 A1 | 10/1999 |
| JP | 7-330714 | 12/1995 |
| JP | 10-231284 | 9/1998 |
| WO | 93/09093 A1 | 5/1993 |
| WO | WO 94/28707 | 5/1994 |
| WO | 94/14766 A1 | 7/1994 |
| WO | WO 94/26707 A1 * | 11/1994 |
| WO | 96/22776 A1 | 8/1996 |

OTHER PUBLICATIONS

Yoshitomo Suhara et al., Bioorganic & Medicinal Chemistry Letters, 10 (2000), 1129-1132).*

* cited by examiner

*Primary Examiner* — Sabiha Qazi
(74) *Attorney, Agent, or Firm* — Browdy and Neimark, PLLC

(57) ABSTRACT

The object of the present invention is to provide vitamin D derivatives that have excellent physiological activities as medicines, particularly as therapeutic agents for skin diseases such as psoriasis, and that have a reduced hypercalcemic effect.

The present invention provides a vitamin D derivative of Formula (1):

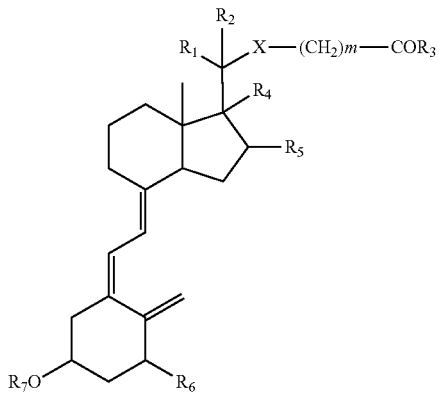

Formula (1)

wherein
X represents an oxygen atom or a sulfur atom;
m represents a number of 1 to 3;
$R_1$ and $R_2$ each represent a hydrogen atom or an alkyl group;
$R_4$ and $R_5$ each represent a hydrogen atom or a hydroxyl group, etc.;
$R_3$ represents —$YR_8$, etc.;
$R_6$ represents a hydrogen atom, etc.;
$R_7$ represents a hydrogen atom, etc.

6 Claims, No Drawings

VITAMIN D DERIVATIVES

TECHNICAL FIELD

The present invention relates to novel vitamin D derivatives, more specifically vitamin D derivatives useful as medicines (e.g., therapeutic agents for skin diseases such as psoriasis).

BACKGROUND ART

In vivo, vitamin $D_3$ is first metabolized into 25-hydroxyvitamin $D_3$ in the liver through hydroxylation at the 25-position, which in turn is metabolized into $1\alpha$, 25-dihydroxyvitamin $D_3$ or 24R,25-dihydroxyvitamin $D_3$ in the kidneys through hydroxylation at the $1\alpha$- or 24-position, respectively. Among these metabolites, $1\alpha$,25-dihydroxyvitamin $D_3$ and its synthetic analogs are known to have a wide variety of physiological activities including calcium metabolism-regulatory activity, growth or differentiation-inhibitory activity against tumor cells or the like, and immunoregulatory activity.

Vitamin $D_3$ has involved a problem that it would be likely to cause hypercalcemia when continuously used for a long period of time. To overcome this problem, attempts have been made to synthesize various vitamin D derivatives; there have been proposed some vitamin D derivatives that have a reduced hypercalcemic effect (e.g., JP 7-330714 A and JP 10-231284 A).

The object of the present invention is to provide vitamin D derivatives that have excellent physiological activities as medicines, particularly as therapeutic agents for skin diseases such as psoriasis, and that have a reduced hypercalcemic effect.

DISCLOSURE OF THE INVENTION

Under these circumstances, the inventors of the present invention focused on compounds having an ester or amide structure in their side chains and made extensive and intensive efforts to provide vitamin D derivatives with a reduced hypercalcemic effect. As a result, the inventors found that the intended object was accomplished by a vitamin D derivative of the following Formula (1):

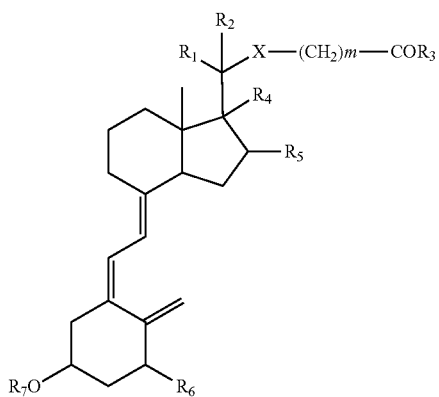

Formula (1)

wherein

X represents an oxygen atom or a sulfur atom;
m represents a number of 1 to 3;
$R_1$ and $R_2$ each represent a hydrogen atom or an alkyl group;
$R_4$ and $R_5$ each represent a hydrogen atom or a hydroxyl group, or $R_4$ and $R_5$ together form a double bond between the 16- and 17-positions;
$R_3$ represents —$YR_8$ (wherein Y represents an oxygen atom or a sulfur atom, $R_8$ represents a hydrogen atom, a linear or branched alkyl group which may be substituted with a fluorine atom or a cyclic alkyl group, or a cyclic alkyl group which may be substituted with a fluorine atom) or —$NR_9R_{10}$ (wherein $R_9$ and $R_{10}$ each represent a hydrogen atom, a linear or branched alkyl group which may be substituted with a fluorine atom or a cyclic alkyl group, or a cyclic alkyl group which may be substituted with a fluorine atom, or $R_9$ and $R_{10}$ may form a ring together with the nitrogen atom when $R_4$ and $R_5$ together form a double bond between the 16- and 17-positions);
$R_6$ represents a hydrogen atom or —$OR_{11}$ (wherein $R_{11}$ represents a hydrogen atom or a protecting group); and
$R_7$ represents a hydrogen atom or a protecting group;
and thus the inventors finally completed one aspect of the invention.

Namely, the present invention provides vitamin D derivatives having Formula (1).

In Formula (1), preferably, X represents an oxygen atom or a sulfur atom, m represents a number of 1 to 3, $R_1$ and $R_2$ each represent a hydrogen atom or a $C_1$-$C_4$ alkyl group, $R_4$ and $R_5$ each represent a hydrogen atom or a hydroxyl group, or $R_4$ and $R_5$ together form a double bond between the 16- and 17-positions, $R_3$ represents —$YR_8$ (wherein Y represents an oxygen atom or a sulfur atom, $R_8$ represents a hydrogen atom, a linear or branched $C_1$-$C_{15}$ alkyl group which may be substituted with a fluorine atom or a cyclic $C_3$-$C_{10}$ alkyl group, or a cyclic $C_3$-$C_{15}$ alkyl group which may be substituted with a fluorine atom) or —$NR_9R_{10}$ (wherein $R_9$ and $R_{10}$ each represent a hydrogen atom, a linear or branched $C_1$-$C_{15}$ alkyl group which may be substituted with a fluorine atom or a cyclic $C_3$-$C_{10}$ alkyl group, or a cyclic $C_3$-$C_{15}$ alkyl group which may be substituted with a fluorine atom, or $R_9$ and $R_{10}$ form a 3- to 10-membered ring together with the nitrogen atom when $R_4$ and $R_5$ together form a double bond between the 16- and 17-positions), $R_6$ represents a hydrogen atom or a hydroxyl group, and $R_7$ represents a hydrogen atom.

Also preferably, in Formula (1), X represents an oxygen atom or a sulfur atom, m represents a number of 1 to 2, $R_1$ and $R_2$ each represent a hydrogen atom or a methyl group, $R_4$ and $R_5$ simultaneously represent a hydrogen atom, or $R_4$ represents a hydrogen atom while $R_5$ represents a hydroxyl group, or $R_4$ and $R_5$ together form a double bond between the 16- and 17-positions, $R_3$ represents —$YR_8$ (wherein Y represents an oxygen atom or a sulfur atom, $R_8$ represents a hydrogen atom, a linear or branched $C_1$-$C_{10}$ alkyl group which may be substituted with a fluorine atom or a cyclic $C_3$-$C_8$ alkyl group, or a cyclic $C_3$-$C_{12}$ alkyl group which may be substituted with a fluorine atom) or —$NR_9R_{10}$ (wherein $R_9$ and $R_{10}$ each represent a hydrogen atom, a linear or branched $C_1$-$C_{10}$ alkyl group which may be substituted with a fluorine atom or a cyclic $C_3$-$C_8$ alkyl group, or a cyclic $C_3$-$C_{12}$ alkyl group which may be substituted with a fluorine atom, or $R_9$ and $R_{10}$ form a 3- to 10-membered ring together with the nitrogen atom when $R_4$ and $R_5$ together form a double bond between the 16- and 17-positions), $R_6$ represents a hydroxyl group, and $R_7$ represents a hydrogen atom.

In Formula (1), preferably, X represents an oxygen atom or a sulfur atom, m represents a number of 1 to 2, $R_1$ and $R_2$ each represent a hydrogen atom or a methyl group, $R_4$ and $R_5$ each represent a hydrogen atom, or $R_4$ and $R_5$ together form a double bond between the 16- and 17-positions, $R_3$ represents —$YR_8$ (wherein Y represents an oxygen atom or a sulfur atom, $R_8$ represents a hydrogen atom, a linear or branched $C_1$-$C_8$ alkyl group which may be substituted with a fluorine atom or a cyclic $C_3$-$C_8$ alkyl group, or a cyclic $C_3$-$C_8$ alkyl group which may be substituted with a fluorine atom) or —$NR_9R_{10}$ (wherein $R_9$ and $R_{10}$ each represent a hydrogen atom, a linear or branched $C_1$-$C_8$ alkyl group which may be substituted with a fluorine atom or a cyclic $C_3$-$C_8$ alkyl group, or a cyclic $C_3$-$C_8$ alkyl group which may be substituted with a fluorine atom, or $R_9$ and $R_{10}$ form a 3- to 8-membered ring together with the nitrogen atom when $R_4$ and $R_5$ together form a double bond between the 16- and 17-positions), $R_6$ represents a hydroxyl group, and $R_7$ represents a hydrogen atom.

In Formula (1), preferably, X represents an oxygen atom or a sulfur atom, m represents a number of 1 to 2, $R_1$ and $R_2$ each represent a hydrogen atom or a methyl group, $R_3$ represents —$YR_8$ (wherein Y represents an oxygen atom or a sulfur atom, $R_8$ represents a hydrogen atom, a linear or branched $C_1$-$C_8$ alkyl group which may be substituted with a fluorine atom or a cyclic $C_3$-$C_6$ alkyl group, or a cyclic $C_3$-$C_8$ alkyl group which may be substituted with a fluorine atom), $R_4$ and $R_5$ each represent a hydrogen atom, or $R_4$ and $R_5$ together form a double bond between the 16- and 17-positions, $R_6$ represents a hydroxyl group, and $R_7$ represents a hydrogen atom.

In Formula (1), preferably, X represents an oxygen atom or a sulfur atom, m represents 1, $R_1$ and $R_2$ each represent a hydrogen atom or a methyl group, $R_4$ and $R_5$ each represent a hydrogen atom, or $R_4$ and $R_5$ together form a double bond between the 16- and 17-positions, $R_3$ represents —$NR_9R_{10}$ (wherein $R_9$ and $R_{10}$ each represent a hydrogen atom, a linear or branched $C_1$-$C_8$ alkyl group which may be substituted with a fluorine atom or a cyclic $C_3$-$C_6$ alkyl group, or a cyclic $C_3$-$C_8$ alkyl group which may be substituted with a fluorine atom, or $R_9$ and $R_{10}$ form a 3- to 6-membered ring together with the nitrogen atom when $R_4$ and $R_5$ together form a double bond between the 16- and 17-positions), $R_6$ represents a hydroxyl group, and $R_7$ represents a hydrogen atom.

In Formula (1), preferably, X represents an oxygen atom or a sulfur atom, m represents a number of 1 to 2, $R_1$ and $R_2$ each represent a hydrogen atom or a methyl group, $R_3$ represents —$OR_8$ (wherein $R_8$ represents a branched $C_3$-$C_8$ alkyl group), $R_4$ and $R_5$ each represent a hydrogen atom, or $R_4$ and $R_5$ together form a double bond between the 16- and 17-positions, $R_6$ represents a hydroxyl group, and $R_7$ represents a hydrogen atom.

In Formula (1), preferably, X represents an oxygen atom or a sulfur atom, m represents a number of 1 to 2, $R_1$ and $R_2$ each represent a hydrogen atom or a methyl group, $R_3$ represents —$SR_8$ (wherein $R_8$ represents a branched $C_3$-$C_8$ alkyl group), $R_4$ and $R_5$ each represent a hydrogen atom, or $R_4$ and $R_5$ together form a double bond between the 16- and 17-positions, $R_6$ represents a hydroxyl group, and $R_7$ represents a hydrogen atom.

In Formula (1), preferably, X represents an oxygen atom or a sulfur atom, m represents 1, $R_1$ and $R_2$ each represent a hydrogen atom or a methyl group, $R_3$ represents —$NR_9R_{10}$ (wherein $R_9$ represents a hydrogen atom or a linear or branched $C_1$-$C_4$ alkyl group, $R_{10}$ represents a linear or branched $C_1$-$C_8$ alkyl group which may be substituted with a fluorine atom), $R_4$ and $R_5$ each represent a hydrogen atom, or $R_4$ and $R_5$ together form a double bond between the 16- and 17-positions, $R_6$ represents a hydroxyl group, and $R_7$ represents a hydrogen atom.

In Formula (1), preferably, X represents an oxygen atom, m represents a number of 1 to 2, $R_1$ and $R_2$ each represent a hydrogen atom or a methyl group, $R_3$ represents —$OR_8$ (wherein $R_8$ represents a branched $C_6$-$C_8$ alkyl group), $R_4$ and $R_5$ each represent a hydrogen atom, or $R_4$ and $R_5$ together form a double bond between the 16- and 17-positions, $R_6$ represents a hydroxyl group, and $R_7$ represents a hydrogen atom.

In Formula (1), preferably, X represents an oxygen atom, m represents a number of 1 to 2, $R_1$ and $R_2$ each represent a hydrogen atom or a methyl group, provided that one of $R_1$ and $R_2$ should represent a methyl group, $R_3$ represents —$OR_8$ (wherein $R_8$ represents a branched $C_6$-$C_8$ alkyl group), $R_4$ and $R_5$ together form a double bond between the 16- and 17-positions, $R_6$ represents a hydroxyl group, and $R_7$ represents a hydrogen atom.

In Formula (1), preferably, X represents an oxygen atom, m represents 1, $R_1$ and $R_2$ each represent a hydrogen atom or a methyl group, provided that one of $R_1$ and $R_2$ should represent a methyl group, $R_3$ represents —$NR_9R_{10}$ (wherein $R_9$ represents a hydrogen atom or a methyl group, $R_{10}$ represents a linear or branched $C_1$-$C_4$ alkyl group which may be substituted with a fluorine atom), $R_4$ and $R_5$ together form a double bond between the 16- and 17-positions, $R_6$ represents a hydroxyl group, and $R_7$ represents a hydrogen atom.

In Formula (1), preferably, X represents an oxygen atom, m represents 1, $R_1$ and $R_2$ each represent a hydrogen atom or a methyl group, provided that one of $R_1$ and $R_2$ should represent a methyl group, $R_3$ represents —$NR_9R_{10}$ (wherein $R_9$ represents a hydrogen atom, $R_{10}$ represents a propyl group which may by substituted with a fluorine atom), $R_4$ and $R_5$ together form a double bond between the 16- and 17-positions, $R_6$ represents a hydroxyl group, and $R_7$ represents a hydrogen atom.

Preferred vitamin D derivatives according to the present invention include 1α,3β-dihydroxy-20(S)-(1-ethyl-1-methylpropoxycarbonylmethoxy)-9,10-secopregna-5,7,10(19), 16-tetraene, 1α,3β-dihydroxy-20(S)-(1-isopropyl-2-methylpropoxycarbonylmethoxy)-9,10-secopregna-5,7,10(19),16-tetraene, 1α,3β-dihydroxy-20(S)-(1,1-dimethylbutoxycarbonylmethoxy)-9,10-secopregna-5,7,10 (19),16-tetraene, 1α,3β-dihydroxy-20(S)-(1,1-dimethylhexyloxycarbonylmethoxy)-9,10-secopregna-5,7, 10(19),16-tetraene, 1α,3β-dihydroxy-20(S)-{2-(1-ethyl-1-methylpropoxycarbonyl)ethoxy}-9,10-secopregna-5,7,10 (19),16-tetraene, {(1α,3β-dihydroxy-9,10-secopregna-5,7, 10(19),16-tetraen-20(S)-yl)oxy}-N-(2,2,3,3,3-pentafluoropropyl)acetamide and 1α,3β-dihydroxy-20(S)-(1-ethyl-1-methylpropoxycarbonylmethoxy)-9,10-secopregna-5,7,10(19)-triene.

In another aspect, the present invention provides a pharmaceutical composition comprising the above vitamin D derivative.

In yet another aspect, the present invention provides a therapeutic agent for skin disease, which comprises the above vitamin D derivative as a active ingredient. The skin disease is preferably psoriasis.

In still another aspect, the present invention provides the use of the above vitamin D derivative for the preparation of a therapeutic agent for skin diseases. The therapeutic agent for skin diseases is preferably a therapeutic agent for psoriasis.

In still another aspect, the present invention provides a method for treating a skin disease using the above vitamin D derivative, for example, a method which comprises the step of administering a therapeutically effective amount of the vitamin D derivative to a patient in need of such reaction. The skin disease is preferably psoriasis.

Also, the present invention provides an advantageous method for preparing a compound usable as an intermediate for the preparation of the above vitamin D derivative. Namely, the present invention provides a method for carbonylating a compound of the following Formula (2):

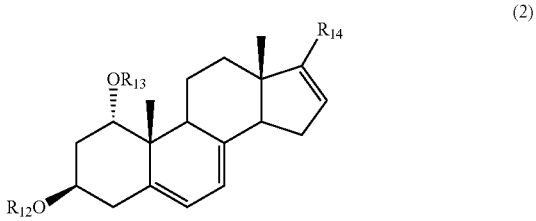

(2)

wherein
$R_{12}$ and $R_{13}$ each represent a protecting group,
and $R_{14}$ represents a leaving group,
in a solvent in the presence of an organoaluminum reagent and a palladium catalyst under a carbon monoxide atmosphere to prepare a compound of the following Formula (3):

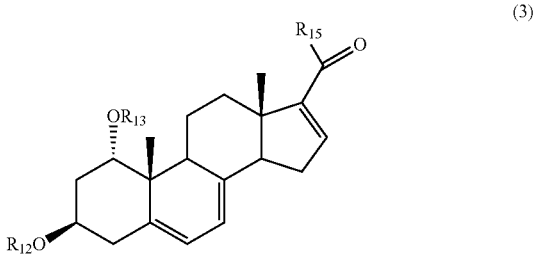

(3)

wherein
$R_{12}$ and $R_{13}$ are as defined in Formula (2), and $R_{15}$ represents an alkyl group, an aryl group, an alkenyl group or an alkynyl group).
In the above method, the organoaluminum reagent preferably has Formula (4):

$(R_{15})_n AlW_{3-n}$ (4)

wherein
n represents an integer of 1 to 3, $R_{15}$ represents an alkyl group, an aryl group, an alkenyl group or an alkynyl group, and W represents a halogen atom.

BEST MODE FOR CARRYING OUT THE INVENTION

Embodiments and implementation procedures for the vitamin D derivative of Formula (1) according to the present invention and the pharmaceutical composition comprising the same will be described below in more detail.

This application claims the priority of Japanese Patent Application Nos. 2000-179251, 2000-351412 and 2000-375024, the disclosures of which are hereby incorporated by reference in their entirety.

As used herein, an alkyl group generally refers to a linear or branched $C_1$-$C_{15}$ alkyl group or a cyclic $C_3$-$C_{15}$ alkyl group, unless otherwise specified. The alkyl group as $R_1$ and $R_2$ preferably contains 1 to 6 carbon atoms, more preferably 1 to 4 carbon atoms. Specific examples include methyl, ethyl and n-butyl, with methyl being preferred. The linear or branched alkyl group as $R_8$, $R_9$ and $R_{10}$ preferably contains 1 to 10 carbon atoms, more preferably 1 to 8 carbon atoms. Most preferably, $R_8$ is a branched $C_6$-$C_8$ alkyl group and $R_9$ and $R_{10}$ are each a linear or branched $C_1$-$C_4$ alkyl group. Specific examples include, methyl, ethyl, n-propyl, i-propyl, n-butyl, s-butyl, i-butyl, t-butyl, n-pentyl, t-pentyl, 1-ethyl-1-methylpropyl, 1-i-propyl-2-methylpropyl, 1,1-diethylpropyl, 1,1-dimethylbutyl, 1,1-dimethylhexyl, n-hexyl, n-heptyl, n-octyl, nonyl and decanyl. Preferred are methyl, ethyl, n-propyl, i-propyl, i-butyl, t-butyl, t-pentyl, 1-ethyl-1-methylpropyl, 1-i-propyl-2-methylpropyl, 1,1-diethylpropyl, 1,1-dimethylbutyl and 1,1-dimethylhexyl, and more preferred are methyl, ethyl, n-propyl, t-butyl, t-pentyl, 1-ethyl-1-methylpropyl, 1-i-propyl-2-methylpropyl, 1,1-dimethylbutyl and 1,1-dimethylhexyl. Most preferably, $R_8$ is 1-ethyl-1-methylpropyl or 1,1-dimethylhexyl, $R_9$ is methyl, and $R_{10}$ is n-propyl.

Examples of a cyclic alkyl group usually include those which contain 3 to 15 carbon atoms, preferably 3 to 12 carbon atoms, and more preferably 3 to 8 carbon atoms. In particular, a cyclic $C_3$-$C_6$ alkyl group is preferred as a substituent on a linear or branched alkyl group. Specific examples include cyclopropyl, cyclobutyl, cyclopentyl, cyclohexyl, cycloheptyl, cyclooctyl, cyclononyl, cyclodecanyl, cyclododecanyl and cyclopentadecanyl.

A linear or branched alkyl group which may be substituted with a fluorine atom or a cyclic alkyl group, or a cyclic alkyl group which may be substituted with a fluorine atom generally refers to a linear, branched or cyclic alkyl group such as the ones stated above, at least one hydrogen atom of which is substituted with a fluorine atom or cyclic alkyl group. Different types of alkyl groups may be substituted with different numbers of fluorine atoms, usually 3 to 20 fluorine atoms, preferably 3 to 15 fluorine atoms, more preferably 3 to 12 fluorine atoms, and most preferably 3 to 8 fluorine atoms.

The protecting groups as $R_7$, $R_{11}$, $R_{12}$ and $R_{13}$ may be the same or different and examples include an acyl group, an optionally substituted alkyl group and a substituted silyl group. Specific examples include methyl, methoxymethyl, methylthiomethyl, t-butylthiomethyl, (phenyldimethylsilyl) methoxymethyl, benzyloxymethyl, p-methoxybenzyloxymethyl, p-chlorobenzyloxymethyl, (4-methoxyphenoxy)methyl, t-butoxymethyl, 2-methoxyethoxymethyl, 2,2,2-trichloroethoxymethyl, 2-(trimethylsilyl) ethoxymethyl, phenylthiomethyl, cyclopropylmethyl, tetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-dioxide, 1,4-dioxan-2-yl, tetrahydrofuranyl, tetrahydrothiofuranyl, phenacyl, p-bromophenacyl, 1-ethoxyethyl, methoxyisopropyl, 1-(2-chloroethoxy)ethyl, 1-methyl-1-methoxyethyl, 1-methyl-benzyloxyethyl, 1-methyl-1-benzyloxy-2-fluoroethyl, 2,2,2-trichloroethyl, 2-trimethylsilylethyl, 2,2-dichloro-1,1-difluoroethyl, allyl, t-butyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-chlorobenzyl, p-bromobenzyl, 2,6-dichlorobenzyl, p-cyanobenzyl, p-phenylbenzyl, 4-(dimethylaminocarbonyl)benzyl, 2-picolyl, 4-picolyl, diphenylmethyl, p,p'-dinitrobenzhydryl, 5-dibenzosuberyl, triphenylmethyl, p-methoxyphenyldiphenylmethyl, di(p-methoxyphenyl)phenylmethyl, tri(p-methoxyphenyl)methyl, 9-anthryl, 1,3-benzodithiolan-2-yl, benzisothiazolyl S,S-dioxide, trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, t-butylmethoxyphenylsilyl, formyl, acetyl, chloroacetyl, dichloroacetyl, trichloroacetyl, trifluoroacetyl, methoxyacetyl, propionyl, butyryl, isobutyryl, pivaloyl, adamantyl, cyclohexanecarbonyl, benzoyl, 4-nitrobenzoyl, 4-chlorobenzoyl, 4-methoxybenzoyl, naphthoyl, toluoyl, 9-fluorenecarbonyl, methoxycarbonyl, ethoxycarbonyl, t-butoxycarbonyl, benzyloxycarbonyl, 4-methoxybenzyloxycarbonyl, 9-fluorenylmethyloxycarbonyl, 2,2,2-trichloroethoxycarbonyl, 2-(trimethylsilyl)ethoxycarbonyl, 2-(methylthiomethoxy)ethoxycarbonyl, propoxycarbonyl, isopropoxycarbonyl, i-butoxycarbonyl, vinyloxycarbonyl, allyloxycarbonyl, p-nitrophenyloxycarbonyl, 3,4-dimethoxybenzyloxycarbonyl, o-nitrobenzyloxycarbonyl, p-nitrobenzyloxycarbonyl, benzylthiocarbonyl, 4-ethoxy-1-naphthyloxycarbonyl, (methylthio)thiocarbonyl, i-butylaminocarbonyl and phenylaminocarbonyl. Preferred are substituted silyl groups such as trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl and t-butylmethoxyphenylsilyl, or acyl groups such as formyl, acetyl, chloroacetyl, dichloroacetyl, trichloroacetyl, trifluoroacetyl, methoxyacetyl, triphenylmethoxyacetyl, phenoxyacetyl, propionyl, butyryl, isobutyryl, 4-(methylthiomethoxy)butyryl, pivaloyl, adamantyl, cyclohexanecarbonyl, benzoyl, 4-nitrobenzoyl, 4-chlorobenzoyl, 2-iodobenzoyl, 4-methoxybenzoyl, p-phenylbenzoyl, naphthoyl, toluoyl and 9-fluorenecarbonyl. More preferred are triethylsilyl, triisopropylsilyl, dimethylisopropylsilyl, diethylisopropylsilyl, t-butyldimethylsilyl, t-butyldiphenylsilyl, triphenylsilyl, diphenylmethylsilyl, acetyl, pivaloyl, benzoyl and 4-methoxybenzoyl.

Examples of the leaving group as $R_{14}$ include halogen atoms such as chlorine, bromine and iodine, sulfonyloxy groups such as trifluoromethanesulfonyloxy, pentafluoroethanesulfonyloxy, nonafluorobutanesulfonyloxy, methanesulfonyloxy, benzenesulfonyloxy and toluenesulfonyloxy, or phosphate ester groups such as dimethylphosphoryloxy, diethylphosphoryloxy and diphenylphosphoryloxy, with bromine, iodine, trifluoromethanesulfonyloxy and nonafluorobutanesulfonyloxy being preferred.

In preparing a compound of Formula (3) according to the present invention, a solvent for use in carbonylation may be selected as appropriate, but an organic solvent is preferred. An organic solvent refers to a liquid material inert to reaction substrates and may be exemplified by N,N-dimethylacetamide, N,N-dimethylformamide, 1,3-dimethyl-2-imidazolidinone, dimethyl sulfoxide, tetrahydrofuran, 1,2-dimethoxyethane, 1,4-dioxane, tert-butyl methyl ether, ethyl ether, isopropyl ether, acetone, methyl ethyl ketone, ethyl acetate, methylene chloride, 1,2-dichloroethane, toluene, benzene and chlorobenzene. Preferred are N,N-dimethylacetamide, N,N-dimethylformamide and 1,3-dimethyl-2-imidazolidinone, and more preferred is N,N-dimethylacetamide.

In preparing a compound of Formula (3) according to the present invention, an organoaluminum reagent refers to a compound having Formula (4):

$$(R_{15})_n AlW_{3-n} \quad (4)$$

wherein
n represents an integer of 1, 2 or 3;
$R_{15}$ represents an alkyl group, an aryl group, an alkenyl group or an alkynyl group, wherein an alkyl group refers to a linear or branched $C_1$-$C_{15}$ alkyl group or a cyclic $C_3$-$C_{15}$ alkyl group, an aryl group refers to a phenyl group which may have a substituent such as alkyl, halogen or nitro, an alkenyl group refers to a linear or branched $C_2$-$C_{15}$ substituent having a double bond, and an alkynyl group refers to a linear or branched $C_2$-$C_{15}$ substituent having a triple bond; and W represents a halogen atom such as chlorine, bromine and iodine.

Examples include trimethylaluminum, dimethylaluminum chloride, dimethylaluminum bromide, dimethylaluminum iodide, methylaluminum dichloride, methylaluminum dibromide, methylaluminum diiodide, triethylaluminum, diethylaluminum chloride, diethylaluminum bromide, diethylaluminum iodide, ethylaluminum dichloride, ethylaluminum dibromide, ethylaluminum diiodide, tri-n-propylaluminum, di-n-propylaluminum chloride, di-n-propylaluminum bromide, di-n-propylaluminum iodide, n-propylaluminum dichloride, n-propylaluminum dibromide, n-propylaluminum diiodide, tri-n-butylaluminum, di-n-butylaluminum chloride, di-n-butylaluminum bromide, di-n-butylaluminum iodide, n-butylaluminum dichloride, n-butylaluminum dibromide, n-butylaluminum diiodide, triphenylaluminum, diphenylaluminum chloride, diphenylaluminum bromide, diphenylaluminum iodide, phenylaluminum dichloride, phenylaluminum dibromide and phenylaluminum diiodide. Preferred are trimethylaluminum, dimethylaluminum chloride, methylaluminum dichloride, triethylaluminum, diethylaluminum chloride, ethylaluminum dichloride, tri-n-propylaluminum, di-n-propylaluminum chloride, n-propylaluminum dichloride, tri-n-butylaluminum, di-n-butylaluminum chloride, n-butylaluminum dichloride, triphenylaluminum, diphenylaluminum chloride and phenylaluminum dichloride. More preferred are dimethylaluminum chloride, diethylaluminum chloride, di-n-propylaluminum chloride, di-n-butylaluminum chloride and diphenylaluminum chloride.

A palladium catalyst refers to a zero- or di-valent palladium compound which may have an appropriate ligand. Examples include tetrakis(triphenylphosphine)palladium, dichlorobis(triphenylphosphine)palladium, dichloro[1,3-bis(diphenylphosphino)propane]palladium, dichloro[1,2-bis(diphenylphosphino)ethane]palladium, bis(dibenzylideneacetone)palladium and tris(dibenzylideneacetone)dipalladium, with tetrakis(triphenylphosphine)palladium being preferred.

The following Tables 1 to 44 show non-limiting examples of the vitamin D derivative of Formula (1) according to the present invention.

In Tables 1 to 23, $R_3$ represents $OR_8$; in Table 24, it represents $SR_8$; and in Tables 25 to 44, it represents $NR_9R_{10}$.

TABLE 1

| | | | | | R3 = OR8 | | | | |
|---|---|---|---|---|---|---|---|---|---|
| | X | R1 | R2 | m | R8 | R4 | R5 | R6 | R7 |
| 1 | O | H | H | 1 | H | H | H | OH | H |
| 2 | O | H | H | 1 | $CH_3$ | H | H | OH | H |
| 3 | O | H | H | 1 | $OH_2CH_3$ | H | H | OH | H |
| 4 | O | H | H | 1 | $(CH_2)_2OH_3$ | H | H | OH | H |
| 5 | O | H | H | 1 | $CH(OH_3)_2$ | H | H | OH | H |
| 6 | O | H | H | 1 | $(CH_2)_3OH_3$ | H | H | OH | H |
| 7 | O | H | H | 1 | $CH_2CH(CH_3)_2$ | H | H | OH | H |
| 8 | O | H | H | 1 | $C(CH_3)_3$ | H | H | OH | H |
| 9 | O | H | H | 1 | H | H | OH | OH | H |
| 10 | O | H | H | 1 | $CH_3$ | H | OH | OH | H |
| 11 | O | H | H | 1 | $CH_2OH_3$ | H | OH | OH | H |
| 12 | O | H | H | 1 | $(CH_2)_2CH_3$ | H | OH | OH | H |
| 13 | O | H | H | 1 | $CH(CH_3)_2$ | H | OH | OH | H |
| 14 | O | H | H | 1 | $(CH_2)_3CH_3$ | H | OH | OH | H |
| 15 | O | H | H | 1 | $CH_2CH(CH_3)_2$ | H | OH | OH | H |
| 16 | O | H | H | 1 | $C(CH_3)_3$ | H | OH | OH | H |
| 17 | O | H | H | 1 | H | | = | OH | H |
| 18 | O | H | H | 1 | $CH_3$ | | = | OH | H |
| 19 | O | H | H | 1 | $CH_2CH_3$ | | = | OH | H |
| 20 | O | H | H | 1 | $(CH_2)_2CH_3$ | | = | OH | H |
| 21 | O | H | H | 1 | $CH(CH_3)_2$ | | = | OH | H |

TABLE 1-continued

R3 = OR8

| | X | R1 | R2 | m | R8 | R4 | R5 | R6 | R7 |
|---|---|---|---|---|---|---|---|---|---|
| 22 | O | H | H | 1 | $(CH_2)_3CH_3$ | | = | OH | H |
| 23 | O | H | H | 1 | $CH_2CH(CH_3)_2$ | | = | OH | H |
| 24 | O | H | H | 1 | $C(CH_3)_3$ | | = | OH | H |
| 25 | O | H | H | 1 | $C(CH_3)_2CH_2CH_3$ | | = | OH | H |
| 26 | O | H | H | 1 | $C(CH_3)(CH_2CH_3)_2$ | | = | OH | H |

TABLE 2

| | X | R1 | R2 | m | R8 | R4 | R5 | R6 | R7 |
|---|---|---|---|---|---|---|---|---|---|
| 27 | O | H | H | 1 | $C(CH_2CH_3)_3$ | | = | OH | H |
| 28 | O | H | H | 1 | cyclopropyl | | = | OH | H |
| 29 | O | H | H | 1 | cyclobutyl | | = | OH | H |
| 30 | O | H | H | 1 | cyclopentyl | | = | OH | H |
| 31 | O | H | H | 1 | cyclohexyl | | = | OH | H |
| 32 | O | H | H | 1 | cycloheptyl | | = | OH | H |
| 33 | O | H | H | 1 | $CH(CF_3)_2$ | | = | OH | H |
| 34 | O | H | H | 2 | H | H | H | OH | H |
| 35 | O | H | H | 2 | $CH_3$ | H | H | OH | H |
| 36 | O | H | H | 2 | $CH_2CH_3$ | H | H | OH | H |
| 37 | O | H | H | 2 | $(CH_2)_2CH_3$ | H | H | OH | H |
| 38 | O | H | H | 2 | $CH(CH_3)_2$ | H | H | OH | H |
| 39 | O | H | H | 2 | $(CH_2)_3CH_3$ | H | H | OH | H |
| 40 | O | H | H | 2 | $CH_2CH(CH_3)_2$ | H | H | OH | H |
| 41 | O | H | H | 2 | $C(CH_3)_3$ | H | H | OH | H |
| 42 | O | H | H | 2 | H | H | OH | OH | H |
| 43 | O | H | H | 2 | $CH_3$ | H | OH | OH | H |
| 44 | O | H | H | 2 | $CH_2CH_3$ | H | OH | OH | H |
| 45 | O | H | H | 2 | $(CH_2)_2CH_3$ | H | OH | OH | H |
| 46 | O | H | H | 2 | $CH(CH_3)_2$ | H | OH | OH | H |
| 47 | O | H | H | 2 | $(CH_2)_3CH_3$ | H | OH | OH | H |
| 48 | O | H | H | 2 | $CH_2CH(CH_3)_2$ | H | OH | OH | H |
| 49 | O | H | H | 2 | $C(CH_3)_3$ | H | OH | OH | H |
| 50 | O | H | H | 2 | H | | = | OH | H |
| 51 | O | H | H | 2 | $CH_3$ | | = | OH | H |
| 52 | O | H | H | 2 | $CH_2CH_3$ | | = | OH | H |
| 53 | O | H | H | 2 | $(CH_2)_2CH_3$ | | = | OH | H |

TABLE 3

| | X | R1 | R2 | m | R8 | R4 | R5 | R6 | R7 |
|---|---|---|---|---|---|---|---|---|---|
| 54 | O | H | H | 2 | $CH(CH_3)_2$ | | = | OH | H |
| 55 | O | H | H | 2 | $(CH_2)_3CH_3$ | | = | OH | H |
| 56 | O | H | H | 2 | $CH_2CH(CH_3)_2$ | | = | OH | H |
| 57 | O | H | H | 2 | $C(CH_3)_3$ | | = | OH | H |
| 58 | O | H | H | 3 | H | H | H | OH | H |
| 59 | O | H | H | 3 | $CH_3$ | H | H | OH | H |
| 60 | O | H | H | 3 | $CH_2CH_3$ | H | H | OH | H |
| 61 | O | H | H | 3 | $(CH_2)_2CH_3$ | H | H | OH | H |
| 62 | O | H | H | 3 | $CH(CH_3)_2$ | H | H | OH | H |
| 63 | O | H | H | 3 | $(CH_2)_3CH_3$ | H | H | OH | H |
| 64 | O | H | H | 3 | $CH_2CH(CH_3)_2$ | H | H | OH | H |
| 65 | O | H | H | 3 | $C(CH_3)_3$ | H | H | OH | H |
| 66 | O | H | H | 3 | H | H | OH | OH | H |
| 67 | O | H | H | 3 | $CH_3$ | H | OH | OH | H |
| 68 | O | H | H | 3 | $CH_2CH_3$ | H | OH | OH | H |
| 69 | O | H | H | 3 | $(CH_2)_2CH_3$ | H | OH | OH | H |

TABLE 3-continued

| | X | R1 | R2 | m | R8 | R4 | R5 | R6 | R7 |
|---|---|---|---|---|---|---|---|---|---|
| 70 | O | H | H | 3 | $CH(CH_3)_2$ | H | OH | OH | H |
| 71 | O | H | H | 3 | $(CH_2)_3CH_3$ | H | OH | OH | H |
| 72 | O | H | H | 3 | $CH_2CH(CH_3)_2$ | H | OH | OH | H |
| 73 | O | H | H | 3 | $C(CH_3)_3$ | H | OH | OH | H |
| 74 | O | H | H | 3 | H | | = | OH | H |
| 75 | O | H | H | 3 | $CH_3$ | | = | OH | H |
| 76 | O | H | H | 3 | $CH_2CH_3$ | | = | OH | H |
| 77 | O | H | H | 3 | $(CH_2)_2CH_3$ | | = | OH | H |
| 78 | O | H | H | 3 | $CH(CH_3)_2$ | | = | OH | H |
| 79 | O | H | H | 3 | $(CH_2)_3CH_3$ | | = | OH | H |
| 80 | O | H | H | 3 | $CH_2CH(CH_3)_2$ | | = | OH | H |

TABLE 4

| | X | R1 | R2 | m | R8 | R4 | R5 | R6 | R7 |
|---|---|---|---|---|---|---|---|---|---|
| 81 | O | H | H | 3 | $C(CH_3)_3$ | | = | OH | H |
| 82 | O | $CH_3$ | H | 1 | H | H | H | OH | H |
| 83 | O | $CH_3$ | H | 1 | $CH_3$ | H | H | OH | H |
| 84 | O | $CH_3$ | H | 1 | $CH_2CH_3$ | H | H | OH | H |
| 85 | O | $CH_3$ | H | 1 | $(CH_2)_2CH_3$ | H | H | OH | H |
| 86 | O | $CH_3$ | H | 1 | $CH(CH_3)_2$ | H | H | OH | H |
| 87 | O | $CH_3$ | H | 1 | $(CH_2)_3CH_3$ | H | H | OH | H |
| 88 | O | $CH_3$ | H | 1 | $CH_2CH(CH_3)_2$ | H | H | OH | H |
| 89 | O | $CH_3$ | H | 1 | $C(CH_3)_3$ | H | H | OH | H |
| 90 | O | $CH_3$ | H | 1 | $CH(CH_2CH_3)_2$ | H | H | OH | H |
| 91 | O | $CH_3$ | H | 1 | $C(CH_3)(CH_2CH_3)_2$ | H | H | OH | H |
| 92 | O | $CH_3$ | H | 1 | H | H | OH | OH | H |
| 93 | O | $CH_3$ | H | 1 | $CH_3$ | H | OH | OH | H |
| 94 | O | $CH_3$ | H | 1 | $CH_2CH_3$ | H | OH | OH | H |
| 95 | O | $CH_3$ | H | 1 | $(CH_2)_2CH_3$ | H | OH | OH | H |
| 96 | O | $CH_3$ | H | 1 | $CH(CH_3)_2$ | H | OH | OH | H |
| 97 | O | $CH_3$ | H | 1 | $(CH_2)_3CH_3$ | H | OH | OH | H |
| 98 | O | $CH_3$ | H | 1 | $CH_2OH(OH_3)_2$ | H | OH | OH | H |
| 99 | O | $CH_3$ | H | 1 | $C(CH_3)_3$ | H | OH | OH | H |
| 100 | O | $CH_3$ | H | 1 | H | | = | OH | H |
| 101 | O | $CH_3$ | H | 1 | $CH_3$ | | = | OH | H |
| 102 | O | $CH_3$ | H | 1 | $CH_2CH_3$ | | = | OH | H |
| 103 | O | $CH_3$ | H | 1 | $(CH_2)_2CH_3$ | | = | OH | H |
| 104 | O | $CH_3$ | H | 1 | $CH(CH_3)_2$ | | = | OH | H |
| 105 | O | $CH_3$ | H | 1 | $(CH_2)_3CH_3$ | | = | OH | H |
| 106 | O | $CH_3$ | H | 1 | $CH_2CH(CH_3)_2$ | | = | OH | H |
| 107 | O | $CH_3$ | H | 1 | $C(CH_3)_3$ | | = | OH | H |

TABLE 5

| | X | R1 | R2 | m | R8 | R4 | R5 | R6 | R7 |
|---|---|---|---|---|---|---|---|---|---|
| 108 | O | $CH_3$ | H | 1 | $C(CH_3)_2CH_2CH_3$ | | = | OH | H |
| 109 | O | $CH_3$ | H | 1 | $CH(CH_2CH_3)_2$ | | = | OH | H |
| 110 | O | $CH_3$ | H | 1 | $C(CH_3)(CH_2CH_3)_2$ | | = | OH | H |
| 111 | O | $CH_3$ | H | 1 | $C(CH_3)_2(CH(CH_3)_2)$ | | = | OH | H |
| 112 | O | $CH_3$ | H | 1 | $C(CH_3)_2((CH_2)_2CH_3)$ | | = | OH | H |
| 113 | O | $CH_3$ | H | 1 | $C(CH_2CH_3)_3$ | | = | OH | H |
| 114 | O | $CH_3$ | H | 1 | $CH(CH(CH_3)_2)_2$ | | = | OH | H |

TABLE 5-continued

|     | X | R1  | R2 | m | R8                          | R4 | R5 | R6 | R7 |
|-----|---|-----|----|---|-----------------------------|----|----|----|----|
| 115 | O | CH₃ | H  | 1 | CH((CH₂)₂CH₃)₂              |    | =  | OH | H  |
| 116 | O | CH₃ | H  | 1 | C(CH₃)₂((CH₂)₃CH₃)          |    | =  | OH | H  |
| 117 | O | CH₃ | H  | 1 | C(CH₃)₂(CH₂CH(CH₃)₂)        |    | =  | OH | H  |
| 118 | O | CH₃ | H  | 1 | C(CH₃)₂(C(CH₃)₃)            |    | =  | OH | H  |
| 119 | O | CH₃ | H  | 1 | C(CH₃)((CH₂)₂CH₃)₂          |    | =  | OH | H  |
| 120 | O | CH₃ | H  | 1 | C(CH₂CH₃)₂(CH(CH₃)₂)        |    | =  | OH | H  |
| 121 | O | CH₃ | H  | 1 | C(CH₃)₂((CH₂)₄CH₃)          |    | =  | OH | H  |
| 122 | O | CH₃ | H  | 1 | C(CH₃)₂(CH₂C(CH₃)₃)         |    | =  | OH | H  |
| 123 | O | CH₃ | H  | 1 | C(CH₂CH₃)₂(C(CH₃)₃)         |    | =  | OH | H  |
| 124 | O | CH₃ | H  | 1 | CH((CH₂)₃CH₃)₂              |    | =  | OH | H  |
| 125 | O | CH₃ | H  | 1 | CH(C(CH₃)₃)₂                |    | =  | OH | H  |
| 126 | O | CH₃ | H  | 1 | CH((CH₂)₂CH(CH₃)₂)₂         |    | =  | OH | H  |
| 127 | O | CH₃ | H  | 1 | CH(CH₂C(CH₃)₃)₂             |    | =  | OH | H  |
| 128 | O | CH₃ | H  | 1 | cyclopropyl                 |    | =  | OH | H  |
| 129 | O | CH₃ | H  | 1 | cyclobutyl                  |    | =  | OH | H  |
| 130 | O | CH₃ | H  | 1 | cyclopentyl                 |    | =  | OH | H  |
| 131 | O | CH₃ | H  | 1 | cyclohexyl                  |    | =  | OH | H  |
| 132 | O | CH₃ | H  | 1 | cycloheptyl                 |    | =  | OH | H  |
| 133 | O | CH₃ | H  | 1 | cyclooctyl                  |    | =  | OH | H  |
| 134 | O | CH₃ | H  | 1 | cyclodecyl                  |    | =  | OH | H  |

TABLE 6

|     | X | R1  | R2 | m | R8                      | R4 | R5 | R6 | R7 |
|-----|---|-----|----|---|-------------------------|----|----|----|----|
| 135 | O | CH₃ | H  | 1 | cyclododecyl            |    | =  | OH | H  |
| 136 | O | CH₃ | H  | 1 | cyclopropylmethyl       |    | =  | OH | H  |
| 137 | O | CH₃ | H  | 1 | C(CH₃)₂-(cyclopropyl)   |    | =  | OH | H  |
| 138 | O | CH₃ | H  | 1 | cyclopentylmethyl       |    | =  | OH | H  |
| 139 | O | CH₃ | H  | 1 | cyclohexylmethyl        |    | =  | OH | H  |
| 140 | O | CH₃ | H  | 1 | 1-methylcyclopentyl     |    | =  | OH | H  |
| 141 | O | CH₃ | H  | 1 | 1-ethylcyclopentyl      |    | =  | OH | H  |
| 142 | O | CH₃ | H  | 1 | 1-methylcyclohexyl      |    | =  | OH | H  |
| 143 | O | CH₃ | H  | 1 | 1-methylcycloheptyl     |    | =  | OH | H  |
| 144 | O | CH₃ | H  | 1 | 1-ethylcyclohexyl       |    | =  | OH | H  |
| 145 | O | CH₃ | H  | 1 | 1-methylcyclooctyl      |    | =  | OH | H  |
| 146 | O | CH₃ | H  | 1 | 1-adamantyl             |    | =  | OH | H  |
| 147 | O | CH₃ | H  | 1 | 2-adamantyl             |    | =  | OH | H  |
| 148 | O | H   | H  | 1 | CH(CF₃)₂                |    | =  | OH | H  |
| 149 | O | CH₃ | H  | 2 | H                       | H  | H  | OH | H  |
| 150 | O | CH₃ | H  | 2 | CH₃                     | H  | H  | OH | H  |
| 151 | O | CH₃ | H  | 2 | CD₂CH₃                  | H  | H  | OH | H  |
| 152 | O | CH₃ | H  | 2 | (CH₂)₂CH₃               | H  | H  | OH | H  |
| 153 | O | CH₃ | H  | 2 | CH(CH₃)₂                | H  | H  | OH | H  |
| 154 | O | CH₃ | H  | 2 | (CH₂)₃CH₃               | H  | H  | OH | H  |
| 155 | O | CH₃ | H  | 2 | CH₂CH(CH₃)₂             | H  | H  | OH | H  |
| 156 | O | CH₃ | H  | 2 | C(CH₃)₃                 | H  | H  | OH | H  |
| 157 | O | CH₃ | H  | 2 | H                       | H  | OH | OH | H  |
| 158 | O | CH₃ | H  | 2 | CH₃                     | H  | OH | OH | H  |
| 159 | O | CH₃ | H  | 2 | CH₂CH₃                  | H  | OH | OH | H  |
| 160 | O | CH₃ | H  | 2 | (CH₂)₂CH₃               | H  | OH | OH | H  |
| 161 | O | CH₃ | H  | 2 | CH(CH₃)₂                | H  | OH | OH | H  |

TABLE 7

|     | X | R1  | R2 | m | R8                      | R4 | R5 | R6 | R7 |
|-----|---|-----|----|---|-------------------------|----|----|----|----|
| 162 | O | CH₃ | H  | 2 | (CH₂)₃CH₃               | H  | OH | OH | H  |
| 163 | O | CH₃ | H  | 2 | CH₂CH(CH₃)₂             | H  | OH | OH | H  |
| 164 | O | CH₃ | H  | 2 | C(CH₃)₃                 | H  | OH | OH | H  |
| 165 | O | CH₃ | H  | 2 | H                       |    | =  | OH | H  |
| 166 | O | CH₃ | H  | 2 | CH₃                     |    | =  | OH | H  |
| 167 | O | CH₃ | H  | 2 | CH₂CH₃                  |    | =  | OH | H  |
| 168 | O | CH₃ | H  | 2 | (CH₂)₂CH₃               |    | =  | OH | H  |
| 169 | O | CH₃ | H  | 2 | CH(CH₃)₂                |    | =  | OH | H  |
| 170 | O | CH₃ | H  | 2 | (CH₂)₃CH₃               |    | =  | OH | H  |
| 171 | O | CH₃ | H  | 2 | CH₂CH(CH₃)₂             |    | =  | OH | H  |
| 172 | O | CH₃ | H  | 2 | C(CH₃)₃                 |    | =  | OH | H  |
| 173 | O | CH₃ | H  | 2 | C(CH₃)(CH₂CH₃)₂         |    | =  | OH | H  |
| 174 | O | CH₃ | H  | 3 | H                       | H  | H  | OH | H  |
| 175 | O | CH₃ | H  | 3 | CH₃                     | H  | H  | OH | H  |
| 176 | O | CH₃ | H  | 3 | CH₂CH₃                  | H  | H  | OH | H  |

TABLE 7-continued

|     | X | R1  | R2  | m | R8          | R4 | R5 | R6 | R7 |
|-----|---|-----|-----|---|-------------|----|----|----|----|
| 177 | O | CH₃ | H   | 3 | (CH₂)₂CH₃   | H  | H  | OH | H  |
| 178 | O | CH₃ | H   | 3 | CH(CH₃)₂    | H  | H  | OH | H  |
| 179 | O | CH₃ | H   | 3 | (CH₂)₃CH₃   | H  | H  | OH | H  |
| 180 | O | CH₃ | H   | 3 | CH₂CH(CH₃)₂ | H  | H  | OH | H  |
| 181 | O | CH₃ | H   | 3 | C(CH₃)₃     | H  | H  | OH | H  |
| 182 | O | CH₃ | H   | 3 | H           | H  | OH | OH | H  |
| 183 | O | CH₃ | H   | 3 | CH₃         | H  | OH | OH | H  |
| 184 | O | CH₃ | H   | 3 | CH₂CH₃      | H  | OH | OH | H  |
| 165 | O | CH₃ | H   | 3 | (CH₂)₂CH₃   | H  | OH | OH | H  |
| 186 | O | CH₃ | H   | 3 | CH(CH₃)₂    | H  | OH | OH | H  |
| 187 | O | CH₃ | H   | 3 | (CH₂)₃CH₃   | H  | OH | OH | H  |
| 188 | O | CH₃ | H   | 3 | CH₂CH(CH₃)₂ | H  | OH | OH | H  |

TABLE 8

|     | X | R1  | R2  | m | R8           | R4 | R5 | R6 | R7 |
|-----|---|-----|-----|---|--------------|----|----|----|----|
| 189 | O | CH₃ | H   | 3 | C(CH₃)₃      | H  | OH | OH | H  |
| 190 | O | CH₃ | H   | 3 | H            |    | =  | OH | H  |
| 191 | O | CH₃ | H   | 3 | CH₃          |    | =  | OH | H  |
| 192 | O | CH₃ | H   | 3 | CH₂CH₃       |    | =  | OH | H  |
| 193 | O | CH₃ | H   | 3 | (CH₂)₂CH₃    |    | =  | OH | H  |
| 194 | O | CH₃ | H   | 3 | CH(CH₃)₂     |    | =  | OH | H  |
| 195 | O | CH₃ | H   | 3 | (CH₂)₃CH₃    |    | =  | OH | H  |
| 196 | O | CH₃ | H   | 3 | CH₂OH(CH₃)₂  |    | =  | OH | H  |
| 197 | O | CH₃ | H   | 3 | C(CH₃)₃      |    | =  | OH | H  |
| 198 | O | H   | CH₃ | 1 | H            | H  | H  | OH | H  |
| 199 | O | H   | CH₃ | 1 | CH₃          | H  | H  | OH | H  |
| 200 | O | H   | CH₃ | 1 | CH₂CH₃       | H  | H  | OH | H  |
| 201 | O | H   | CH₃ | 1 | (CH₂)₂CH₃    | H  | H  | OH | H  |
| 202 | O | H   | CH₃ | 1 | CH(CH₃)₂     | H  | H  | OH | H  |
| 203 | O | H   | CH₃ | 1 | (CH₂)₃CH₃    | H  | H  | OH | H  |
| 204 | O | H   | CH₃ | 1 | CH₂CH(CH₃)₂  | H  | H  | OH | H  |
| 205 | O | H   | CH₃ | 1 | C(CH₃)₃      | H  | H  | OH | H  |
| 206 | O | H   | CH₃ | 1 | H            | H  | OH | OH | H  |
| 207 | O | H   | CH₃ | 1 | CH₃          | H  | OH | OH | H  |
| 208 | O | H   | CH₃ | 1 | CH₂CH₃       | H  | OH | OH | H  |
| 209 | O | H   | CH₃ | 1 | (CH₂)₂CH₃    | H  | OH | OH | H  |
| 210 | O | H   | CH₃ | 1 | CH(CH₃)₂     | H  | OH | OH | H  |
| 211 | O | H   | CH₃ | 1 | (CH₂)₃CH₃    | H  | OH | OH | H  |
| 212 | O | H   | CH₃ | 1 | CH₂CH(CH₃)₂  | H  | OH | OH | H  |
| 213 | O | H   | CH₃ | 1 | C(CH₃)₃      | H  | OH | OH | H  |
| 214 | O | H   | CH₃ | 1 | H            |    | =  | OH | H  |
| 215 | O | H   | CH₃ | 1 | CH₃          |    | =  | OH | H  |

TABLE 9

|     | X | R1 | R2  | m | R8              | R4 | R5 | R6 | R7 |
|-----|---|----|-----|---|-----------------|----|----|----|----|
| 216 | O | H  | CH₃ | 1 | CH₂CH₃          |    | =  | OH | H  |
| 217 | O | H  | CH₃ | 1 | (CH₂)₂CH₃       |    | =  | OH | H  |
| 218 | O | H  | CH₃ | 1 | CH(CH₃)₂        |    | =  | OH | H  |
| 219 | O | H  | CH₃ | 1 | (CH₂)₃CH₃       |    | =  | OH | H  |
| 220 | O | H  | CH₃ | 1 | CH₂CH(CH₃)₂     |    | =  | OH | H  |
| 221 | O | H  | CH₃ | 1 | C(CH₃)₃         |    | =  | OH | H  |
| 222 | O | H  | CH₃ | 1 | C(CH₃)₂CH₂CH₃   |    | =  | OH | H  |
| 223 | O | H  | CH₃ | 1 | CH(CH₂CH₃)₂     |    | =  | OH | H  |
| 224 | O | H  | CH₃ | 1 | C(CH₃)(CH₂CH₃)₂ |    | =  | OH | H  |
| 225 | O | H  | CH₃ | 1 | C(CH₂CH₃)₃      |    | =  | OH | H  |
| 226 | O | H  | CH₃ | 1 | cyclopropyl     |    | =  | OH | H  |
| 227 | O | H  | CH₃ | 1 | cyclobutyl      |    | =  | OH | H  |
| 228 | O | H  | CH₃ | 1 | cyclopentyl     |    | =  | OH | H  |
| 229 | O | H  | CH₃ | 1 | cyclohexyl      |    | =  | OH | H  |
| 230 | O | H  | CH₃ | 1 | cycloheptyl     |    | =  | OH | H  |
| 231 | O | H  | CH₃ | 1 | CH(CF₃)₂        |    | =  | OH | H  |
| 232 | O | H  | CH₃ | 2 | H               | H  | H  | OH | H  |
| 233 | O | H  | CH₃ | 2 | CH₃             | H  | H  | OH | H  |
| 234 | O | H  | CH₃ | 2 | CH₂CH₃          | H  | H  | OH | H  |
| 235 | O | H  | CH₃ | 2 | (CH₂)₂CH₃       | H  | H  | OH | H  |
| 236 | O | H  | CH₃ | 2 | CH(CH₃)₂        | H  | H  | OH | H  |
| 237 | O | H  | CH₃ | 2 | (CH₂)₃CH₃       | H  | H  | OH | H  |
| 238 | O | H  | CH₃ | 2 | CH₂CH(CH₃)₂     | H  | H  | OH | H  |
| 239 | O | H  | CH₃ | 2 | C(CH₃)₃         | H  | H  | OH | H  |
| 240 | O | H  | CH₃ | 2 | H               | H  | OH | OH | H  |
| 241 | O | H  | CH₃ | 2 | CH₃             | H  | OH | OH | H  |
| 242 | O | H  | CH₃ | 2 | CH₂CH₃          | H  | OH | OH | H  |

TABLE 10

|     | X | R1 | R2  | m | R8            | R4 | R5 | R6 | R7 |
|-----|---|----|-----|---|---------------|----|----|----|----|
| 243 | O | H  | CH₃ | 2 | (CH₂)₂CH₃     | H  | OH | OH | H  |
| 244 | O | H  | CH₃ | 2 | CH(CH₃)₂      | H  | OH | OH | H  |
| 245 | O | H  | CH₃ | 2 | (CH₂)₃CH₃     | H  | OH | OH | H  |
| 246 | O | H  | CH₃ | 2 | CH₂CH(CH₃)₂   | H  | OH | OH | H  |
| 247 | O | H  | CH₃ | 2 | C(CH₃)₃       | H  | OH | OH | H  |
| 248 | O | H  | CH₃ | 2 | H             |    | =  | OH | H  |
| 249 | O | H  | CH₃ | 2 | CH₃           |    | =  | OH | H  |
| 250 | O | H  | CH₃ | 2 | CH₂CH₃        |    | =  | OH | H  |
| 251 | O | H  | CH₃ | 2 | (CH₂)₂CH₃     |    | =  | OH | H  |
| 252 | O | H  | CH₃ | 2 | CH(CH₃)₂      |    | =  | OH | H  |
| 253 | O | H  | CH₃ | 2 | (CH₂)₃CH₃     |    | =  | OH | H  |
| 254 | O | H  | CH₃ | 2 | CH₂CH(CH₃)₂   |    | =  | OH | H  |
| 255 | O | H  | CH₃ | 2 | C(CH₃)₃       |    | =  | OH | H  |
| 256 | O | H  | CH₃ | 3 | H             | H  | H  | OH | H  |
| 257 | O | H  | CH₃ | 3 | CH₃           | H  | H  | OH | H  |
| 258 | O | H  | CH₃ | 3 | CH₂CH₃        | H  | H  | OH | H  |
| 259 | O | H  | CH₃ | 3 | (CH₂)₂CH₃     | H  | H  | OH | H  |
| 260 | O | H  | CH₃ | 3 | CH(CH₃)₂      | H  | H  | OH | H  |
| 261 | O | H  | CH₃ | 3 | (CH₂)₃CH₃     | H  | H  | OH | H  |
| 262 | O | H  | CH₃ | 3 | CH₂CH(CH₃)₂   | H  | H  | OH | H  |
| 263 | O | H  | CH₃ | 3 | C(CH₃)₃       | H  | H  | OH | H  |
| 264 | O | H  | CH₃ | 3 | H             | H  | OH | OH | H  |
| 265 | O | H  | CH₃ | 3 | CH₃           | H  | OH | OH | H  |
| 266 | O | H  | CH₃ | 3 | CH₂CH₃        | H  | OH | OH | H  |
| 267 | O | H  | CH₃ | 3 | (CH₂)₂CH₃     | H  | OH | OH | H  |
| 268 | O | H  | CH₃ | 3 | CH(CH₃)₂      | H  | OH | OH | H  |
| 269 | O | H  | CH₃ | 3 | (CH₂)₃CH₃     | H  | OH | OH | H  |

TABLE 11

|     | X | R1  | R2  | m | R8            | R4 | R5 | R6 | R7 |
|-----|---|-----|-----|---|---------------|----|----|----|----|
| 270 | O | H   | CH₃ | 3 | CH₂CH(CH₃)₂   | H  | OH | OH | H  |
| 271 | O | H   | CH₃ | 3 | C(CH₃)₃       | H  | OH | OH | H  |
| 272 | O | H   | CH₃ | 3 | H             |    | =  | OH | H  |
| 273 | O | H   | CH₃ | 3 | CH₃           |    | =  | OH | H  |
| 274 | O | H   | CH₃ | 3 | CH₂CH₃        |    | =  | OH | H  |
| 275 | O | H   | CH₃ | 3 | (CH₂)₂CH₃     |    | =  | OH | H  |
| 276 | O | H   | CH₃ | 3 | CH(CH₃)₂      |    | =  | OH | H  |
| 277 | O | H   | CH₃ | 3 | (CH₂)₃CH₃     |    | =  | OH | H  |
| 278 | O | H   | CH₃ | 3 | CH₂CH(CH₃)₂   |    | =  | OH | H  |
| 279 | O | H   | CH₃ | 3 | C(CH₃)₃       |    | =  | OH | H  |
| 280 | O | CH₃ | CH₃ | 1 | H             | H  | H  | OH | H  |
| 281 | O | CH₃ | CH₃ | 1 | CH₃           | H  | H  | OH | H  |
| 282 | O | CH₃ | CH₃ | 1 | CH₂CH₃        | H  | H  | OH | H  |
| 283 | O | CH₃ | CH₃ | 1 | (CH₂)₂CH₃     | H  | H  | OH | H  |
| 284 | O | CH₃ | CH₃ | 1 | CH(CH₃)₂      | H  | H  | OH | H  |
| 285 | O | CH₃ | CH₃ | 1 | (CH₂)₃CH₃     | H  | H  | OH | H  |
| 286 | O | CH₃ | CH₃ | 1 | CH₂CH(CH₃)₂   | H  | H  | OH | H  |
| 287 | O | CH₃ | CH₃ | 1 | C(CH₃)₃       | H  | H  | OH | H  |
| 288 | O | CH₃ | CH₃ | 1 | H             | H  | OH | OH | H  |
| 289 | O | CH₃ | CH₃ | 1 | CH₃           | H  | OH | OH | H  |
| 290 | O | CH₃ | CH₃ | 1 | CH₂CH₃        | H  | OH | OH | H  |
| 291 | O | CH₃ | CH₃ | 1 | (CH₂)₂CH₃     | H  | OH | OH | H  |
| 292 | O | CH₃ | CH₃ | 1 | CH(CH₃)₂      | H  | OH | OH | H  |
| 293 | O | CH₃ | CH₃ | 1 | (CH₂)₃CH₃     | H  | OH | OH | H  |
| 294 | O | CH₃ | CH₃ | 1 | CH₂CH(CH₃)₂   | H  | OH | OH | H  |
| 295 | O | CH₃ | CH₃ | 1 | C(CH₃)₃       | H  | OH | OH | H  |
| 296 | O | CH₃ | CH₃ | 1 | H             |    | =  | OH | H  |

TABLE 12

|     | X | R1  | R2  | m | R8            | R4 | R5 | R6 | R7 |
|-----|---|-----|-----|---|---------------|----|----|----|----|
| 297 | O | CH₃ | CH₃ | 1 | CH₃           |    | =  | OH | H  |
| 298 | O | CH₃ | CH₃ | 1 | CH₂CH₃        |    | =  | OH | H  |
| 299 | O | CH₃ | CH₃ | 1 | (CH₂)₂CH₃     |    | =  | OH | H  |
| 300 | O | CH₃ | CH₃ | 1 | CH(CH₃)₂      |    | =  | OH | H  |
| 301 | O | CH₃ | CH₃ | 1 | (CH₂)₃CH₃     |    | =  | OH | H  |
| 302 | O | CH₃ | CH₃ | 1 | CH₂CH(CH₃)₂   |    | =  | OH | H  |
| 303 | O | CH₃ | CH₃ | 1 | C(CH₃)₃       |    | =  | OH | H  |
| 304 | O | CH₃ | CH₃ | 1 | cyclopropyl   |    | =  | OH | H  |
| 305 | O | CH₃ | CH₃ | 1 | cyclobutyl    |    | =  | OH | H  |
| 306 | O | CH₃ | CH₃ | 1 | cyclopentyl   |    | =  | OH | H  |
| 307 | O | CH₃ | CH₃ | 1 | cyclohexyl    |    | =  | OH | H  |
| 308 | O | CH₃ | CH₃ | 1 | cycloheptyl   |    | =  | OH | H  |
| 309 | O | CH₃ | CH₃ | 1 | CH(CF₃)₂      |    | =  | OH | H  |
| 310 | O | CH₃ | CH₃ | 2 | H             | H  | H  | OH | H  |
| 311 | O | CH₃ | CH₃ | 2 | CH₃           | H  | H  | OH | H  |
| 312 | O | CH₃ | CH₃ | 2 | CH₂CH₃        | H  | H  | OH | H  |
| 313 | O | CH₃ | CH₃ | 2 | (CH₂)₂CH₃     | H  | H  | OH | H  |
| 314 | O | CH₃ | CH₃ | 2 | CH(CH₃)₂      | H  | H  | OH | H  |
| 315 | O | CH₃ | CH₃ | 2 | (CH₂)₃CH₃     | H  | H  | OH | H  |
| 316 | O | CH₃ | CH₃ | 2 | CH₂CH(CH₃)₂   | H  | H  | OH | H  |
| 317 | O | CH₃ | CH₃ | 2 | C(CH₃)₃       | H  | H  | OH | H  |
| 318 | O | CH₃ | CH₃ | 2 | H             | H  | OH | OH | H  |
| 319 | O | CH₃ | CH₃ | 2 | CH₃           | H  | OH | OH | H  |
| 320 | O | CH₃ | CH₃ | 2 | CH₂CH₃        | H  | OH | OH | H  |
| 321 | O | CH₃ | CH₃ | 2 | (CH₂)₂CH₃     | H  | OH | OH | H  |
| 322 | O | CH₃ | CH₃ | 2 | CH(CH₃)₂      | H  | OH | OH | H  |
| 323 | O | CH₃ | CH₃ | 2 | (CH₂)₃CH₃     | H  | OH | OH | H  |

TABLE 13

|     | X | R1  | R2  | m | R8            | R4 | R5 | R6 | R7 |
|-----|---|-----|-----|---|---------------|----|----|----|----|
| 324 | O | CH₃ | CH₃ | 2 | CH₂CH(CH₃)₂   | H  | OH | OH | H  |
| 325 | O | CH₃ | CH₃ | 2 | C(CH₃)₃       | H  | OH | OH | H  |
| 326 | O | CH₃ | CH₃ | 2 | H             |    | =  | OH | H  |
| 327 | O | CH₃ | CH₃ | 2 | CH₃           |    | =  | OH | H  |
| 328 | O | CH₃ | CH₃ | 2 | CH₂CH₃        |    | =  | OH | H  |
| 329 | O | CH₃ | CH₃ | 2 | (CH₂)₂CH₃     |    | =  | OH | H  |
| 330 | O | CH₃ | CH₃ | 2 | CH(CH₃)₂      |    | =  | OH | H  |
| 331 | O | CH₃ | CH₃ | 2 | (CH₂)₃CH₃     |    | =  | OH | H  |
| 332 | O | CH₃ | CH₃ | 2 | CH₂CH(CH₃)₂   |    | =  | OH | H  |
| 333 | O | CH₃ | CH₃ | 2 | C(CH₃)₃       |    | =  | OH | H  |
| 334 | O | CH₃ | CH₃ | 3 | H             | H  | H  | OH | H  |
| 335 | O | CH₃ | CH₃ | 3 | CH₃           | H  | H  | OH | H  |
| 336 | O | CH₃ | CH₃ | 3 | CH₂CH₃        | H  | H  | OH | H  |
| 337 | O | CH₃ | CH₃ | 3 | (CH₂)₂CH₃     | H  | H  | OH | H  |
| 338 | O | CH₃ | CH₃ | 3 | CH(CH₃)₂      | H  | H  | OH | H  |
| 339 | O | CH₃ | CH₃ | 3 | (CH₂)₃CH₃     | H  | H  | OH | H  |
| 340 | O | CH₃ | CH₃ | 3 | CH₂CH(CH₃)₂   | H  | H  | OH | H  |
| 341 | O | CH₃ | CH₃ | 3 | C(CH₃)₃       | H  | H  | OH | H  |

TABLE 13-continued

| | X | R1 | R2 | m | R8 | R4 | R5 | R6 | R7 |
|---|---|---|---|---|---|---|---|---|---|
| 342 | O | CH$_3$ | CH$_3$ | 3 | H | | H | OH | OH | H |
| 343 | O | CH$_3$ | CH$_3$ | 3 | CH$_3$ | H | OH | OH | H |
| 344 | O | CH$_3$ | CH$_3$ | 3 | CH$_2$CH$_3$ | H | OH | OH | H |
| 345 | O | CH$_3$ | CH$_3$ | 3 | (CH$_2$)$_2$CH$_3$ | H | OH | OH | H |
| 346 | O | CH$_3$ | CH$_3$ | 3 | CH(CH$_3$)$_2$ | H | OH | OH | H |
| 347 | O | CH$_3$ | CH$_3$ | 3 | (CH$_2$)$_3$CH$_3$ | H | OH | OH | H |
| 348 | O | CH$_3$ | CH$_3$ | 3 | CH$_2$CH(CH$_3$)$_2$ | H | OH | OH | H |
| 349 | O | CH$_3$ | CH$_3$ | 3 | C(CH$_3$)$_3$ | H | OH | OH | H |
| 350 | O | CH$_3$ | CH$_3$ | 3 | H | | = | OH | H |

TABLE 14

| | X | R1 | R2 | m | R8 | R4 | R5 | R6 | R7 |
|---|---|---|---|---|---|---|---|---|---|
| 351 | O | CH$_3$ | CH$_3$ | 3 | CH$_3$ | | = | OH | H |
| 352 | O | CH$_3$ | CH$_3$ | 3 | CH$_2$CH$_3$ | | = | OH | H |
| 353 | O | CH$_3$ | CH$_3$ | 3 | (CH$_2$)$_2$CH$_3$ | | = | OH | H |
| 354 | O | CH$_3$ | CH$_3$ | 3 | CH(CH$_3$)$_2$ | | = | OH | H |
| 355 | O | CH$_3$ | CH$_3$ | 3 | (CH$_2$)$_3$CH$_3$ | | = | OH | H |
| 356 | O | CH$_3$ | CH$_3$ | 3 | CH$_2$CH(CH$_3$)$_2$ | | = | OH | H |
| 357 | O | CH$_3$ | CH$_3$ | 3 | C(CH$_3$)$_3$ | | = | OH | H |
| 358 | S | H | H | 1 | H | H | H | OH | H |
| 359 | S | H | H | 1 | CH$_3$ | H | H | OH | H |
| 360 | S | H | H | 1 | CH$_2$CH$_3$ | H | H | OH | H |
| 361 | S | H | H | 1 | (CH$_2$)$_2$CH$_3$ | H | H | OH | H |
| 362 | S | H | H | 1 | CH(CH$_3$)$_2$ | H | H | OH | H |
| 363 | S | H | H | 1 | (CH$_2$)$_3$CH$_3$ | H | H | OH | H |
| 364 | S | H | H | 1 | CH$_2$CH(CH$_3$)$_2$ | H | H | OH | H |
| 365 | S | H | H | 1 | C(CH$_3$)$_3$ | H | H | OH | H |
| 366 | S | H | H | 1 | H | H | OH | OH | H |
| 367 | S | H | H | 1 | CH$_3$ | H | OH | OH | H |
| 368 | S | H | H | 1 | CH$_2$CH$_3$ | H | OH | OH | H |
| 369 | S | H | H | 1 | (CH$_2$)$_2$CH$_3$ | H | OH | OH | H |
| 370 | S | H | H | 1 | CH(CH$_3$)$_2$ | H | OH | OH | H |
| 371 | S | H | H | 1 | (CH$_2$)$_3$CH$_3$ | H | OH | OH | H |
| 372 | S | H | H | 1 | CH$_2$CH(CH$_3$)$_2$ | H | OH | OH | H |
| 373 | S | H | H | 1 | C(CH$_3$)$_3$ | H | OH | OH | H |
| 374 | S | H | H | 1 | H | | = | OH | H |
| 375 | S | H | H | 1 | CH$_3$ | | = | OH | H |
| 376 | S | H | H | 1 | CH$_2$CH$_3$ | | = | OH | H |
| 377 | S | H | H | 1 | (CH$_2$)$_2$CH$_3$ | | = | OH | H |

TABLE 15

| | X | R1 | R2 | m | R8 | R4 | R5 | R6 | R7 |
|---|---|---|---|---|---|---|---|---|---|
| 378 | S | H | H | 1 | CH(CH$_3$)$_2$ | | = | OH | H |
| 379 | S | H | H | 1 | (CH$_2$)$_3$CH$_3$ | | = | OH | H |
| 380 | S | H | H | 1 | CH$_2$CH(CH$_3$)$_2$ | | = | OH | H |
| 381 | S | H | H | 1 | C(CH$_3$)$_3$ | | = | OH | H |
| 382 | S | H | H | 1 | C(CH$_3$)$_2$CH$_2$CH$_3$ | | = | OH | H |
| 383 | S | H | H | 1 | C(CH$_3$)(CH$_2$CH$_3$)$_2$ | | = | OH | H |
| 384 | S | H | H | 1 | C(CH$_2$CH$_3$)$_3$ | | = | OH | H |
| 385 | S | H | H | 1 | cyclopropyl | | = | OH | H |
| 386 | S | H | H | 1 | cyclobutyl | | = | OH | H |
| 387 | S | H | H | 1 | cyclopentyl | | = | OH | H |
| 388 | S | H | H | 1 | cyclohexyl | | = | OH | H |
| 389 | S | H | H | 1 | cycloheptyl | | = | OH | H |
| 390 | S | H | H | 1 | CH(CF$_3$)$_2$ | | = | OH | H |
| 391 | S | H | H | 2 | H | H | H | OH | H |
| 392 | S | H | H | 2 | CH$_3$ | H | H | OH | H |
| 393 | S | H | H | 2 | CH$_2$CH$_3$ | H | H | OH | H |
| 394 | S | H | H | 2 | (CH$_2$)$_2$CH$_3$ | H | H | OH | H |
| 395 | S | H | H | 2 | CH(CH$_3$)$_2$ | H | H | OH | H |
| 396 | S | H | H | 2 | (CH$_2$)$_3$CH$_3$ | H | H | OH | H |
| 397 | S | H | H | 2 | CH$_2$CH(CH$_3$)$_2$ | H | H | OH | H |
| 398 | S | H | H | 2 | C(CH$_3$)$_3$ | H | H | OH | H |
| 399 | S | H | H | 2 | H | H | OH | OH | H |
| 400 | S | H | H | 2 | CH$_3$ | H | OH | OH | H |
| 401 | S | H | H | 2 | CH$_2$CH$_3$ | H | OH | OH | H |
| 402 | S | H | H | 2 | (CH$_2$)$_2$CH$_3$ | H | OH | OH | H |
| 403 | S | H | H | 2 | CH(CH$_3$)$_2$ | H | OH | OH | H |
| 404 | S | H | H | 2 | (CH$_2$)$_3$CH$_3$ | H | OH | OH | H |

TABLE 16

| | X | R1 | R2 | m | R8 | R4 | R5 | R6 | R7 |
|---|---|---|---|---|---|---|---|---|---|
| 405 | S | H | H | 2 | CH$_2$CH(CH$_3$)$_2$ | H | OH | OH | H |
| 406 | S | H | H | 2 | C(CH$_3$)$_3$ | H | OH | OH | H |
| 407 | S | H | H | 2 | H | | = | OH | H |
| 408 | S | H | H | 2 | CH$_3$ | | = | OH | H |
| 409 | S | H | H | 2 | CH$_2$CH$_3$ | | = | OH | H |
| 410 | S | H | H | 2 | (CH$_2$)$_2$CH$_3$ | | = | OH | H |
| 411 | S | H | H | 2 | CH(CH$_3$)$_2$ | | = | OH | H |
| 412 | S | H | H | 2 | (CH$_2$)$_3$CH$_3$ | | = | OH | H |
| 413 | S | H | H | 2 | CH$_2$CH(CH$_3$)$_2$ | | = | OH | H |
| 414 | S | H | H | 2 | C(CH$_3$)$_3$ | | = | OH | H |
| 415 | S | H | H | 3 | H | H | H | OH | H |
| 416 | S | H | H | 3 | CH$_3$ | H | H | OH | H |
| 417 | S | H | H | 3 | CH$_2$CH$_3$ | H | H | OH | H |
| 418 | S | H | H | 3 | (CH$_2$)$_2$CH$_3$ | H | H | OH | H |
| 419 | S | H | H | 3 | CH(CH$_3$)$_2$ | H | H | OH | H |
| 420 | S | H | H | 3 | (CH$_2$)$_3$CH$_3$ | H | H | OH | H |
| 421 | S | H | H | 3 | CH$_2$CH(CH$_3$)$_2$ | H | H | OH | H |
| 422 | S | H | H | 3 | C(CH$_3$)$_3$ | H | H | OH | H |
| 423 | S | H | H | 3 | H | H | OH | OH | H |
| 424 | S | H | H | 3 | CH$_3$ | H | OH | OH | H |
| 425 | S | H | H | 3 | CH$_2$CH$_3$ | H | OH | OH | H |
| 426 | S | H | H | 3 | (CH$_2$)$_2$CH$_3$ | H | OH | OH | H |
| 427 | S | H | H | 3 | CH(CH$_3$)$_2$ | H | OH | OH | H |
| 428 | S | H | H | 3 | (CH$_2$)$_3$CH$_3$ | H | OH | OH | H |
| 429 | S | H | H | 3 | CH$_2$CH(CH$_3$)$_2$ | H | OH | OH | H |
| 430 | S | H | H | 3 | C(CH$_3$)$_3$ | H | OH | OH | H |
| 431 | S | H | H | 3 | H | | = | OH | H |

TABLE 17

| | X | R1 | R2 | m | R8 | R4 | R5 | R6 | R7 |
|---|---|---|---|---|---|---|---|---|---|
| 432 | S | H | H | 3 | CH$_3$ | | = | OH | H |
| 433 | S | H | H | 3 | CH$_2$CH$_3$ | | = | OH | H |
| 434 | S | H | H | 3 | (CH$_2$)$_2$CH$_3$ | | = | OH | H |
| 435 | S | H | H | 3 | CH(CH$_3$)$_2$ | | = | OH | H |
| 436 | S | H | H | 3 | (CH$_2$)$_3$CH$_3$ | | = | OH | H |
| 437 | S | H | H | 3 | CH$_2$CH(CH$_3$)$_2$ | | = | OH | H |
| 438 | S | H | H | 3 | C(CH$_3$)$_3$ | | = | OH | H |
| 439 | S | CH$_3$ | H | 1 | H | H | H | OH | H |
| 440 | S | CH$_3$ | H | 1 | CH$_3$ | H | H | OH | H |
| 441 | S | CH$_3$ | H | 1 | CH$_2$CH$_3$ | H | H | OH | H |
| 442 | S | CH$_3$ | H | 1 | (CH$_2$)$_2$CH$_3$ | H | H | OH | H |
| 443 | S | CH$_3$ | H | 1 | CH(CH$_3$)$_2$ | H | H | OH | H |
| 444 | S | CH$_3$ | H | 1 | (CH$_2$)$_3$CH$_3$ | H | H | OH | H |
| 445 | S | CH$_3$ | H | 1 | CH$_2$CH(CH$_3$)$_2$ | H | H | OH | H |
| 446 | S | CH$_3$ | H | 1 | C(CH$_3$)$_3$ | H | H | OH | H |
| 447 | S | CH$_3$ | H | 1 | H | H | OH | OH | H |
| 448 | S | CH$_3$ | H | 1 | CH$_3$ | H | OH | OH | H |
| 449 | S | CH$_3$ | H | 1 | CH$_2$CH$_3$ | H | OH | OH | H |
| 450 | S | CH$_3$ | H | 1 | (CH$_2$)$_2$CH$_3$ | H | OH | OH | H |
| 451 | S | CH$_3$ | H | 1 | CH(CH$_3$)$_2$ | H | OH | OH | H |
| 452 | S | CH$_3$ | H | 1 | (CH$_2$)$_3$CH$_3$ | H | OH | OH | H |
| 453 | S | CH$_3$ | H | 1 | CH$_2$CH(CH$_3$)$_2$ | H | OH | OH | H |
| 454 | S | CH$_3$ | H | 1 | C(CH$_3$)$_3$ | H | OH | OH | H |
| 455 | S | CH$_3$ | H | 1 | H | | = | OH | H |
| 456 | S | CH$_3$ | H | 1 | CH$_3$ | | = | OH | H |
| 457 | S | CH$_3$ | H | 1 | CH$_2$CH$_3$ | | = | OH | H |
| 458 | S | CH$_3$ | H | 1 | (CH$_2$)$_2$CH$_3$ | | = | OH | H |

TABLE 18

| | X | R1 | R2 | m | R8 | R4 | R5 | R6 | R7 |
|---|---|---|---|---|---|---|---|---|---|
| 459 | S | CH$_3$ | H | 1 | CH(CH$_3$)$_2$ | | = | OH | H |
| 460 | S | CH$_3$ | H | 1 | (CH$_2$)$_3$CH$_3$ | | = | OH | H |
| 461 | S | CH$_3$ | H | 1 | CH$_2$CH(CH$_3$)$_2$ | | = | OH | H |
| 462 | S | CH$_3$ | H | 1 | C(CH$_3$)$_3$ | | = | OH | H |
| 463 | S | CH$_3$ | H | 1 | C(CH$_3$)$_2$CH$_2$CH$_3$ | | = | OH | H |
| 464 | S | CH$_3$ | H | 1 | C(CH$_3$)(CH$_2$CH$_3$)$_2$ | | = | OH | H |
| 465 | S | CH$_3$ | H | 1 | C(CH$_2$CH$_3$)$_3$ | | = | OH | H |
| 466 | S | CH$_3$ | H | 1 | cyclopropyl | | = | OH | H |
| 467 | S | CH$_3$ | H | 1 | cyclobutyl | | = | OH | H |

TABLE 18-continued

| | X | R1 | R2 | m | R8 | R4 | R5 | R6 | R7 |
|---|---|---|---|---|---|---|---|---|---|
| 468 | S | CH₃ | H | 1 | cyclopentyl | | = | OH | H |
| 469 | S | CH₃ | H | 1 | cyclohexyl | | = | OH | H |
| 470 | S | CH₃ | H | 1 | cycloheptyl | | = | OH | H |
| 471 | S | CH₃ | H | 1 | CH(CF₃)₂ | | = | OH | H |
| 472 | S | CH₃ | H | 2 | H | H | H | OH | H |
| 473 | S | CH₃ | H | 2 | CH₃ | H | H | OH | H |
| 474 | S | CH₃ | H | 2 | CH₂CH₃ | H | H | OH | H |
| 475 | S | CH₃ | H | 2 | (CH₂)₂CH₃ | H | H | OH | H |
| 476 | S | CH₃ | H | 2 | CH(CH₃)₂ | H | H | OH | H |
| 477 | S | CH₃ | H | 2 | (CH₂)₃CH₃ | H | H | OH | H |
| 478 | S | CH₃ | H | 2 | CH₂CH(CH₃)₂ | H | H | OH | H |
| 479 | S | CH₃ | H | 2 | C(CH₃)₃ | H | H | OH | H |
| 480 | S | CH₃ | H | 2 | H | H | OH | OH | H |
| 481 | S | CH₃ | H | 2 | CH₃ | H | OH | OH | H |
| 482 | S | CH₃ | H | 2 | CH₂CH₃ | H | OH | OH | H |
| 483 | S | CH₃ | H | 2 | (CH₂)₂CH₃ | H | OH | OH | H |
| 484 | S | CH₃ | H | 2 | CH(CH₃)₂ | H | OH | OH | H |
| 485 | S | CH₃ | H | 2 | (CH₂)₃CH₃ | H | OH | OH | H |

TABLE 19

| | X | R1 | R2 | m | R8 | R4 | R5 | R6 | R7 |
|---|---|---|---|---|---|---|---|---|---|
| 486 | S | CH₃ | H | 2 | CH₂CH(CH₃)₂ | H | OH | OH | H |
| 487 | S | CH₃ | H | 2 | C(CH₃)₃ | H | OH | OH | H |
| 488 | S | CH₃ | H | 2 | H | | = | OH | H |
| 489 | S | CH₃ | H | 2 | CH₃ | | = | OH | H |
| 490 | S | CH₃ | H | 2 | CH₂CH₃ | | = | OH | H |
| 491 | S | CH₃ | H | 2 | (CH₂)₂CH₃ | | = | OH | H |
| 492 | S | CH₃ | H | 2 | CH(CH₃)₂ | | = | OH | H |
| 493 | S | CH₃ | H | 2 | (CH₂)₃CH₃ | | = | OH | H |
| 494 | S | CH₃ | H | 2 | CH₂CH(CH₃)₂ | | = | OH | H |
| 495 | S | CH₃ | H | 2 | C(CH₃)₃ | | = | OH | H |
| 496 | S | CH₃ | H | 3 | H | H | H | OH | H |
| 497 | S | CH₃ | H | 3 | CH₃ | H | H | OH | H |
| 498 | S | CH₃ | H | 3 | CH₂CH₃ | H | H | OH | H |
| 499 | S | CH₃ | H | 3 | (CH₂)₂CH₃ | H | H | OH | H |
| 500 | S | CH₃ | H | 3 | CH(CH₃)₂ | H | H | OH | H |
| 501 | S | CH₃ | H | 3 | (CH₂)₃CH₃ | H | H | OH | H |
| 502 | S | CH₃ | H | 3 | CH₂CH(CH₃)₂ | H | H | OH | H |
| 503 | S | CH₃ | H | 3 | C(CH₃)₃ | H | H | OH | H |
| 504 | S | CH₃ | H | 3 | H | H | OH | OH | H |
| 505 | S | CH₃ | H | 3 | CH₃ | H | OH | OH | H |
| 506 | S | CH₃ | H | 3 | CH₂CH₃ | H | OH | OH | H |
| 507 | S | CH₃ | H | 3 | (CH₂)₂CH₃ | H | OH | OH | H |
| 508 | S | CH₃ | H | 3 | CH(CH₃)₂ | H | OH | OH | H |
| 509 | S | CH₃ | H | 3 | (CH₂)₃CH₃ | H | OH | OH | H |
| 510 | S | CH₃ | H | 3 | CH₂CH(CH₃)₂ | H | OH | OH | H |
| 511 | S | CH₃ | H | 3 | C(CH₃)₃ | H | OH | OH | H |
| 512 | S | CH₃ | H | 3 | H | | = | OH | H |

TABLE 20

| | X | R1 | R2 | m | R8 | R4 | R5 | R6 | R7 |
|---|---|---|---|---|---|---|---|---|---|
| 513 | S | CH₃ | H | 3 | CH₃ | | = | OH | H |
| 514 | S | CH₃ | H | 3 | CH₂CH₃ | | = | OH | H |
| 515 | S | CH₃ | H | 3 | (CH₂)₂CH₃ | | = | OH | H |
| 516 | S | CH₃ | H | 3 | CH(CH₃)₂ | | = | OH | H |
| 517 | S | CH₃ | H | 3 | (CH₂)₃CH₃ | | = | OH | H |
| 518 | S | CH₃ | H | 3 | CH₂CH(CH₃)₂ | | = | OH | H |
| 519 | S | CH₃ | H | 3 | C(CH₃)₃ | | = | OH | H |
| 520 | S | H | CH₃ | 1 | H | H | H | OH | H |
| 521 | S | H | CH₃ | 1 | CH₃ | H | H | OH | H |
| 522 | S | H | CH₃ | 1 | CH₂CH₃ | H | H | OH | H |
| 523 | S | H | CH₃ | 1 | (CH₂)₂CH₃ | H | H | OH | H |
| 524 | S | H | CH₃ | 1 | CH(CH₃)₂ | H | H | OH | H |
| 525 | S | H | CH₃ | 1 | (CH₂)₃CH₃ | H | H | OH | H |
| 526 | S | H | CH₃ | 1 | CH₂CH(CH₃)₂ | H | H | OH | H |
| 527 | S | H | CH₃ | 1 | C(CH₃)₃ | H | H | OH | H |
| 528 | S | H | CH₃ | 1 | H | H | OH | OH | H |
| 529 | S | H | CH₃ | 1 | CH₃ | H | OH | OH | H |
| 530 | S | H | CH₃ | 1 | CH₂CH₃ | H | OH | OH | H |

TABLE 20-continued

| | X | R1 | R2 | m | R8 | R4 | R5 | R6 | R7 |
|---|---|---|---|---|---|---|---|---|---|
| 531 | S | H | CH₃ | 1 | (CH₂)₂CH₃ | H | OH | OH | H |
| 532 | S | H | CH₃ | 1 | CH(CH₃)₂ | H | OH | OH | H |
| 533 | S | H | CH₃ | 1 | (CH₂)₃CH₃ | H | OH | OH | H |
| 534 | S | H | CH₃ | 1 | CH₂CH(CH₃)₂ | H | OH | OH | H |
| 535 | S | H | CH₃ | 1 | C(CH₃)₃ | H | OH | OH | H |
| 536 | S | H | CH₃ | 1 | H | | = | OH | H |
| 537 | S | H | CH₃ | 1 | CH₃ | | = | OH | H |
| 538 | S | H | CH₃ | 1 | CH₂CH₃ | | = | OH | H |
| 539 | S | H | CH₃ | 1 | (CH₂)₂CH₃ | | = | OH | H |

TABLE 21

| | X | R1 | R2 | m | R8 | R4 | R5 | R6 | R7 |
|---|---|---|---|---|---|---|---|---|---|
| 540 | S | H | CH₃ | 1 | CH(CH₃)₂ | | = | OH | H |
| 541 | S | H | CH₃ | 1 | (CH₂)₃CH₃ | | = | OH | H |
| 542 | S | H | CH₃ | 1 | CH₂CH(CH₃)₂ | | = | OH | H |
| 543 | S | H | CH₃ | 1 | C(CH₃)₃ | | = | OH | H |
| 544 | S | H | CH₃ | 1 | C(CH₃)₂CH₂CH₃ | | = | OH | H |
| 545 | S | H | CH₃ | 1 | C(CH₃)(CH₂CH₃)₂ | | = | OH | H |
| 546 | S | H | CH₃ | 1 | C(CH₂CH₃)₃ | | = | OH | H |
| 547 | S | H | CH₃ | 1 | cyclopropyl | | = | OH | H |
| 548 | S | H | CH₃ | 1 | cyclobutyl | | = | OH | H |
| 549 | S | H | CH₃ | 1 | cyclopentyl | | = | OH | H |
| 550 | S | H | CH₃ | 1 | cyclohexyl | | = | OH | H |
| 551 | S | H | CH₃ | 1 | cycloheptyl | | = | OH | H |
| 552 | S | H | CH₃ | 1 | CH(CF₃)₂ | | = | OH | H |
| 553 | S | H | CH₃ | 2 | H | H | H | OH | H |
| 554 | S | H | CH₃ | 2 | CH₃ | H | H | OH | H |
| 555 | S | H | CH₃ | 2 | CH₂CH₃ | H | H | OH | H |
| 556 | S | H | CH₃ | 2 | (CH₂)₂CH₃ | H | H | OH | H |
| 557 | S | H | CH₃ | 2 | CH(CH₃)₂ | H | H | OH | H |
| 558 | S | H | CH₃ | 2 | (CH₂)₃CH₃ | H | H | OH | H |
| 559 | S | H | CH₃ | 2 | CH₂CH(CH₃)₂ | H | H | OH | H |
| 560 | S | H | CH₃ | 2 | C(CH₃)₃ | H | H | OH | H |
| 561 | S | H | CH₃ | 2 | H | H | OH | OH | H |
| 562 | S | H | CH₃ | 2 | CH₃ | H | OH | OH | H |
| 563 | S | H | CH₃ | 2 | CH₂CH₃ | H | OH | OH | H |
| 564 | S | H | CH₃ | 2 | (CH₂)₂CH₃ | H | OH | OH | H |
| 565 | S | H | CH₃ | 2 | CH(CH₃)₂ | H | OH | OH | H |
| 566 | S | H | CH₃ | 2 | (CH₂)₃CH₃ | H | OH | OH | H |

TABLE 22

| | X | R1 | R2 | m | R8 | R4 | R5 | R6 | R7 |
|---|---|---|---|---|---|---|---|---|---|
| 567 | S | H | CH₃ | 2 | CH₂CH(CH₃)₂ | H | OH | OH | H |
| 568 | S | H | CH₃ | 2 | C(CH₃)₃ | H | OH | OH | H |
| 569 | S | H | CH₃ | 2 | H | | = | OH | H |
| 570 | S | H | CH₃ | 2 | CH₃ | | = | OH | H |
| 571 | S | H | CH₃ | 2 | CH₂CH₃ | | = | OH | H |
| 572 | S | H | CH₃ | 2 | (CH₂)₂CH₃ | | = | OH | H |
| 573 | S | H | CH₃ | 2 | CH(CH₃)₂ | | = | OH | H |
| 574 | S | H | CH₃ | 2 | (CH₂)₃CH₃ | | = | OH | H |
| 575 | S | H | CH₃ | 2 | CH₂CH(CH₃)₂ | | = | OH | H |
| 576 | S | H | CH₃ | 2 | C(CH₃)₃ | | = | OH | H |
| 577 | S | H | CH₃ | 3 | H | H | H | OH | H |
| 578 | S | H | CH₃ | 3 | CH₃ | H | H | OH | H |
| 579 | S | H | CH₃ | 3 | CH₂CH₃ | H | H | OH | H |
| 580 | S | H | CH₃ | 3 | (CH₂)₂CH₃ | H | H | OH | H |
| 581 | S | H | CH₃ | 3 | CH(CH₃)₂ | H | H | OH | H |
| 582 | S | H | CH₃ | 3 | (CH₂)₃CH₃ | H | H | OH | H |
| 583 | S | H | CH₃ | 3 | CH₂CH(CH₃)₂ | H | H | OH | H |
| 584 | S | H | CH₃ | 3 | C(CH₃)₃ | H | H | OH | H |
| 585 | S | H | CH₃ | 3 | H | H | OH | OH | H |
| 586 | S | H | CH₃ | 3 | CH₃ | H | OH | OH | H |
| 587 | S | H | CH₃ | 3 | CH₂CH₃ | H | OH | OH | H |
| 588 | S | H | CH₃ | 3 | (CH₂)₂CH₃ | H | OH | OH | H |
| 589 | S | H | CH₃ | 3 | CH(CH₃)₂ | H | OH | OH | H |
| 590 | S | H | CH₃ | 3 | (CH₂)₃CH₃ | H | OH | OH | H |
| 591 | S | H | CH₃ | 3 | CH₂CH(CH₃)₂ | H | OH | OH | H |
| 592 | S | H | CH₃ | 3 | C(CH₃)₃ | H | OH | OH | H |
| 593 | S | H | CH₃ | 3 | H | | = | OH | H |

TABLE 23

| | X | R1 | R2 | m | R8 | R4 | R5 | R6 | R7 |
|---|---|---|---|---|---|---|---|---|---|
| 594 | S | H | CH$_3$ | 3 | CH$_3$ | | = | OH | H |
| 595 | S | H | CH$_3$ | 3 | CH$_2$CH$_3$ | | = | OH | H |
| 596 | S | H | CH$_3$ | 3 | (CH$_2$)$_2$CH$_3$ | | = | OH | H |
| 597 | S | H | CH$_3$ | 3 | CH(CH$_3$)$_2$ | | = | OH | H |
| 598 | S | H | CH$_3$ | 3 | (CH$_2$)$_3$CH$_3$ | | = | OH | H |
| 599 | S | H | CH$_3$ | 3 | CH$_2$CH(CH$_3$)$_2$ | | = | OH | H |
| 600 | S | H | CH$_3$ | 3 | C(CH$_3$)$_3$ | | = | OH | H |

TABLE 24

R3 = SR8

| | X | R1 | R2 | m | R8 | R4 | R5 | R6 | R7 |
|---|---|---|---|---|---|---|---|---|---|
| 1 | O | H | H | 1 | CH$_2$CH$_3$ | | = | OH | H |
| 2 | O | H | H | 1 | CH(CH$_3$)$_2$ | | = | OH | H |
| 3 | O | H | H | 1 | C(CH$_3$)$_3$ | | = | OH | H |
| 4 | O | CH$_3$ | H | 1 | CH$_2$CH$_3$ | | = | OH | H |
| 5 | O | CH$_3$ | H | 1 | CH(CH$_3$)$_2$ | | = | OH | H |
| 6 | O | CH$_3$ | H | 1 | C(CH$_3$)$_3$ | | = | OH | H |
| 7 | O | H | CH$_3$ | 1 | CH$_2$CH$_3$ | | = | OH | H |
| 8 | O | H | CH$_3$ | 1 | CH(CH$_3$)$_2$ | | = | OH | H |
| 9 | O | H | CH$_3$ | 1 | C(CH$_3$)$_3$ | | = | OH | H |
| 10 | O | CH$_3$ | CH$_3$ | 1 | CH$_2$CH$_3$ | | = | OH | H |
| 11 | O | CH$_3$ | CH$_3$ | 1 | CH(CH$_3$)$_2$ | | = | OH | H |
| 12 | O | CH$_3$ | CH$_3$ | 1 | C(CH$_3$)$_3$ | | = | OH | H |
| 13 | S | H | H | 1 | CH$_2$CH$_3$ | | = | OH | H |
| 14 | S | H | H | 1 | CH(CH$_3$)$_2$ | | = | OH | H |
| 15 | S | H | H | 1 | C(CH$_3$)$_3$ | | = | OH | H |
| 16 | S | CH$_3$ | H | 1 | CH$_2$CH$_3$ | | = | OH | H |
| 17 | S | CH$_3$ | H | 1 | CH(CH$_3$)$_2$ | | = | OH | H |
| 18 | S | CH$_3$ | H | 1 | C(CH$_3$)$_3$ | | = | OH | H |
| 19 | S | H | CH$_3$ | 1 | CH$_2$CH$_3$ | | = | OH | H |
| 20 | S | H | CH$_3$ | 1 | CH(CH$_3$)$_2$ | | = | OH | H |
| 21 | S | H | CH$_3$ | 1 | C(CH$_3$)$_3$ | | = | OH | H |

TABLE 25

R3 = NR9R10

| | X | R1 | R2 | m | R9 | R10 | R4 | R5 | R6 | R7 |
|---|---|---|---|---|---|---|---|---|---|---|
| 1 | O | H | H | 1 | H | H | H | H | OH | H |
| 2 | O | H | H | 1 | H | CH$_3$ | H | H | OH | H |
| 3 | O | H | H | 1 | H | CH(CH$_3$)$_2$ | H | H | OH | H |
| 4 | O | H | H | 1 | H | C(CH$_3$)$_3$ | H | H | OH | H |
| 5 | O | H | H | 1 | H | H | H | OH | OH | H |
| 6 | O | H | H | 1 | H | CH$_3$ | H | OH | OH | H |
| 7 | O | H | H | 1 | H | CH(CH$_3$)$_2$ | H | OH | OH | H |
| 8 | O | H | H | 1 | H | C(CH$_3$)$_3$ | H | OH | OH | H |
| 9 | O | H | H | 1 | H | H | | = | OH | H |
| 10 | O | H | H | 1 | H | CH$_3$ | | = | OH | H |
| 11 | O | H | H | 1 | H | CH$_2$CH$_3$ | | = | OH | H |
| 12 | O | H | H | 1 | H | (CH$_2$)$_2$CH$_3$ | | = | OH | H |
| 13 | O | H | H | 1 | H | CH(CH$_3$)$_2$ | | = | OH | H |
| 14 | O | H | H | 1 | H | (CH$_2$)$_3$CH$_3$ | | = | OH | H |
| 15 | O | H | H | 1 | H | CH$_2$CH(CH$_3$)$_2$ | | = | OH | H |
| 16 | O | H | H | 1 | H | CH(CH$_3$)CH$_2$CH$_3$ | | = | OH | H |
| 17 | O | H | H | 1 | H | C(CH$_3$)$_3$ | | = | OH | H |
| 18 | O | H | H | 1 | H | cyclopropyl | | = | OH | H |
| 19 | O | H | H | 1 | H | cyclobutyl | | = | OH | H |
| 20 | O | H | H | 1 | H | cyclopentyl | | = | OH | H |
| 21 | O | H | H | 1 | H | cyclohexyl | | = | OH | H |
| 22 | O | H | H | 1 | H | cycloheptyl | | = | OH | H |
| 23 | O | H | H | 1 | H | CH(CF$_3$)$_2$ | | = | OH | H |
| 24 | O | H | H | 1 | CH$_3$ | CH$_3$ | H | H | OH | H |
| 25 | O | H | H | 1 | CH$_3$ | CH(CH$_3$)$_2$ | H | H | OH | H |
| 26 | O | H | H | 1 | CH$_3$ | C(CH$_3$)$_3$ | H | H | OH | H |
| 27 | O | H | H | 1 | CH$_3$ | CH$_3$ | H | OH | OH | H |

TABLE 26

| | X | R1 | R2 | m | R9 | R10 | R4 | R5 | R6 | R7 |
|---|---|---|---|---|---|---|---|---|---|---|
| 28 | O | H | H | 1 | CH$_3$ | CH(CH$_3$)$_2$ | H | OH | OH | H |
| 29 | O | H | H | 1 | CH$_3$ | C(CH$_3$)$_3$ | H | OH | OH | H |
| 30 | O | H | H | 1 | CH$_3$ | CH$_3$ | | = | OH | H |
| 31 | O | H | H | 1 | CH$_3$ | CH$_2$CH$_3$ | | = | OH | H |
| 32 | O | H | H | 1 | CH$_3$ | (CH$_2$)$_2$CH$_3$ | | = | OH | H |
| 33 | O | H | H | 1 | CH$_3$ | CH(CH$_3$)$_2$ | | = | OH | H |
| 34 | O | H | H | 1 | CH$_3$ | (CH$_2$)$_3$CH$_3$ | | = | OH | H |
| 35 | O | H | H | 1 | CH$_3$ | CH$_2$CH(CH$_3$)$_2$ | | = | OH | H |
| 36 | O | H | H | 1 | CH$_3$ | CH(CH$_3$)CH$_2$CH$_3$ | | = | OH | H |
| 37 | O | H | H | 1 | CH$_3$ | C(CH$_3$)$_3$ | | = | OH | H |
| 38 | O | H | H | 1 | —(CH$_2$)$_2$— | | | = | OH | H |
| 39 | O | H | H | 1 | —(CH$_2$)$_3$— | | | = | OH | H |
| 40 | O | H | H | 1 | —(CH$_2$)$_4$— | | | = | OH | H |
| 41 | O | H | H | 1 | —(CH$_2$)$_5$— | | | = | OH | H |
| 42 | O | H | H | 1 | —(CH$_2$)$_6$— | | | = | OH | H |
| 43 | O | H | H | 2 | H | H | H | H | OH | H |
| 44 | O | H | H | 2 | H | CH$_3$ | H | H | OH | H |
| 45 | O | H | H | 2 | H | CH(CH$_3$)$_2$ | H | H | OH | H |
| 46 | O | H | H | 2 | H | C(CH$_3$)$_3$ | H | H | OH | H |
| 47 | O | H | H | 2 | H | H | H | OH | OH | H |
| 48 | O | H | H | 2 | H | CH$_3$ | H | OH | OH | H |
| 49 | O | H | H | 2 | H | CH(CH$_3$)$_2$ | H | OH | OH | H |
| 50 | O | H | H | 2 | H | C(CH$_3$)$_3$ | H | OH | OH | H |
| 51 | O | H | H | 2 | H | H | | = | OH | H |
| 52 | O | H | H | 2 | H | CH$_3$ | | = | OH | H |
| 53 | O | H | H | 2 | H | CH(CH$_3$)$_2$ | | = | OH | H |
| 54 | O | H | H | 2 | H | C(CH$_3$)$_3$ | | = | OH | H |
| 55 | O | H | H | 2 | CH$_3$ | CH$_3$ | H | H | OH | H |

TABLE 27

| | X | R1 | R2 | m | R9 | R10 | R4 | R5 | R6 | R7 |
|---|---|---|---|---|---|---|---|---|---|---|
| 56 | O | H | H | 2 | CH$_3$ | CH(CH$_3$)$_2$ | H | H | OH | H |
| 57 | O | H | H | 2 | CH$_3$ | C(CH$_3$)$_3$ | H | H | OH | H |
| 58 | O | H | H | 2 | CH$_3$ | CH$_3$ | H | OH | OH | H |
| 59 | O | H | H | 2 | CH$_3$ | CH(CH$_3$)$_2$ | H | OH | OH | H |
| 60 | O | H | H | 2 | CH$_3$ | C(CH$_3$)$_3$ | H | OH | OH | H |
| 61 | O | H | H | 2 | CH$_3$ | CH$_3$ | | = | OH | H |
| 62 | O | H | H | 2 | CH$_3$ | CH(CH$_3$)$_2$ | | = | OH | H |
| 63 | O | H | H | 2 | CH$_3$ | C(CH$_3$)$_3$ | | = | OH | H |
| 64 | O | H | H | 3 | H | H | H | H | OH | H |
| 65 | O | H | H | 3 | H | CH$_3$ | H | H | OH | H |
| 66 | O | H | H | 3 | H | CH(CH$_3$)$_2$ | H | H | OH | H |
| 67 | O | H | H | 3 | H | C(CH$_3$)$_3$ | H | H | OH | H |
| 68 | O | H | H | 3 | H | H | H | OH | OH | H |
| 69 | O | H | H | 3 | H | CH$_3$ | H | OH | OH | H |
| 70 | O | H | H | 3 | H | CH(CH$_3$)$_2$ | H | OH | OH | H |
| 71 | O | H | H | 3 | H | C(CH$_3$)$_3$ | H | OH | OH | H |
| 72 | O | H | H | 3 | H | H | | = | OH | H |
| 73 | O | H | H | 3 | H | CH$_3$ | | = | OH | H |
| 74 | O | H | H | 3 | H | CH(CH$_3$)$_2$ | | = | OH | H |
| 75 | O | H | H | 3 | H | C(CH$_3$)$_3$ | | = | OH | H |
| 76 | O | H | H | 3 | CH$_3$ | CH$_3$ | H | H | OH | H |
| 77 | O | H | H | 3 | CH$_3$ | CH(CH$_3$)$_2$ | H | H | OH | H |
| 78 | O | H | H | 3 | CH$_3$ | C(CH$_3$)$_3$ | H | H | OH | H |
| 79 | O | H | H | 3 | CH$_3$ | CH$_3$ | H | OH | OH | H |
| 80 | O | H | H | 3 | CH$_3$ | CH(CH$_3$)$_2$ | H | OH | OH | H |
| 81 | O | H | H | 3 | CH$_3$ | C(CH$_3$)$_3$ | H | OH | OH | H |
| 82 | O | H | H | 3 | CH$_3$ | CH$_3$ | | = | OH | H |
| 83 | O | H | H | 3 | CH$_3$ | CH(CH$_3$)$_2$ | | = | OH | H |

TABLE 28

| | X | R1 | R2 | m | R9 | R10 | R4 | R5 | R6 | R7 |
|---|---|---|---|---|---|---|---|---|---|---|
| 84 | O | H | H | 3 | CH₃ | C(CH₃)₃ | | = | OH | H |
| 85 | O | CH₃ | H | 1 | H | H | H | H | OH | H |
| 86 | O | CH₃ | H | 1 | H | CH₃ | H | H | OH | H |
| 87 | O | CH₃ | H | 1 | H | CH(CH₃)₂ | H | H | OH | H |
| 88 | O | CH₃ | H | 1 | H | C(CH₃)₃ | H | H | OH | H |
| 89 | O | CH₃ | H | 1 | H | H | H | OH | OH | H |
| 90 | O | CH₃ | H | 1 | H | CH₃ | H | OH | OH | H |
| 91 | O | CH₃ | H | 1 | H | CH(CH₃)₂ | H | OH | OH | H |
| 92 | O | CH₃ | H | 1 | H | C(CH₃)₃ | H | OH | OH | H |
| 93 | O | CH₃ | H | 1 | H | H | | = | OH | H |
| 94 | O | CH₃ | H | 1 | H | CH₃ | | = | OH | H |
| 95 | O | CH₃ | H | 1 | H | OCH₃ | | = | OH | H |
| 96 | O | CH₃ | H | 1 | H | CH₂CH₃ | | = | OH | H |
| 97 | O | CH₃ | H | 1 | H | (CH₂)₂CH₃ | | = | OH | H |
| 98 | O | CH₃ | H | 1 | H | CH(CH₃)₂ | | = | OH | H |
| 99 | O | CH₃ | H | 1 | H | (CH₂)₃CH₃ | | = | OH | H |
| 100 | O | CH₃ | H | 1 | H | CH₂CH(CH₃)₂ | | = | OH | H |
| 101 | O | CH₃ | H | 1 | H | CH(CH₃)CH₂CH₃ | | = | OH | H |
| 102 | O | CH₃ | H | 1 | H | C(CH₃)₃ | | = | OH | H |
| 103 | O | CH₃ | H | 1 | H | CH₂(CH(CH₃)₂) | | = | OH | H |
| 104 | O | CH₃ | H | 1 | H | CH(CH₂CH₃)₂ | | = | OH | H |
| 105 | O | CH₃ | H | 1 | H | CH₂C(CH₃)₃ | | = | OH | H |
| 106 | O | CH₃ | H | 1 | H | CH₂(CH(CH₂CH₃)₂) | | = | OH | H |
| 107 | O | CH₃ | H | 1 | H | CH((CH₂)₂CH₃)₂ | | = | OH | H |
| 108 | O | CH₃ | H | 1 | H | cyclopropyl | | = | OH | H |
| 109 | O | CH₃ | H | 1 | H | cyclobutyl | | = | OH | H |
| 110 | O | CH₃ | H | 1 | H | cyclopentyl | | = | OH | H |
| 111 | O | CH₃ | H | 1 | H | cyclohexyl | | = | OH | H |

TABLE 29

| | X | R1 | R2 | m | R9 | R10 | R4 | R5 | R6 | R7 |
|---|---|---|---|---|---|---|---|---|---|---|
| 112 | O | CH₃ | H | 1 | H | cycloheptyl | | = | OH | H |
| 113 | O | CH₃ | H | 1 | H | CH(CF₃)₂ | | = | OH | H |
| 114 | O | CH₃ | H | 1 | H | CH₂CF₃ | | = | OH | H |
| 115 | O | CH₃ | H | 1 | H | CH₂CF₂CF₃ | | = | OH | H |
| 116 | O | CH₃ | H | 1 | CH₃ | CH₃ | H | H | OH | H |
| 117 | O | CH₃ | H | 1 | CH₃ | CH(CH₃)₂ | H | H | OH | H |
| 118 | O | CH₃ | H | 1 | CH₃ | C(CH₃)₃ | H | H | OH | H |
| 119 | O | CH₃ | H | 1 | CH₃ | CH₃ | H | OH | OH | H |
| 120 | O | CH₃ | H | 1 | CH₃ | CH(CH₃)₂ | H | OH | OH | H |
| 121 | O | CH₃ | H | 1 | CH₃ | C(CH₃)₃ | H | OH | OH | H |
| 122 | O | CH₃ | H | 1 | CH₃ | CH₃ | | = | OH | H |
| 123 | O | CH₃ | H | 1 | CH₃ | OCH₃ | | = | OH | H |
| 124 | O | CH₃ | H | 1 | CH₃ | CH₂CH₃ | | = | OH | H |
| 125 | O | CH₃ | H | 1 | CH₃ | (CH₂)₂CH₃ | | = | OH | H |
| 126 | O | CH₃ | H | 1 | CH₃ | CH(CH₃)₂ | | = | OH | H |
| 127 | O | CH₃ | H | 1 | CH₃ | (CH₂)₃CH₃ | | = | OH | H |
| 128 | O | CH₃ | H | 1 | CH₃ | CH₂CH(CH₃)₂ | | = | OH | H |
| 129 | O | CH₃ | H | 1 | CH₃ | CH(CH₃)CH₂CH₃ | | = | OH | H |
| 130 | O | CH₃ | H | 1 | CH₃ | C(CH₃)₃ | | = | OH | H |
| 131 | O | CH₃ | H | 1 | —(CH₂)₂— | | | = | OH | H |
| 132 | O | CH₃ | H | 1 | —(CH₂)₃— | | | = | OH | H |
| 133 | O | CH₃ | H | 1 | —(CH₂)₄— | | | = | OH | H |
| 134 | O | CH₃ | H | 1 | —(CH₂)₅— | | | = | OH | H |
| 135 | O | CH₃ | H | 1 | —(CH₂)₆— | | | = | OH | H |
| 136 | O | CH₃ | H | 2 | H | H | H | H | OH | H |
| 137 | O | CH₃ | H | 2 | H | CH₃ | H | H | OH | H |
| 138 | O | CH₃ | H | 2 | H | CH(CH₃)₂ | H | H | OH | H |
| 139 | O | CH₃ | H | 2 | H | C(CH₃)₃ | H | H | OH | H |

TABLE 30

| | X | R1 | R2 | m | R9 | R10 | R4 | R5 | R6 | R7 |
|---|---|---|---|---|---|---|---|---|---|---|
| 140 | O | CH₃ | H | 2 | H | H | H | OH | OH | H |
| 141 | O | CH₃ | H | 2 | H | CH₃ | H | OH | OH | H |
| 142 | O | CH₃ | H | 2 | H | CH(CH₃)₂ | H | OH | OH | H |
| 143 | O | CH₃ | H | 2 | H | C(CH₃)₃ | H | OH | OH | H |
| 144 | O | CH₃ | H | 2 | H | H | | = | OH | H |
| 145 | O | CH₃ | H | 2 | H | CH₃ | | = | OH | H |
| 146 | O | CH₃ | H | 2 | H | CH(CH₃)₂ | | = | OH | H |
| 147 | O | CH₃ | H | 2 | H | C(CH₃)₃ | | = | OH | H |
| 148 | O | CH₃ | H | 2 | CH₃ | CH₃ | H | H | OH | H |
| 149 | O | CH₃ | H | 2 | CH₃ | CH(CH₃)₂ | H | H | OH | H |

TABLE 30-continued

| | X | R1 | R2 | m | R9 | R10 | R4 | R5 | R6 | R7 |
|---|---|---|---|---|---|---|---|---|---|---|
| 150 | O | CH₃ | H | 2 | CH₃ | C(CH₃)₃ | H | H | OH | H |
| 151 | O | CH₃ | H | 2 | CH₃ | CH₃ | H | OH | OH | H |
| 152 | O | CH₃ | H | 2 | CH₃ | CH(CH₃)₂ | H | OH | OH | H |
| 153 | O | CH₃ | H | 2 | CH₃ | C(CH₃)₃ | H | OH | OH | H |
| 154 | O | CH₃ | H | 2 | CH₃ | CH₃ | | = | OH | H |
| 155 | O | CH₃ | H | 2 | CH₃ | CH(CH₃)₂ | | = | OH | H |
| 156 | O | CH₃ | H | 2 | CH₃ | C(CH₃)₃ | | = | OH | H |
| 157 | O | CH₃ | H | 3 | H | H | H | H | OH | H |
| 158 | O | CH₃ | H | 3 | H | CH₃ | H | H | OH | H |
| 159 | O | CH₃ | H | 3 | H | CH(CH₃)₂ | H | H | OH | H |
| 160 | O | CH₃ | H | 3 | H | C(CH₃)₃ | H | H | OH | H |
| 161 | O | CH₃ | H | 3 | H | H | H | OH | OH | H |
| 162 | O | CH₃ | H | 3 | H | CH₃ | H | OH | OH | H |
| 163 | O | CH₃ | H | 3 | H | CH(CH₃)₂ | H | OH | OH | H |
| 164 | O | CH₃ | H | 3 | H | C(CH₃)₃ | H | OH | OH | H |
| 165 | O | CH₃ | H | 3 | H | H | | = | OH | H |
| 166 | O | CH₃ | H | 3 | H | CH₃ | | = | OH | H |
| 167 | O | CH₃ | H | 3 | H | CH(CH₃)₂ | | = | OH | H |

TABLE 31

| | X | R1 | R2 | m | R9 | R10 | R4 | R5 | R6 | R7 |
|---|---|---|---|---|---|---|---|---|---|---|
| 168 | O | CH₃ | H | 3 | H | C(CH₃)₃ | | = | OH | H |
| 169 | O | CH₃ | H | 3 | CH₃ | CH₃ | H | H | OH | H |
| 170 | O | CH₃ | H | 3 | CH₃ | CH(CH₃)₂ | H | H | OH | H |
| 171 | O | CH₃ | H | 3 | CH₃ | C(CH₃)₃ | H | H | OH | H |
| 172 | O | CH₃ | H | 3 | CH₃ | CH₃ | H | OH | OH | H |
| 173 | O | CH₃ | H | 3 | CH₃ | CH(CH₃)₂ | H | OH | OH | H |
| 174 | O | CH₃ | H | 3 | CH₃ | C(CH₃)₃ | H | OH | OH | H |
| 175 | O | CH₃ | H | 3 | CH₃ | CH₃ | | = | OH | H |
| 176 | O | CH₃ | H | 3 | CH₃ | CH(CH₃)₂ | | = | OH | H |
| 177 | O | CH₃ | H | 3 | CH₃ | C(CH₃)₃ | | = | OH | H |
| 178 | O | H | CH₃ | 1 | H | H | H | H | OH | H |
| 179 | O | H | CH₃ | 1 | H | CH₃ | H | H | OH | H |
| 180 | O | H | CH₃ | 1 | H | CH(CH₃)₂ | H | H | OH | H |
| 181 | O | H | CH₃ | 1 | H | C(CH₃)₃ | H | H | OH | H |
| 182 | O | H | CH₃ | 1 | H | H | H | OH | OH | H |
| 183 | O | H | CH₃ | 1 | H | CH₃ | H | OH | OH | H |
| 184 | O | H | CH₃ | 1 | H | CH(CH₃)₂ | H | OH | OH | H |
| 185 | O | H | CH₃ | 1 | H | C(CH₃)₃ | H | OH | OH | H |
| 186 | O | H | CH₃ | 1 | H | H | | = | OH | H |
| 187 | O | H | CH₃ | 1 | H | CH₃ | | = | OH | H |
| 188 | O | H | CH₃ | 1 | H | CH₂CH₃ | | = | OH | H |
| 189 | O | H | CH₃ | 1 | H | (CH₂)₂CH₃ | | = | OH | H |
| 190 | O | H | CH₃ | 1 | H | CH(CH₃)₂ | | = | OH | H |
| 191 | O | H | CH₃ | 1 | H | (CH₂)₃CH₃ | | = | OH | H |
| 192 | O | H | CH₃ | 1 | H | CH₂CH(CH₃)₂ | | = | OH | H |
| 193 | O | H | CH₃ | 1 | H | CH(CH₃)CH₂CH₃ | | = | OH | H |
| 194 | O | H | CH₃ | 1 | H | C(CH₃)₃ | | = | OH | H |
| 195 | O | H | CH₃ | 1 | CH₃ | CH₃ | H | H | OH | H |

TABLE 32

| | X | R1 | R2 | m | R9 | R10 | R4 | R5 | R6 | R7 |
|---|---|---|---|---|---|---|---|---|---|---|
| 196 | O | H | CH₃ | 1 | CH₃ | CH(CH₃)₂ | H | H | OH | H |
| 197 | O | H | CH₃ | 1 | CH₃ | C(CH₃)₃ | H | H | OH | H |
| 198 | O | H | CH₃ | 1 | CH₃ | CH₃ | H | OH | OH | H |
| 199 | O | H | CH₃ | 1 | CH₃ | CH(CH₃)₂ | H | OH | OH | H |
| 200 | O | H | CH₃ | 1 | CH₃ | C(CH₃)₃ | H | OH | OH | H |
| 201 | O | H | CH₃ | 1 | CH₃ | CH₃ | | = | OH | H |
| 202 | O | H | CH₃ | 1 | CH₃ | CH₂CH₃ | | = | OH | H |
| 203 | O | H | CH₃ | 1 | CH₃ | (CH₂)₂CH₃ | | = | OH | H |
| 204 | O | H | CH₃ | 1 | CH₃ | CH(CH₃)₂ | | = | OH | H |
| 205 | O | H | CH₃ | 1 | CH₃ | (CH₂)₃CH₃ | | = | OH | H |
| 206 | O | H | CH₃ | 1 | CH₃ | CH₂CH(CH₃)₂ | | = | OH | H |
| 207 | O | H | CH₃ | 1 | CH₃ | CH(CH₃)CH₂CH₃ | | = | OH | H |
| 208 | O | H | CH₃ | 1 | CH₃ | C(CH₃)₃ | | = | OH | H |
| 209 | O | H | CH₃ | 2 | H | H | H | H | OH | H |
| 210 | O | H | CH₃ | 2 | H | CH₃ | H | H | OH | H |
| 211 | O | H | CH₃ | 2 | H | CH(CH₃)₂ | H | H | OH | H |
| 212 | O | H | CH₃ | 2 | H | C(CH₃)₃ | H | H | OH | H |
| 213 | O | H | CH₃ | 2 | H | H | H | OH | OH | H |
| 214 | O | H | CH₃ | 2 | H | CH₃ | H | OH | OH | H |
| 215 | O | H | CH₃ | 2 | H | CH(CH₃)₂ | H | OH | OH | H |
| 216 | O | H | CH₃ | 2 | H | C(CH₃)₃ | H | OH | OH | H |
| 217 | O | H | CH₃ | 2 | H | H | | = | OH | H |
| 218 | O | H | CH₃ | 2 | H | CH₃ | | = | OH | H |
| 219 | O | H | CH₃ | 2 | H | CH(CH₃)₂ | | = | OH | H |
| 220 | O | H | CH₃ | 2 | H | C(CH₃)₃ | | = | OH | H |
| 221 | O | H | CH₃ | 2 | CH₃ | CH₃ | H | H | OH | H |

TABLE 32-continued

| | X | R1 | R2 | m | R9 | R10 | R4 | R5 | R6 | R7 |
|---|---|---|---|---|---|---|---|---|---|---|
| 222 | O | H | CH₃ | 2 | CH₃ | CH(CH₃)₂ | H | H | OH | H |
| 223 | O | H | CH₃ | 2 | CH₃ | C(CH₃)₃ | H | H | OH | H |

TABLE 33

| | X | R1 | R2 | m | R9 | R10 | R4 | R5 | R6 | R7 |
|---|---|---|---|---|---|---|---|---|---|---|
| 224 | O | H | CH₃ | 2 | CH₃ | CH₃ | H | OH | OH | H |
| 225 | O | H | CH₃ | 2 | CH₃ | CH(CH₃)₂ | H | OH | OH | H |
| 226 | O | H | CH₃ | 2 | CH₃ | C(CH₃)₃ | H | OH | OH | H |
| 227 | O | H | CH₃ | 2 | CH₃ | CH₃ | | = | OH | H |
| 228 | O | H | CH₃ | 2 | CH₃ | CH(CH₃)₂ | | = | OH | H |
| 229 | O | H | CH₃ | 2 | CH₃ | C(CH₃)₃ | | = | OH | H |
| 230 | O | H | CH₃ | 3 | H | H | H | H | OH | H |
| 231 | O | H | CH₃ | 3 | H | CH₃ | H | H | OH | H |
| 232 | O | H | CH₃ | 3 | H | CH(CH₃)₂ | H | H | OH | H |
| 233 | O | H | CH₃ | 3 | H | C(CH₃)₃ | H | H | OH | H |
| 234 | O | H | CH₃ | 3 | H | H | H | OH | OH | H |
| 235 | O | H | CH₃ | 3 | H | CH₃ | H | OH | OH | H |
| 236 | O | H | CH₃ | 3 | H | CH(CH₃)₂ | H | OH | OH | H |
| 237 | O | H | CH₃ | 3 | H | C(CH₃)₃ | H | OH | OH | H |
| 238 | O | H | CH₃ | 3 | H | H | | = | OH | H |
| 239 | O | H | CH₃ | 3 | H | CH₃ | | = | OH | H |
| 240 | O | H | CH₃ | 3 | H | CH(CH₃)₂ | | = | OH | H |
| 241 | O | H | CH₃ | 3 | H | C(CH₃)₃ | | = | OH | H |
| 242 | O | H | CH₃ | 3 | CH₃ | CH₃ | H | H | OH | H |
| 243 | O | H | CH₃ | 3 | CH₃ | CH(CH₃)₂ | H | H | OH | H |
| 244 | O | H | CH₃ | 3 | CH₃ | C(CH₃)₃ | H | H | OH | H |
| 245 | O | H | CH₃ | 3 | CH₃ | CH₃ | H | OH | OH | H |
| 246 | O | H | CH₃ | 3 | CH₃ | CH(CH₃)₂ | H | OH | OH | H |
| 247 | O | H | CH₃ | 3 | CH₃ | C(CH₃)₃ | H | OH | OH | H |
| 248 | O | H | CH₃ | 3 | CH₃ | CH₃ | | = | OH | H |
| 249 | O | H | CH₃ | 3 | CH₃ | CH(CH₃)₂ | | = | OH | H |
| 250 | O | H | CH₃ | 3 | CH₃ | C(CH₃)₃ | | = | OH | H |
| 251 | O | CH₃ | CH₃ | 1 | H | H | H | H | OH | H |

TABLE 34

| | X | R1 | R2 | m | R9 | R10 | R4 | R5 | R6 | R7 |
|---|---|---|---|---|---|---|---|---|---|---|
| 252 | O | CH₃ | CH₃ | 1 | H | CH₃ | H | H | OH | H |
| 253 | O | CH₃ | CH₃ | 1 | H | CH(CH₃)₂ | H | H | OH | H |
| 254 | O | CH₃ | CH₃ | 1 | H | C(CH₃)₃ | H | H | OH | H |
| 255 | O | CH₃ | CH₃ | 1 | H | H | H | OH | OH | H |
| 256 | O | CH₃ | CH₃ | 1 | H | CH₃ | H | OH | OH | H |
| 257 | O | CH₃ | CH₃ | 1 | H | CH(CH₃)₂ | H | OH | OH | H |
| 258 | O | CH₃ | CH₃ | 1 | H | C(CH₃)₃ | H | OH | OH | H |
| 259 | O | CH₃ | CH₃ | 1 | H | H | | = | OH | H |
| 260 | O | CH₃ | CH₃ | 1 | H | CH₃ | | = | OH | H |
| 261 | O | CH₃ | CH₃ | 1 | H | CH(CH₃)₂ | | = | OH | H |
| 262 | O | CH₃ | CH₃ | 1 | H | C(CH₃)₃ | | = | OH | H |
| 263 | O | CH₃ | CH₃ | 1 | CH₃ | CH₃ | H | H | OH | H |
| 264 | O | CH₃ | CH₃ | 1 | CH₃ | CH(CH₃)₂ | H | H | OH | H |
| 265 | O | CH₃ | CH₃ | 1 | CH₃ | C(CH₃)₃ | H | H | OH | H |
| 266 | O | CH₃ | CH₃ | 1 | CH₃ | CH₃ | H | OH | OH | H |

TABLE 34-continued

| | X | R1 | R2 | m | R9 | R10 | R4 | R5 | R6 | R7 |
|---|---|---|---|---|---|---|---|---|---|---|
| 267 | O | CH₃ | CH₃ | 1 | CH₃ | CH(CH₃)₂ | H | OH | OH | H |
| 268 | O | CH₃ | CH₃ | 1 | CH₃ | C(CH₃)₃ | H | OH | OH | H |
| 269 | O | CH₃ | CH₃ | 1 | CH₃ | CH₃ | | = | OH | H |
| 270 | O | CH₃ | CH₃ | 1 | CH₃ | CH(CH₃)₂ | | = | OH | H |
| 271 | O | CH₃ | CH₃ | 1 | CH₃ | C(CH₃)₃ | | = | OH | H |
| 272 | O | CH₃ | CH₃ | 2 | H | H | H | H | OH | H |
| 273 | O | CH₃ | CH₃ | 2 | H | CH₃ | H | H | OH | H |
| 274 | O | CH₃ | CH₃ | 2 | H | CH(CH₃)₂ | H | H | OH | H |
| 275 | O | CH₃ | CH₃ | 2 | H | C(CH₃)₃ | H | H | OH | H |
| 276 | O | CH₃ | CH₃ | 2 | H | H | H | OH | OH | H |
| 277 | O | CH₃ | CH₃ | 2 | H | CH₃ | H | OH | OH | H |
| 278 | O | CH₃ | CH₃ | 2 | H | CH(CH₃)₂ | H | OH | OH | H |
| 279 | O | CH₃ | CH₃ | 2 | H | C(CH₃)₃ | H | OH | OH | H |

TABLE 35

| | X | R1 | R2 | m | R9 | R10 | R4 | R5 | R6 | R7 |
|---|---|---|---|---|---|---|---|---|---|---|
| 280 | O | CH₃ | CH₃ | 2 | H | H | | = | OH | H |
| 281 | O | CH₃ | CH₃ | 2 | H | CH₃ | | = | OH | H |
| 282 | O | CH₃ | CH₃ | 2 | H | CH(CH₃)₂ | | = | OH | H |
| 283 | O | CH₃ | CH₃ | 2 | H | C(CH₃)₃ | | = | OH | H |
| 284 | O | CH₃ | CH₃ | 2 | CH₃ | CH₃ | H | H | OH | H |
| 285 | O | CH₃ | CH₃ | 2 | CH₃ | CH(CH₃)₂ | H | H | OH | H |
| 286 | O | CH₃ | CH₃ | 2 | CH₃ | C(CH₃)₃ | H | H | OH | H |
| 287 | O | CH₃ | CH₃ | 2 | CH₃ | CH₃ | H | OH | OH | H |
| 288 | O | CH₃ | CH₃ | 2 | CH₃ | CH(CH₃)₂ | H | OH | OH | H |
| 289 | O | CH₃ | CH₃ | 2 | CH₃ | C(CH₃)₃ | H | OH | OH | H |
| 290 | O | CH₃ | CH₃ | 2 | CH₃ | CH₃ | | = | OH | H |
| 291 | O | CH₃ | CH₃ | 2 | CH₃ | CH(CH₃)₂ | | = | OH | H |
| 292 | O | CH₃ | CH₃ | 2 | CH₃ | C(CH₃)₃ | | = | OH | H |
| 293 | O | CH₃ | CH₃ | 3 | H | H | H | H | OH | H |
| 294 | O | CH₃ | CH₃ | 3 | H | CH₃ | H | H | OH | H |
| 295 | O | CH₃ | CH₃ | 3 | H | CH(CH₃)₂ | H | H | OH | H |
| 296 | O | CH₃ | CH₃ | 3 | H | C(CH₃)₃ | H | H | OH | H |
| 297 | O | CH₃ | CH₃ | 3 | H | H | H | OH | OH | H |
| 298 | O | CH₃ | CH₃ | 3 | H | CH₃ | H | OH | OH | H |
| 299 | O | CH₃ | CH₃ | 3 | H | CH(CH₃)₂ | H | OH | OH | H |
| 300 | O | CH₃ | CH₃ | 3 | H | C(CH₃)₃ | H | OH | OH | H |
| 301 | O | CH₃ | CH₃ | 3 | H | H | | = | OH | H |
| 302 | O | CH₃ | CH₃ | 3 | H | CH₃ | | = | OH | H |
| 303 | O | CH₃ | CH₃ | 3 | H | CH(CH₃)₂ | | = | OH | H |
| 304 | O | CH₃ | CH₃ | 3 | H | C(CH₃)₃ | | = | OH | H |
| 305 | O | CH₃ | CH₃ | 3 | CH₃ | CH₃ | H | H | OH | H |
| 306 | O | CH₃ | CH₃ | 3 | CH₃ | CH(CH₃)₂ | H | H | OH | H |
| 307 | O | CH₃ | CH₃ | 3 | CH₃ | C(CH₃)₃ | H | H | OH | H |

TABLE 36

| | X | R1 | R2 | m | R9 | R10 | R4 | R5 | R6 | R7 |
|---|---|---|---|---|---|---|---|---|---|---|
| 308 | O | CH₃ | CH₃ | 3 | CH₃ | CH₃ | H | OH | OH | H |
| 309 | O | CH₃ | CH₃ | 3 | CH₃ | CH(CH₃)₂ | H | OH | OH | H |
| 310 | O | CH₃ | CH₃ | 3 | CH₃ | C(CH₃)₃ | H | OH | OH | H |
| 311 | O | CH₃ | CH₃ | 3 | CH₃ | CH₃ | | = | OH | H |
| 312 | O | CH₃ | CH₃ | 3 | CH₃ | CH(CH₃)₂ | | = | OH | H |
| 313 | O | CH₃ | CH₃ | 3 | CH₃ | C(CH₃)₃ | | = | OH | H |
| 314 | S | H | H | 1 | H | H | H | H | OH | H |
| 315 | S | H | H | 1 | H | CH₃ | H | H | OH | H |
| 316 | S | H | H | 1 | H | CH(CH₃)₂ | H | H | OH | H |
| 317 | S | H | H | 1 | H | C(CH₃)₃ | H | H | OH | H |
| 318 | S | H | H | 1 | H | H | H | OH | OH | H |
| 319 | S | H | H | 1 | H | CH₃ | H | OH | OH | H |

TABLE 36-continued

| | X | R1 | R2 | m | R9 | R10 | R4 | R5 | R6 | R7 |
|---|---|---|---|---|---|---|---|---|---|---|
| 320 | S | H | H | 1 | H | CH(CH$_3$)$_2$ | H | OH | OH | H |
| 321 | S | H | H | 1 | H | C(CH$_3$)$_3$ | H | OH | OH | H |
| 322 | S | H | H | 1 | H | H | | = | OH | H |
| 323 | S | H | H | 1 | H | CH$_3$ | | = | OH | H |
| 324 | S | H | H | 1 | H | CH$_2$CH$_3$ | | = | OH | H |
| 325 | S | H | H | 1 | H | (CH$_2$)$_2$CH$_3$ | | = | OH | H |
| 326 | S | H | H | 1 | H | CH(CH$_3$)$_2$ | | = | OH | H |
| 327 | S | H | H | 1 | H | (CH$_2$)$_3$CH$_3$ | | = | OH | H |
| 328 | S | H | H | 1 | H | CH$_2$CH(CH$_3$)$_2$ | | = | OH | H |
| 329 | S | H | H | 1 | H | CH(CH$_3$)CH$_2$CH$_3$ | | = | OH | H |
| 330 | S | H | H | 1 | H | C(CH$_3$)$_3$ | | = | OH | H |
| 331 | S | H | H | 1 | H | cyclopropyl | | = | OH | H |
| 332 | S | H | H | 1 | H | cyclobutyl | | = | OH | H |
| 333 | S | H | H | 1 | H | cyclopentyl | | = | OH | H |
| 334 | S | H | H | 1 | H | cyclohexyl | | = | OH | H |
| 335 | S | H | H | 1 | H | cycloheptyl | | = | OH | H |

TABLE 37

| | X | R1 | R2 | m | R9 | R10 | R4 | R5 | R6 | R7 |
|---|---|---|---|---|---|---|---|---|---|---|
| 336 | S | H | H | 1 | H | CH(CF$_3$)$_2$ | | = | OH | H |
| 337 | S | H | H | 1 | CH$_3$ | CH$_3$ | H | H | OH | H |
| 338 | S | H | H | 1 | CH$_3$ | CH(CH$_3$)$_2$ | H | H | OH | H |
| 339 | S | H | H | 1 | CH$_3$ | C(CH$_3$)$_3$ | H | H | OH | H |
| 340 | S | H | H | 1 | CH$_3$ | CH$_3$ | H | OH | OH | H |
| 341 | S | H | H | 1 | CH$_3$ | CH(CH$_3$)$_2$ | H | OH | OH | H |
| 342 | S | H | H | 1 | CH$_3$ | C(CH$_3$)$_3$ | H | OH | OH | H |
| 343 | S | H | H | 1 | CH$_3$ | CH$_3$ | | = | OH | H |
| 344 | S | H | H | 1 | CH$_3$ | CH$_2$CH$_3$ | | = | OH | H |
| 345 | S | H | H | 1 | CH$_3$ | (CH$_2$)$_2$CH$_3$ | | = | OH | H |
| 346 | S | H | H | 1 | CH$_3$ | CH(CH$_3$)$_2$ | | = | OH | H |
| 347 | S | H | H | 1 | CH$_3$ | (CH$_2$)$_3$CH$_3$ | | = | OH | H |
| 348 | S | H | H | 1 | CH$_3$ | CH$_2$CH(CH$_3$)$_2$ | | = | OH | H |
| 349 | S | H | H | 1 | CH$_3$ | CH(CH$_3$)CH$_2$CH$_3$ | | = | OH | H |
| 350 | S | H | H | 1 | CH$_3$ | C(CH$_3$)$_3$ | | = | OH | H |
| 351 | S | H | H | 1 | —(CH$_2$)$_2$— | | | = | OH | H |
| 352 | S | H | H | 1 | —(CH$_2$)$_3$— | | | = | OH | H |
| 353 | S | H | H | 1 | —(CH$_2$)$_4$— | | | = | OH | H |
| 354 | S | H | H | 1 | —(CH$_2$)$_5$— | | | = | OH | H |
| 355 | S | H | H | 1 | —(CH$_2$)$_6$— | | | = | OH | H |
| 356 | S | H | H | 2 | H | H | H | H | OH | H |
| 357 | S | H | H | 2 | H | CH$_3$ | H | H | OH | H |
| 358 | S | H | H | 2 | H | CH(CH$_3$)$_2$ | H | H | OH | H |
| 359 | S | H | H | 2 | H | C(CH$_3$)$_3$ | H | H | OH | H |
| 360 | S | H | H | 2 | H | H | H | OH | OH | H |
| 361 | S | H | H | 2 | H | CH$_3$ | H | OH | OH | H |
| 362 | S | H | H | 2 | H | CH(CH$_3$)$_2$ | H | OH | OH | H |
| 363 | S | H | H | 2 | H | C(CH$_3$)$_3$ | H | OH | OH | H |

TABLE 38

| | X | R1 | R2 | m | R9 | R10 | R4 | R5 | R6 | R7 |
|---|---|---|---|---|---|---|---|---|---|---|
| 364 | S | H | H | 2 | H | H | | = | OH | H |
| 365 | S | H | H | 2 | H | CH$_3$ | | = | OH | H |
| 366 | S | H | H | 2 | H | CH(CH$_3$)$_2$ | | = | OH | H |
| 367 | S | H | H | 2 | H | C(CH$_3$)$_3$ | | = | OH | H |
| 368 | S | H | H | 2 | CH$_3$ | CH$_3$ | H | H | OH | H |
| 369 | S | H | H | 2 | CH$_3$ | CH(CH$_3$)$_2$ | H | H | OH | H |
| 370 | S | H | H | 2 | CH$_3$ | C(CH$_3$)$_3$ | H | H | OH | H |
| 371 | S | H | H | 2 | CH$_3$ | CH$_3$ | H | OH | OH | H |
| 372 | S | H | H | 2 | CH$_3$ | CH(CH$_3$)$_2$ | H | OH | OH | H |
| 373 | S | H | H | 2 | CH$_3$ | C(CH$_3$)$_3$ | H | OH | OH | H |
| 374 | S | H | H | 2 | CH$_3$ | CH$_3$ | | = | OH | H |
| 375 | S | H | H | 2 | CH$_3$ | CH(CH$_3$)$_2$ | | = | OH | H |
| 376 | S | H | H | 2 | CH$_3$ | C(CH$_3$)$_3$ | | = | OH | H |
| 377 | S | H | H | 3 | H | H | H | H | OH | H |
| 378 | S | H | H | 3 | H | CH$_3$ | H | H | OH | H |
| 379 | S | H | H | 3 | H | CH(CH$_3$)$_2$ | H | H | OH | H |
| 380 | S | H | H | 3 | H | C(CH$_3$)$_3$ | H | H | OH | H |
| 381 | S | H | H | 3 | H | H | H | OH | OH | H |
| 382 | S | H | H | 3 | H | CH$_3$ | H | OH | OH | H |
| 383 | S | H | H | 3 | H | CH(CH$_3$)$_2$ | H | OH | OH | H |
| 384 | S | H | H | 3 | H | C(CH$_3$)$_3$ | H | OH | OH | H |
| 385 | S | H | H | 3 | H | H | | = | OH | H |
| 386 | S | H | H | 3 | H | CH$_3$ | | = | OH | H |
| 387 | S | H | H | 3 | H | CH(CH$_3$)$_2$ | | = | OH | H |
| 388 | S | H | H | 3 | H | C(CH$_3$)$_3$ | | = | OH | H |
| 389 | S | H | H | 3 | CH$_3$ | CH$_3$ | H | H | OH | H |
| 390 | S | H | H | 3 | CH$_3$ | CH(CH$_3$)$_2$ | H | H | OH | H |
| 391 | S | H | H | 3 | CH$_3$ | C(CH$_3$)$_3$ | H | H | OH | H |

TABLE 39

|     | X | R1 | R2 | m | R9 | R10 | R4 | R5 | R6 | R7 |
|-----|---|----|----|---|----|----|----|----|----|----|
| 392 | S | H | H | 3 | CH$_3$ | CH$_3$ | H | OH | OH | H |
| 393 | S | H | H | 3 | CH$_3$ | CH(CH$_3$)$_2$ | H | OH | OH | H |
| 394 | S | H | H | 3 | CH$_3$ | C(CH$_3$)$_3$ | H | OH | OH | H |
| 395 | S | H | H | 3 | CH$_3$ | CH$_3$ |  | = | OH | H |
| 396 | S | H | H | 3 | CH$_3$ | CH(CH$_3$)$_2$ |  | = | OH | H |
| 397 | S | H | H | 3 | CH$_3$ | C(CH$_3$)$_3$ |  | = | OH | H |
| 398 | S | CH$_3$ | H | 1 | H | H | H | H | OH | H |
| 399 | S | CH$_3$ | H | 1 | H | CH$_3$ | H | H | OH | H |
| 400 | S | CH$_3$ | H | 1 | H | CH(CH$_3$)$_2$ | H | H | OH | H |
| 401 | S | CH$_3$ | H | 1 | H | C(CH$_3$)$_3$ | H | H | OH | H |
| 402 | S | CH$_3$ | H | 1 | H | H | H | OH | OH | H |
| 403 | S | CH$_3$ | H | 1 | H | CH$_3$ | H | OH | OH | H |
| 404 | S | CH$_3$ | H | 1 | H | CH(CH$_3$)$_2$ | H | OH | OH | H |
| 405 | S | CH$_3$ | H | 1 | H | C(CH$_3$)$_3$ | H | OH | OH | H |
| 406 | S | CH$_3$ | H | 1 | H | H |  | = | OH | H |
| 407 | S | CH$_3$ | H | 1 | H | CH$_3$ |  | = | OH | H |
| 408 | S | CH$_3$ | H | 1 | H | CH$_2$CH$_3$ |  | = | OH | H |
| 409 | S | CH$_3$ | H | 1 | H | (CH$_2$)$_2$CH$_3$ |  | = | OH | H |
| 410 | S | CH$_3$ | H | 1 | H | CH(CH$_3$)$_2$ |  | = | OH | H |
| 411 | S | CH$_3$ | H | 1 | H | (CH$_2$)$_3$CH$_3$ |  | = | OH | H |
| 412 | S | CH$_3$ | H | 1 | H | CH$_2$CH(CH$_3$)$_2$ |  | = | OH | H |
| 413 | S | CH$_3$ | H | 1 | H | CH(CH$_3$)CH$_2$CH$_3$ |  | = | OH | H |
| 414 | S | CH$_3$ | H | 1 | H | C(CH$_3$)$_3$ |  | = | OH | H |
| 415 | S | CH$_3$ | H | 1 | H | cyclopropyl |  | = | OH | H |
| 416 | S | CH$_3$ | H | 1 | H | cyclobutyl |  | = | OH | H |
| 417 | S | CH$_3$ | H | 1 | H | cyclopentyl |  | = | OH | H |
| 418 | S | CH$_3$ | H | 1 | H | cyclohexyl |  | = | OH | H |
| 419 | S | CH$_3$ | H | 1 | H | cycloheptyl |  | = | OH | H |

TABLE 40

|     | X | R1 | R2 | m | R9 | R10 | R4 | R5 | R6 | R7 |
|-----|---|----|----|---|----|----|----|----|----|----|
| 420 | S | CH$_3$ | H | 1 | H | CH(CF$_3$)$_2$ |  | = | OH | H |
| 421 | S | CH$_3$ | H | 1 | CH$_3$ | CH$_3$ | H | H | OH | H |
| 422 | S | CH$_3$ | H | 1 | CH$_3$ | CH(CH$_3$)$_2$ | H | H | OH | H |
| 423 | S | CH$_3$ | H | 1 | CH$_3$ | C(CH$_3$)$_3$ | H | H | OH | H |
| 424 | S | CH$_3$ | H | 1 | CH$_3$ | CH$_3$ | H | OH | OH | H |
| 425 | S | CH$_3$ | H | 1 | CH$_3$ | CH(CH$_3$)$_2$ | H | OH | OH | H |
| 426 | S | CH$_3$ | H | 1 | CH$_3$ | C(CH$_3$)$_3$ | H | OH | OH | H |
| 427 | S | CH$_3$ | H | 1 | CH$_3$ | CH$_3$ |  | = | OH | H |
| 428 | S | CH$_3$ | H | 1 | CH$_3$ | OCH$_3$ |  | = | OH | H |
| 429 | S | CH$_3$ | H | 1 | CH$_3$ | CH$_2$CH$_3$ |  | = | OH | H |
| 430 | S | CH$_3$ | H | 1 | CH$_3$ | (CH$_2$)$_2$CH$_3$ |  | = | OH | H |
| 431 | S | CH$_3$ | H | 1 | CH$_3$ | CH(CH$_3$)$_2$ |  | = | OH | H |
| 432 | S | CH$_3$ | H | 1 | CH$_3$ | (CH$_2$)$_3$CH$_3$ |  | = | OH | H |
| 433 | S | CH$_3$ | H | 1 | CH$_3$ | CH$_2$CH(CH$_3$)$_2$ |  | = | OH | H |
| 434 | S | CH$_3$ | H | 1 | CH$_3$ | CH(CH$_3$)CH$_2$CH$_3$ |  | = | OH | H |
| 435 | S | CH$_3$ | H | 1 | CH$_3$ | C(CH$_3$)$_3$ |  | = | OH | H |
| 436 | S | CH$_3$ | H | 1 |  | —(CH$_2$)$_2$— |  | = | OH | H |
| 437 | S | CH$_3$ | H | 1 |  | —(CH$_2$)$_3$— |  | = | OH | H |
| 438 | S | CH$_3$ | H | 1 |  | —(CH$_2$)$_4$— |  | = | OH | H |
| 439 | S | CH$_3$ | H | 1 |  | —(CH$_2$)$_5$— |  | = | OH | H |
| 440 | S | CH$_3$ | H | 1 |  | —(CH$_2$)$_6$— |  | = | OH | H |
| 441 | S | CH$_3$ | H | 2 | H | H | H | H | OH | H |
| 442 | S | CH$_3$ | H | 2 | H | CH$_3$ | H | H | OH | H |
| 443 | S | CH$_3$ | H | 2 | H | CH(CH$_3$)$_2$ | H | H | OH | H |
| 444 | S | CH$_3$ | H | 2 | H | C(CH$_3$)$_3$ | H | H | OH | H |
| 445 | S | CH$_3$ | H | 2 | H | H | H | OH | OH | H |
| 446 | S | CH$_3$ | H | 2 | H | CH$_3$ | H | OH | OH | H |
| 447 | S | CH$_3$ | H | 2 | H | CH(CH$_3$)$_2$ | H | OH | OH | H |

TABLE 41

|     | X | R1 | R2 | m | R9 | R10 | R4 | R5 | R6 | R7 |
|-----|---|----|----|---|----|----|----|----|----|----|
| 448 | S | CH$_3$ | H | 2 | H | C(CH$_3$)$_3$ | H | OH | OH | H |
| 449 | S | CH$_3$ | H | 2 | H | H |  | = | OH | H |
| 450 | S | CH$_3$ | H | 2 | H | CH$_3$ |  | = | OH | H |
| 451 | S | CH$_3$ | H | 2 | H | CH(CH$_3$)$_2$ |  | = | OH | H |
| 452 | S | CH$_3$ | H | 2 | H | C(CH$_3$)$_3$ |  | = | OH | H |
| 453 | S | CH$_3$ | H | 2 | CH$_3$ | CH$_3$ | H | H | OH | H |
| 454 | S | CH$_3$ | H | 2 | CH$_3$ | CH(CH$_3$)$_2$ | H | H | OH | H |
| 455 | S | CH$_3$ | H | 2 | CH$_3$ | C(CH$_3$)$_3$ | H | H | OH | H |
| 456 | S | CH$_3$ | H | 2 | CH$_3$ | CH$_3$ | H | OH | OH | H |
| 457 | S | CH$_3$ | H | 2 | CH$_3$ | CH(CH$_3$)$_2$ | H | OH | OH | H |

TABLE 41-continued

| | X | R1 | R2 | m | R9 | R10 | R4 | R5 | R6 | R7 |
|---|---|---|---|---|---|---|---|---|---|---|
| 458 | S | CH₃ | H | 2 | CH₃ | C(CH₃)₃ | H | OH | OH | H |
| 459 | S | CH₃ | H | 2 | CH₃ | CH₃ | | = | OH | H |
| 460 | S | CH₃ | H | 2 | CH₃ | CH(CH₃)₂ | | = | OH | H |
| 461 | S | CH₃ | H | 2 | CH₃ | C(CH₃)₃ | | = | OH | H |
| 462 | S | CH₃ | H | 3 | H | H | H | H | OH | H |
| 463 | S | CH₃ | H | 3 | H | CH₃ | H | H | OH | H |
| 464 | S | CH₃ | H | 3 | H | CH(CH₃)₂ | H | H | OH | H |
| 465 | S | CH₃ | H | 3 | H | C(CH₃)₃ | H | H | OH | H |
| 466 | S | CH₃ | H | 3 | H | H | H | OH | OH | H |
| 467 | S | CH₃ | H | 3 | H | CH₃ | H | OH | OH | H |
| 468 | S | CH₃ | H | 3 | H | CH(CH₃)₂ | H | OH | OH | H |
| 469 | S | CH₃ | H | 3 | H | C(CH₃)₃ | H | OH | OH | H |
| 470 | S | CH₃ | H | 3 | H | H | | = | OH | H |
| 471 | S | CH₃ | H | 3 | H | CH₃ | | = | OH | H |
| 472 | S | CH₃ | H | 3 | H | CH(CH₃)₂ | | = | OH | H |
| 473 | S | CH₃ | H | 3 | H | C(CH₃)₃ | | = | OH | H |
| 474 | S | CH₃ | H | 3 | CH₃ | CH₃ | H | H | OH | H |
| 475 | S | CH₃ | H | 3 | CH₃ | CH(CH₃)₂ | H | H | OH | H |

TABLE 42

| | X | R1 | R2 | m | R9 | R10 | R4 | R5 | R6 | R7 |
|---|---|---|---|---|---|---|---|---|---|---|
| 476 | S | CH₃ | H | 3 | CH₃ | C(CH₃)₃ | H | H | OH | H |
| 477 | S | CH₃ | H | 3 | CH₃ | CH₃ | H | OH | OH | H |
| 478 | S | CH₃ | H | 3 | CH₃ | CH(CH₃)₂ | H | OH | OH | H |
| 479 | S | CH₃ | H | 3 | CH₃ | C(CH₃)₃ | H | OH | OH | H |
| 480 | S | CH₃ | H | 3 | CH₃ | CH₃ | | = | OH | H |
| 481 | S | CH₃ | H | 3 | CH₃ | CH(CH₃)₂ | | = | OH | H |
| 482 | S | CH₃ | H | 3 | CH₃ | C(CH₃)₃ | | = | OH | H |
| 483 | S | H | CH₃ | 1 | H | H | H | H | OH | H |
| 484 | S | H | CH₃ | 1 | H | CH₃ | H | H | OH | H |
| 485 | S | H | CH₃ | 1 | H | CH(CH₃)₂ | H | H | OH | H |
| 486 | S | H | CH₃ | 1 | H | C(CH₃)₃ | H | H | OH | H |
| 487 | S | H | CH₃ | 1 | H | H | H | OH | OH | H |
| 488 | S | H | CH₃ | 1 | H | CH₃ | H | OH | OH | H |
| 489 | S | H | CH₃ | 1 | H | CH(CH₃)₂ | H | OH | OH | H |
| 490 | S | H | CH₃ | 1 | H | C(CH₃)₃ | H | OH | OH | H |
| 491 | S | H | CH₃ | 1 | H | H | | = | OH | H |
| 492 | S | H | CH₃ | 1 | H | CH₃ | | = | OH | H |
| 493 | S | H | CH₃ | 1 | H | CH₂CH₃ | | = | OH | H |
| 494 | S | H | CH₃ | 1 | H | (CH₂)₂CH₃ | | = | OH | H |
| 495 | S | H | CH₃ | 1 | H | CH(CH₃)₂ | | = | OH | H |
| 496 | S | H | CH₃ | 1 | H | (CH₂)₃CH₃ | | = | OH | H |
| 497 | S | H | CH₃ | 1 | H | CH₂CH(CH₃)₂ | | = | OH | H |
| 498 | S | H | CH₃ | 1 | H | CH(CH₃)CH₂CH₃ | | = | OH | H |
| 499 | S | H | CH₃ | 1 | H | C(CH₃)₃ | | = | OH | H |
| 500 | S | H | CH₃ | 1 | CH₃ | CH₃ | H | H | OH | H |
| 501 | S | H | CH₃ | 1 | CH₃ | CH(CH₃)₂ | H | H | OH | H |
| 502 | S | H | CH₃ | 1 | CH₃ | C(CH₃)₃ | H | H | OH | H |
| 503 | S | H | CH₃ | 1 | CH₃ | CH₃ | H | OH | OH | H |

TABLE 43

| | X | R1 | R2 | m | R9 | R10 | R4 | R5 | R6 | R7 |
|---|---|---|---|---|---|---|---|---|---|---|
| 504 | S | H | CH₃ | 1 | CH₃ | CH(CH₃)₂ | H | OH | OH | H |
| 505 | S | H | CH₃ | 1 | CH₃ | C(CH₃)₃ | H | OH | OH | H |
| 506 | S | H | CH₃ | 1 | CH₃ | CH₃ | | = | OH | H |
| 507 | S | H | CH₃ | 1 | CH₃ | CH₂CH₃ | | = | OH | H |
| 508 | S | H | CH₃ | 1 | CH₃ | (CH₂)₂CH₃ | | = | OH | H |
| 509 | S | H | CH₃ | 1 | CH₃ | CH(CH₃)₂ | | = | OH | H |
| 510 | S | H | CH₃ | 1 | CH₃ | (CH₂)₃CH₃ | | = | OH | H |
| 511 | S | H | CH₃ | 1 | CH₃ | CH₂CH(CH₃)₂ | | = | OH | H |
| 512 | S | H | CH₃ | 1 | CH₃ | CH(CH₃)CH₂CH₃ | | = | OH | H |
| 513 | S | H | CH₃ | 1 | CH₃ | C(CH₃)₃ | | = | OH | H |
| 514 | S | H | CH₃ | 2 | H | H | H | H | OH | H |
| 515 | S | H | CH₃ | 2 | H | CH₃ | H | H | OH | H |
| 516 | S | H | CH₃ | 2 | H | CH(CH₃)₂ | H | H | OH | H |
| 517 | S | H | CH₃ | 2 | H | C(CH₃)₃ | H | H | OH | H |
| 518 | S | H | CH₃ | 2 | H | H | H | OH | OH | H |
| 519 | S | H | CH₃ | 2 | H | CH₃ | H | OH | OH | H |
| 520 | S | H | CH₃ | 2 | H | CH(CH₃)₂ | H | OH | OH | H |
| 521 | S | H | CH₃ | 2 | H | C(CH₃)₃ | H | OH | OH | H |
| 522 | S | H | CH₃ | 2 | H | H | | = | OH | H |
| 523 | S | H | CH₃ | 2 | H | CH₃ | | = | OH | H |
| 524 | S | H | CH₃ | 2 | H | CH(CH₃)₂ | | = | OH | H |
| 525 | S | H | CH₃ | 2 | H | C(CH₃)₃ | | = | OH | H |
| 526 | S | H | CH₃ | 2 | CH₃ | CH₃ | H | H | OH | H |
| 527 | S | H | CH₃ | 2 | CH₃ | CH(CH₃)₂ | H | H | OH | H |
| 528 | S | H | CH₃ | 2 | CH₃ | C(CH₃)₃ | H | H | OH | H |
| 529 | S | H | CH₃ | 2 | CH₃ | CH₃ | H | OH | OH | H |

TABLE 43-continued

| | X | R1 | R2 | m | R9 | R10 | R4 | R5 | R6 | R7 |
|---|---|---|---|---|---|---|---|---|---|---|
| 530 | S | H | CH₃ | 2 | CH₃ | CH(CH₃)₂ | H | OH | OH | H |
| 531 | S | H | CH₃ | 2 | CH₃ | C(CH₃)₃ | H | OH | OH | H |

TABLE 44

| | X | R1 | R2 | m | R9 | R10 | R4 | R5 | R6 | R7 |
|---|---|---|---|---|---|---|---|---|---|---|
| 532 | S | H | CH₃ | 2 | CH₃ | CH₃ | | = | OH | H |
| 533 | S | H | CH₃ | 2 | CH₃ | CH(CH₃)₂ | | = | OH | H |
| 534 | S | H | CH₃ | 2 | CH₃ | C(CH₃)₃ | | = | OH | H |
| 535 | S | H | CH₃ | 3 | H | H | H | H | OH | H |
| 536 | S | H | CH₃ | 3 | H | CH₃ | H | H | OH | H |
| 537 | S | H | CH₃ | 3 | H | CH(CH₃)₂ | H | H | OH | H |
| 538 | S | H | CH₃ | 3 | H | C(CH₃)₃ | H | H | OH | H |
| 539 | S | H | CH₃ | 3 | H | H | H | OH | OH | H |
| 540 | S | H | CH₃ | 3 | H | CH₃ | H | OH | OH | H |
| 541 | S | H | CH₃ | 3 | H | CH(CH₃)₂ | H | OH | OH | H |
| 542 | S | H | CH₃ | 3 | H | C(CH₃)₃ | H | OH | OH | H |
| 543 | S | H | CH₃ | 3 | H | H | | = | OH | H |
| 544 | S | H | CH₃ | 3 | H | CH₃ | | = | OH | H |
| 545 | S | H | CH₃ | 3 | H | CH(CH₃)₂ | | = | OH | H |
| 546 | S | H | CH₃ | 3 | H | C(CH₃)₃ | | = | OH | H |
| 547 | S | H | CH₃ | 3 | CH₃ | CH₃ | H | H | OH | H |
| 548 | S | H | CH₃ | 3 | CH₃ | CH(CH₃)₂ | H | H | OH | H |
| 549 | S | H | CH₃ | 3 | CH₃ | C(CH₃)₃ | H | H | OH | H |
| 550 | S | H | CH₃ | 3 | CH₃ | CH₃ | H | OH | OH | H |
| 551 | S | H | CH₃ | 3 | CH₃ | CH(CH₃)₂ | H | OH | OH | H |
| 552 | S | H | CH₃ | 3 | CH₃ | C(CH₃)₃ | H | OH | OH | H |
| 553 | S | H | CH₃ | 3 | CH₃ | CH₃ | | = | OH | H |
| 554 | S | H | CH₃ | 3 | CH₃ | CH(CH₃)₂ | | = | OH | H |
| 555 | S | H | CH₃ | 3 | CH₃ | C(CH₃)₃ | | = | OH | H |

The vitamin D derivative of Formula (1) according to the present invention may be prepared in the following manners. However, the preparation is not particularly limited to these manners and other procedures may be used for synthesis.

I. Synthesis of Vitamin D Derivatives of Formula (1) wherein X is an Oxygen Atom Vitamin D derivatives of Formula (1) wherein X is an oxygen atom, $R_6$ is a hydroxyl group, and $R_7$ is a hydrogen atom can be prepared as follows, starting with a compound of Formula (A) found in JP 61-267550 A or E. Murayama et al., Chem. Pharm. Bull. 34 (10), 1986, 4410-4413:

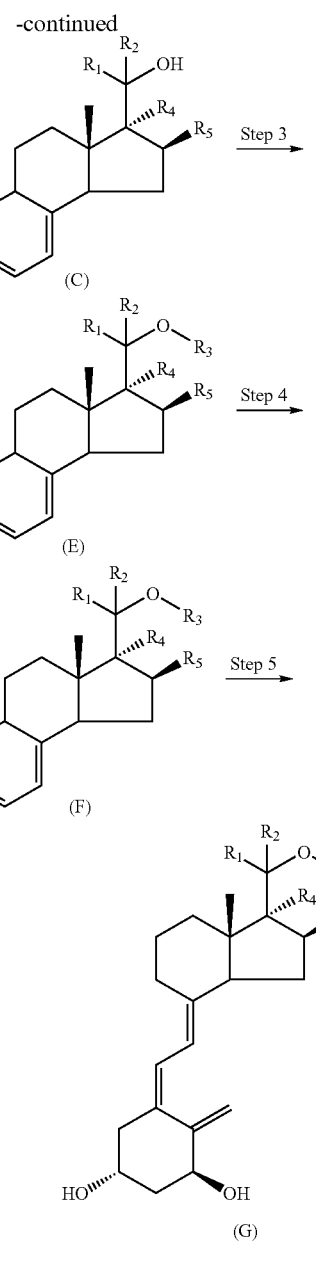

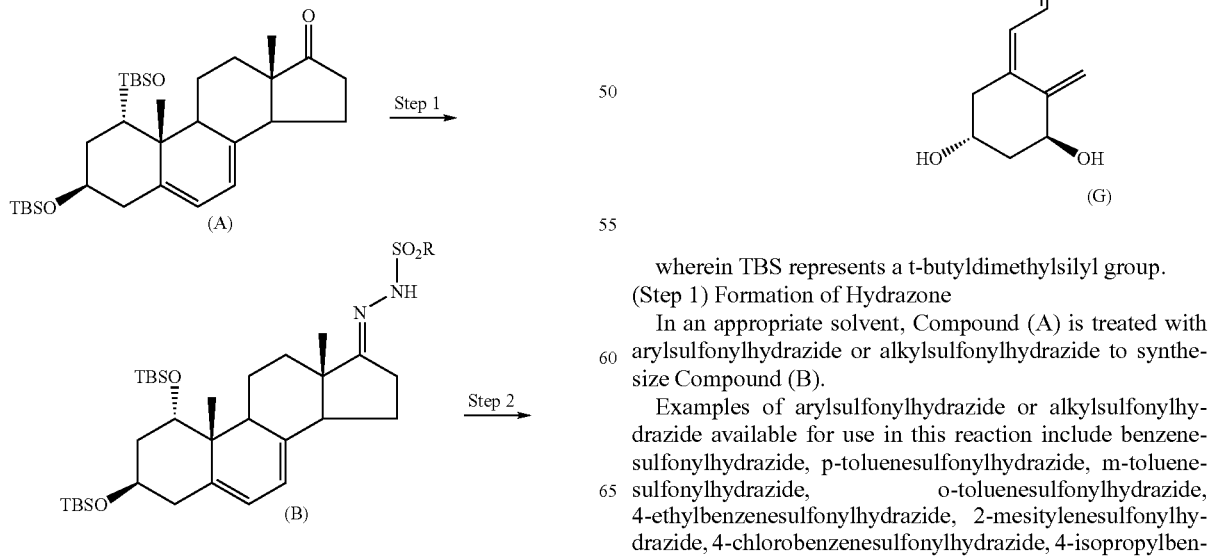

wherein TBS represents a t-butyldimethylsilyl group.

(Step 1) Formation of Hydrazone

In an appropriate solvent, Compound (A) is treated with arylsulfonylhydrazide or alkylsulfonylhydrazide to synthesize Compound (B).

Examples of arylsulfonylhydrazide or alkylsulfonylhydrazide available for use in this reaction include benzenesulfonylhydrazide, p-toluenesulfonylhydrazide, m-toluenesulfonylhydrazide, o-toluenesulfonylhydrazide, 4-ethylbenzenesulfonylhydrazide, 2-mesitylenesulfonylhydrazide, 4-chlorobenzenesulfonylhydrazide, 4-isopropylbenzenesulfonylhydrazide, 2,4,6-triisopropylbenzenesulfonylhydrazide, methanesulfonylhydrazide, 2-methyl-2-propanesulfonylhydrazide, 2-propanesulfonylhydrazide and ethanesulfonylhydrazide. Preferred are benzenesulfonylhydrazide, p-toluenesulfonylhydrazide and 2,4,6-triisopropylbenzenesulfonylhydrazide, and more preferred is 2,4,6-triisopropylbenzenesulfonylhydrazide.

Examples of a solvent available for use in this reaction include hydrocarbon-, ether-, halogen-, ester-, amide-, alcohol-, sulfoxide- and nitrile-based solvents. Specific examples include hexane, benzene, toluene, diethyl ether, tetrahydrofuran, 1,4-dioxane, 1,2-dimethoxyethane, t-butyl methyl ether, diisopropyl ether, dichloromethane, chloroform, 1,2-dichloroethane, chlorobenzene, ethyl acetate, methyl acetate, propyl acetate, N,N-dimethylformamide, N,N-dimethylacetamide, 1,3-dimethyl-2-imidazolidinone, 1,3-dimethyl-3,4,5,6-tetrahydro-2(1H)-pyrimidinone, methanol, ethanol, isopropanol, dimethyl sulfoxide, acetonitrile and propionitrile. Preferred are toluene, diethyl ether, tetrahydrofuran, dichloromethane and ethyl acetate, and more preferred are tetrahydrofuran and ethyl acetate.

The reaction may be performed at any temperature as long as the reaction can proceed, preferably at 0° C. to 100° C., more preferably at room temperature.

(Step 2) Alkylation

In an appropriate solvent, Compound (B) is then treated with a base, followed by formaldehyde (or its equivalent such as 1,3,5-trioxane and paraformaldehyde) or acetone to synthesize Compound (C).

Examples of a base available for use in the above reaction include n-butyllithium, s-butyllithium, t-butyllithium, methyllithium, phenyllithium, methylmagnesium bromide, methylmagnesium chloride, methylmagnesium iodide, isopropylmagnesium bromide, diisopropylmagnesium, lithium diisopropylamide, lithium bis(trimethylsilyl)amide, lithium 2,2,6,6-tetramethylpiperidide, lithium amide, sodium hydride, sodium bis(trimethylsilyl)amide, potassium hydride and potassium bis(trimethylsilyl)amide. Preferred are n-butyllithium, s-butyllithium, t-butyllithium and lithium diisopropylamide, and more preferred are n-butyllithium and s-butyllithium.

In the above reaction, an appropriate metal salt may be added after the reaction with a base. Examples of a metal salt include cerium chloride, magnesium bromide, magnesium chloride, zinc chloride, titanium tetrachloride, chlorotitanium triisopropoxide, samarium chloride and indium chloride, with cerium chloride being preferred.

Examples of a solvent available for use in the above reaction include hydrocarbon- and ether-based solvents. Specific examples include pentane, hexane, benzene, toluene, diethyl ether, t-butyl methyl ether, tetrahydrofuran, 1,2-dimethoxyethane, 1,4-dioxane and anisole. Preferred are hexane, diethyl ether and tetrahydrofuran, and more preferred are hexane and tetrahydrofuran.

This reaction may also be performed in the presence of an amide or amine compound. Examples of an amide or amine compound include 1,4-diazabicyclo[2,2,2]octane, N,N,N',N'-tetramethylethylenediamine, 1,3-dimethyl-2-imidazolidinone, 1,3-dimethyl-3,4,5,6-tetrahydro-2(1H)-pyrimidinone, N,N-dimethylformamide, N,N-dimethylacetamide and hexamethylphosphortriamide. Preferred are N,N,N',N'-tetramethylethylenediamine, 1,3-dimethyl-3,4,5,6-tetrahydro-2 (1H)-pyrimidinone and hexamethylphosphortriamide, and more preferred is N,N,N',N'-tetramethylethylenediamine.

The reaction with a base may be performed at any temperature as long as the reaction can proceed, preferably at −100° C. to 50° C., more preferably at −80° C. to 20° C.

The reaction with formaldehyde (or its equivalent such as 1,3,5-trioxane, paraformaldehyde) or acetone may be performed at any temperature as long as the reaction can proceed, preferably at −100° C. to 50° C., more preferably at −80° C. to 20° C.

In a case where $R_1$ and $R_2$ are each a hydrogen atom and $R_4$ and $R_5$ together form a double bond between the 16- and 17-positions, Compound (C) can also be synthesized as follows.

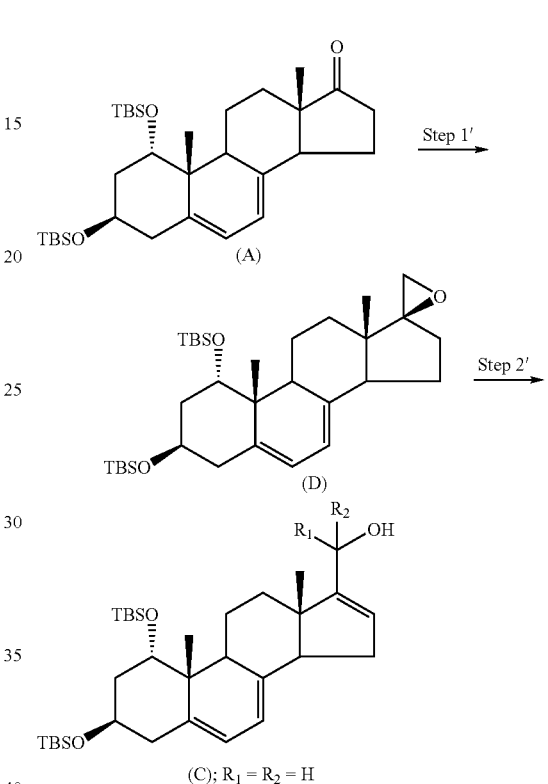

(Step 1') Epoxidation

In an appropriate solvent, Compound (A) is treated with a trimethylsulfonium salt or a trimethylsulfoxonium salt in the presence of a base to synthesize Compound (D).

Examples of a trimethylsulfonium salt or a trimethylsulfoxonium salt available for use in this reaction include trimethylsulfonium iodide, trimethylsulfonium bromide, trimethylsulfonium chloride, trimethylsulfonium methylsulfate, trimethylsulfonium tetrafluoroborate, trimethylsulfonium perchlorate, trimethylsulfoxonium iodide, trimethylsulfoxonium bromide, trimethylsulfoxonium chloride, trimethylsulfoxonium methylsulfate, trimethylsulfoxonium tetrafluoroborate and trimethylsulfoxonium perchlorate, with trimethylsulfonium bromide and trimethylsulfoxonium iodide being preferred.

Examples of a base available for use in this reaction include n-butyllithium, s-butyllithium, t-butyllithium, methyllithium, phenyllithium, methylmagnesium bromide, methylmagnesium chloride, methylmagnesium iodide, isopropylmagnesium bromide, lithium diisopropylamide, lithium bis(trimethylsilyl)amide, lithium 2,2,6,6-tetramethylpiperidide, lithium amide, sodium hydride, sodium bis(trimethylsilyl) amide, potassium hydride, potassium bis(trimethylsilyl) amide, sodium hydroxide and potassium hydroxide. Preferred are sodium hydride, potassium hydride, n-butyllithium, s-butyllithium, t-butyllithium, sodium hydroxide and potassium hydroxide, and more preferred are sodium hydride and potassium hydride.

Examples of a solvent available for use in this reaction include hydrocarbon-, ether-, amide- and sulfoxide-based solvents. Specific examples include pentane, hexane, benzene, toluene, diethyl ether, t-butyl methyl ether, tetrahydrofuran, 1,2-dimethoxyethane, 1,4-dioxane, anisole, diglyme, N,N-dimethylformamide, N,N-dimethylacetamide, 1,3-dimethyl-2-imidazolidinone, 1,3-dimethyl-3,4,5,6-tetrahydro-2(1H)-pyrimidinone and dimethyl sulfoxide, with dimethyl sulfoxide being preferred. Such a solvent may be used in combination with an ether-based solvent (e.g., tetrahydrofuran), if necessary.

The reaction may be performed at any temperature as long as the reaction can proceed, preferably at −20° C. to 20° C.

(Step 2') Ring-opening of Epoxide

In an appropriate solvent, Compound (D) is treated with an acid to synthesize Compound (C).

Examples of an acid available for use in this reaction include hydrochloric acid, sulfuric acid, acetic acid, phosphoric acid, aluminum trimethoxide, aluminum triethoxide, aluminum triisopropoxide, aluminum tri-t-butoxide, aluminum chloride, zinc chloride, tin(II) chloride, tin(IV) chloride, titanium(IV) chloride, titanium tetramethoxide, titanium tetraethoxide and titanium tetraisopropoxide. Preferred are aluminum trimethoxide, aluminum triethoxide, aluminum triisopropoxide and aluminum tri-t-butoxide, and more preferred is aluminum triisopropoxide.

Examples of a solvent available for use in this reaction include hydrocarbon-, ether-, halogen- and amide-based solvents. Specific examples include pentane, hexane, benzene, 1,2-dichlorobenzene, toluene, diethyl ether, tetrahydrofuran, 1,4-dioxane, t-butyl methyl ether, diglyme, 1,2-dimethoxyethane, 1,4-dioxane, anisole, dichloromethane, chloroform, carbon tetrachloride, 1,2-dichloroethane, N,N-dimethylformamide, N,N-dimethylacetamide, 1,3-dimethyl-2-imidazolidinone, 1,3-dimethyl-3,4,5,6-tetrahydro-2(1H)-pyrimidinone and dimethyl sulfoxide. Preferred are benzene, 1,2-dichlorobenzene and toluene, and more preferred is 1,2-dichlorobenzene.

This reaction may be performed at any temperature as long as the reaction can proceed, preferably at 0° C. to 200° C., more preferably at 80° C. to 180° C.

The above reaction may be performed using a base instead of an acid. Examples of a base include n-butyllithium, s-butyllithium, t-butyllithium, methyllithium, phenyllithium, methylmagnesium bromide, methylmagnesium chloride, methylmagnesium iodide, isopropylmagnesium bromide, lithium diethylamide, lithium diisopropylamide, lithium bis(trimethylsilyl)amide, lithium 2,2,6,6-tetramethylpiperidide, lithium amide, sodium hydride, sodium bis(trimethylsilyl)amide, potassium hydride, potassium bis(trimethylsilyl)amide, diethylaluminum diisopropylamide, diethylaluminum 2,2,6,6-tetramethylpiperidide, sodium hydroxide and potassium hydroxide. Preferred are lithium diethylamide, diisopropylmagnesium, lithium diisopropylamide, lithium bis(trimethylsilyl)amide, lithium 2,2,6,6-tetramethylpiperidide, lithium amide, sodium hydride, sodium bis(trimethylsilyl)amide, potassium hydride, potassium bis(trimethylsilyl)amide, diethylaluminum diisopropylamide and diethylaluminum 2,2,6,6-tetramethylpiperidide, and more preferred is lithium diethylamide.

Examples of a solvent available for use in the reaction with a base include hydrocarbon-, ether-, halogen- and amide-based solvents. Specific examples include pentane, hexane, benzene, 1,2-dichlorobenzene, toluene, diethyl ether, tetrahydrofuran, 1,4-dioxane, t-butyl methyl ether, diglyme, 1,2-dimethoxyethane, 1,4-dioxane, anisole, dichloromethane, chloroform, carbon tetrachloride, 1,2-dichloroethane, N,N-dimethylformamide, N,N-dimethylacetamide, 1,3-dimethyl-2-imidazolidinone, 1,3-dimethyl-3,4,5,6-tetrahydro-2(1H)-pyrimidinone and dimethyl sulfoxide, with benzene, toluene, diethyl ether and tetrahydrofuran being preferred.

The reaction with a base may be performed at any temperature as long as the reaction can proceed, preferably at −40° C. to 200° C., more preferably at 0° C. to 100° C.

(Step 3) Introduction of a Side Chain

In order to introduce a side chain, Compound (C) prepared in the above Steps (1) and (2) or Steps (1') and (2') is reacted with an alkylating agent corresponding to the side chain in the presence of a base, thereby obtaining Compound (E).

An alkylating agent available for use corresponds to $R_3$ in the compound of Formula (1) according to the present invention. Namely, examples include alkylating agents represented by the following Formula corresponding to the side chain $R_3$:

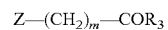

$$Z-(CH_2)_m-COR_3$$

wherein Z represents a leaving group such as a halogen atom, a mesyloxy group, a tosyloxy group or a trifluoromethanesulfonyloxy group, or

$$CH_2=CH-COR_3$$

(JP 6-72994 A, T. Mikami, T. Iwaoka, M. Kato, H. Watanabe and N. Kubodera, Synth. Commun. 27 (14), 1997, 2363-2369).

Examples of $Z-(CH_2)_m-COR_3$ include t-butyl bromoacetate, N-t-butylbromoacetamide and N-t-butyl-N-methylbromoacetamide.

Examples of $CH_2=CH-COR_3$ include acrylic acid, methyl acrylate, ethyl acrylate, n-propyl acrylate, i-propyl acrylate, butyl acrylate, t-butyl acrylate, acrylamide, N-methylacrylamide, N,N-dimethylacrylamide, N-ethylacrylamide, N,N-diethylacrylamide and N-t-butylacrylamide.

Examples of a base include alkali metal hydrides, alkali metal alkoxides, metal dialkylamides and metal alkyls. Preferred are sodium hydride, potassium hydride, potassium t-butoxide, lithium diisopropylamide, lithium bistrimethylsilylamide, methyllithium, n-butyllithium and ethylmagnesium bromide, and more preferred are sodium hydride and potassium hydride.

This reaction may be performed in the presence of a crown ether. Examples of a crown ether include 15-crown-5, 18-crown-6 and dibenzo-18-crown-6.

Examples of a solvent include hydrocarbon-, ether- and amide-based solvents. Specific examples include benzene, toluene, diethyl ether, tetrahydrofuran, 1,2-dimethoxyethane, 1,4-dioxane, N,N-dimethylacetamide, N,N-dimethylformamide, 1,3-dimethyl-2-imidazolidinone and 1,3-dimethyl-3,4,5,6-tetrahydro-2 (1H)-pyrimidinone. Preferred are tetrahydrofuran, 1,2-dimethoxyethane, N,N-dimethylformamide and 1,3-dimethyl-2-imidazolidinone, and more preferred is tetrahydrofuran.

The reaction is performed at a temperature varying according to the type of substrate, generally at a temperature ranging from −40° C. to the boiling point or decomposition point of the solvent used, preferably at 0° C. to 200° C., more preferably around room temperature to around 120° C.

The introduction of the side chain is not particularly limited to the above-stated manner and may also be performed in other manners known to those skilled in the art.

(Step 4) Deprotection

According to conventional procedures, protecting groups are removed from Compound (E) to give Compound (F).

Examples of a deprotection regent available for use include hydrochloric acid, sulfuric acid, acetic acid, acidic ion exchange resins, tetrabutylammonium fluoride, hydrogen fluoride/pyridine, hydrogen fluoride/triethylamine and hydrofluoric acid, with acidic ion exchange resins, tetrabutylammonium fluoride and hydrogen fluoride/pyridine being preferred.

The deprotection is generally performed in an ether-based solvent, preferably in tetrahydrofuran. The reaction temperature for deprotection will vary according to the type of substrate, but it is generally preferable to perform the deprotection at a temperature ranging from room temperature to 65° C.

(Step 5) Photoreaction and Thermal Isomerization

According to conventional procedures, Compound (F) is subjected to photoreaction and thermal isomerization to give Compound (G).

Steps 3, 4 and 5 are not always performed in the order stated above. These steps may be performed in the following order: Step 3→Step 5→Step 4 or Step 5→Step 3→Step 4, provided that Step 4 should not precede Step 3.

In each step, the side chain may be modified, if necessary, in a known manner such as solvolysis (including hydrolysis)-esterification/amidation, ester exchange reaction (Larock, R. C., Comprehensive Organic Transformations, 2nd ed., Wiley-VCH: New York, 1999).

In addition, any one of the compounds as listed below may be used as a compound of Formula (C) to start treatment from Step 3 or 5.

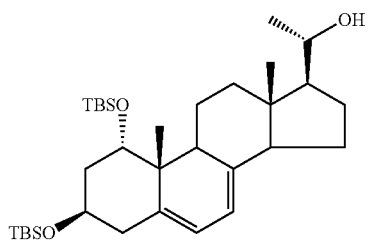

This compound can be found in JP 61-267550 A or E. Murayama, K. Miyamoto, N. Kubodera, T. Mori and I. Matsunaga, Chem. Pharm. Bull. 34 (10), 1986, 4410-4413.

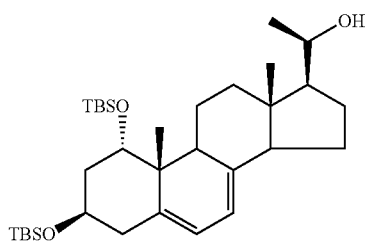

This compound can be found in JP 6-86626 A and N. Kubodera, H. Watanabe, K. Miyamoto and M. Matsumoto, Bioorg. Med. Chem. Lett. 3 (9), 1993, 1869-1872.

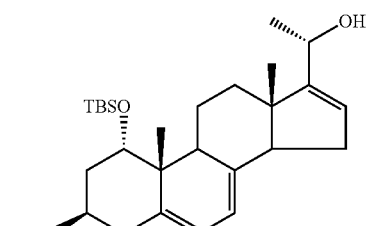

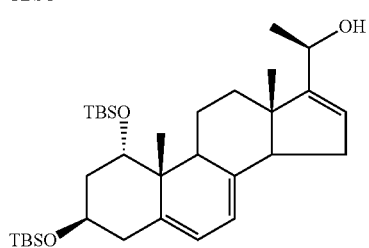

These compounds can be found in JP 10-231284 A.

II. Synthesis of Vitamin D Derivatives of Formula (1) wherein X is a Sulfur Atom Vitamin D derivatives of Formula (1) wherein X is a sulfur atom, $R_6$ is a hydroxyl group, and $R_7$ is a hydrogen atom can be prepared as follows, starting with Compound (C) obtained through the above Steps 1, 2, etc.

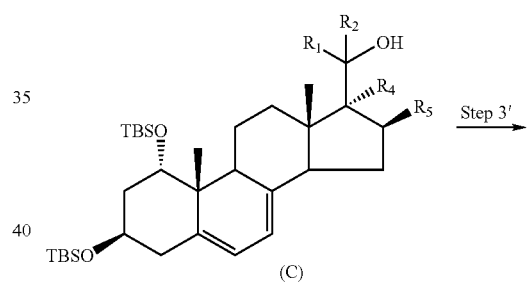

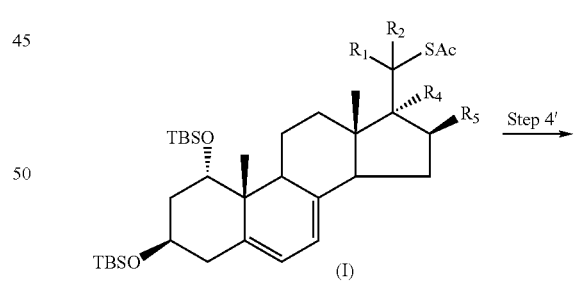

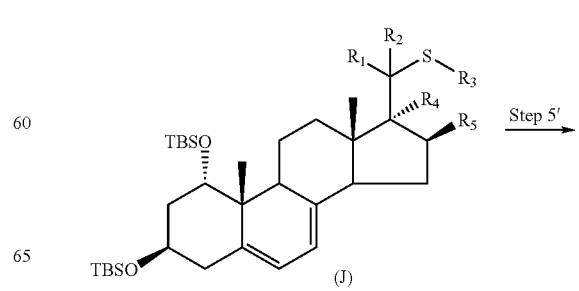

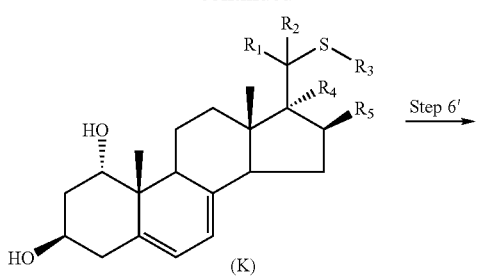

(K)

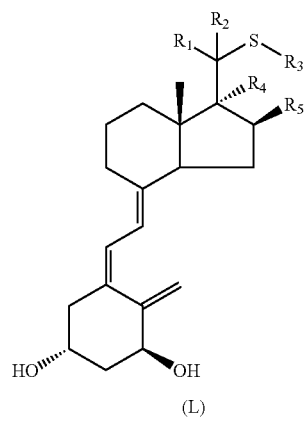

(L)

(Step 3') Introduction of a Sulfur Functional Group

Compound (C) is subjected to, for example, the following two reactions to give Compound (I):

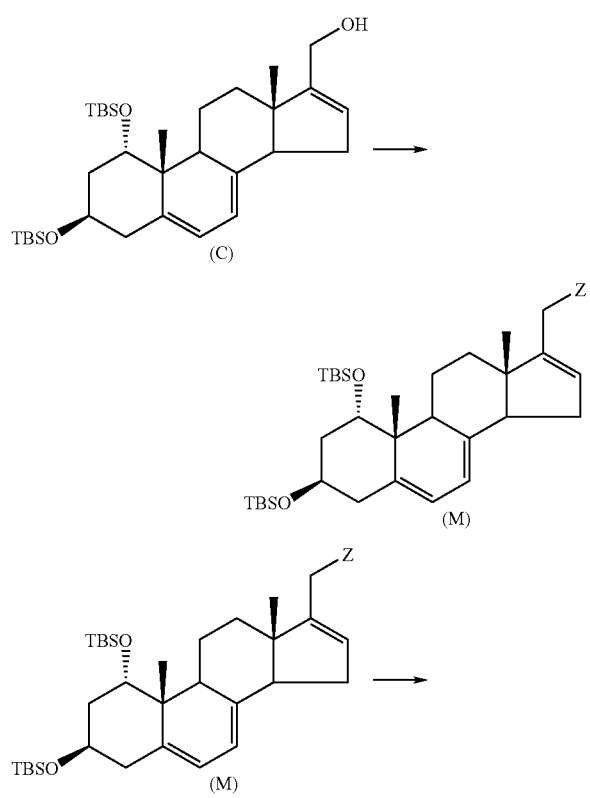

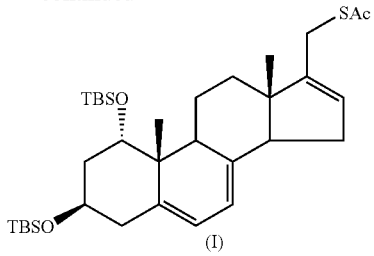

(I)

wherein Z represents a leaving group such as a chlorine atom, a bromine atom, an iodine atom, a methanesulfonyloxy group or a toluenesulfonyloxy group.

Compound (C) can be converted into Compound (M) having a leaving group, according to conventional procedures (Larock, R. C. Comprehensive Organic Transformations, 2nd ed., Wiley-VCH: New York, 1999).

Although the above scheme shows the reaction of Compound (C) wherein $R_1$ and $R_2$ are each a hydrogen atom, and $R_4$ and $R_5$ together form a double bond between the 16- and 17-positions, other cases may also be treated similarly.

In an appropriate solvent, Compound (M) is then treated with a metal salt of thiocarboxylic or dithiocarboxylic acid to synthesize Compound (I).

Examples of a metal salt of thiocarboxylic or dithiocarboxylic acid include sodium thioacetate, potassium thioacetate, sodium thiobenzoate, potassium thiobenzoate, sodium dithioacetate, potassium dithioacetate, sodium dithiobenzoate and potassium dithiobenzoate, with potassium thioacetate being preferred.

Examples of a solvent include hydrocarbon-, ether-, halogen-, ketone/ester/amide-, sulfoxide- and nitrile-based solvents. Specific examples include hexane, benzene, toluene, diethyl ether, tetrahydrofuran, 1,4-dioxane, 1,2-dimethoxyethane, dichloromethane, chloroform, carbon tetrachloride, acetone, ethyl acetate, N,N-dimethylformamide, N,N-dimethylacetamide, 1,3-dimethyl-2-imidazolidinone, 1,3-dimethyl-3,4,5,6-tetrahydro-2 (1H)-pyrimidinone, dimethyl sulfoxide and acetonitrile. Preferred are diethyl ether, tetrahydrofuran, 1,4-dioxane, 1,2-dimethoxyethane, acetone, N,N-dimethylformamide, N,N-dimethylacetamide, 1,3-dimethyl-2-imidazolidinone and dimethyl sulfoxide, and more preferred are tetrahydrofuran, acetone and dimethyl sulfoxide. Further, these solvents may be used in combination.

The reaction may be performed at any temperature as long as the reaction can proceed, generally at −50° C. to 100° C., preferably at 0° C. to room temperature.

The above two reactions may be performed continuously, that is, after conversion of the hydroxyl group into a leaving group, Compound (M) without work-up may be treated with a metal salt of thiocarboxylic or dithiocarboxylic acid.

(Step 4') Alkali Solvolysis and S-alkylation

Compound (I) is solvolyzed under alkaline conditions simultaneously with S-alkylation to give Compound (J).

Examples of a base available for use in alkali solvolysis and S-alkylation include lithium hydroxide, sodium hydroxide, potassium hydroxide, sodium methoxide and potassium t-butoxide, with sodium hydroxide, potassium hydroxide and sodium methoxide being preferred.

Examples of a solvent available for use include water and alcohol-based solvents. For example, methanol, ethanol, propanol and butanol may be used alone or in combination with an ether-based solvent such as diethyl ether, tetrahydrofuran, 1,2-dimethoxyethane, 1,4-dioxane or diglyme.

An alkylating agent available for use may correspond to the side chain, as stated in Section I., Step 3.

The reaction is generally performed at −40° C. to 100° C., preferably at 0° C. to 50° C., more preferably at room temperature.

(Step 5') Deprotection

According to conventional procedures, protecting groups are removed from Compound (J) to give Compound (K).

Examples of a deprotection reagent available for use include hydrochloric acid, sulfuric acid, acetic acid, acidic ion exchange resins, tetrabutylammonium fluoride, hydrogen fluoride/pyridine, hydrogen fluoride/triethylamine and hydrofluoric acid, with acidic ion exchange resins and tetrabutylammonium fluoride being preferred.

The deprotection is generally performed in an ether-based solvent, preferably in tetrahydrofuran. The reaction temperature for deprotection will vary according to the type of substrate, but it is generally preferable to perform the deprotection at a temperature ranging from room temperature to 65° C.

(Step 6') Photoreaction and Thermal Isomerization

According to conventional procedures, Compound (K) is subjected to photoreaction and thermal isomerization to give Compound (L).

Steps 3', 4', 5' and 6 may be performed in any order, provided that Steps 4' and 5' should not precede Step 3'.

In addition, either of the compounds as listed below, which can be found in JP 10-231284 A, may be used as a compound of Formula (I) to start reaction from Step 4'.

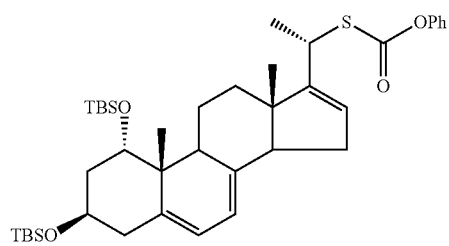

Further, either of the compounds as listed below, which can be found in JP 10-231284 A, may be used as a compound of Formula (I) to start reaction from Step 4'. In this case, Step 6' can be omitted.

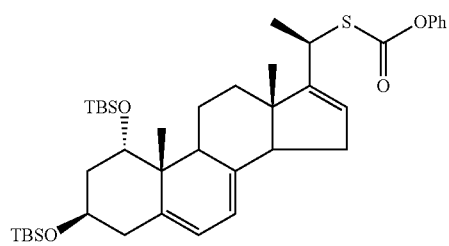

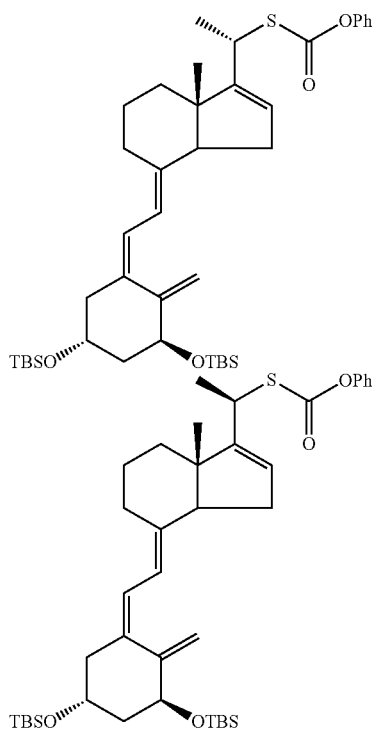

In the respective steps of synthesis schemes I and II stated above, the respective intermediates and final products can be purified and isolated by standard techniques such as silica gel column chromatography, thin layer chromatography and recrystallization.

The present invention enables the advantageous preparation of a compound represented by the above Formula (3), which may be used as an intermediate for the preparation of the vitamin D derivative of Formula (1) according to the present invention.

In preparing a compound of Formula (3) from a compound of Formula (2), tetramethyltin and dimethylzinc have been conventionally used as a reaction reagent. However, the former has required improvement in view of toxicity and reactivity because its low reactivity allows side reactions to proceed simultaneously with the desired reaction, while the latter has required improvement in view of reactivity because its high reactivity allows side reactions to occur preferentially over the desired reaction.

In contrast, when an organoaluminum reagent is used for the preparation of Compound (3) in accordance with the present invention, the reagent causes few side reactions to occur and enables the desired reaction to proceed in high selectivity, thereby resulting in an increased yield of the reaction product. The reagent used is also less toxic. The present invention therefore achieves a more advantageous preparation of a compound of Formula (3), as compared to conventional techniques. This means that the present invention is also more advantageous in preparing a compound of Formula (1) than conventional techniques because the benefits in preparing Compound (3), when applied to the preparation of Compound (1), result in an increased yield of Compound (1) and reduced toxicity of the reagent used.

In Formula (2), examples of the protecting group as $R_{12}$ and $R_{13}$ include an acetyl group and a tert-butyldimethylsilyl group. Examples of the leaving group as $R_{14}$ include a bromine atom, an iodine atom, a trifluoromethanesulfonyloxy group and a nonafluorobutanesulfonyloxy group. A compound of Formula (2) can be prepared by, for example, the method described in Example 24 below.

The compound of Formula (2) can then be carbonylated with carbon monoxide in an organic solvent (e.g., N,N-dimethylformamide, dimethyl sulfoxide, N,N-dimethylacetamide, 1,3-dimethyl-2-imidazolidinone, tetrahydrofuran, toluene) in the presence of an organoaluminum reagent of Formula (4) and a palladium catalyst to give the desired compound of Formula (3) advantageously.

Examples of an organoaluminum reagent include dimethylaluminum chloride, diethylaluminum chloride, di-n-propylaluminum chloride, di-n-butylaluminum chloride and diphenylaluminum chloride.

Examples of a palladium catalyst include tetrakis(triphenylphosphine)palladium, dichlorobis(triphenylphosphine)palladium, dichloro[1,3-bis(diphenylphosphino)propane]palladium, dichloro[1,2-bis(diphenylphosphino)ethane]palladium, bis(dibenzylideneacetone)palladium and tris(dibenzylideneacetone)dipalladium.

In the present invention, these catalysts may be used in combination with a ligand such as triphenylphosphine, tributylphosphine, tricyclohexylphosphine or tri-tert-butylphosphine, if necessary, in order to attain higher catalytic activity or higher reaction selectivity.

The carbonylation is performed at a temperature of 0° C. to 150° C. under a carbon monoxide atmosphere at normal to elevated pressure (up to about 20 atm) for around 10 minutes to around 12 hours.

The compound of Formula (3) thus prepared can be used as an intermediate for the synthesis of the vitamin D derivative of Formula (1) according to the present invention.

Namely, the compound of Formula (1) can be prepared from the compound of Formula (3) by, for example, the method described in Example 25 below.

In Formula (3), $R_{12}$ and $R_{13}$ are as defined in Formula (2) and $R_{15}$ represents an alkyl group such as methyl, ethyl, propyl and butyl, an aryl group such as phenyl, an alkenyl group such as vinyl, or an alkynyl group such as ethynyl.

The vitamin D derivative of Formula (1) thus prepared is a pharmaceutically useful compound with a reduced hypercalcemic effect, as shown in Examples below.

A pharmaceutical composition comprising the vitamin D derivative of the present invention may be formulated into the desired dosage form such as tablets, granules, fine granules, capsules, powders, injections, solutions, suspensions, emulsions, percutaneous absorption formulations or suppositories in combination with pharmaceutically acceptable carriers, excipients, disintegrating agents, lubricants, binders, flavoring agents, coloring agents and the like.

In a case where a therapeutic agent for skin diseases comprising the vitamin D derivative of the present invention as an active ingredient is used for the reaction of psoriasis or the like, the agent may be formulated into a dosage form suitable for external application such as ointments, creams or lotions.

The dose of the therapeutic agent comprising the vitamin D derivative of the present invention as an active ingredient can be determined as appropriate for the type of disease to be treated, the condition, physique, diathesis, age and sex of a patient, the intended route of administration, or the type of dosage form, etc. The agent is generally used in an amount as the active ingredient of 0.001 to 10,000 μg/day, preferably 0.01 to 1,000 μg/day for oral administration, in an amount of 0.01 to 10,000 μg/day, preferably 0.1 to 1,000 μg/day for injection, and in an amount of 1 to 50,000 μg/day, preferably 10 to 5,000 μg/day for external application, which doses may be administered at a time or in divided portions twice or three times a day.

In a case where a therapeutic agent for skin diseases comprising the vitamin D derivative of the present invention as an active ingredient is used for the reaction of psoriasis or the like, the agent is preferably administered by topical application such as external application, but in some cases, it may be systemically administered by oral or parenteral route.

EXAMPLES

The present invention will be further described in the following Examples, which are provided for illustrative purposes only and are not intended to limit the scope of the invention.

In these Examples, each NMR spectrum was measured in $CDCl_3$, unless otherwise specified, and using tetramethylenesilane or chloroform as an internal standard. Each mass spectrum (MS) was measured in EI mode and at an ionizing voltage of 70 eV. Each ultraviolet absorption spectrum (UV) was measured in an ethanol solvent. Column chromatography and preparative thin layer chromatography were performed using silica gel (75 to 150 μm or 40 to 63 μm) and silica gel (thickness: 1 mm, 0.5 mm or 0.25 mm, 20×20 cm each), respectively.

Example 1

Preparation of 17-acetylthiomethyl-1α,3β-bis(tert-butyldimethylsilyloxy)androsta-5,7,16-triene (1) Preparation of 1α,3β-bis(tert-butyldimethylsilyloxy)-17-(2,4,6-triisopropylbenzenesulfonylhydrazono)androsta-5,7-diene 1α,3β-Bis(tert-butyldimethylsilyloxy)-17-oxoandrosta-5,7-diene (1.64 g, 3.08 mmol) and 2,4,6-triisopropylbenzenesulfonylhydrazide (1.01 g, 3.39 mmol) were dissolved in ethyl acetate (6 ml) and stirred at room temperature for 16 hours. After evaporation under reduced pressure to remove the solvent, the resulting residue was purified by column chromatography (hexane:ethyl acetate=15:1) to give the titled compound (1.86 g, 75%).

$^1$H NMR δ: 7.15 (s, 2H), 6.98 (brs, 1H), 5.58 (d, J=5.8 Hz, 1H), 5.40-5.33(m, 1H), 4.28-4.20(m, 2H), 4.18-3.93(m, 1H), 3.70-3.63(m, 1H), 2.95-2.74(m, 2H), 1.30-1.22(m, 24H), 0.88(s, 9H), 0.85(s, 9H), 0.68(s, 3H), 0.09(s, 3H), 0.06(s, 3H), 0.04(s, 3H), 0.03(s, 3H). IR(KBr): 3232, 2956, 2860, 1600, 1462, 1426, 1384, 1372, 1362, 1328, 1254, 1214, 1194, 1166, 1154, 1102, 1038, 1006, 968, 952, 938, 928, 916, 878, 834, 774, 716, 666, 548 cm$^{-1}$.

(2) Preparation of 1α,3β-bis(tert-butyldimethylsilyloxy)-17-(hydroxymethyl)androsta-5,7,16-triene A solution of 1α,3β-bis(tert-butyldimethylsilyloxy)-17-(2,4,6-triisopropylbenzenesulfonylhydrazono)androsta-5,7-diene (32.7 mg, 0.0403 mmol) in hexane (0.8 ml) and tetramethylethylenediamine (0.16 ml) was cooled to −78° C., followed by addition of 1.53 M n-butyllithium (0.106 ml, 0.161 mmol). The reaction mixture was stirred at −78° C. for 2 hours and then warmed to 0° C. and stirred for 15 minutes. After addition of paraformaldehyde (10 mg, 0.33 mmol), the reaction mixture was stirred at 0° C. for 1 hour and then at room temperature for 1 hour. Aqueous sodium chloride was added to the reaction mixture, which was then extracted with dichloromethane, dried over anhydrous sodium sulfate and evaporated to remove the solvent. The resulting residue was purified by column chromatography (hexane:ethyl acetate=6:1) to give the titled compound (13.6 mg, 62%).

(3) Preparation of 17-acetylthiomethyl-1α,3β-bis(tert-butyldimethylsilyloxy)androsta-5,7,16-triene To a solution of 1α,3β-bis(tert-butyldimethylsilyloxy)-17-(hydroxymethyl)androsta-5,7,16-triene (4.00 g, 7.34 mmol) in tetrahydrofuran (70 ml), triethylamine (4.10 ml, 29.4 mmol) was added and methanesulfonyl chloride (1.70 ml, 22.0 mmol) was further added dropwise at −10° C., followed by stirring for 20 minutes. After warming to room temperature, a solution of potassium thioacetate (3.73 g, 29.4 mmol) in dimethyl sulfoxide (70 ml) was added to the reaction mixture. The reaction mixture was stirred for 30 minutes, diluted with hexane, washed with water and then dried over anhydrous magnesium sulfate. After evaporation under reduced pressure to remove the solvent, the resulting residue was purified by silica gel column chromatography (hexane:ethyl acetate=15:1) to give the titled compound (3.91 g, 88%) as a colorless oil.

IR(neat): 2954, 2929, 2897, 2856, 1695, 1471, 1462, 1371, 1360, 1254, 1099 cm$^{-1}$. $^1$H NMR δ: 0.05(s, 1H), 0.07 (s, 3H), 0.07(s, 3H), 0.11(s, 3H), 0.82(s, 3H), 0.88 (s, 18H), 0.94(s, 3H), 2.34(s, 3H), 2.79-2.90(m, 1H), 3.52-3.68(m, 2H), 3.68-3.73(m, 1H), 3.98-4.12(m, 1H), 5.35-5.41(m, 1H), 5.57-5.64 (m, 2H). MS m/z: 602(M$^+$), 413(100%). UV λ$_{max}$nm: 234, 261, 271, 281, 294.

Example 2

Steps (1) and (2) in Example 1 were replaced by the following Steps (1) and (2).

(1) Preparation of 1α,3β-bis(tert-butyldimethylsilyloxy)androsta-5,7-diene-(17S)-spiro-2'-oxirane Sodium hydride (60% in oil, 0.2821 g, 7.06 mmol) was added to dimethyl sulfoxide (13 ml) and stirred at 80° C. for 1 hour. The resulting suspension was cooled to 0° C. and diluted with tetrahydrofuran (19 ml), to which a solution of trimethylsulfonium iodide (1.33 g, 6.50 mmol) in dimethyl sulfoxide (9 ml) was then added dropwise and stirred at 0° C. for 35 minutes. Subsequently, a solution of 1α,3β-bis(tert-butyldimethylsilyloxy)-17-oxoandrosta-5,7-diene (1.0 g, 1.88 mmol) in tetrahydrofuran (7 ml) was added and stirred at room temperature for 14 hours. The reaction mixture was poured into saturated aqueous ammonium chloride, extracted with ethyl acetate, washed with water and saturated aqueous sodium chloride, and then dried over anhydrous sodium sulfate. After evaporation under reduced pressure to remove the solvent, the residue was purified by column chromatography (hexane:ethyl acetate=6:1) to give the titled compound (0.93 g, 91%) as a white foam.

$^1$H NMR δ: 0.05(s, 3H), 0.06(s, 3H), 0.07(s, 3H), 0.11(s, 3H), 0.88(s, 3H), 0.89(s, 3H), 2.65(d, J=4.9 Hz, 1H), 2.93(d, J=4.9 Hz, 1H), 3.71(brs, 1H), 3.98-4.12(m, 1H), 5.35-5.43 (m, 1H), 5.57-5.64(m, 1H).

(2) Preparation of 1α,3β-bis(tert-butyldimethylsilyloxy)-17-(hydroxymethyl)androsta-5,7,16-triene To a solution of 1α,3β-bis(tert-butyldimethylsilyloxy)androsta-5,7-diene-(17S)-spiro-2'-oxirane (20 g, 36.7 mmol) in 1,2-dichlorobenzene (130 ml), aluminum isopropoxide (22 g, 108 mmol) was added under an argon atmosphere and stirred at 130° C. for 1.5 hours. An aqueous solution of Rochelle salt was added to the reaction mixture, which was then extracted with ethyl acetate (twice), followed by washing with water and drying over anhydrous sodium sulfate. After evaporation under reduced pressure to remove the solvent, the residue was purified by column chromatography (hexane:ethyl acetate=6:1) to give the titled compound (10 g, 50%) as a white solid.

IR(neat): 3392, 2954, 2929, 2856, 1462, 1254, 1097, 1082 cm$^{-1}$. $^1$H NMR δ: 0.05(s, 3H), 0.07(s, 6H), 0.11(s, 3H), 0.88(s, 3H), 0.89(s, 3H), 3.71(brs, 1H), 4.00(brs, 1H), 4.22(s, 2H), 5.40(brs, 1H), 5.57-5.66(m, 2H). MS m/z: 544(M$^+$), 355(100%). UV λ$_{max}$nm: 270, 281, 293.

Example 3

Preparation of 17-acetylthiomethyl-1α,3β-bis(tert-butyldimethylsilyloxy)androsta-5,7,16-triene Steps (1) and (2) in Example 1 were followed by the step shown below instead of Step (3).

To a solution of 1α,3β-bis(tert-butyldimethylsilyloxy)-17-(hydroxymethyl)androsta-5,7,16-triene (100 mg, 0.183 mmol), triphenylphosphine (96.0 mg, 0.366 mmol) and imidazole (49.8 mg, 0.732 mmol) in dichloromethane (2 ml), N-bromosuccinimide (65.1 mg, 0.366 mmol) was added at 0° C. and stirred at room temperature. After 1 hour, hexane was added to the reaction mixture, which was then washed with water and saturated aqueous sodium chloride. After drying over anhydrous magnesium sulfate, the solvent was removed under reduced pressure to give a mixture (150 mg) containing 1α,3β-bis(tert-butyldimethylsilyloxy)-17-(bromomethyl)androsta-5,7,16-triene. This mixture was dissolved in acetone (1.5 ml), followed by addition of potassium thioacetate (31.4 mg, 0.275 mmol) and stirring for 30 minutes. The reaction mixture was diluted with hexane and filtered. The resulting filtrate was evaporated under reduced pressure to remove the solvent and the residue was purified by preparative thin layer chromatography (0.5 mm×2 plates, hexane:ethyl acetate=20:1, developed once) to give the titled compound (70.2 mg, 64%) as a colorless oil.

Example 4

(1) Preparation of 1α,3β-bis(tert-butyldimethylsilyloxy)-20(S)-(N,N-dimethylaminocarbonylethoxy) pregna-5,7,16-triene To a solution of 1α,3β-bis(tert-butyldimethylsilyloxy)-20(S)-hydroxypregna-5,7,16-triene (400 mg, 0.72 mmol) in tetrahydrofuran (7.2 ml), sodium hydride (60% in oil, 46 mg, 1.15 mmol) was added and stirred at room temperature for 30 minutes under a nitrogen stream. After addition of N,N-dimethylacrylamide (308 mg, 3.11 mmol), the reaction mixture was further stirred at the same temperature for 3 hours, poured into saturated aqueous ammonium chloride, extracted with ethyl acetate (3 times) and washed with saturated aqueous sodium chloride and water. The organic layer was dried over anhydrous magnesium sulfate. After evaporation under reduced pressure to remove the solvent, the resulting residue was purified by column chromatography (hexane:ethyl acetate=2:1) to give the titled compound (459 mg, 96.9%) as a colorless oil.

IR(neat): 2954, 2929, 2895, 2856, 1655, 1462, 1389, 1371, 1254, 1149, 1097 cm$^{-1}$. $^1$H NMR δ: 0.05(s, 3H), 0.06(s, 6H), 0.11(s, 3H), 0.88(s, 21H), 0.94(s, 3H), 1.30(d, J=6.6 Hz, 3H), 2.60(t, J=6.9 Hz, 2H), 2.78-2.90(m, 1H), 2.94(s, 3H), 3.02(s, 3H), 3.57-3.80(m, 3H), 3.90-4.11(m, 2H), 5.35-5.43(m, 1H), 5.57-5.64(m, 2H). MS m/z: 540 (M$^+$-HO (CH$_2$)$_2$CONMe$_2$), 73(100%). UV $\lambda_{max}$nm: 271, 282, 294.

(2) Preparation of 1α,3β-dihydroxy-20(S)-(N,N-dimethylaminocarbonylethoxy)pregna-5,7,16-triene To a solution of 1α,3β-bis(tert-butyldimethylsilyloxy)-20(S)-(N,N-dimethylaminocarbonylethoxy)pregna-5,7,16-triene (100 mg, 0.15 mmol) in tetrahydrofuran (6.0 ml), a 1M tetrahydrofuran solution of tetra-n-butylammonium fluoride (1.5 ml) was added and stirred at 50° C. for 1 hour under a nitrogen stream. After cooling to room temperature, the reaction mixture was diluted with ethyl acetate, washed sequentially with 0.5N hydrochloric acid, saturated aqueous sodium bicarbonate and saturated aqueous sodium chloride, and then dried over anhydrous magnesium sulfate. After evaporation under reduced pressure to remove the solvent, the resulting residue was purified by preparative thin layer chromatography (1.0 mm×2 plates, chloroform:methanol=10:1) to give the titled compound (45 mg, 70.3%) as a colorless foam.

IR(neat): 3359, 2970, 2935, 2918, 2873, 2837, 1624, 1417, 1361, 1257, 1196, 1151, 1097, 1053 cm$^{-1}$. $^1$H NMR δ: 0.87(s, 3H), 0.97(s, 3H), 1.29(d, J=6.3 Hz, 3H), 2.59(t, J=6.9 Hz, 2H), 2.73-2.85(m, 1H), 2.93(s, 3H), 3.02 (s, 3H), 3.53-3.66 (m, 1H), 3.69-3.81(m, 2H), 3.92-4.13(m, 2H), 5.40-5.48(m, 1H), 5.60(brs, 1H), 5.70-5.76(m, 1H). MS m/z: 312(M$^+$-HO(CH$_2$)$_2$CONMe$_2$), 72(100%). UV $\lambda_{max}$nm: 271, 282, 293.

(3) Preparation of 1α,3β-dihydroxy-20(S)-(N,N-dimethylaminocarbonylethoxy)-9,10-secopregna-5,7,10(19),16-tetraene 1α,3β-Dihydroxy-20(S)-(N,N-dimethylaminocarbonylethoxy)pregna-5,7,16-triene (60 mg, 0.14 mmol) was dissolved in ethanol (200 ml). While bubbling with argon at 0° C. under stirring, the resulting solution was irradiated using a 400 W high-pressure mercury lamp with a Vycor filter for 5 minutes, and then heated at reflux for 2 hours. After cooling to room temperature, the reaction mixture was evaporated under reduced pressure to remove the solvent and the resulting residue was purified by preparative thin layer chromatography (0.5 mm×3 plates, dichloromethane:ethanol=20:1, developed three times; 0.5 mm×2 plates, hexane:ethyl acetate:ethanol=3:7:0.5, developed three times; and then 0.5 mm×1 plate, hexane:ethyl acetate:ethanol=2:8:0.5, developed three times) to give the titled compound (5.333 mg, 8.9%) as a colorless oil.

IR(neat): 3400, 2930, 2848, 1633, 1628, 1103, 1055 cm$^{-1}$. $^1$H NMR δ: 0.77(s, 3H), 1.29(d, J=6.6 Hz, 3H), 2.59(t, J=6.9 Hz, 2H), 2.74-2.86(m, 1H), 2.93(s, 3H), 3.02 (s, 3H), 3.52-3.65(m, 1H), 3.68-3.80(m, 1H), 3.94(q, J=6.6 Hz, 1H), 4.17-4.29(m, 1H), 4.39-4.48(m, 1H), 5.01(brs, 1H), 5.33(brs, 1H), 5.57(brs, 1H), 6.10(d, J=11.2 Hz, 1H), 6.37(d, J=11.2 Hz, 1H). MS m/z: 429(M$^+$), 118 (100%). UV $_{max}$nm: 264.

Example 5

(1) Preparation of 1α,3β-bis(tert-butyldimethylsilyloxy)-20(R)-(N,N-dimethylaminocarbonylethoxy)pregna-5,7,16-triene 1α,3β-Bis(tert-butyldimethylsilyloxy)-20(R)-hydroxypregna-5,7,16-triene (316 mg, 0.57 mmol) was treated with N,N-dimethylacrylamide (175 mg, 1.77 mmol) and sodium hydride (60% in oil, 36 mg, 0.91 mmol) in tetrahydrofuran (5.7 ml) in the same manner as shown in Example 4(1) (at 0° C. for 1.5 hours and then at room temperature for 1.5 hours), followed by work up and purification using column chromatography (hexane:ethyl acetate=2:1) to give the titled compound (352 mg, 93.9%) as a colorless oil.

IR(neat): 3280, 2954, 2929, 2885, 2856, 1628, 1464, 1402, 1373, 1255, 1097 cm$^{-1}$. $^1$H NMR δ: 0.05(s, 3H), 0.07(s, 6H), 0.11(s, 3H), 0.83(s, 3H), 0.88(s, 18H), 0.94(s, 3H), 1.32(d, J=6.3 Hz, 3H), 2.63(t, J=6.9 Hz, 2H), 2.79-2.90(m, 1H), 2.94(s, 3H), 3.01(s, 3H), 3.66-3.79(m, 3H), 3.96-4.09(m, 2H), 5.34-5.42(m, 1H), 5.56-5.66(m, 2H). MS m/z: 540(M$^+$-HO(CH$_2$)$_2$CONMe$_2$), 73 (100%). UV $\lambda_{max}$nm: 271, 282, 294.

(2) Preparation of 1α,3β-dihydroxy-20(R)-(N,N-dimethylaminocarbonylethoxy)pregna-5,7,16-triene 1α,3β-Bis(tert-butyldimethylsilyloxy)-20(R)-(N,N-dimethylaminocarbonylethoxy)pregna-5,7,16-triene (100 mg, 0.15 mmol) was treated with a 1M tetrahydrofuran solution of tetra-n-butylammonium fluoride (1.5 ml) in tetrahydrofuran (6.0 ml) in the same manner as shown in Example 4(2) (at room temperature for 30 minutes and then at 50° C. for 1.5 hours), followed by work up and purification using preparative thin layer chromatography (0.5 mm×2 plates, chloroform:methanol=10:1) to give the titled compound (52 mg, 83.0%) as a colorless foam.

IR(neat): 3390, 2962, 2933, 2875, 1624, 1456, 1398, 1373, 1267, 1157, 1097, 1057 cm$^{-1}$. $^1$H NMR δ: 0.84(s, 3H), 0.98(s, 3H), 1.32(d, J=6.6 Hz, 3H), 2.60(t, J=7.3 Hz, 2H), 2.73-2.85 (m, 1H), 2.94(s, 3H), 3.01(s, 3H), 3.72(t, J=7.3 Hz, 2H), 3.78(brs, 1H), 3.97-4.13(m, 2H), 5.42-5.49(m, 1H), 5.65(brs, 1H), 5.72-5.78(m, 1H). MS m/z: 312(M$^+$-HO(CH$_2$)$_2$CONMe$_2$), 72 (100%). UV $\lambda_{max}$nm: 271, 281, 293.

(3) Preparation of 1α,3β-dihydroxy-20(R)(N,N-dimethylaminocarbonylethoxy)-9,10-secopregna-5,7,10(19),16-tetraene 1α,3β-Dihydroxy-20(R)-(N,N-dimethylaminocarbonylethoxy)pregna-5,7,16-triene (50 mg, 0.12 mmol) was treated in ethanol (200 ml) in the same manner as shown in Example 4(3) (irradiated with light for 4 minutes and 45 seconds, heated at reflux for 2 hours), followed by purification using preparative thin layer chromatography (0.5 mm×2 plates, dichloromethane:ethanol=20:1, developed three times and then 0.5 mm×1 plate, hexane:ethyl acetate:ethanol=2:8:0.5, developed three times) to give the titled compound (3.427 mg, 6.9%) as a colorless oil.

IR(neat): 3400, 2929, 1633, 1055 cm$^{-1}$. $^1$H NMR δ: 0.73(s, 3H), 1.31(d, J=6.6 Hz, 3H), 2.59(t, J=7.3 Hz, 2H), 2.75-2.85 (m, 1H), 2.94(s, 3H), 3.02(s, 3H), 3.72(t, J=7.3 Hz, 2H), 3.99(q, J=6.6 Hz, 1H), 4.18-4.30(m, 1H), 4.39-4.49(m, 1H), 5.01(brs, 1H), 5.33(brs, 1H), 5.60(brs, 1H), 6.10(d, J=11.6 Hz, 1H), 6.37(d, J=11.2 Hz, 1H). MS m/z: 429(M$^+$), 72 (100%). UV $\lambda_{max}$nm: 265.

Example 6

(1) Preparation of 1α,3β-bis(tert-butyldimethylsilyloxy)-17-(N,N-dimethylaminocarbonylethoxymethyl)androsta-5,7,16-triene 1α,3β-Bis(tert-butyldimethylsilyloxy)-17-(hydroxymethyl)androsta-5,7,16-triene (951 mg, 1.75 mmol) was treated with N,N-dimethylacrylamide (540 mg, 5.44 mmol) and sodium hydride (60% in oil, 105 mg, 2.62 mmol) in tetrahydrofuran (17.5 ml) in the same manner as shown in Example 4(1) (at 5° C. for 14 hours), followed by work up and purification using column chromatography (hexane:ethyl acetate=2:1) to give the titled compound (1.05 g, 92.7%) as a yellow oil.

IR(neat): 2954, 2929, 2895, 2856, 1653, 1462, 1398, 1371, 1254, 1097, 1074 cm$^{-1}$. $^1$H NMR δ: 0.05(s, 3H), 0.06(m, 6H), 0.11(s, 3H), 0.82(s, 3H), 0.877(s, 9H), 0.881 (s, 9H), 0.94(s, 3H), 2.62(t, J=6.6 Hz, 2H), 2.80-2.90(m, 1H), 2.94(s, 3H), 3.02(s, 3H), 3.70(brs, 1H), 3.76(t, J=6.6 Hz, 2H), 3.96-4.12 (m, 4H), 5.34-5.42(m, 1H), 5.55-5.67(m, 2H). MS m/z: 644 (M$^+$−1), 73 (100%). UV λ$_{max}$nm: 271, 281, 293.

(2) Preparation of 1α,3β-bis(tert-butyldimethylsilyloxy)-17-(N,N-dimethylaminocarbonylethoxymethyl)-9,10-secoandrosta-5,7,10(19),16-tetraene 1α,3β-Bis(tert-butyldimethylsilyloxy)-17-(N,N-dimethylaminocarbonylethoxymethyl)androsta-5,7,16-triene (300 mg, 0.47 mmol) was treated in ethanol (350 ml) in the same manner as shown in Example 4(3) (irradiated with light for 13 minutes and 30 seconds, heated at reflux for 2 hours) and then evaporated under reduced pressure to remove the solvent, thereby giving a yellow oil (300 mg) containing the desired product.

(3) Preparation of 1α,3β-dihydroxy-17-(N,N-dimethylaminocarbonylethoxymethyl)-9,10-secoandrosta-5,7,10(19),16-tetraene The oil from Example 6(2) (300 mg) was dissolved in tetrahydrofuran (30 ml) and methanol (30 ml), to which AMBERLYST 15 (11.1 g) was then added and stirred in the dark at room temperature for 4 hours under a nitrogen stream. Insoluble products were filtered through CELITE and washed with methanol. Sodium bicarbonate was added to the filtrate and stirred for 5 minutes, followed by re-filtration. The filtrate was concentrated under reduced pressure and the resulting residue was purified by preparative thin layer chromatography (1.0 mm×3 plates, dichloromethane:ethanol=20:1, developed three times and then 0.5 mm×3 plates, hexane:ethyl acetate:ethanol=2:8:0.5, developed three times) to give the titled compound (10.282 mg, 5.5%) as a colorless oil.

IR(neat): 3400, 2929, 2875, 2850, 1633, 1500, 1402, 1159, 1059 cm$^{-1}$. $^1$H NMR δ: 0.72(s, 3H), 2.62(t, J=6.6 Hz, 2H), 2.54-2.66(m, 1H), 2.75-2.86(m, 1H), 2.94(s, 3H), 3.02(s, 3H), 3.68-3.78(m, 2H), 3.96-4.09(m, 2H), 4.18-4.29(m, 1H), 4.39-4.48(m, 1H), 5.00(brs, 1H), 5.33(brs, 1H), 5.60 (brs, 1H), 6.09(d, J=11.6 Hz, 1H), 6.36(d, J=11.2 Hz, 1H). MS m/z: 298(M$^+$−HO(CH$_2$)$_2$CONMe$_2$), 72 (100%). UV λ$_{max}$nm: 264.

Example 7

Preparation of 1α,3β-dihydroxy-20(S)-(N,N-dimethylaminocarbonylethoxy)-9,10-secopregna-5,7,10(19)-triene 1α,3β-Bis(tert-butyldimethylsilyloxy)-20(S)-(N,N-dimethylaminocarbonylethoxy)pregna-5,7-diene (220 mg, 0.33 mmol) was treated in ethanol (200 ml) in the same manner as shown in Example 4(3) (irradiated with light for 12 minutes, heated at reflux for 2 hours) and then evaporated under reduced pressure to remove the solvent. The resulting residue (210 mg) was treated in tetrahydrofuran (20 ml) and methanol (20 ml) with AMBERLYST 15 (7.4 g) in the same manner as shown in Example 6(3) (at room temperature for 5 hours), followed by work up and purification using preparative thin layer chromatography (0.5 mm×7 plates, dichloromethane:ethanol=20:1, developed three times; 0.5 mm×2 plates, hexane:ethyl acetate:ethanol=2:8:0.5, developed three times; and then 0.5 mm×2 plates, dichloromethane:ethanol=10:1, developed twice) to give the titled compound (7.202 mg, 5.1% for 2 steps) as a colorless oil.

IR(neat): 3400, 2927, 2873, 1633, 1628, 1446, 1417, 1149, 1095, 1059 cm$^{-1}$. $^1$H NMR δ: 0.51 (s, 3H), 1.16 (d, J=5.9 Hz, 3H), 2.75-2.88 (m, 1H), 2.93 (s, 3H), 3.02 (s, 3H), 3.20-3.33 (m, 1H), 3.51-3.63 (m, 1H), 3.80-3.92 (m, 1H), 4.17-4.27 (m, 1H), 4.38-4.47 (m, 1H), 4.99 (brs, 1H), 5.32 (brs, 1H), 6.02 (d, J=11.2 Hz, 1H), 6.36 (d, J=11.2 Hz, 1H). MS m/z: 296 (M$^+$−HO(CH$_2$)$_2$CONMe$_2$—H$_2$O), 72 (100%). UV λ$_{max}$nm: 264.

Example 8

(1) Preparation of 1α,3β-bis(tert-butyldimethylsilyloxy)-20(S)-(tert-butoxycarbonylmethoxy)pregna-5,7,16-triene A solution of 1α,3β-bis(tert-butyldimethylsilyloxy)-20 (S)-hydroxypregna-5,7,16-triene (55.5 mg, 0.0993 mmol), sodium hydride (95%, 15 mg, 0.594 mmol) and 15-crown-5 (15 mg, 0.0681 mmol) in tetrahydrofuran (1 ml) was stirred at an external temperature of 72° C. for 1 hour, to which t-butyl bromoacetate (0.05 ml, 0.336 mmol) was then added at room temperature and further stirred at an external temperature of 72° C. for 5 hours and 15 minutes. After the reaction mixture was diluted with ethyl acetate, water was added dropwise under ice cooling. After washing with saturated aqueous sodium chloride, the organic layer was dried over anhydrous magnesium sulfate. After evaporation under reduced pressure to remove the solvent, the resulting residue was purified by preparative thin layer chromatography (0.5 mm×1 plate, hexane:ethyl acetate=10:1, developed once) to give the titled compound (55.1 mg, 82%) as a colorless oil.

IR(neat): 2928, 2856, 1748, 1088, 832 cm$^{-1}$. $^1$H NMR δ: 0.05 (s, 3H), 0.06 (s, 6H), 0.10 (s, 3H), 0.86 (s, 3H), 0.88 (s, 18H), 0.94 (s, 3H), 1.36 (d, J=6.3 Hz, 3H), 1.46 (s, 9H), 2.79-2.91 (m, 1H), 3.69 (brs, 1H), 3.82 (d, J=16.5 Hz, 1H), 3.94 (d, J=16.5 Hz, 1H), 3.98-4.15 (m, 2H), 4.09 (q, J=6.3 Hz, 1H), 5.35-5.43 (m, 1H), 5.57-5.66 (m, 2H). UV λ$_{max}$nm: 271, 282, 294.

(2) Preparation of 1α,3β-bis(tert-butyldimethylsilyloxy)-20(S)-(tert-butoxycarbonylmethoxy)-9,10-secopregna-5,7,10(19),16-tetraene 1α,3β-Bis(tert-butyldimethylsilyloxy)-20(S)-(tert-butoxycarbonylmethoxy)pregna-5,7,16-triene (52.2 mg, 0.0775 mmol) was treated in ethanol (200 ml) in the same manner as shown in Example 4(3) (irradiated with light for 4 minutes and 20 seconds, heated at reflux for 2 hours), followed by purification using preparative thin layer chromatography (0.5 mm×2 plates, hexane:ethyl acetate=20:1, developed twice) to give a mixture (16.6 mg) containing the titled compound.

(3) Preparation of 20(S)-(tert-butoxycarbonylmethoxy)-1α,3β-dihydroxy-9,10-secopregna-5,7,10 (19),16-tetraene The mixture from Example 8(2) (16.6 mg) was dissolved in tetrahydrofuran (2.5 ml), to which hydrogen fluoride/pyridine (70%, 1 ml) was then added and stirred at room temperature for 30 minutes. The reaction mixture was diluted with ethyl acetate, washed sequentially with water (twice), saturated aqueous sodium bicarbonate (three times) and saturated aqueous sodium chloride (once), dried over anhydrous magnesium sulfate, and then evaporated under reduced pressure to remove the solvent. The resulting residue was purified by preparative thin layer chromatography (0.25 mm×1 plate, dichloromethane:ethanol=20:1, developed three times; 0.25 mm×1 plate, hexane:ethyl acetate:ethanol=10:5:1, developed five times; and then 0.25 mm×1 plate, dichloromethane:ethyl acetate=3:1, developed three times) to give the titled compound (1.77 mg, 5% for 2 steps) as a colorless oil.

IR(neat): 3400, 2976, 2932, 1746, 1122 cm$^{-1}$. $^1$H NMR δ: 0.77 (s, 3H), 1.36 (d, J=6.4 Hz, 3H), 1.47 (s, 9H), 2.37-2.47 (m, 1H), 2.55-2.66 (m, 1H), 2.76-2.89 (m, 1H), 3.81 (d, J=16.3 Hz, 1H), 3.94 (d, J=16.3 Hz, 1H), 4.07 (q, J=6.4 Hz, 1H), 4.19-4.31 (m, 1H), 4.41-4.50 (m, 1H), 5.01 (s, 1H), 5.34 (s, 1H), 5.60 (brs, 1H), 6.11 (d, J=11.4 Hz, 1H), 6.37 (d, J=11.2 Hz, 1H). MS m/z: 312 (M$^+$-HOCH$_2$CO$_2$C(CH$_3$)$_3$), 57 (100%). UV λ$_{max}$nm: 263.

Example 9

(1) Preparation of 1α,3β-bis(tert-butyldimethylsilyloxy)-20(R)-(tert-butoxycarbonylmethoxy)pregna-5,7,16-triene 1α,3β-Bis(tert-butyldimethylsilyloxy)-20(R)-hydroxypregna-5,7,16-triene (158 mg, 0.283 mmol) was treated with sodium hydride (60% in oil, 77 mg, 1.925 mmol), tetrahydrofuran (6 ml), 15-crown-5 (67 mg, 0.304 mmol) and t-butyl bromoacetate (0.25 ml, 1.679 mmol) in the same manner as shown in Example 8(1) (at an external temperature of 85° C. for 11 hours and 40 minutes) and then worked up. The resulting residue was purified by column chromatography (hexane:ethyl acetate=10:1) and preparative thin layer chromatography (0.5 mm×3 plates, hexane:ethyl acetate=20:1, developed twice) to give the titled compound (142.6 mg, 75%) as a colorless oil.

IR(neat): 2932, 2856, 1748, 1100, 834 cm$^{-1}$. $^1$H NMR δ: 0.05 (s, 3H), 0.07 (s, 6H), 0.11 (s, 3H), 0.85 (s, 3H), 0.88 (s, 18H), 0.94 (s, 3H), 1.37 (d, J=6.6 Hz, 3H), 1.47 (s, 9H), 2.78-2.91 (m, 1H), 3.70 (brs, 1H), 3.86 (d, J=16.4 Hz, 1H), 3.96 (d, J=16.4 Hz, 1H), 3.98-4.13 (m, 1H), 4.15 (q, J=6.6 Hz, 1H), 5.35-5.46 (m, 1H), 5.61 (d, J=5.4 Hz, 1H), 5.66 (brs, 1H). UV λ$_{max}$nm: 271, 282, 294.

(2) Preparation of 1α,3β-bis(tert-butyldimethylsilyloxy)-20(R)-(tert-butoxycarbonylmethoxy)-9,10-secopregna-5,7,10(19),16-tetraene 1α,3β-Bis(tert-butyldimethylsilyloxy)-20(R)-(tert-butoxycarbonylmethoxy)pregna-5,7,16-triene (108.3 mg, 0.161 mmol) was treated in ethanol (200 ml) in the same manner as shown in Example 4(3) (irradiated with light for 6.5 minutes, heated at reflux for 1.5 hours), followed by purification using preparative thin layer chromatography (0.5 mm×1 plate, hexane:ethyl acetate=20:1, developed twice) to give a mixture (25.6 mg) containing the titled compound.

(3) Preparation of 20(R)-(tert-butoxycarbonylmethoxy)-1α,3β-dihydroxy-9,10-secopregna-5,7,10(19),16-tetraene The mixture from Example 9(2) (25.6 mg) was treated in tetrahydrofuran (2.5 ml) with a 1M tetrahydrofuran solution of tetra-n-butylammonium fluoride (0.35 ml, 0.35 mmol) in the same manner as shown in Example 4(2) (at an external temperature of 47.5° C. for 4 hours) and then worked up. The resulting residue was purified by preparative thin layer chromatography (0.5 mm×1 plate, dichloromethane:ethanol=15:1, developed four times; 0.25 mm×1 plate, hexane:ethyl acetate:ethanol=10:5:1, developed three times; and then 0.25 mm×1 plate, dichloromethane:ethyl acetate=3:1, developed three times) to give the titled compound (3.169 mg, 4% for 2 steps) as a colorless oil.

IR(neat): 3400, 2932, 1744, 1162, 1124, 1056, 732 cm$^{-1}$. $^1$H NMR δ: 0.76 (s, 3H), 1.37 (d, J=6.4 Hz, 3H), 1.47 (s, 9H), 2.41-2.54 (m, 1H), 2.54-2.69 (m, 1H), 2.76-2.91 (m, 1H), 3.85 (d, J=16.3 Hz, 1H), 3.95 (d, J=16.3 Hz, 1H), 4.12 (q, J=6.6 Hz, 1H), 4.17-4.31 (m, 1H), 4.39-4.52 (m, 1H), 5.01 (s, 1H), 5.34 (s, 1H), 5.64 (brs, 1H), 6.10 (d, J=11.3 Hz, 1H), 6.37 (d, J=11.3 Hz, 1H). MS m/z: 312 (M$^+$-HOCH$_2$C(O)OC(CH$_3$)$_3$), 57 (100%). UV λ$_{max}$nm: 263.

Example 10

(1) Preparation of 1α,3β-bis(tert-butyldimethylsilyloxy)-17-(tert-butoxycarbonylmethoxymethyl)androsta-5,7,16-triene A solution of 1α,3β-bis(tert-butyldimethylsilyloxy)-17-(hydroxymethyl)androsta-5,7,16-triene (1.0 g, 1.84 mmol), sodium hydride (60% in oil, 220 mg, 5.50 mmol), 15-crown-5 (400 mg, 1.82 mmol) and t-butyl bromoacetate (0.55 ml, 3.69 mmol) in tetrahydrofuran (20 ml) was stirred at an external temperature of 88° C. for 1 hour and 15 minutes. The reaction mixture was diluted with ethyl acetate and filtered through CELITE. Water was added dropwise to the filtrate under ice cooling, followed by washing with saturated aqueous sodium chloride. The organic layer was dried over anhydrous magnesium sulfate. After evaporation under reduced pressure to remove the solvent, the resulting residue was purified by column chromatography (hexane:ethyl acetate=20:1) to give the titled compound (946.6 mg, 78%) as a colorless oil.

IR(neat): 2952, 2928, 2892, 2856, 1748, 1460, 1370, 1252, 1098, 968, 834, 774 cm$^{-1}$. $^1$H NMR δ: 0.05 (s, 3H), 0.06 (s, 6H), 0.11 (s, 3H), 0.84 (s, 3H), 0.88 (s, 18H), 0.94 (s, 3H), 1.48 (s, 9H), 2.79-2.92 (m, 1H), 3.70 (brs, 1H), 3.95 (s, 2H), 4.13 (s, 2H), 3.97-4.20 (m, 1H), 5.35-5.43 (m, 1H), 5.60 (d, J=5.4 Hz, 1H), 5.69 (s, 1H). MS m/z: 526 (M$^+$-HOCH$_2$CO$_2$C(CH$_3$)$_3$), 57 (100%). UV λ$_{max}$nm: 271, 281, 294.

(2) Preparation of 1α,3β-bis(tert-butyldimethylsilyloxy)-17-(tert-butoxycarbonylmethoxymethyl)-9,10-secoandrosta-5,7,10(19),16-tetraene 1α,3β-Bis(tert-butyldimethylsilyloxy)-17-(tert-butoxycarbonylmethoxymethyl)androsta-5,7,16-triene (168 mg, 0.255 mmol) was treated in ethanol (200 ml) in the same manner as shown in Example 4(3) (irradiated with light for 10 minutes, heated at reflux for 1.5 hours), followed by purification using preparative thin layer chromatography (0.5 mm×3 plates, hexane:ethyl acetate=15:1, developed twice) to give a mixture (35.8 mg) containing the titled compound.

(3) Preparation of 1α,3β-dihydroxy-17-(tert-butoxycarbonylmethoxymethyl)-9,10-secoandrosta-5,7,10(19),16-tetraene The mixture from Example 10(1) (35.8 mg) was treated in tetrahydrofuran (1 ml) with a 1M tetrahydrofuran solution of tetra-n-butylammonium fluoride (0.35 ml, 0.35 mmol) in the same manner as shown in Example 4(2) (at an external temperature of 45° C. for 2 hours) and then worked up. The resulting residue was purified by preparative thin layer chromatography (0.5 mm×1 plate, dichloromethane:ethanol=15:1, developed once; 0.25 mm×1 plate, hexane:ethyl acetate:ethanol=10:5:1, developed three times; 0.25 mm×1 plate, dichloromethane:ethanol=20:1, developed twice and dichloromethane:ethanol=15:1, developed twice; and then 0.25 mm×1 plate, dichloromethane:ethyl acetate=3:1, developed twice) to give the titled compound (0.649 mg, 0.6% for 2 steps) as a colorless oil.

IR(neat): 3352, 2928, 1744, 1452, 1368, 1226, 1162, 1130, 1056 cm$^{-1}$. $^1$H NMR δ: 0.74 (s, 3H), 1.48 (s, 9H), 2.53-2.67 (m, 1H), 2.75-2.89 (m, 1H), 3.95 (s, 2H), 4.12 (brs, 2H), 4.17-4.30 (m, 1H), 4.39-4.50 (m, 1H), 5.01 (s, 1H), 5.33 (s, 1H), 5.65 (s, 1H), 6.09 (d, J=11.5 Hz, 1H), 6.37 (d, J=11.5 Hz, 1H). MS m/z: 430 (M$^+$), 57 (100%). UV λ$_{max}$nm: 263.

Example 11

(1) Preparation of 1α,3β-bis(tert-butyldimethylsilyloxy)-20(S)-hydroxy-9,10-secopregna-5,7,10(19),16-tetraene 1α,3β-Bis(tert-butyldimethylsilyloxy)-20(S)-hydroxypregna-5,7,16-triene (1.0 g, 1.79 mmol) was treated in ethanol (270 ml) in the same manner as shown in Example 4 (3) (irradiated with light for 1 hour, heated at reflux for 2 hours), followed by separation using column chromatography (hexane:dichloromethane:ethyl acetate=9:1:0.5) to give a fraction containing the desired product as a colorless foam (250 mg).

(2) Preparation of 1α,3β-dihydroxy-20(S)-(tert-butoxycarbonylethoxy)-9,10-secopregna-5,7,10(19),16-tetraene The fraction containing 1α,3β-bis(tert-butyldimethylsilyloxy)-20(S)-hydroxy-9,10-secopregna-5,7,10(19),16-tetraene from Example 11(1) (40 mg) was treated with sodium hydride (60% in oil, 4.5 mg, 0.11 mmol), tetrahydrofuran (0.7 ml) and t-butyl acrylate (55 mg, 0.43 mmol) under the same conditions as shown in Example 4(1), followed by work up and separation using preparative thin layer chromatography (0.5 mm×3 plates, hexane:dichloromethane:ethanol=9:1:0.5) to give a colorless oily fraction (42 mg) containing the desired product. The fraction (42 mg) was further treated in tetrahydrofuran (2.4 ml) with a 1M tetrahydrofuran solution of tetra-n-butylammonium fluoride (0.6 ml) in the same manner as shown in Example 4(2) (for 1.5 hours), followed by work up and purification using preparative thin layer chromatography (0.5 mm×2 plates, dichloromethane:ethanol=20:1, developed twice; 0.5 mm×1 plate, hexane:ethyl acetate:ethanol=10:5:1, developed four times; and then 0.5 mm×1 plate, dichloromethane:ethyl acetate=1:3, developed four times) to give the titled compound (3.276 mg, 1.22% for 3 steps) as a colorless oil.

IR(neat): 3383, 2976, 2931, 2869, 2850, 1732, 1448, 1367, 1255, 1159, 1105, 1054 cm$^{-1}$. $^1$H NMR δ: 0.78 (s, 3H), 1.28 (d, J=6.6 Hz, 3H), 1.45 (s, 9H), 2.46 (t, J=6.6 Hz, 2H), 2.56-2.65 (m, 1H), 2.76-2.87 (m, 1H), 3.45-3.57 (m, 1H), 3.60-3.72 (m, 1H), 3.92 (q, J=6.6 Hz, 1H), 4.18-4.31 (m, 1H), 4.39-4.50 (m, 1H), 5.01 (brs, 1H), 5.34 (brs, 1H), 5.57 (brs, 1H), 6.10 (d, J=11.2 Hz, 1H), 6.37 (d, J=11.2 Hz, 1H). MS m/z: 458 (M$^+$), 57 (100%). UV λ$_{max}$nm: 263.

Example 12

Preparation of 1α,3β-dihydroxy-20(R)-(N,N-dimethylaminocarbonylethoxy)-9,10-secopregna-5,7,10(19)-triene 1α,3β-Bis(tert-butyldimethylsilyloxy)-20(R)-hydroxypregna-5,7-diene (100 mg, 0.18 mmol) was treated in ethanol (200 ml) in the same manner as shown in Example 4 (3) (irradiated with light for 5 minutes and 45 seconds, heated at reflux for 2 hours), followed by separation using preparative thin layer chromatography (0.5 mm×3 plates, hexane:ethyl acetate=5:1) to give a yellow oily fraction containing the desired product (18 mg). The fraction was then treated with N,N-dimethylacrylamide (9.8 mg, 0.099 mol) and sodium hydride (60% in oil, 2 mg, 0.047 mmol) in tetrahydrofuran (0.32 ml) in the same manner as shown in Example 4(1) (at 0° C. for 2 hours and then at room temperature for 24 hours), followed by work up and separation using preparative thin layer chromatography (0.5 mm×2 plates, ethyl acetate) to give a colorless oily fraction containing the desired product (11 mg). These fraction (11 mg) was further treated in tetrahydrofuran (2 ml) and methanol (2 ml) with AMBERLYST 15 (1.3 g) in the same manner as shown in Example 6(3) (at room temperature for 5 hours), followed by work up and purification using preparative thin layer chromatography (0.25 mm×1 plate, dichloromethane:ethanol=10:1, developed three times and then 0.25 mm×1 plate, toluene:ethyl acetate=1:9, developed five times) to give the titled compound (1.261 mg, 1.62%) as a colorless oil.

IR(neat): 3429, 2925, 2871, 1628, 1103, 1057 cm$^{-1}$. $^1$H NMR δ: 0.55 (s, 3H), 1.09 (t, J=5.9 Hz, 3H), 2.78-2.89 (m, 1H), 2.93 (s, 3H), 3.02 (s, 3H), 3.25-3.37 (m, 1H), 3.54-3.66 (m, 1H), 3.79-3.90 (m, 1H), 4.16-4.29 (m, 1H), 4.38-4.48 (m, 1H), 5.00 (brs, 1H), 5.32 (brs, 1H), 5.99 (d, J=11.2 Hz, 1H), 6.38 (d, J=11.2 Hz, 1H). MS m/z: 431 (M$^+$), 118 (100%). UV λ$_{max}$nm: 264.

Example 13

Preparation of 1α,3β-dihydroxy-20(S)-(N-tert-butyl-N-methylaminocarbonylmethoxy)-9,10-secopregna-5,7,10(19),16-tetraene The fraction containing 1α,3β-bis(tert-butyldimethylsilyloxy)-20(S)-hydroxy-9,10-secopregna-5,7,10(19),16-tetraene from Example 11(1) (100 mg) was treated with sodium hydride (60% in oil, 86 mg, 2.14 mmol), tetrahydrofuran (4.8 ml), 15-crown-5 (80 mg, 0.36 mmol) and N-t-butyl-N-methylbromoacetamide (446 mg, 2.14 mmol) in the same manner as shown in Example 8(1), followed by work up and separation using preparative thin layer chromatography (0.5 mm×4 plates, hexane:ethyl acetate=10:1, developed four times) to give a colorless oil fraction containing the desired product (63 mg). The fraction (63 mg) was further treated in tetrahydrofuran (6.0 ml) with a 1M tetrahydrofuran solution of tetra-n-butylammonium fluoride (1.38 ml) in the same manner as shown in Example 4(2) (for 2 hours), followed by work up and purification using preparative thin layer chromatography (0.5 mm×2 plates, dichloromethane:ethanol=20:1, developed four times and then 0.5 mm×2 plates, hexane:ethyl acetate:ethanol=10:5:1, developed five times) to give the titled compound (10.683 mg, 2.35% for 3 steps) as a colorless oil.

IR(neat): 3390, 2974, 2931, 2850, 1651, 1633, 1446, 1392, 1365, 1211, 1140, 1053 cm$^{-1}$. $^1$H NMR δ: 0.76 (s, 3H), 1.35 (d, J=6.6 Hz, 3H), 1.40 (s, 9H), 2.54-2.67 (m, 1H), 2.87 (s, 3H), 3.89 (d, J=13.9 Hz, 1H), 3.99-4.14 (m, 2H), 4.18-4.31 (m, 1H), 4.40-4.52 (m, 1H), 5.01 (brs, 1H), 5.33 (brs, 1H), 5.60 (brs, 1H), 6.10 (d, J=11.2 Hz, 1H), 6.37 (d, J=11.2 Hz, 1H). MS m/z: 312 (M$^+$-HOCH$_2$CON(Me)t-Bu), 57 (100%). UV λ$_{max}$nm: 264.

Example 14

Preparation of 1α,3β-dihydroxy-20(S)-(N-tert-butylaminocarbonylmethoxy)-9,10-secopregna-5,7,10(19),16-tetraene The fraction containing 1α,3β-bis(tert-butyldimethylsilyloxy)-20(S)-hydroxy-9,10-secopregna-5,7,10(19),16-tetraene from Example 11(1) (100 mg) was treated with sodium hydride (60% in oil, 43 mg, 1.07 mmol), tetrahydrofuran (1.9 ml), N,N-dimethylformamide (80 mg, 1.9 mmol) and N-t-butylbromoacetamide (208 mg, 1.07 mmol) in the same manner as shown in Example 8(1), followed by work up and separation using preparative thin layer chromatography (0.5 mm×4 plates, hexane:ethyl acetate=10:1, developed three times) to give a yellow oily fraction containing the desired product (35 mg). The fraction (35 mg) was further treated in tetrahydrofuran (3.3 ml) with a 1M tetrahydrofuran solution of tetra-n-butylammonium fluoride (0.78 ml) in the same manner as shown in Example 4(2) (for 2 hours), followed by work up and purification using preparative thin layer chromatography (0.5 mm×2 plates, dichloromethane:ethanol=20:1, developed three times and then 0.5 mm×1 plate, hexane:ethyl acetate:ethanol=10:5:1, developed five times) to give the titled compound (5.267 mg, 1.20% for 3 steps) as a colorless oil.

IR(neat): 3400, 3323, 2968, 2931, 2850, 1666, 1531, 1456, 1365, 1227, 1109, 1055 cm$^{-1}$. $^1$H NMR δ: 0.79 (s, 3H), 1.36 (d, J=6.6 Hz, 3H), 1.37 (s, 9H), 2.19-2.47 (m, 3H), 2.55-2.65 (m, 1H), 2.77-2.88 (m, 1H), 3.69 (d, J=15.2 Hz, 1H), 3.81 (d, J=15.2 Hz, 1H), 3.98 (q, J=6.3 Hz, 1H), 4.17-4.33 (m, 1H), 4.40-4.53 (m, 1H), 5.01 (brs, 1H), 5.34 (brs, 1H), 5.60 (brs, 1H), 6.11 (d, J=11.2 Hz, 1H), 6.37 (d, J=11.2 Hz, 1H), 6.44 (brs, 1H). MS m/z: 312 (M$^+$-HOCH$_2$CONHt-Bu), 57 (100%). UV λ$_{max}$nm: 263.

Example 15

Preparation of 1α,3β-dihydroxy-20(S)-(isopropoxycarbonylmethoxy)-9,10-secopregna-5,7,10(19),16-tetraene The fraction containing 1α,3β-bis(tert-butyldimethylsilyloxy)-20(S)-hydroxy-9,10-secopregna-5,7,10(19),16-tetraene from Example 11(1) (100 mg) was treated with sodium hydride (60% in oil, 43 mg, 1.07 mmol), tetrahydrofuran (4.8 ml), 15-crown-5 (80 mg, 0.36 mmol) and isopropyl bromoacetate (388 mg, 2.14 mmol) in the same manner as shown in Example 8(1), followed by work up and separation using preparative thin layer chromatography (0.5 mm×4 plates, hexane:ethyl acetate=10:1) to give a colorless oily fraction containing the desired product (20 mg). The fraction (20 mg) was further treated in tetrahydrofuran (2.0 ml) with a 1M tetrahydrofuran solution of tetra-n-butylammonium fluoride (0.46 ml) in the same manner as shown in Example 4(2) (for 2 hours), followed by work up and purification using preparative thin layer chromatography (0.5 mm×2 plates, dichloromethane:ethanol=20:1, developed twice; 0.5 mm×1 plate, hexane:ethyl acetate:ethanol=10:5:1, developed four times; and then 0.5 mm×1 plate, dichloromethane:ethyl acetate=1:3, developed four times) to give the titled compound (1.386 mg, 0.32% for 3 steps) as a colorless oil.

IR(neat): 3386, 2978, 2931, 2850, 1747, 1444, 1373, 1286, 1207, 1126, 1105, 1052 cm$^{-1}$. $^1$H NMR δ: 0.78 (s, 3H), 1.25 (d, J=6.3 Hz, 6H), 1.37 (d, J=6.6 Hz, 3H), 2.55-2.66 (m, 1H), 2.77-2.87 (m, 1H), 3.89 (d, J=16.5 Hz, 1H), 4.02 (d, J=16.2 Hz, 1H), 4.07 (q, J=6.3 Hz, 1H), 4.19-4.30 (m, 1H), 4.40-4.50 (m, 1H), 5.01 (brs, 1H), 5.03-5.15 (m, 1H), 5.34 (brs, 1H), 5.61 (brs, 1H), 6.10 (d, J=11.2 Hz, 1H), 6.37 (d, J=11.2 Hz, 1H). MS m/z: 430 (M$^+$), 133 (100%). UV λ$_{max}$nm: 264.

Example 16

(1) Preparation of 17-acetylthiomethyl-1α,3β-dihydroxy-9,10-secoandrosta-5,7,10(19),16-tetraene 1α,3β-Bis(tert-butyldimethylsilyloxy)-17-(hydroxymethyl)androsta-5,7,16-triene (750 mg, 1.38 mmol) was treated in ethanol (600 ml) in the same manner as shown in Example 4(3) (irradiated with light for 30 minutes, heated at reflux for 2 hours), followed by purification using column chromatography (hexane:ethyl acetate=10:1) to give a fraction containing the titled compound (550 mg). The fraction was then treated with methanesulfonyl chloride (0.23 ml, 2.97 mmol) and triethylamine (0.56 ml, 4.02 mmol) in tetrahydrofuran (5 ml) and with potassium thioacetate (0.457 g, 4.00 mmol) in dimethyl sulfoxide (5 ml) in the same manner as shown in Example 1(3) (mesylated for 15 minutes, thioacetylated for 30 minutes), followed by work up and purification using preparative thin layer chromatography (1.0 mm×7 plates, hexane:ethyl acetate=10:1, developed once) to give a fraction containing the titled compound (430 mg). The fraction was further treated in tetrahydrofuran (40 ml) and methanol (40 ml) with AMBERLYST 15 (18 g) in the same manner as shown in Example 6 (3), followed by work up and purification using preparative thin layer chromatography (1.0 mm×7 plates, hexane:ethyl acetate:ethanol=5:5:1, developed once) to give the titled compound (30 mg) as a colorless oil.

$^1$H NMR δ: 0.72 (s, 3H), 2.33 (s, 3H), 3.50-3.68 (m, 2H), 4.10 (brs, 1H), 4.43 (brs, 1H), 5.00 (s, 1H), 5.33 (s, 1H), 5.57 (s, 1H), 6.10 (d, J=11.2 Hz, 1H), 6.34 (d, J=11.2 Hz, 1H).

(2) Preparation of 17-(tert-butoxycarbonylmethylthiomethyl)-1α,3β-dihydroxy-9,10-secoandrosta-5,7,10(19),16-tetraene To a solution of 17-acetylthiomethyl-1α,3β-dihydroxy-9,10-secoandrosta-5,7,10(19),16-tetraene (10 mg, 0.0267 mmol) in tetrahydrofuran (0.5 ml), t-butyl bromoacetate (10 mg, 0.0513 mmol) was added under a nitrogen atmosphere and stirred at room temperature for 5 minutes. A 1M methanol solution of potassium hydroxide (0.5 ml) was added and further stirred at room temperature for 14 hours. The reaction mixture was diluted with ethyl acetate, washed with water and saturated aqueous sodium chloride, and then dried over anhydrous sodium sulfate. After evaporation under reduced pressure to remove the solvent, the residue was purified by preparative thin layer chromatography (0.25 mm×1 plate, ethyl acetate:toluene=1:1, developed twice) to give the titled compound (0.479 mg, 4%) as a colorless oil.

IR(neat): 2924, 2848, 1722, 1564, 1367, 1294, 1259, 1124, 1053 cm$^{-1}$. $^1$H NMR δ: 0.76 (s, 3H), 1.48 (s, 9H), 3.08 (s, 2H), 3.28-3.31 (m, 2H), 4.22 (brs, 1H), 4.46 (brs, 1H), 5.01 (s, 1H), 5.34 (s, 1H), 5.59 (s, 1H), 6.10 (d, J=10.9 Hz, 1H), 6.37 (d, J=10.9 Hz, 1H). MS m/z: 389 (M$^+$-(CH$_3$)$_3$C), 57 (100%). UV λ$_{max}$nm: 264.

Example 17

(1) Preparation of 1α,3β-bis(tert-butyldimethylsilyloxy)-20(S)-(tert-butoxycarbonylmethoxy)-9,10-secopregna-5,7,10(19),16-tetraene To a solution of 1α,3β-bis(tert-butyldimethylsilyloxy)-20(S)-hydroxy-9,10-secopregna-5,7,10(19),16-tetraene (848 mg, 1.52 mmol) in tetrahydrofuran (25 ml), sodium hydride (60% in oil, 374 mg, 9.34 mmol) was added and stirred at room temperature for 15 minutes under a nitrogen stream. A solution of 15-crown-5 (335 mg, 1.52 mmol) and tert-butyl bromoacetate (1.82 g, 9.34 mmol) in tetrahydrofuran (8 ml) was further added dropwise, followed by heating at reflux for 4 hours and 30 minutes. The reaction mixture was poured into water, extracted with ethyl acetate, washed sequentially with saturated aqueous ammonium chloride, saturated aqueous sodium bicarbonate and saturated aqueous sodium chloride, and then dried over anhydrous magnesium sulfate. After evaporation under reduced pressure to remove the solvent, the resulting residue was purified by column chromatography (n-hexane:ethyl acetate=20:1) to give a mixture (1.47 g) containing the titled compound as a colorless oil.

(2) Preparation of [{1α,3β-bis(tert-butyldimethylsilyloxy)-9,10-secopregna-5,7,10(19),16-tetraen-20(S)-yl}oxy]acetic Acid The mixture containing 1α,3β-bis(tert-butyldimethylsilyloxy)-20(S)-(tert-butoxycarbonylmethoxy)-9,10-secopregna-5,7,10(19),16-tetraene from Example 17(1) (1.47 g) was dissolved in tetrahydrofuran (30.0 ml). A 1M methanol solution of sodium methoxide (11 ml) was added to this solution and stirred at room temperature for 30 minutes. A 1M aqueous sodium hydroxide (11 ml) was further added and stirred at room temperature for 30 minutes. The reaction mixture was diluted with dichloromethane, poured into saturated aqueous sodium dihydrogenphosphate, extracted with dichloromethane, and then dried over anhydrous magnesium sulfate. After evaporation under reduced pressure to remove the solvent, the resulting residue was purified by column chromatography (dichloromethane:ethanol=20:1) to give the titled compound (651 mg, 69% for 2 steps) as a colorless oil.

IR(neat): 3300-2500, 2952, 2929, 2886, 2856, 1727, 1471, 1461, 1369, 1253, 1083, 1078 cm$^{-1}$. $^1$H NMR δ: 0.04-0.09 (m, 12H), 0.78 (s, 3H), 0.88 (s, 18H), 1.40 (d, J=6.4 Hz, 3H), 2.78-2.88 (m, 1H), 3.93 (d, J=16.3 Hz, 1H), 4.01-4.25 (m, 3H), 4.34-4.43 (m, 1H), 4.87 (d, J=2.1 Hz, 1H), 5.20 (d, J=1.7 Hz, 1H), 5.64 (brs, 1H), 6.10 (d, J=11.4 Hz, 1H), 6.23 (d, J=11.2 Hz, 1H). MS m/z: 616 (M$^+$−1), 73 (100%). UV λ$_{max}$nm: 264.

(3) Preparation of 1α,3β-bis(tert-butyldimethylsilyloxy)-20(S)-(1-ethyl-1-methylpropoxycarbonylmethoxy)-9,10-secopregna-5,7,10(19),16-tetraene To a solution of [{1α,3β-bis(tert-butyldimethylsilyloxy)-9,10-secopregna-5,7,10(19),16-tetraen-20(S)-yl}oxy]acetic acid (326 mg, 0.53 mmol) in tetrahydrofuran (5.3 ml), 3-methyl-3-pentanol (87 mg, 0.85 mmol), N,N'-dicyclohexylcarbodiimide (175 mg, 0.85 mmol) and 4-(dimethylamino)pyridine (65 mg, 0.53 mmol) were added and stirred at room temperature for 17 hours under a nitrogen stream. The reaction mixture was poured into water and extracted with ethyl acetate. The organic layer was dried over anhydrous magnesium sulfate. After evaporation under reduced pressure to remove the solvent, the resulting residue was purified by column chromatography (hexane:ethyl acetate=20:1) to give a mixture (319 mg) containing the titled compound as a colorless oil.

(4) Preparation of 1α,3β-dihydroxy-20(S)-(1-ethyl-1-methylpropoxycarbonylmethoxy)-9,10-secopregna-5,7,10(19),16-tetraene The mixture containing 1α,3β-bis(tert-butyldimethylsilyloxy)-20(S)-(1-ethyl-1-methylpropoxycarbonylmethoxy)-9,10-secopregna-5,7,10(19),16-tetraene from Example 17(3) (319 mg) was dissolved in tetrahydrofuran (10 ml). A 1M tetrahydrofuran solution of tetra-n-butylammonium fluoride (4.55 ml) was added to this solution and stirred at 50° C. for 2 hours under a nitrogen stream. The reaction mixture was poured into water, extracted with ethyl acetate, and then washed sequentially with saturated aqueous ammonium chloride, saturated aqueous sodium bicarbonate and saturated aqueous sodium chloride. The organic layer was dried over anhydrous magnesium sulfate. After evaporation under reduced pressure to remove the solvent, the resulting residue was purified by column chromatography (dichloromethane:ethanol=20:1) and then preparative thin layer chromatography (0.5 mm×3 plates, dichloromethane:ethanol=20:1, developed three times) to give the titled compound (125.3 mg, 50% for 2 steps) as a colorless oil.

IR(neat): 3400, 2973, 2931, 2883, 2850, 1745, 1727, 1459, 1373, 1218, 1122, 1052 cm$^{-1}$. $^1$H NMR δ: 0.77 (s, 3H), 0.85 (t, J=7.6 Hz, 6H), 1.36 (d, J=6.6 Hz, 3H), 2.56-2.66 (m, 1H), 2.77-2.87 (m, 1H), 3.84 (d, J=16.5 Hz, 1H), 3.96 (d, J=16.3 Hz, 1H), 4.08 (q, J=6.4 Hz, 1H), 4.19-4.29 (m, 1H), 4.40-4.49 (m, 1H), 5.01 (brs, 1H), 5.34 (brs, 1H), 5.59 (brs, 1H), 6.11 (d, J=11.4 Hz, 1H), 6.37 (d, J=11.1 Hz, 1H). MS m/z: 472 (M$^+$), 85 (100%). UV λ$_{max}$nm: 263.

Example 18

(1) Preparation of 1α,3β-bis(tert-butyldimethylsilyloxy)-20(S)-(1,1-dimethylbutoxycarbonylmethoxy)-9,10-secopregna-5,7,10(19),16-tetraene

[{1α,3β-Bis(tert-butyldimethylsilyloxy)-9,10-secopregna-5,7,10(19),16-tetraen-20(S)-yl}oxy]acetic acid (26 mg, 0.042 mmol) was treated with 2-methyl-2-pentanol (0.1 ml, 1.208 mmol), N,N'-dicyclohexylcarbodiimide (14 mg, 0.067 mmol) and 4-(dimethylamino)pyridine (5 mg, 0.042 mmol) in tetrahydrofuran (1.0 ml) in the same manner as shown in Example 17(3) (at room temperature for 18 hours), followed by work up and purification using preparative thin layer chromatography (0.5 mm×1 plate, hexane:ethyl acetate=6:1, developed once) to give a mixture (20 mg) containing the titled compound.

(2) Preparation of 1α,3β-dihydroxy-20(S)-(1,1-dimethylbutoxycarbonylmethoxy)-9,10-secopregna-5,7,10(19),16-tetraene The mixture containing 1α,3β-bis(tert-butyldimethylsilyloxy)-20(S)-(1,1-dimethylbutoxycarbonylmethoxy)-9,10-secopregna-5,7,10(19),16-tetraene from Example 18(1) (20 mg) was treated with a 1M tetrahydrofuran solution of tetra-n-butylammonium fluoride (1.0 ml) in tetrahydrofuran (1.0 ml) in the same manner as shown in Example 17(4) (at an external temperature of 45° C. for 1 hour), followed by work up and purification using preparative thin layer chromatography (0.5 mm×1 plate, hexane:ethyl acetate:ethanol=10:10:1, developed twice) to give the titled compound (2.724 mg, 14% for 2 steps) as a colorless oil.

IR(neat): 2929, 2852, 1747, 1635, 1455, 1369, 1218, 1122, 1052 cm$^{-1}$. $^1$H NMR δ: 0.77 (s, 3H), 0.91 (t, J=7.0 Hz, 3H), 1.36 (d, J=6.2 Hz, 3H), 2.56-2.66 (m, 1H), 2.77-2.89 (m, 1H), 3.82 (d, J=16.5 Hz, 1H), 3.93 (d, J=16.5 Hz, 1H), 4.08 (q, J=6.2 Hz, 1H), 4.19-4.30 (m, 1H), 4.40-4.93 (m, 1H), 5.01 (s, 1H), 5.34 (s, 1H), 5.60 (s, 1H), 6.11 (d, J=11.3 Hz, 1H), 6.37 (d, J=11.3 Hz, 1H). MS(ESI) m/z: 495 (M$^+$+Na). UV λ$_{max}$nm: 263.

Example 19

(1) Preparation of 1α,3β-bis(tert-butyldimethylsilyloxy)-20(S)-(1,1-dimethylhexyloxycarbonylmethoxy)-9,10-secopregna-5,7,10(19),16-tetraene

[{1α,3β-Bis(tert-butyldimethylsilyloxy)-9,10-secopregna-5,7,10(19),16-tetraen-20(S)-yl}oxy]acetic acid (50.7 mg, 0.0822 mmol) was treated with 2-methyl-2-heptanol (0.1 ml, 0.936 mmol), N,N'-dicyclohexylcarbodiimide (27 mg, 0.131 mmol) and 4-(dimethylamino)pyridine (0.01 g, 0.0822 mmol) in dichloromethane (1.0 ml) in the same manner as shown in Example 17(3) (at room temperature for 18 hours), followed by work up and purification using preparative thin layer chromatography (0.5 mm×2 plates, hexane:ethyl acetate=6:1, developed twice) to give a mixture (30 mg) containing the titled compound.

(2) Preparation of 1α,3β-dihydroxy-20(S)-(1,1-dimethylhexyloxycarbonylmethoxy)-9,10-secopregna-5,7,10(19),16-tetraene The mixture containing 1α,3β-bis(tert-butyldimethylsilyloxy)-20(S)-(1,1-dimethylhexyloxycarbonylmethoxy)-9,10-secopregna-5,7,10(19),16-tetraene from Example 19(1) (30 mg) was treated with a 1M tetrahydrofuran solution of tetra-n-butylammonium fluoride (1.0 ml) in tetrahydrofuran (1.0 ml) in the same manner as shown in Example 17(4) (at an external temperature of 50° C. for 1 hour), followed by work up and purification using preparative thin layer chromatography (0.5 mm×2 plates, hexane:ethyl acetate:ethanol=5:5:1, developed twice) to give the titled compound (7.414 mg, 18% for 2 steps) as a colorless oil.

IR(neat): 2929, 2852, 1745, 1727, 1625, 1562, 1450, 1369, 1122, 1052 cm$^{-1}$. $^1$H NMR δ: 0.77 (s, 3H), 0.88 (t, J=7.0 Hz, 3H), 1.36 (d, J=6.5 Hz, 3H), 2.56-2.65 (m, 1H), 2.77-2.87 (m, 1H), 3.82 (d, J=16.5 Hz, 1H), 3.92 (d, J=16.5 Hz, 1H), 4.07 (q, J=6.5 Hz, 1H), 4.21-4.29 (m, 1H), 4.40-4.49 (m, 1H), 5.01 (s, 1H), 5.34 (s, 1H), 5.59 (s, 1H), 6.11 (d, J=11.3 Hz, 1H), 6.37 (d, J=11.3 Hz, 1H). MS m/z: 482 (M$^+$-H$_2$O), 57 (100%). UV λ$_{max}$nm: 264.

Example 20

(1) Preparation of 1-ethyl-1-methylpropyl Acrylate

To a solution of acryloyl chloride (5.0 g, 55.2 mmol) and 3-methyl-3-pentanol (7.6 ml, 60.8 mmol) in dichloromethane, triethylamine (23 ml, 166 mmol) was added at room temperature under a nitrogen atmosphere. After stirring at room temperature for 14 hours, the reaction mixture was diluted with dichloromethane and washed with water and saturated aqueous sodium chloride. The organic layer was dried over anhydrous sodium sulfate. After evaporation under reduced pressure to remove the solvent, the resulting residue was purified by column chromatography (hexane:ethyl acetate=10:1) to give the titled compound (5.45 g, 63%) as a colorless oil.

$^1$H NMR δ: 0.82 (t, J=7.6 Hz, 6H), 1.37 (s, 3H), 1.66-1.96 (m, 4H), 5.66 (dd, J=10.3, 1.7 Hz, 1H), 6.00 (dd, J=17.3, 10.3 Hz, 1H), 6.24 (dd, J=17.3, 1.7 Hz, 1H).

(2) Preparation of 1α,3β-bis(tert-butyldimethylsilyloxy)-20(S)-{2-(1-ethyl-1-methylpropoxycarbonyl)ethoxy}-9,10-secopregna-5,7,10(19),16-tetraene To a solution of 1α,3β-bis(tert-butyldimethylsilyloxy)-20(S)-hydroxy-9,10-secopregna-5,7,10(19),16-tetraene (50 mg, 0.0894 mmol) and 1-ethyl-1-methylpropyl acrylate (0.1 g, 0.640 mmol) in tetrahydrofuran (1.0 ml), sodium hydride (60% in oil, 3.4 mg, 0.085 mmol) was added at 0° C. under a nitrogen atmosphere. After stirring at 5° C. for 18 hours, the reaction mixture was diluted with ethyl acetate and washed with saturated aqueous ammonium chloride and water. The organic layer was dried over anhydrous sodium sulfate. After evaporation under reduced pressure to remove the solvent, the resulting residue was purified by preparative thin layer chromatography (0.5 mm×2 plates, hexane:ethyl acetate=10:1, developed once) to give a mixture (77.3 mg) containing the titled compound.

(3) Preparation of 1α,3β-dihydroxy-20(S)-{2-(1-ethyl-1-methylpropoxycarbonyl)ethoxy}-9,10-secopregna-5,7,10(19),16-tetraene The mixture containing 1α,3β-bis(tert-butyldimethylsilyloxy)-20(S)-{2-(1-ethyl-1-methylpropoxycarbonyl)ethoxy}-9,10-secopregna-5,7,10(19),16-tetraene from Example 20(2) (77.3 mg) was treated with a 1M tetrahydrofuran solution of tetra-n-butylammonium fluoride (1.0 ml) in tetrahydrofuran (1.0 ml) in the same manner as shown in Example 17(4) (at an external temperature of 50° C. for 1 hour), followed by work up and purification using preparative thin layer chromatography (0.5 mm×4 plates, hexane:ethyl acetate:ethanol=5:5:1, developed twice) to give the titled compound (15.8 mg, 36% for 2 steps) as a colorless oil.

IR(neat): 2973, 2931, 2881, 2850, 1727, 1461, 1444, 1367, 1263, 1195, 1056 cm$^{-1}$. $^1$H NMR δ: 0.77 (s, 3H), 0.85 (t, J=7.6 Hz, 6H), 1.28 (d, J=6.5 Hz, 3H), 1.37 (s, 3H), 2.48 (t, J=6.8 Hz, 2H), 2.55-2.66 (m, 1H), 2.76-2.88 (m, 1H), 3.44-3.56 (m, 1H), 3.57-3.71 (m, 1H), 3.92 (q, J=6.5 Hz, 1H), 4.19-4.28 (m, 1H), 4.40-4.49 (m, 1H), 5.01 (s, 1H), 5.34 (s, 1H), 5.57 (s, 1H), 6.10 (d, J=11.3 Hz, 1H), 6.37 (d, J=11.3 Hz, 1H). MS m/z: 486 (M$^+$), 312 (100%). UV λ$_{max}$nm: 264.

Example 21

(1) Preparation of 1α,3β-bis(tert-butyldimethylsilyloxy)-20(S)-(1-isopropyl-2-methylpropoxycarbonylmethoxy)-9,10-secopregna-5,7,10(19),16-tetraene

[{1α,3β-Bis(tert-butyldimethylsilyloxy)-9,10-secopregna-5,7,10(19),16-tetraen-20(S)-yl}oxy]acetic acid (30 mg, 0.049 mmol), 2,4-dimethyl-3-pentanol (17 mg, 0.15 mmol), 1-ethyl-3-(3-dimethylaminopropyl)carbodiimide hydrochloride (19 mg, 0.099 mmol), 4-(dimethylamino)pyridine (18 mg, 0.15 mmol) and dichloromethane (1 ml) were mixed and stirred overnight at room temperature, followed by separation using preparative thin layer chromatography (0.5 mm×2 plates, hexane:ethyl acetate=5:1, developed once) to give a mixture (22 mg) containing the desired product as a colorless foam.

(2) Preparation of 1α,3β-dihydroxy-20(S)-(1-isopropyl-2-methylpropoxycarbonylmethoxy)-9,10-secopregna-5,7,10(19),16-tetraene The mixture containing 1α,3β-bis(tert-butyldimethylsilyloxy)-20(S)-(1-isopropyl-2-methylpropoxycarbonylmethoxy)-9,10-secopregna-5,7,10(19),16-tetraene from Example 21(1) (22 mg, 0.031 mmol) was treated in tetrahydrofuran (0.62 ml) with a 1M tetrahydrofuran solution of tetra-n-butylammonium fluoride (0.31 ml) in the same manner as shown in Example 17(4) (at an external temperature of 50° C. for 2 hours), followed by work up and purification using preparative thin layer chromatography (0.5 mm×2 plates, hexane:ethyl acetate:ethanol=10:10:1, developed twice) to give the titled compound (9.336 mg, 39% for 2 steps) as a colorless glass.

IR(neat): 3370, 2966, 2933, 2877, 2850, 1751, 1464, 1203, 1122, 1053 cm$^{-1}$. $^1$H NMR δ: 0.78 (s, 3H), 0.83-0.91 (m, 12H), 1.38 (d, J=6.4 Hz, 3H), 2.56-2.65 (m, 1H), 2.77-2.87 (m, 1H), 3.98 (d, J=16.7 Hz, 1H), 4.08 (d, J=16.7 Hz, 1H), 4.04-4.16 (m, 1H), 4.18-4.36 (br, 1H), 4.40-4.50 (br, 1H), 4.67 (t, J=6.3 Hz, 1H), 5.01 (brs, 1H), 5.34 (s, 1H), 5.61 (brs, 1H), 6.11 (d, J=11.4 Hz, 1H), 6.37 (d, J=11.4 Hz, 1H). MS m/z: 312 (M$^+$-HOCH$_2$CO$_2$CH(i-Pr)$_2$), 57 (100%). UV $\lambda_{max}$nm: 264.

Example 22

(1) Preparation of [{1α,3β-bis(tert-butyldimethylsilyloxy)-9,10-secopregna-5,7,10(19),16-tetraen-20(S)-yl}oxy]-N-(2,2,3,3,3-pentafluoropropyl)acetamide

[{1α,3β-Bis(tert-butyldimethylsilyloxy)-9,10-secopregna-5,7,10(19),16-tetraen-20(S)-yl}oxy]acetic acid (34.1 mg, 0.055 mmol), 2,2,3,3,3-pentafluoropropylamine (41 mg, 0.28 mmol), 1-ethyl-3-(3-dimethylaminopropyl)carbodiimide hydrochloride (21 mg, 0.11 mmol), 1-hydroxybenzotriazole monohydrate (8 mg, 0.052 mmol) and dichloromethane (0.55 ml) were mixed and stirred overnight at room temperature, followed by separation using preparative thin layer chromatography (0.5 mm×1 plate, hexane:ethyl acetate=5:1, developed once) to give (29 mg) a mixture containing the desired product as a colorless foam.

(2) Preparation of {(1α,3β-dihydroxy-9,10-secopregna-5,7,10(19),16-tetraen-20(S)-yl)oxy}-N-(2,2,3,3,3-pentafluoropropyl)acetamide The mixture containing [{1α,3β-bis(tert-butyldimethylsilyloxy)-9,10-secopregna-5,7,10(19),16-tetraen-20(S)-yl}oxy]-N-(2,2,3,3,3-pentafluoropropyl)acetamide from Example 22(1) (29 mg, 0.039 mmol) was treated in tetrahydrofuran (0.78 ml) with a 1M tetrahydrofuran solution of tetra-n-butylammonium fluoride (0.39 ml) in the same manner as shown in Example 17(4) (at an external temperature of 50° C. for 1.5 hours), followed by work up and purification using preparative thin layer chromatography (0.5 mm×2 plates, hexane:ethyl acetate:ethanol=10:10:1, developed once and then 0.5 mm×2 plates, dichloromethane:acetonitrile=1:1, developed once) to give the titled compound (9.603 mg, 33% for 2 steps) as a colorless foam.

IR(neat): 3419, 3357, 2927, 2852, 1684, 1533, 1437, 1346, 1198, 1155, 1115, 1053, 1028 cm$^{-1}$. $^1$H NMR δ: 0.79 (s, 3H), 1.36 (d, J=6.6 Hz, 3H), 2.55-2.65 (m, 1H), 2.77-2.87 (m, 1H), 3.86 (d, J=15.5 Hz, 1H), 4.02 (d, J=15.5 Hz, 1H), 3.91-4.09 (m, 3H), 4.19-4.30 (m, 1H), 4.41-4.49 (m, 1H), 5.01 (brs, 1H), 5.34 (s, 1H), 5.61 (brs, 1H), 6.11 (d, J=11.2 Hz, 1H), 6.36 (d, J=11.2 Hz, 1H), 6.85-6.97 (m, 1H). MS m/z: 519 (M$^+$), 91 (100%). UV $\lambda_{max}$nm: 264.

Example 23

(1) Preparation of 1-ethyl-1-methylpropyl Bromoacetate

To a solution of 3-methyl-3-pentanol (10.6 g, 103 mmol) in dichloromethane (49 ml), N,N-dimethylaniline (15.0 g, 124 mmol) and bromoacetyl bromide (25.0 g, 124 mmol) were added and stirred at room temperature for 2 hours under a nitrogen stream. The reaction mixture was poured into water, extracted with tert-butyl methyl ether, washed sequentially with saturated aqueous potassium bisulfate and saturated aqueous sodium bicarbonate, and then dried over sodium sulfate. After evaporation under reduced pressure to remove the solvent, the resulting residue was purified by vacuum distillation (5 mmHg, 71° C. to 72° C.) to give the titled compound (20.4 g, 89%) as a colorless oil.

IR(neat): 2975, 2942, 2883, 1731, 1461, 1382, 1290, 1180, 1133, 1108 cm$^{-1}$. $^1$H NMR δ: 0.88 (t, J=7.5 Hz, 6H), 1.41 (s, 3H), 1.70-1.99 (m, 4H), 3.76 (s, 2H).

(2) Preparation of 1α,3β-bis(tert-butyldimethylsilyloxy)-20(S)-(1-ethyl-1-methylpropoxycarbonylmethoxy)pregna-5,7-diene To a solution of 1α,3β-bis(tert-butyldimethylsilyloxy)-20(S)-hydroxypregna-5,7-diene (5.00 g, 8.91 mmol) in tetrahydrofuran (90 ml), sodium hydride (60% in oil, 2.14 g, 53.5 mmol), 15-crown-5 (1.77 ml, 8.91 mmol) and 1-ethyl-1-methylpropyl bromoacetate (11.9 g, 53.5 mmol) were added, followed by heating at reflux for 16 hours under an argon atmosphere. After cooling to room temperature, the reaction mixture was poured into saturated aqueous ammonium chloride and extracted with ethyl acetate (twice). The combined organic layers were washed with saturated aqueous sodium chloride and dried over anhydrous magnesium sulfate. After evaporation under reduced pressure to remove the solvent, the resulting residue was purified by column chromatography (hexane:t-butyl methyl ether=30:1 and then hexane:toluene=2:1) to give a mixture (5.59 g) containing the titled compound.

(3) Preparation of 1α,3β-dihydroxy-20(S)-(1-ethyl-1-methylpropoxycarbonylmethoxy)pregna-5,7-diene The mixture containing 1α,3β-bis(tert-butyldimethylsilyloxy)-20(S)-(1-ethyl-1-methylpropoxycarbonylmethoxy)pregna-5,7-diene from Example 23(2) (5.59 g), a 1M tetrahydrofuran solution of tetra-n-butylammonium fluoride (79.5 ml, 79.5 ml) and acetic acid (2 ml) were mixed and stirred at an external temperature of 65° C. for 17 hours. After cooling to room temperature, the reaction mixture was diluted with ethyl acetate, washed sequentially with aqueous potassium bisulfate, saturated aqueous sodium bicarbonate and saturated aqueous sodium chloride, and then dried over anhydrous magnesium sulfate. After evaporation under reduced pressure to remove the solvent, the resulting residue was purified by column chromatography (hexane:ethyl acetate:ethanol=5:5:0.3) to give the titled compound (2.43 g, 57% for 2 steps) as a pale yellow foam.

IR(neat): 3369, 2968, 2939, 2875, 1751, 1722, 1460, 1375, 1294, 1209, 1132, 1055, 1032 cm$^{-1}$. $^1$H NMR δ: 0.62 (s, 3H), 0.85 (t, J=7.5 Hz, 6H), 0.94 (s, 3H), 1.20 (d, J=6.1 Hz, 3H), 1.40 (s, 3H), 2.27-2.41 (m, 1H), 2.48-2.59 (m, 1H), 2.66-2.79 (m, 1H), 3.39 (m, 1H), 3.76 (brs, 1H), 3.93 (d, J=16.0 Hz, 1H), 4.01 (d, J=16.0 Hz, 1H), 4.07 (m, 1H), 5.36-5.45 (m, 1H), 5.69-5.76 (m, 1H). MS m/z: 474 (M$^+$), 315 (100*). UV $\lambda_{max}$nm: 271, 282, 294.

(4) Preparation of 1α,3β-dihydroxy-20(S)-(1-ethyl-1-methylpropoxycarbonylmethoxy)-9,10-secopregna-5,7,10(19)-triene 1α,3β-Dihydroxy-20(S)-(1-ethyl-1-methylpropoxycarbonylmethoxy)pregna-5,7-diene (2.42 g, 5.10 mmol) was treated in tetrahydrofuran (650 ml) in the same manner as shown in Example 4(3), except that light irradiation was continued for 2 hours and 15 minutes, followed by purification using column chromatography (hexane:ethyl acetate: ethanol=7:3:0.3 and then dichloromethane:ethyl acetate: ethanol=6:1:0.1) to give the titled compound (773 mg, 32%) as a colorless foam.

IR(neat): 3377, 2968, 2939, 2879, 1749, 1716, 1458, 1375, 1296, 1213, 1128, 1057 cm$^{-1}$. $^1$H NMR δ: 0.53 (s, 3H), 0.85 (t, J=7.5 Hz, 6H), 1.19 (d, J=6.0 Hz, 3H), 1.39 (s, 3H), 2.25-2.37 (m, 1H), 2.55-2.65 (m, 1H), 2.77-2.88 (m, 1H), 3.36 (m, 1H), 3.92 (d, J=16.0 Hz, 1H), 4.00 (d, J=16.0 Hz, 1H), 4.17-4.29 (br, 1H), 4.39-4.48 (br, 1H), 4.99 (m, 1H), 5.32 (m, 1H), 6.03 (d, J=11.3 Hz, 1H), 6.37 (d, J=11.3 Hz, 1H). MS m/z: 474 (M$^+$), 134 (100%). UV $\lambda_{max}$nm: 264.

Example 24

Synthesis of (1α,3β)-1,3-bis((tert-butyl(dimethyl) silyl)oxy)pregna-5,7,16-trien-20-one (1) Synthesis of (1α,3β)-1,3-bis((tert-butyl(dimethyl)silyl)oxy)androsta-5,7,16-trien-17-yl trifluoromethanesulfonate (1α,3β)-1,3-Bis((tert-butyl(dimethyl)silyl)oxy)androsta-5,7-dien-17-one (21.0 g) was dissolved in tetrahydrofuran (140 ml), to which 2-(N,N-bis(trifluoromethylsulfonyl) amino)pyridine (19.1 g) was then added at room temperature. After the reaction mixture was cooled to −78° C., a 1.0 M tetrahydrofuran solution of sodium bis(trimethylsilyl)amide (48.3 ml) was further added dropwise. After continued stirring at −78° C. for 30 minutes, saturated aqueous sodium bicarbonate was added to the reaction mixture, which was then extracted with hexane/ethyl acetate=5/1. The extracted solution was dried over anhydrous sodium sulfate and evaporated under reduced pressure to remove the solvent. The resulting residue was washed with acetonitrile (100 ml) to give the titled compound (23.3 g, yield 89%).

$^1$H-NMR(270 MHz, CDCl$_3$) δ: 5.64-5.58 (m, 2H), 5.43-5.37 (m, 1H), 4.12-3.98 (m, 1H), 3.74-3.68 (m, 1H), 2.96-2.84 (m, 1H), 2.48-2.26 (m, 5H), 2.00-1.42 (m, 1H), 0.97 (s, 3H), 0.95 (s, 3H), 0.89 (s, 18H), 0.12 (s, 3H), 0.107 (s, 6H), 0.06 (s, 3H).

(2) Synthesis of (1α,3β)-1,3-bis((tert-butyl(dimethyl)silyl)oxy)pregna-5,7,16-trien-20-one (1α,3β)-1,3-Bis((tert-butyl(dimethyl)silyl)oxy)androsta-5,7,16-trien-17-yl trifluoromethanesulfonate (40.3 g) was dissolved in dimethylacetamide (203 ml), followed by addition of tetrakis(triphenylphosphine)palladium(0) (703 mg). The resulting mixture was placed under reduced pressure and then placed in a carbon monoxide atmosphere. This procedure was further repeated twice. A 0.98 M hexane solution of dimethylaluminum chloride (74.4 ml) was added to the mixture at room temperature and then stirred at room temperature for 20 minutes. After heating to 58° C. and stirring for 2 hours, water was added to the reaction mixture, which was then extracted with hexane/ethyl acetate=1/1. The extracted solution was dried over anhydrous magnesium sulfate and concentrated under reduced pressure to give the titled compound (34.0 g, yield 100%).

$^1$H-NMR(300 MHz, benzene-d$_6$) δ: 6.01 (dd, J=2.5, 2.7 Hz, 1H), 5.72 (d, J=5.8 Hz, 1H), 5.43-5.36 (m, 1H), 4.38-4.23 (m, 1H), 3.58-3.51 (m, 1H), 3.09-2.97 (m, 1H), 2.63-2.53 (m, 2H), 2.41-2.29 (m, 1H), 2.08-1.96 (m, 3H), 1.94 (s, 3H), 1.83-1.67 (m, 2H), 1.05 (s, 9H), 1.04 (s, 3H), 0.95 (s, 9H), 0.86 (s, 3H), 0.19 (s, 3H), 0.17 (s, 3H), 0.11 (s, 3H), 0.02 (s, 3H).

Example 25

Synthesis of 1α,3β-dihydroxy-20(S)-(1-ethyl-1-methylpropoxycarbonylmethoxy)-9,10-secopregna-5,7,10(19),16-tetraene (1) Synthesis of (1α,3β,20S)-1,3-bis((tert-butyl(dimethyl)silyl)oxy)pregna-5,7,16-trien-20-ol The (1α,3β)-1,3-bis((tert-butyl(dimethyl)silyl)oxy)pregna-5,7,16-trien-20-one synthesized in Example 24 (45.0 g) was dissolved in toluene (240 ml) and then cooled to −20° C., followed by stirring for 30 minutes. Borane-dimethylsulfide complex (22.9 ml) was added to the resulting solution at −20° C. and stirred for 5 minutes. A 1M toluene solution of (R)-2-methyl-CBS-oxazaborolidine (22.9 ml) was further added to the solution at −20° C. and stirred for 1 hour. Methanol was added to the reaction mixture, which was then extracted with ethyl acetate. The extracted solution was dried over anhydrous sodium sulfate and evaporated under reduced pressure to remove the solvent. The resulting residue was purified by silica gel column chromatography (liquid phase: hexane/ethyl acetate=9/1) to give the titled compound (23.3 g, yield 89%).

$^1$H-NMR(300 MHz, benzene-d$_6$) δ: 5.71 (d, J=4.9 Hz, 1H), 5.49 (brs, 2H), 4.40-4.15 (m, 2H), 3.59 (brs, 1H), 3.13-3.03 (m, 1H), 2.61 (s, 1H), 2.59 (s, 1H), 2.46-2.37 (m, 1H), 2.20-1.92 (m, 4H), 1.85-1.47 (m, 4H), 1.24 (d, J=6.6 Hz, 3H), 1.06 (s, 9H), 0.99 (s, 3H), 0.95 (s, 9H), 0.91 (s, 3H), 0.20 (s, 3H), 0.18 (s, 3H), 0.06 (s, 3H), 0.05 (s, 3H).

(2) Synthesis of 1-ethyl-1-methylpropyl ((((1α,3β,20S)-1,3-bis(tert-butyl(dimethyl)silyl)oxy)pregna-5,7,16-trien-20-yl)oxy)acetate (1α,3β,20S)-1,3-Bis((tert-butyl(dimethyl)silyl)oxy)pregna-5,7,16-trien-20-ol (210 mg) and 60% sodium hydride (90 mg) were dissolved in tetrahydrofuran (3.7 ml). To the resulting solution, 15-crown-5-ether (83 μl) and then 1-ethyl-1-methylpropylbromoacetate (502 mg) were added at room temperature, followed by heating to 60° C. After stirring at 60° C. for 12 hours, methanol was added to the solution, which was then extracted with tert-butyl methyl ether. The extracted solution was dried over anhydrous sodium sulfate and evaporated under reduced pressure to remove the solvent. The resulting residue was purified by silica gel column chromatography (liquid phase: hexane/diethyl ether=10/1) and then silica gel column chromatography (liquid phase: hexane/methylene chloride=1/2) to give the titled compound (244 mg, yield 93%).

$^1$H-NMR(300 MHz, benzene-d$_6$) δ: 5.70 (d, J=6.9 Hz, 1H), 5.56 (brs, 1H), 5.49-5.41 (m, 1H), 4.38-4.25 (m, 1H), 4.21 (q, J=6.3 Hz, 1H), 3.99 (d, J=16.2 Hz, 1H), 3.92 (d, J=16.2 Hz, 1H), 3.63-3.55 (m, 1H), 3.10-3.00 (m, 1H), 2.64-2.53 (m, 1H), 2.47-2.36 (m, 1H), 2.23-1.44 (m, 12H), 1.41 (d, J=6.3 Hz, 3H), 1.31 (s, 3H), 1.04 (s, 9H), 0.98 (s, 3H), 0.94 (s, 9H), 0.89 (s, 3H), 0.76 (t, J=7.4 Hz, 6H), 0.18 (s, 3H), 0.16 (s, 3H), 0.13 (s, 3H), 0.06 (s, 3H).

(3) Synthesis of 1-ethyl-1-methylpropyl (((1α,3β,20S)-1,3-dihydroxypregna-5,7,16-trien-20-yl)oxy) acetate 1-Ethyl-1-methylpropyl ((((1α,3β,20S)-1,3-bis(tert-butyl (dimethyl)silyl)oxy)pregna-5,7,16-trien-20-yl)oxy)acetate (203 mg) was dissolved in a 1.0 M tetrahydrofuran solution of tetrabutylammonium fluoride (3.0 ml), followed by addition of acetic acid (75 µg). The resulting solution was heated to 60° C., stirred for 12 hours and then extracted with ethyl acetate. The extracted solution was dried over anhydrous sodium sulfate and evaporated under reduced pressure to remove the solvent. The resulting residue was purified by silica gel column chromatography (liquid phase: hexane/ethyl acetate=2/3) to give the titled compound (132 mg, yield 97%).

$^1$H-NMR(300 MHz, acetone-$d_6$) δ: 5.66-5.59 (m, 2H), 5.45-5.39 (m, 1H), 4.14 (q, J=6.6 Hz, 1H), 4.09-3.95 (m, 1H), 3.95 (d, J=16.2 Hz, 1H), 3.86 (d, J=16.2 Hz, 1H), 3.80-3.70 (m, 1.5H), 3.64-3.50 (m, 0.5H), 2.49-2.39 (m, 1H), 2.38-2.17 (m, 4H), 2.12-2.06 (m, 1H), 1.96-1.62 (m, 8H), 1.54-1.42 (m, 1H), 1.37 (s, 3H), 1.30 (d, J=6.6 Hz, 3H), 0.95 (s, 3H), 0.90 (s, 3H), 0.85 (t, J=7.4 Hz, 6H).

(4) Synthesis of 1α,3β-dihydroxy-20(S)-(1-ethyl-1-methylpropoxycarbonylmethoxy)-9,10-secopregna-5,7,10(19),16-tetraene 1-Ethyl-1-methylpropyl (((1α,3β,20S)-1,3-dihydroxypregna-5,7,16-trien-20-yl)oxy)acetate (132 mg) was dissolved in tetrahydrofuran (500 ml). This solution was cooled to 18° C. under an argon stream and irradiated with UV light for 30 minutes using a 5 kW UV irradiator with a xenon-mercury lamp (280 to 320 nm, USHIO INC.)(Japanese Patent Application No. 10-188880, WO00/01477). This solution was further heated at reflux for 2 hours and evaporated under reduced pressure to remove the solvent. The resulting residue was purified by silica gel column chromatography (liquid phase: methylene chloride/ethyl acetate=6/4) to give the titled compound (34.2 mg, yield 26%). The compound thus prepared had the same individual spectra as the compound prepared in Example 17(4).

Example 26

(1) Preparation of 1α,3β-bis(tert-butyldimethylsilyloxy)-20(S)-(1,1-diethylpropoxycarbonylmethoxy)-9,10-secopregna-5,7,10(19),16-tetraene

[{1α,3β-Bis(tert-butyldimethylsilyloxy)-9,10-secopregna-5,7,10(19),16-tetraen-20(S)-yl}oxy]acetic acid (31 mg, 0.05 mmol) was treated with 3-ethyl-3-pentanol (9 mg, 0.08 mmol), N,N'-dicyclohexylcarbodiimide (17 mg, 0.08 mmol) and 4-(dimethylamino)pyridine (6 mg, 0.05 mmol) in dichloromethane (0.5 ml) in the same manner as shown in Example 17(3) (at room temperature for 17 hours), followed by work up and purification using preparative thin layer chromatography (0.5 mm×3 plates, hexane:ethyl acetate=10:1, developed twice) to give a mixture (27.0 mg) containing the titled compound.

(2) Preparation of 1α,3β-dihydroxy-20(S)-(1,1-diethylpropoxycarbonylmethoxy)-9,10-secopregna-5,7,10(19),16-tetraene The mixture containing 1α,3β-bis(tert-butyldimethylsilyloxy)-20(S)-(1,1-diethylpropoxycarbonylmethoxy)-9,10-secopregna-5,7,10(19),16-tetraene from Example 26(1) (27 mg) was treated in tetrahydrofuran (1.7 ml) with a 1M tetrahydrofuran solution of tetra-n-butylammonium fluoride (0.57 ml) in the same manner as shown in Example 17(4) (at an external temperature of 50° C. for 2 hours) and then worked up. The resulting residue was purified by preparative thin layer chromatography (0.5 mm×2 plates, dichloromethane:ethanol=20:1, developed twice; 0.5 mm×2 plates, hexane:ethyl acetate:ethanol=10:5:1, developed three times; and then 0.25 mm×2 plates, dichloromethane:ethyl acetate=3:1, developed twice) to give the titled compound (2.966 mg, 12.2% for 2 steps) as a colorless oil.

IR(neat): 3386, 2969, 2931, 2881, 2852, 1745, 1727, 1457, 1288, 1214, 1122, 1052 cm$^{-1}$. $^1$H NMR δ: 0.78 (s, 3H), 0.81 (t, J=7.3 Hz, 9H), 1.36 (d, J=6.3 Hz, 3H), 1.84 (q, J=7.3 Hz, 6H), 2.18-2.47 (m, 3H), 2.54-2.67 (m, 1H), 2.76-2.88 (m, 1H), 3.85 (d, J=16.5 Hz, 1H), 3.97 (d, J=16.5 Hz, 1H), 4.04-4.13 (m, 1H), 4.19-4.30 (m, 1H), 4.39-4.49 (m, 1H), 5.01 (brs, 1H), 5.34 (brs, 1H), 5.59 (brs, 1H), 6.11 (d, J=11.5 Hz, 1H), 6.37 (d, J=11.2 Hz, 1H). MS m/z: 312 (M$^+$-HOCH$_2$COOCEt$_3$), 57 (100%). UV λ$_{max}$nm: 263.

Example 27

(1) Preparation of 1α,3β-bis(tert-butyldimethylsilyloxy)-20(S)-(cycloheptyloxycarbonylmethoxy)-9,10-secopregna-5,7,10(19),16-tetraene

[{1α,3β-Bis(tert-butyldimethylsilyloxy)-9,10-secopregna-5,7,10(19),16-tetraen-20(S)-yl}oxy]acetic Acid (20 mg, 0.0324 mmol) was treated with cycloheptanol (6 µl, 0.0518 mmol), N,N'-dicyclohexylcarbodiimide (10 mg, 0.0518 mmol) and 4-(dimethylamino)pyridine (4 mg, 0.0324 mmol) in dichloromethane (1.0 ml) in the same manner as shown in Example 17(3) (at room temperature for 2 hours), followed by work up and purification using preparative thin layer chromatography (0.5 mm×1 plate, hexane:ethyl acetate=5:1, developed once) to give a mixture (26.7 mg) containing the titled compound.

(2) Preparation of 1α,3β-dihydroxy-20(S)-(cycloheptyloxycarbonylmethoxy)-9,10-secopregna-5,7,10(19),16-tetraene The mixture containing 1α,3β-bis(tert-butyldimethylsilyloxy)-20(S)-(cycloheptyloxycarbonylmethoxy)-9,10-secopregna-5,7,10(19),16-tetraene from Example 27(1) (26.7 mg) was treated in tetrahydrofuran (0.7 ml) with a 1M tetrahydrofuran solution of tetra-n-butylammonium fluoride (0.3 ml) in the same manner as shown in Example 17(4) (at an external temperature of 50° C. for 1 hour) and then worked up. The resulting residue was purified by preparative thin layer chromatography (0.5 mm×1 plate, hexane:ethyl acetate:ethanol=5:5:1, developed twice) to give the titled compound (4.134 mg, 25% for 2 steps) as a colorless oil.

IR(neat): 3326, 2927, 2852, 2358, 2321, 1749, 1627, 1558, 1448, 1218, 1122, 1053 cm$^{-1}$. $^1$H NMR δ: 0.77 (s, 3H), 1.36 (d, J=6.5 Hz, 3H), 2.55-2.65 (m, 1H), 2.76-2.87 (m, 1H), 3.85-4.17 (m, 3H), 4.18-4.29 (m, 1H), 4.41-4.49 (m, 1H), 4.94-5.07 (m, 2H), 5.34 (s, 1H), 5.61 (brs, 1H), 6.11 (d, J=11.1 Hz, 1H), 6.37 (d, J=11.1 Hz, 1H). MS m/z: 466 (M$^+$-H$_2$O), 55 (100%). UV λ$_{max}$nm: 263.

Example 28

(1) Preparation of 1α,3β-bis(tert-butyldimethylsilyloxy)-20(S)-(1-ethylbutoxycarbonylmethoxy)-9,10-secopregna-5,7,10(19),16-tetraene

[{1α,3β-Bis(tert-butyldimethylsilyloxy)-9,10-secopregna-5,7,10(19),16-tetraen-20(S)-yl}oxy]acetic acid (20 mg, 0.0324 mmol) was treated with 4-heptanol (7 µl, 0.0518 mmol), N,N'-dicyclohexylcarbodiimide (10 mg, 0.0518 mmol) and 4-(dimethylamino)pyridine (4 mg, 0.0324 mmol)

in dichloromethane (1.0 ml) in the same manner as shown in Example 17(3) (at room temperature for 2 hours), followed by work up and purification using preparative thin layer chromatography (0.5 mm×1 plate, hexane:ethyl acetate=5:1, developed once) to give a mixture (21.7 mg) containing the titled compound.

(2) Preparation of 1α,3β-dihydroxy-20(S)-(1-ethyl-butoxycarbonylmethoxy)-9,10-secopregna-5,7,10(19),16-tetraene The mixture containing 1α,3β-bis(tert-butyldimethylsilyloxy)-20(S)-(1-ethylbutoxycarbonylmethoxy)-9,10-secopregna-5,7,10(19),16-tetraene from Example 28(1) (21.7 mg) was treated in tetrahydrofuran (0.7 ml) with a 1M tetrahydrofuran solution of tetra-n-butylammonium fluoride (0.3 ml) in the same manner as shown in Example 17(4) (at an external temperature of 50° C. for 1 hour) and then worked up. The resulting residue was purified by preparative thin layer chromatography (0.5 mm×1 plate, hexane:ethyl acetate:ethanol=5:5:1, developed twice) and then another run of preparative thin layer chromatography (0.5 mm×1 plate, hexane:ethyl acetate:ethanol=10:10:1, developed twice) to give the titled compound (4.266 mg, 27% for 2 steps) as a colorless oil.

IR(neat): 3390, 3325, 2956, 2931, 2852, 1749, 1627, 1448, 1203, 1122, 1053 cm$^{-1}$. $^1$H NMR δ: 0.77 (s, 3H), 0.90 (t, J=7.0 Hz, 6H), 1.37 (d, J=6.2 Hz, 3H), 2.53-2.65 (m, 1H), 2.76-2.88 (m, 1H), 3.87-4.17 (m, 3H), 4.19-4.29 (m, 1H), 4.39-4.49 (m, 1H), 4.92-5.05 (m, 2H), 5.34 (s, 1H), 5.61 (brs, 1H), 6.11 (d, J=11.1 Hz, 1H), 6.38 (d, J=11.1 Hz, 1H). MS m/z: 450 (M$^+$-2H$_2$O), 57 (100%). UV λ$_{max}$nm: 263.

Example 29

(1) Preparation of 1α,3β-bis(tert-butyldimethylsilyloxy)-20(S)-(1-methyl-1-propylbutoxycarbonylmethoxy)-9,10-secopregna-5,7,10(19),16-tetraene

[{1α,3β-Bis(tert-butyldimethylsilyloxy)-9,10-secopregna-5,7,10(19),16-tetraen-20(S)-yl}oxy]acetic acid (20 mg, 0.03 mmol) was treated with 4-methyl-4-heptanol (6.3 mg, 0.048 mmol), N,N'-dicyclohexylcarbodiimide (9.9 mg, 0.048 mmol) and 4-(dimethylamino)pyridine (3.7 mg, 0.03 mmol) in dichloromethane (0.3 ml) in the same manner as shown in Example 17(3) (at room temperature for 15 hours), followed by work up and purification using preparative thin layer chromatography (0.5 mm×1 plate, hexane:ethyl acetate=10:1, developed twice) to give a mixture (14.0 mg) containing the titled compound.

(2) Preparation of 1α,3β-dihydroxy-20(S)-(1-methyl-1-propylbutoxycarbonylmethoxy)-9,10-secopregna-5,7,10(19),16-tetraene The mixture containing 1α,3β-bis(tert-butyldimethylsilyloxy)-20(S)-(1-methyl-1-propylbutoxycarbonylmethoxy)-9,10-secopregna-5,7,10(19),16-tetraene from Example 29(1) (14 mg) was treated in tetrahydrofuran (0.5 ml) with a 1M tetrahydrofuran solution of tetra-n-butylammonium fluoride (0.2 ml) in the same manner as shown in Example 17(4) (at an external temperature of 50° C. for 2 hours) and then worked up. The resulting residue was purified by preparative thin layer chromatography (0.25 mm×2 plates, dichloromethane:ethanol=20:1, developed three times) to give the titled compound (6.351 mg, 42.3% for 2 steps) as a colorless oil.

IR(neat): 3417, 2960, 2931, 2873, 1747, 1467, 1373, 1213, 1122, 1052 cm$^{-1}$. $^1$H NMR δ: 0.77 (s, 3H), 0.90 (t, J=7.3 Hz, 6H), 1.36 (d, J=6.6 Hz, 3H), 1.40 (s, 3H), 2.17-2.47 (m, 3H), 2.56-2.66 (m, 1H), 2.76-2.88 (m, 1H), 3.81 (d, J=16.5 Hz, 1H), 3.94 (d, J=16.5 Hz, 1H), 4.02-4.13 (m, 1H), 4.19-4.29 (m, 1H), 4.40-4.51 (m, 1H), 5.01 (brs, 1H), 5.34 (brs, 1H), 5.59 (brs, 1H), 6.11 (d, J=11.4 Hz, 1H), 6.37 (d, J=11.1 Hz, 1H). MS m/z: 312 (M$^+$-HOCH$_2$COOC(CH$_3$)(C$_3$H$_7$)$_2$), 71 (100%). UV λ$_{max}$nm: 264.

Example 30

(1) Preparation of 1α,3β-bis(tert-butyldimethylsilyloxy)-20(S)-(1-methylcyclohexyloxycarbonylmethoxy)-9,10-secopregna-5,7,10(19),16-tetraene

[{1α,3β-Bis(tert-butyldimethylsilyloxy)-9,10-secopregna-5,7,10(19),16-tetraen-20(S)-yl}oxy]acetic acid (20 mg, 0.0324 mmol) was treated with 1-methylcyclohexanol (7 µl, 0.0518 mmol), N,N'-dicyclohexylcarbodiimide (10 mg, 0.0518 mmol) and 4-(dimethylamino)pyridine (4 mg, 0.0324 mmol) in dichloromethane (1.0 ml) in the same manner as shown in Example 17(3) (at room temperature for 14 hours), followed by work up and purification using preparative thin layer chromatography (0.5 mm×1 plate, hexane:ethyl acetate=7:1, developed once) to give a mixture (14.0 mg) containing the titled compound.

(2) Preparation of 1α,3β-dihydroxy-20(S)-(1-methylcyclohexyloxycarbonylmethoxy)-9,10-secopregna-5,7,10(19),16-tetraene The mixture containing 1α,3β-bis(tert-butyldimethylsilyloxy)-20(S)-(1-methylcyclohexyloxycarbonylmethoxy)-9,10-secopregna-5,7,10(19),16-tetraene from Example 30(1) (14.0 mg) was treated in tetrahydrofuran (0.7 ml) with a 1M tetrahydrofuran solution of tetra-n-butylammonium fluoride (0.3 ml) in the same manner as shown in Example 17(4) (at an external temperature of 50° C. for 1 hour) and then worked up. The resulting residue was purified by preparative thin layer chromatography (0.5 mm×1 plate, hexane:ethyl acetate:ethanol=5:5:1, developed once) to give the titled compound (4.220 mg, 27% for 2 steps) as a colorless oil.

IR(neat): 3446, 2931, 2852, 1747, 1446, 1211, 1124, 1053, 962 cm$^{-1}$. $^1$H NMR δ: 0.78 (s, 3H), 1.37 (d, J=6.8 Hz, 3H), 1.49 (s, 3H), 2.56-2.66 (m, 1H), 2.77-2.89 (m, 1H), 3.85 (d, J=16.5 Hz, 1H), 3.98 (d, J=16.5 Hz, 1H), 4.09 (q, J=6.8 Hz, 1H), 4.19-4.29 (m, 1H), 4.41-4.49 (m, 1H), 5.02 (s, 1H), 5.34 (s, 1H), 5.60 (brs, 1H), 6.11 (d, J=11.6 Hz, 1H), 6.38 (d, J=11.6 Hz, 1H). MS m/z: 466 (M$^+$-H$_2$O), 55 (100%). UV λ$_{max}$nm: 263.

Example 31

(1) Preparation of 1α,3β-bis(tert-butyldimethylsilyloxy)-20(S)-(cyclododecyloxycarbonylmethoxy)-9,10-secopregna-5,7,10(19),16-tetraene

[{1α,3β-Bis(tert-butyldimethylsilyloxy)-9,10-secopregna-5,7,10(19),16-tetraen-20(S)-yl}oxy]acetic acid (20 mg, 0.0324 mmol) was treated with cyclododecanol (9 µl, 0.0518 mmol), N,N'-dicyclohexylcarbodiimide (10 mg, 0.0518 mmol) and 4-(dimethylamino)pyridine (4 mg, 0.0324 mmol) in dichloromethane (1.0 ml) in the same manner as shown in Example 17(3) (at room temperature for 14 hours), followed by work up and purification using preparative thin layer chromatography (0.5 mm×1 plate, hexane:ethyl acetate=7:1, developed once) to give a mixture (21.6 mg) containing the titled compound.

(2) Preparation of 1α,3β-dihydroxy-20(S)-(cyclododecyloxycarbonylmethoxy)-9,10-secopregna-5,7,10(19),16-tetraene The mixture containing 1α,3β-bis(tert-butyldimethylsilyloxy)-20(S)-(cyclododecyloxycarbonylmethoxy)-9,10-secopregna-5,7,10(19),16-tetraene from Example 31(1) (21.6 mg) was treated in tetrahydrofuran (0.7 ml) with a 1M tetrahydrofuran solution of tetra-n-butylammonium fluoride (0.3 ml) in the same manner as shown in Example 17(4) (at an external temperature of 50° C. for 1 hour) and then worked up. The resulting residue was purified by preparative thin layer chromatography (0.5 mm×1 plate, hexane:ethyl acetate:ethanol=5:5:1, developed once) to give the titled compound (4.971 mg, 28% for 2 steps) as a colorless oil.

IR(neat): 3446, 2931, 2850, 1748, 1471, 1446, 1205, 1124, 1053 cm$^{-1}$. $^1$H NMR δ: 0.77 (s, 3H), 2.56-2.66 (m, 1H), 2.77-2.87 (m, 1H), 3.90 (d, J=16.5 Hz, 1H), 4.02 (d, J=16.5 Hz, 1H), 4.09 (q, J=6.5 Hz, 1H), 4.19-4.29 (m, 1H), 4.41-4.49 (m, 1H), 5.01 (s, 1H), 5.04-5.15 (m, 1H), 5.34 (s, 1H), 5.60 (brs, 1H), 6.10 (d, J=11.3 Hz, 1H), 6.37 (d, J=11.3 Hz, 1H). MS m/z: 518 (M$^+$-2H$_2$O), 55 (100%). UV $\lambda_{max}$nm: 263.

Example 32

(1) Preparation of 1α,3β-bis(tert-butyldimethylsilyloxy)-20(S)-(1-methylcyclopentyloxycarbonylmethoxy)-9,10-secopregna-5,7,10(19),16-tetraene

[{1α,3β-Bis(tert-butyldimethylsilyloxy)-9,10-secopregna-5,7,10(19),16-tetraen-20(S)-yl}oxy]acetic acid (30 mg, 0.048 mmol) was treated with 1-methylcyclopentanol (4.8 mg, 0.048 mmol), N,N'-dicyclohexylcarbodiimide (9.9 mg, 0.048 mmol) and 4-(dimethylamino)pyridine (3.7 mg, 0.03 mol) in dichloromethane (0.3 ml) in the same manner as hown in Example 17(3) (at room temperature for 15 hours), ollowed by work up and purification using preparative thin layer chromatography (0.5 mm×2 plates, hexane:ethyl acetate=10:1, developed twice) to give a mixture (20.0 mg) containing the titled compound.

(2) Preparation of 1α,3β-dihydroxy-20(S)-(1-methylcyclopentyloxycarbonylmethoxy)-9,10-secopregna-5,7,10(19),16-tetraene The mixture containing 1α,3β-bis(tert-butyldimethylsilyloxy)-20(S)-(1-methylcyclopentyloxycarbonylmethoxy)-9,10-secopregna-5,7,10(19),16-tetraene from Example 32(1) (20 mg) was treated in tetrahydrofuran (0.5 ml) with a 1M tetrahydrofuran solution of tetra-n-butylammonium fluoride (0.29 ml) in the same manner as shown in Example 17(4) (at an external temperature of 50° C. for 1.5 hours) and then worked up. The resulting residue was purified by preparative thin layer chromatography (0.5 mm×2 plates, dichloromethane:ethanol=20:1, developed three times) to give the titled compound (7.666 mg, 54.3% for 2 steps) as a colorless oil.

IR(neat): 3392, 2965, 2933, 2873, 2850, 1747, 1444, 1375, 1222, 1180, 1122, 1052 cm$^{-1}$. $^1$H NMR δ: 0.77 (s, 3H), 1.36 (d, J=6.4 Hz, 3H), 2.19-2.51 (m, 3H), 2.56-2.68 (m, 1H), 2.77-2.89 (m, 1H), 3.83 (d, J=16.3 Hz, 1H), 3.95 (d, J=16.3 Hz, 1H), 4.02-4.14 (m, 1H), 4.21-4.31 (m, 1H), 4.41-4.51 (m, 1H), 5.01 (brs, 1H), 5.34 (brs, 1H), 5.60 (brs, 1H), 6.11 (d, J=11.4 Hz, 1H), 6.37 (d, J=11.1 Hz, 1H). MS m/z: 470 (M$^+$), 312 (M$^+$-HOCH$_2$COOC$_6$H$_{11}$), 83 (100%). UV $\lambda_{max}$nm: 263.

Example 33

(1) Preparation of 1α,3β-bis(tert-butyldimethylsilyloxy)-20(S)-(cyclooctyloxycarbonylmethoxy)-9,10-secopregna-5,7,10(19),16-tetraene

[{1α,3β-Bis(tert-butyldimethylsilyloxy)-9,10-secopregna-5,7,10(19),16-tetraen-20(S)-yl}oxy]acetic acid (21.3 mg, 0.035 mmol) was treated with cyclooctanol (14.0 mg, 0.109 mmol), N,N'-dicyclohexylcarbodiimide (24.0 mg, 0.116 mmol) and 4-(dimethylamino)pyridine (10.0 mg, 0.082 mmol) in dichloromethane (0.3 ml) in the same manner as shown in Example 17(3) (at room temperature for 15 hours), followed by work up and purification using preparative thin layer chromatography (0.5 mm×2 plates, hexane:ethyl acetate=15:1, developed twice) to give a mixture (16.6 mg) containing the titled compound.

(2) Preparation of 1α,3β-dihydroxy-20(S)-(cyclooctyloxycarbonylmethoxy)-9,10-secopregna-5,7,10(19),16-tetraene The mixture containing 1α,3β-bis(tert-butyldimethylsilyloxy)-20(S)-(cyclooctyloxycarbonylmethoxy)-9,10-secopregna-5,7,10(19),16-tetraene from Example 33(1) (16.5 mg) was treated with a 1M tetrahydrofuran solution of tetra-n-butylammonium fluoride (0.25 ml) in the same manner as shown in Example 17(4) (at an external temperature of 45° C. for 30 minutes). The reaction mixture was purified by preparative thin layer chromatography (0.5 mm×2 plates, dichloromethane:ethanol=15:1, developed twice and then 0.25 mm×1 plate, hexane:ethyl acetate:ethanol=10:5:1, developed four times) to give the titled compound (3.5 mg, 20% for 2 steps) as a colorless oil.

IR(neat): 3392, 2928, 2856, 1744, 1468, 1204, 1124, 1052 cm$^{-1}$. $^1$H NMR δ: 0.77 (s, 3H), 1.36 (d, J=6.7 Hz, 3H), 2.56-2.66 (m, 1H), 2.78-2.89 (m, 1H), 3.89 (d, J=16.3 Hz, 1H), 4.00 (d, J=16.3 Hz, 1H), 4.07 (q, J=6.7 Hz, 1H), 4.19-4.31 (m, 1H), 4.41-4.50 (m, 1H), 4.96-5.10 (m, 1H), 5.02 (brs, 1H), 5.34 (brs, 1H), 5.60 (brs, 1H), 6.10 (d, J=11.7 Hz, 1H), 6.37 (d, J=11.7 Hz, 1H). MS m/z: 480 (M$^+$-H$_2$O), 69 (100%). UV $\lambda_{max}$nm: 263.

Example 34

(1) Preparation of 1α,3β-bis(tert-butyldimethylsilyloxy)-20(S)-(1-butylpentyloxycarbonylmethoxy)-9,10-secopregna-5,7,10(19),16-tetraene

[{1α,3β-Bis(tert-butyldimethylsilyloxy)-9,10-secopregna-5,7,10(19),16-tetraen-20(S)-yl}oxy]acetic acid (22.0 mg, 0.036 mmol) was treated with nonan-5-ol (14.0 mg, 0.097 mmol), N,N'-dicyclohexylcarbodiimide (24.0 mg, 0.116 mmol) and 4-(dimethylamino)pyridine (10.0 mg, 0.082 mmol) in dichloromethane (0.3 ml) in the same manner as shown in Example 17(3) (at room temperature for 15 hours), followed by work up and purification using preparative thin layer chromatography (0.5 mm×2 plates, hexane:ethyl acetate=15:1, developed twice) to give a mixture (17.4 mg) containing the titled compound.

(2) Preparation of 1α,3β-dihydroxy-20(S)-(1-butylpentyloxycarbonylmethoxy)-9,10-secopregna-5,7,10(19),16-tetraene The mixture containing 1α,3β-bis(tert-butyldimethylsilyloxy)-20(S)-(1-butylpentyloxycarbonylmethoxy)-9,10- secopregna-5,7,10(19),16-tetraene from Example 34(1) (16.4 mg) was treated with a 1M tetrahydrofuran solution of tetra-n-butylammonium fluoride (0.25 ml) in the same manner as shown in Example 17(4) (at an external temperature of 45° C. for 30 minutes). The reaction mixture was purified by preparative thin layer chromatography (0.5 mm×2 plates, dichloromethane:ethanol=15:1, developed twice; 0.25 mm×1 plate, hexane:ethyl acetate:ethanol=10:5:1, developed four times; 0.25 mm×1 plate, toluene:ethyl acetate=1:1, developed twice; and then 0.25 mm×1 plate, dichloromethane: ethyl acetate=3:1, developed once) to give the titled compound (1.7 mg, 10% for 2 steps) as a colorless oil.

IR(neat): 3384, 2932, 2860, 1746, 1444, 1370, 1204, 1124, 1054 cm$^{-1}$. $^1$H NMR δ: 0.77 (s, 3H), 0.87 (t, J=6.9 Hz, 3H), 0.88 (t, J=6.9 Hz, 3H), 1.37 (d, J=6.6 Hz, 3H), 2.56-2.66 (m, 1H), 2.78-2.89 (m, 1H), 3.93 (d, J=16.5 Hz, 1H), 4.04 (d, J=16.5 Hz, 1H), 4.08 (q, J=6.6 Hz, 1H), 4.20-4.30 (m, 1H), 4.40-4.50 (m, 1H), 4.96 (quint., J=6.3 Hz, 1H), 5.01 (brs, 1H), 5.34 (brs, 1H), 5.60 (brs, 1H), 6.10 (d, J=11.5 Hz, 1H), 6.38 (d, J=11.5 Hz, 1H). MS m/z: 312 (M$^+$-CH$_3$CO$_2$CH(CH$_2$CH$_2$CH$_2$CH$_3$)$_2$), 57 (100%). UV λ$_{max}$nm: 263.

Example 35

(1) Preparation of 1α,3β-bis(tert-butyldimethylsilyloxy)-20(S)-(1,1-dimethylpropoxycarbonylmethoxy)-9,10-secopregna-5,7,10(19),16-tetraene

[{1α,3β-Bis(tert-butyldimethylsilyloxy)-9,10-secopregna-5,7,10(19),16-tetraen-20(S)-yl}oxy]acetic acid (13.0 mg, 0.021 mmol) was treated with tert-amyl alcohol (7.0 mg, 0.079 mmol), N,N'-dicyclohexylcarbodiimide (7.0 mg, 0.034 mmol) and 4-(dimethylamino)pyridine (3.0 mg, 0.025 mmol) in dichloromethane (0.2 ml) in the same manner as shown in Example 17(3) (at room temperature for 1 hour), followed by work up and purification using preparative thin layer chromatography (0.5 mm×1 plate, hexane:ethyl acetate=15:1, developed twice) to give a mixture (9.2 mg) containing the titled compound.

(2) Preparation of 1α,3β-dihydroxy-20(S)-(1,1-dimethylpropoxycarbonylmethoxy)-9,10-secopregna-5,7,10(19),16-tetraene The mixture containing 1α,3β-bis(tert-butyldimethylsilyloxy)-20(S)-(1,1-dimethylpropoxycarbonylmethoxy)-9,10-secopregna-5,7,10(19),16-tetraene from Example 35(1) (10.0 mg) was treated with a 1M tetrahydrofuran solution of tetra-n-butylammonium fluoride (0.15 ml) in the same manner as shown in Example 17(4) (at an external temperature of 45° C. for 40 minutes). The reaction mixture was purified by preparative thin layer chromatography (0.5 mm×1 plate, dichloromethane:ethanol=15:1, developed once, dichloromethane:ethanol=10:1, developed once) to give the titled compound (3.6 mg, 34% for 2 steps) as a colorless oil.

IR(neat): 3392, 2972, 2932, 2848, 1744, 1444, 1370, 1220, 1122, 1054 cm$^{-1}$. $^1$H NMR δ: 0.77 (s, 3H), 0.87 (t, J=7.4 Hz, 3H), 1.36 (d, J=6.5 Hz, 3H), 1.43 (s, 6H), 2.55-2.66 (m, 1H), 2.76-2.87 (m, 1H), 3.82 (d, J=16.3 Hz, 1H), 3.94 (d, J=16.3 Hz, 1H), 4.07 (q, J=6.5 Hz, 1H), 4.19-4.29 (m, 1H), 4.39-4.49 (m, 1H), 5.01 (brs, 1H), 5.34 (brs, 1H), 5.60 (brs, 1H), 6.10 (d, J=11.8 Hz, 1H), 6.37 (d, J=11.8 Hz, 1H). MS m/z: 312 (M$^+$-CH$_3$CO$_2$C(CH$_3$)$_2$CH$_2$CH$_3$), 71 (100%). UV λ$_{max}$nm: 263.

Example 36

(1) Preparation of 1α,3β-bis(tert-butyldimethylsilyloxy)-20(S)-(adamantan-2-yloxycarbonylmethoxy)-9,10-secopregna-5,7,10(19),16-tetraene

[{1α,3β-Bis(tert-butyldimethylsilyloxy)-9,10-secopregna-5,7,10(19),16-tetraen-20(S)-yl}oxy]acetic acid (30 mg, 0.048 mmol) was treated with 2-adamantanol (12 mg, 0.0768 mmol), N,N'-dicyclohexylcarbodiimide (16 mg, 0.0768 mmol) and 4-(dimethylamino)pyridine (6 mg, 0.048 mmol) in dichloromethane (1.0 ml) in the same manner as shown in Example 17(3) (at room temperature for 14 hours), followed by work up and purification using preparative thin layer chromatography (0.5 mm×1 plate, hexane:ethyl acetate=6:1, developed once) to give a mixture (15.0 mg) containing the titled compound.

(2) Preparation of 1α,3β-dihydroxy-20(S)-(adamantan-2-yloxycarbonylmethoxy)-9,10-secopregna-5,7,10(19),16-tetraene The mixture containing 1α,3β-bis(tert-butyldimethylsilyloxy)-20(S)-(adamantan-2-yloxycarbonylmethoxy)-9,10-secopregna-5,7,10(19),16-tetraene from Example 36(1) (15.0 mg) was treated in tetrahydrofuran (1.0 ml) with a 1M tetrahydrofuran solution of tetra-n-butylammonium fluoride (1.0 ml) in the same manner as shown in Example 17(4) (at an external temperature of 45° C. for 1 hour), followed by work up. The resulting residue was purified by preparative thin layer chromatography (0.5 mm×1 plate, hexane:ethyl acetate:ethanol=10:10:1, developed twice) to give the titled compound (1.024 mg, 4% for 2 steps) as a colorless oil.

IR(neat): 3325, 2927, 2850, 1626, 1576, 1448, 1122, 1045 cm$^{-1}$. $^1$H NMR δ: 0.78 (s, 3H), 2.56-2.67 (m, 1H), 2.77-2.87 (m, 1H), 3.92-4.17 (m, 3H), 4.20-4.30 (m, 1H), 4.40-4.50 (m, 1H), 4.98-5.04 (m, 2H), 5.34 (s, 1H), 5.62 (brs, 1H), 6.11 (d, J=11.6 Hz, 1H), 6.38 (d, J=11.6 Hz, 1H). MS m/z: 504 (M$^+$-H$_2$O), 135 (100%). UV λ$_{max}$nm: 263.

Example 37

(1) Preparation of 1α,3β-bis(tert-butyldimethylsilyloxy)-20(S)-(1,1-dimethylpentyloxycarbonylmethoxy)-9,10-secopregna-5,7,10(19),16-tetraene

[{1α,3β-Bis(tert-butyldimethylsilyloxy)-9,10-secopregna-5,7,10(19),16-tetraen-20(S)-yl}oxy]acetic acid (26 mg, 0.042 mmol) was treated with 2-methyl-2-hexanol (0.1 ml, 0.699 mmol), N,N'-dicyclohexylcarbodiimide (14 mg, 0.067 mmol) and 4-(dimethylamino)pyridine (5 mg, 0.042 mmol) in tetrahydrofuran (1.0 ml) in the same manner as shown in Example 17(3) (at room temperature for 14 hours), followed by work up and purification using preparative thin layer chromatography (0.5 mm×1 plate, hexane:ethyl acetate=6:1, developed once) to give a mixture (15.0 mg) containing the titled compound.

(2) Preparation of 1α,3β-dihydroxy-20(S)-(1,1-dimethylpentyloxycarbonylmethoxy)-9,10-secopregna-5,7,10(19),16-tetraene The mixture containing 1α,3β-bis(tert-butyldimethylsilyloxy)-20(S)-(1,1-dimethylpentyloxycarbonylmethoxy)-9,10-secopregna-5,7,10(19),16-tetraene from Example 37(1) (15.0 mg) was treated in tetrahydrofuran (1.0 ml) with a 1M tetrahydrofuran solution of tetra-n-butylammonium fluoride (1.0 ml) in the same manner as shown in Example 17(4) (at an external temperature of 45° C. for 1 hour) and then worked up. The resulting residue was purified by preparative thin layer chromatography (0.5 mm×1 plate, hexane:ethyl acetate:ethanol=10:10:1, developed twice) to give the titled compound (1.784 mg, 9% for 2 steps) as a colorless oil.

IR(neat): 3323, 2927, 2852, 1749, 1626, 1558, 1448, 1254, 1209, 1122, 1053 cm$^{-1}$. $^1$H NMR δ: 0.78 (s, 3H), 0.90 (t, J=7.0 Hz, 3H), 1.36 (d, J=6.8 Hz, 3H), 2.55-2.66 (m, 1H), 2.77-2.88 (m, 1H), 3.82 (d, J=16.2 Hz, 1H), 3.94 (d, J=16.2 Hz, 1H), 3.99-4.12 (m, 1H), 4.20-4.29 (m, 1H), 4.41-4.50 (m, 1H), 5.01 (s, 1H), 5.34 (s, 1H), 5.60 (brs, 1H), 6.11 (d, J=11.3 Hz, 1H), 6.37 (d, J=11.3 Hz, 1H). MS m/z: 468 (M$^+$-H$_2$O), 57 (100%). UV $\lambda_{max}$nm: 262.

Example 38

(1) Preparation of 1α,3β-bis(tert-butyldimethylsilyloxy)-20(S)-(1,1,2-trimethylpropoxycarbonylmethoxy)-9,10-secopregna-5,7,10(19),16-tetraene

[{1α,3β-Bis(tert-butyldimethylsilyloxy)-9,10-secopregna-5,7,10(19),16-tetraen-20(S)-yl}oxy]acetic acid (20.5 mg, 0.033 mmol) was treated with 2,3-dimethylbutan-2-ol (7.5 mg, 0.073 mmol), N,N'-dicyclohexylcarbodiimide (18.0 mg, 0.087 mmol) and 4-(dimethylamino)pyridine (6.8 mg, 0.056 mmol) in dichloromethane (1.0 ml) in the same manner as shown in Example 17(3) (at room temperature for 16 hours), followed by work up and purification using preparative thin layer chromatography (0.5 mm×3 plates, hexane:ethyl acetate=15:1, developed once) to give a mixture (6.6 mg) containing the titled compound.

(2) Preparation of 1α,3β-dihydroxy-20(S)-(1,1,2-trimethylpropoxycarbonylmethoxy)-9,10-secopregna-5,7,10(19),16-tetraene The mixture containing 1α,3β-bis(tert-butyldimethylsilyloxy)-20(S)-(1,1,2-trimethylpropoxycarbonylmethoxy)-9,10-secopregna-5,7,10(19),16-tetraene from Example 38(1) (6.0 mg) was treated with a 1M tetrahydrofuran solution of tetra-n-butylammonium fluoride (0.1 ml) in the same manner as shown in Example 17(4) (at an external temperature of 45° C. for 20 minutes). The reaction mixture was purified by preparative thin layer chromatography (0.5 mm×1 plate, dichloromethane:ethanol=15:1, developed once) to give the titled compound (1.6 mg, 10% for 2 steps) as a colorless oil.

IR(neat): 3384, 2972, 2932, 2852, 1744, 1444, 1372, 1218, 1124, 1054 cm$^{-1}$. $^1$H NMR δ: 0.77 (s, 3H), 0.89 (d, J=7.2 Hz, 6H), 1.36 (d, J=6.7 Hz, 3H), 1.41 (s, 3H), 1.42 (s, 3H), 2.54-2.66 (m, 1H), 2.76-2.87 (m, 1H), 3.82 (d, J=16.5 Hz, 1H), 3.94 (d, J=16.5 Hz, 1H), 4.07 (q, J=6.7 Hz, 1H), 4.18-4.29 (m, 1H), 4.41-4.49 (m, 1H), 5.01 (brs, 1H), 5.34 (s, 1H), 5.59 (brs, 1H), 6.11 (d, J=11.0 Hz, 1H), 6.37 (d, J=11.0 Hz, 1H). MS m/z: 387 (M$^+$-CH(CH$_3$)$_2$CH(CH$_3$)$_2$), 85 (100%), 85 (100%). UV $\lambda_{max}$nm: 263.

Example 39

(1) Preparation of 1α,3β-bis(tert-butyldimethylsilyloxy)-20(S)-(1-ethylcyclohexyloxycarbonylmethoxy)-9,10-secopregna-5,7,10(19),16-tetraene

[{1α,3β-Bis(tert-butyldimethylsilyloxy)-9,10-secopregna-5,7,10(19),16-tetraen-20(S)-yl}oxy]acetic acid (27 mg, 0.044 mmol) was treated with 1-ethylcyclohexanol (17 mg, 0.133 mmol), N,N'-dicyclohexylcarbodiimide (18 mg, 0.087 mmol) and 4-(dimethylamino)pyridine (16 mg, 0.131 mmol) in dichloromethane (0.4 ml) in the same manner as shown in Example 17(3) (at room temperature for 15 hours), followed by work up and purification using preparative thin layer chromatography (0.5 mm×2 plates, hexane:ethyl acetate=5:1, developed once) to give a mixture (25 mg) containing the titled compound.

(2) Preparation of 1α,3β-dihydroxy-20(S)-(1-ethylcyclohexyloxycarbonylmethoxy)-9,10-secopregna-5,7,10(19),16-tetraene The mixture containing 1α,3β-bis(tert-butyldimethylsilyloxy)-20(S)-(1-ethylcyclohexyloxycarbonylmethoxy)-9,10-secopregna-5,7,10(19),16-tetraene from Example 39(1) (25 mg) was treated in tetrahydrofuran (0.66 ml) with a 1M tetrahydrofuran solution of tetra-n-butylammonium fluoride (0.33 ml) in the same manner as shown in Example 17(4) (at an external temperature of 60° C. for 1.5 hours) and then worked up. The resulting residue was purified by preparative thin layer chromatography (0.5 mm×2 plates, dichloromethane:ethyl acetate:ethanol=10:10:1, developed once) to give the titled compound (7.157 mg, 33% for 2 steps) as a colorless glass.

IR(neat): 3380, 2931, 2852, 1745, 1448, 1211, 1122, 1053 cm$^{-1}$. $^1$H NMR δ: 0.78 (s, 3H), 0.82 (t, J=7.6 Hz, 3H), 1.37 (d, J=6.4 Hz, 3H), 2.57-2.62 (m, 1H), 2.78-2.84 (m, 1H), 3.86 (d, J=16.3 Hz, 1H), 3.99 (d, J=16.3 Hz, 1H), 4.09-4.20 (m, 1H), 4.20-4.30 (m, 1H), 4.40-4.49 (m, 1H), 5.01 (brs, 1H), 5.34 (s, 1H), 5.60 (brs, 1H), 6.11 (d, J=11.4 Hz, 1H), 6.37 (d, J=11.4 Hz, 1H). MS m/z: 312 (M$^+$-HOCH$_2$CO$_2$C$_8$H$_{15}$), 69 (100%). UV $\lambda_{max}$nm: 264.

Example 40

(1) Preparation of 1α,3β-bis(tert-butyldimethylsilyloxy)-20(S)-(1-methylcyclooctyloxycarbonylmethoxy)-9,10-secopregna-5,7,10(19),16-tetraene

[{1α,3β-Bis(tert-butyldimethylsilyloxy)-9,10-secopregna-5,7,10(19),16-tetraen-20(S)-yl}oxy]acetic acid (19 mg, 0.031 mmol) was treated with 1-methylcyclooctanol (13 mg, 0.091 mmol), N,N'-dicyclohexylcarbodiimide (13 mg, 0.063 mmol) and 4-(dimethylamino)pyridine (11 mg, 0.090 mmol) in dichloromethane (0.3 ml) in the same manner as shown in Example 17(3) (at room temperature for 15 hours), followed by work up and purification using preparative thin layer chromatography (0.5 mm×2 plates, hexane:ethyl acetate=5:1, developed once) to give a mixture (15 mg) containing the titled compound.

(2) Preparation of 1α,3β-dihydroxy-20(S)-(1-methylcyclooctyloxycarbonylmethoxy)-9,10-secopregna-5,7,10(19),16-tetraene The mixture containing 1α,3β-bis(tert-butyldimethylsilyloxy)-20(S)-(1-methylcyclooctyloxycarbonylmethoxy)-9,10-secopregna-5,7,10(19),16-tetraene from Example 40(1) (15 mg) was treated in tetrahydrofuran (0.46 ml) with a 1M tetrahydrofuran solution of tetra-n-butylammonium fluoride (0.23 ml) in the same manner as shown in Example 17(4) (at an external temperature of 60° C. for 1.5 hours) and then worked up. The resulting residue was purified by preparative thin layer chromatography (0.5 mm×2 plates, dichloromethane:ethyl acetate:ethanol=10:10:1, developed once) to give the titled compound (5.527 mg, 35% for 2 steps) as a colorless foam.

IR(neat): 3390, 2927, 2852, 1743, 1448, 1373, 1205, 1115, 1053 cm$^{-1}$. $^1$H NMR δ: 0.77 (s, 3H), 1.36 (d, J=6.4 Hz, 3H), 2.57-2.63 (m, 1H), 2.79-2.84 (m, 1H), 3.81 (d, J=16.3 Hz, 1H), 3.94 (d, J=16.3 Hz, 1H), 4.04-4.16 (m, 1H), 4.20-4.30 (m, 1H), 4.40-4.49 (m, 1H), 5.01 (brs, 1H), 5.34 (s, 1H), 5.60 (brs, 1H), 6.11 (d, J=11.2 Hz, 1H), 6.37 (d, J=11.2 Hz, 1H). MS m/z: 312 (M$^+$-HOCH$_2$CO$_2$C$_9$H$_{17}$), 69 (100%). UV $\lambda_{max}$nm: 263.

Example 41

(1) Preparation of 1α,3β-bis(tert-butyldimethylsilyloxy)-20(S)-{4-methyl-1-(3-methylbutyl)pentyloxycarbonylmethoxy}-9,10-secopregna-5,7,10(19),16-tetraene

[{1α,3β-Bis(tert-butyldimethylsilyloxy)-9,10-secopregna-5,7,10(19),16-tetraen-20(S)-yl}oxy]acetic acid (26 mg, 0.042 mmol) was treated with 2,8-dimethyl-5-nonanol (0.1 g, 0.580 mmol), N,N'-dicyclohexylcarbodiimide (14 mg, 0.067 mmol) and 4-(dimethylamino)pyridine (5 mg, 0.042 mmol) in dichloromethane (1.0 ml) in the same manner as shown in Example 17(3) (at room temperature for 14 hours), followed by work up and purification using preparative thin layer chromatography (0.5 mm×1 plate, hexane:ethyl acetate=6:1, developed once) to give a mixture (30.0 mg) containing the titled compound.

(2) Preparation of 1α,3β-dihydroxy-20(S)-{4-methyl-1-(3-methylbutyl)pentyloxycarbonylmethoxy}-9,10-secopregna-5,7,10(19),16-tetraene The mixture containing 1α,3β-bis(tert-butyldimethylsilyloxy)-20(S)-{4-methyl-1-(3-methylbutyl)pentyloxycarbonylmethoxy}-9,10-secopregna-5,7,10(19),16-tetraene from Example 41 (1) (30.0 mg) was treated in tetrahydrofuran (1.0 ml) with a 1M tetrahydrofuran solution of tetra-n-butylammonium fluoride (0.8 ml) in the same manner as shown in Example 17(4) (at an external temperature of 50° C. for 1 hour) and then worked up. The resulting residue was purified by preparative thin layer chromatography (0.5 mm×1 plate, hexane:ethyl acetate:ethanol=10:10:1, developed twice) to give the titled compound (8.820 mg, 39% for 2 steps) as a colorless oil.

IR(neat): 2953, 2931, 2870, 2852, 1749, 1732, 1653, 1558, 1468, 1367, 1201, 1122, 1053 cm$^{-1}$. $^1$H NMR δ: 0.78 (s, 3H), 0.86 (t, J=6.4 Hz, 12H), 1.37 (d, J=6.5 Hz, 3H), 2.54-2.67 (m, 1H), 2.76-2.90 (m, 1H), 3.93 (d, J=17.6 Hz, 1H), 4.04 (d, J=17.6 Hz, 1H), 4.09 (q, J=6.8 Hz, 1H), 4.20-4.29 (m, 1H), 4.41-4.49 (m, 1H), 4.86-4.98 (m, 1H), 5.01 (s, 1H), 5.34 (s, 1H), 5.61 (brs, 1H), 6.11 (d, J=10.8 Hz, 1H), 6.38 (d, J=10.8 Hz, 1H). MS m/z: 524 (M$^+$-H$_2$O), 57 (100%). UV λ$_{max}$nm: 264.

Example 42

(1) Preparation of 1α,3β-bis(tert-butyldimethylsilyloxy)-20(S)-(1,1,2,2-tetramethylpropyloxycarbonylmethoxy)-9,10-secopregna-5,7,10(19),16-tetraene

[{1α,3β-Bis(tert-butyldimethylsilyloxy)-9,10-secopregna-5,7,10(19),16-tetraen-20(S)-yl}oxy]acetic acid (26 mg, 0.042 mmol) was treated with 1,1,2,2-tetramethylpropanol (0.1 g, 0.861 mmol), N,N'-dicyclohexylcarbodiimide (14 mg, 0.067 mmol) and 4-(dimethylamino)pyridine (5 mg, 0.042 mmol) in dichloromethane (1.0 ml) in the same manner as shown in Example 17(3) (at room temperature for 14 hours), followed by work up and purification using preparative thin layer chromatography (0.5 mm×1 plate, hexane:ethyl acetate=6:1, developed once) to give a mixture (25.0 mg) containing the titled compound.

(2) Preparation of 1α,3β-dihydroxy-20(S)-(1,1,2,2-tetramethylpropyloxycarbonylmethoxy)-9,10-secopregna-5,7,10(19),16-tetraene The mixture containing 1α,3β-bis(tert-butyldimethylsilyloxy)-20(S)-(1,1,2,2-tetramethylpropyloxycarbonylmethoxy)-9,10-secopregna-5,7,10(19),16-tetraene from Example 42 (1) (25.0 mg) was treated in tetrahydrofuran (1.0 ml) with a 1M tetrahydrofuran solution of tetra-n-butylammonium fluoride (0.8 ml) in the same manner as shown in Example 17(4) (at an external temperature of 50° C. for 1 hour) and then worked up. The resulting residue was purified by preparative thin layer chromatography (0.5 mm×1 plate, hexane:ethyl acetate:ethanol=10:10:1, developed twice) to give the titled compound (1.558 mg, 8% for 2 steps) as a colorless oil.

IR(neat): 2960, 2929, 2850, 1747, 1724, 1371, 1120, 1053 cm$^{-1}$. $^1$H NMR δ: 0.77 (s, 3H), 0.96 (s, 9H), 1.36 (d, J=6.5 Hz, 3H), 2.54-2.66 (m, 1H), 2.75-2.88 (m, 1H), 3.81 (d, J=16.2 Hz, 1H), 3.94 (d, J=16.2 Hz, 1H), 4.08 (q, J=5.9 Hz, 1H), 4.19-4.30 (m, 1H), 4.40-4.49 (m, 1H), 5.02 (s, 1H), 5.34 (s, 1H), 5.60 (brs, 1H), 6.11 (d, J=11.3 Hz, 1H), 6.37 (d, J=11.3 Hz, 1H). MS m/z: 387 (M$^+$-C$_7$H$_{15}$), 57 (100%). UV λ$_{max}$nm: 264.

Example 43

(1) Preparation of 1α,3β-bis(tert-butyldimethylsilyloxy)-20(S)-(1-ethylcyclopentyloxycarbonylmethoxy)-9,10-secopregna-5,7,10(19),16-tetraene

[{1α,3β-Bis(tert-butyldimethylsilyloxy)-9,10-secopregna-5,7,10(19),16-tetraen-20(S)-yl}oxy]acetic acid (22.0 mg, 0.036 mmol) was treated with 1-ethylcyclopentanol (11.3 mg, 0.099 mmol), N,N'-dicyclohexylcarbodiimide (13.1 mg, 0.064 mmol) and 4-(dimethylamino)pyridine (4.7 mg, 0.039 mmol) in dichloromethane (0.5 ml) in the same manner as shown in Example 17(3) (at room temperature for 4 hours), followed by work up and purification using preparative thin layer chromatography (0.5 mm×3 plates, hexane:ethyl acetate=15:1, developed once) to give a mixture (13.5 mg) containing the titled compound.

(2) Preparation of 1α,3β-dihydroxy-20(S)-(1-ethylcyclopentyloxycarbonylmethoxy)-9,10-secopregna-5,7,10(19),16-tetraene The mixture containing 1α,3β-bis(tert-butyldimethylsilyloxy)-20(S)-(1-ethylcyclopentyloxycarbonylmethoxy)-9,10-secopregna-5,7,10(19),16-tetraene from Example 43 (1) (12.5 mg) was treated with a 1M tetrahydrofuran solution of tetra-n-butylammonium fluoride (0.2 ml) in the same manner as shown in Example 17(4) (at an external temperature of 45° C. for 20 minutes). The reaction mixture was purified by preparative thin layer chromatography (0.5 mm×2 plates, dichloromethane:ethanol=15:1, developed twice) to give the titled compound (4.2 mg, 26% for 2 steps) as a colorless oil.

IR(neat): 3400, 2932, 2876, 1742, 1446, 1370, 1218, 1120, 1054 cm$^{-1}$. $^1$H NMR δ: 0.77 (s, 3H), 0.85 (t, J=7.4 Hz, 3H), 1.36 (d, J=6.6 Hz, 3H), 2.55-2.64 (m, 1H), 2.76-2.89 (m, 1H), 3.84 (d, J=16.3 Hz, 1H), 3.96 (d, J=16.3 Hz, 1H), 4.08 (q, J=6.6 Hz, 1H), 4.19-4.30 (m, 1H), 4.40-4.50 (m, 1H), 5.01 (brs, 1H), 5.34 (brs, 1H), 5.59 (brs, 1H), 6.10 (d, J=11.1 Hz, 1H), 6.37 (d, J=11.1 Hz, 1H). MS m/z: 484 (M$^+$), 55 (100%). UV λ$_{max}$nm: 263.

Example 44

(1) Preparation of 1α,3β-bis(tert-butyldimethylsilyloxy)-20(S)-(1-cyclopropyl-1-methylethoxycarbonylmethoxy)-9,10-secopregna-5,7,10(19),16-tetraene

[{1α,3β-Bis(tert-butyldimethylsilyloxy)-9,10-secopregna-5,7,10(19),16-tetraen-20(S)-yl}oxy]acetic acid (58.4 mg, 0.095 mmol) was treated with 2-cyclopropyl-2-propanol (29 mg, 0.290 mmol), N,N'-dicyclohexylcarbodiimide (39 mg, 0.189 mmol) and 4-(dimethylamino)pyridine (35 mg, 0.286 mmol) in dichloromethane (0.95 ml) in the same manner as shown in Example 17(3) (at room temperature for 15 hours), followed by work up and purification using column chromatography (hexane:ethyl acetate=10:1) to give a mixture(54 mg) containing the titled compound.

(2) Preparation of 1α,3β-dihydroxy-20(S)-(1-cyclopropyl-1-methylethoxycarbonylmethoxy)-9,10-secopregna-5,7,10(19),16-tetraene The mixture containing 1α,3β-bis(tert-butyldimethylsilyloxy)-20(S)-(1-cyclopropyl-1-methylethoxycarbonylmethoxy)-9,10-secopregna-5,7,10(19),16-tetraene from Example 44 (1) (49 mg) was treated in tetrahydrofuran (1.4 ml) with a 1M tetrahydrofuran solution of tetra-n-butylammonium fluoride (0.7 ml) in the same manner as shown in Example 17(4) (at an external temperature of 60° C. for 2 hours) and then worked up. The resulting residue was purified by preparative thin layer chromatography (0.5 mm×4 plates, hexane:ethyl acetate:ethanol=10:10:1, developed once and then 0.5 mm×2 plates, toluene:ethyl acetate=5:6, developed once) to give the titled compound (3.561 mg, 9% for 2 steps) as a colorless foam.

IR(neat): 3388, 2972, 2931, 2850, 1745, 1442, 1371, 1221, 1119, 1053 cm$^{-1}$. $^1$H NMR δ: 0.40-0.49 (m, 4H), 0.77 (s, 3H), 2.21-2.45 (m, 3H), 2.57-2.62 (m, 1H), 2.79-2.84 (m, 1H), 3.81 (d, J=16.3 Hz, 1H), 3.93 (d, J=16.3 Hz, 1H), 4.03-4.22 (m, 1H), 4.20-4.30 (m, 1H), 4.40-4.50 (m, 1H), 5.01 (brs, 1H), 5.34 (s, 1H), 5.60 (brs, 1H), 6.10 (d, J=11.3 Hz, 1H), 6.37 (d, J=11.3 Hz, 1H). MS m/z: 312 (M$^+$-HOCH$_2$CO$_2$C$_6$H$_{11}$), 83 (100%). UV λ$_{max}$nm: 264.

Example 45

(1) Preparation of 1α,3β-bis(tert-butyldimethylsilyloxy)-20(S)-(1,1,2-trimethylpropoxycarbonylmethoxy)-9,10-secopregna-5,7,10(19),16-tetraene

[{1α,3β-Bis(tert-butyldimethylsilyloxy)-9,10-secopregna-5,7,10(19),16-tetraen-20(S)-yl}oxy]acetic acid (43.1 mg, 0.070 mmol) was treated with 2,4-dimethyl-2-pentanol (0.1 g, 0.861 mmol), N,N'-dicyclohexylcarbodiimide (23 mg, 0.112 mmol) and 4-(dimethylamino)pyridine (10 mg, 0.070 mmol) in dichloromethane (1.0 ml) in the same manner as shown in Example 17(3) (at room temperature for 14 hours), followed by work up and purification using preparative thin layer chromatography (0.5 mm×2 plates, hexane:ethyl acetate=6:1, developed twice) to give a mixture (28.0 mg) containing the titled compound. (2) Preparation of 1α,3β-dihydroxy-20(S)-(1,1,2-trimethylpropoxycarbonylmethoxy)-9,10-secopregna-5,7,10(19),16-tetraene The mixture containing 1α,3β-bis(tert-butyldimethylsilyloxy)-20(S)-(1,1,2-trimethylpropoxycarbonylmethoxy)-9,10-secopregna-5,7,10(19),16-tetraene from Example 45 (1) (28.0 mg) was treated in tetrahydrofuran (1.0 ml) with a 1M tetrahydrofuran solution of tetra-n-butylammonium fluoride (1.0 ml) in the same manner as shown in Example 17(4) (at an external temperature of 50° C. for 1 hour) and then worked up. The resulting residue was purified by preparative thin layer chromatography (0.5 mm×2 plates, hexane:ethyl acetate:ethanol=5:5:1, developed once) and then another run of preparative thin layer chromatography (0.5 mm×1 plate, dichloromethane:methanol=20:1, developed once) to give the titled compound (2.195 mg, 7% for 2 steps) as a colorless oil.

IR(neat): 2952, 2929, 1747, 1456, 1369, 1215, 1124, 1053 cm$^{-1}$. $^1$H NMR δ: 0.77 (s, 3H), 0.93 (d, J=6.5 Hz, 6H), 1.36 (d, J=6.8 Hz, 3H), 2.56-2.66 (m, 1H), 2.77-2.87 (m, 1H), 3.80 (d, J=16.2 Hz, 1H), 3.92 (d, J=16.2 Hz, 1H), 4.07 (q, J=6.2 Hz, 1H), 4.20-4.30 (m, 1H), 4.40-4.50 (m, 1H), 5.02 (s, 1H), 5.34 (s, 1H), 5.60 (brs, 1H), 6.11 (d, J=11.1 Hz, 1H), 6.38 (d, J=11.1 Hz, 1H). MS m/z: 468 (M$^+$-H$_2$O), 57 (100%). UV λ$_{max}$nm: 264.

Example 46

(1) Preparation of 1α,3β-bis(tert-butyldimethylsilyloxy)-20(S)-(1-methylcycloheptyloxycarbonylmethoxy)-9,10-secopregna-5,7,10(19),16-tetraene

[{1α,3β-Bis(tert-butyldimethylsilyloxy)-9,10-secopregna-5,7,10(19),16-tetraen-20(S)-yl}oxy]acetic acid (29.4 mg, 0.048 mmol) was treated with 1-methylcycloheptanol (11.3 mg, 0.088 mmol), N,N'-dicyclohexylcarbodiimide (29.0 mg, 0.141 mmol) and 4-(dimethylamino)pyridine (6.9 mg, 0.056 mmol) in dichloromethane (0.6 ml) in the same manner as shown in Example 17(3) (at room temperature for 14 hours), followed by work up and purification using preparative thin layer chromatography (0.5 mm×3 plates, hexane:ethyl acetate=15:1, developed twice) to give a mixture (10.4 mg) containing the titled compound.

(2) Preparation of 1α,3β-dihydroxy-20(S)-(1-methylcycloheptyloxycarbonylmethoxy)-9,10-secopregna-5,7,10(19),16-tetraene The mixture containing 1α,3β-bis(tert-butyldimethylsilyloxy)-20(S)-(1-methylcycloheptyloxycarbonylmethoxy)-9,10-secopregna-5,7,10(19),16-tetraene from Example 46 (1) (9.3 mg) was treated with a 1M tetrahydrofuran solution of tetra-n-butylammonium fluoride (0.15 ml) in the same manner as shown in Example 17(4) (at an external temperature of 48° C. for 20 minutes). The reaction mixture was purified by preparative thin layer chromatography (0.5 mm×2 plates, dichloromethane:ethanol=15:1, developed twice and then 0.25 mm×1 plate, hexane:ethyl acetate:ethanol=10:5:1, developed twice) to give the titled compound (3.0 mg, 14% for 2 steps) as a colorless oil.

IR(neat): 3376, 2928, 2852, 1744, 1444, 1372, 1220, 1122, 1050 cm$^1$. $^1$H NMR δ: 0.77 (s, 3H), 1.36 (d, J=6.5 Hz, 3H), 2.54-2.65 (m, 1H), 2.75-2.87 (m, 1H), 3.83 (d, J=16.5 Hz, 1H), 3.95 (d, J=16.5 Hz, 1H), 4.08 (q, J=6.5 Hz, 1H), 4.19-4.29 (m, 1H), 4.40-4.49 (m, 1H), 5.01 (brs, 1H), 5.34 (brs, 1H), 5.60 (brs, 1H), 6.10 (d, J=12.1 Hz, 1H), 6.37 (d, J=12.1 Hz, 1H). MS m/z: 387 (M$^+$-C$_8$H$_{15}$), 67 (100%). UV λ$_{max}$nm: 264.

Example 47

(1) Preparation of 1α,3β-bis(tert-butyldimethylsilyloxy)-20(S)-{3,3-dimethyl-1-(2,2-dimethylpropyl)butoxycarbonylmethoxy}-9,10-secopregna-5,7,10(19),16-tetraene

[{1α,3β-Bis(tert-butyldimethylsilyloxy)-9,10-secopregna-5,7,10(19),16-tetraen-20(S)-yl}oxy]acetic acid (30 mg, 0.049 mmol) was treated with 2,2,6,6-tetramethyl-heptan-4-ol (26 mg, 0.156 mmol), N,N'-dicyclohexylcarbodiimide (16 mg, 0.078 mmol) and 4-(dimethylamino)pyridine (6.0 mg, 0.049 mmol) in dichloromethane (0.5 ml) in the same manner as shown in Example 17(3) (at room temperature for 2 hours), followed by work up and purification using preparative thin layer chromatography (0.5 mm×3 plates, hexane:ethyl acetate 10:1, developed once) to give a mixture (20.0 mg) containing the titled compound.

(2) Preparation of 1α,3β-dihydroxy-20(S)-{3,3-dimethyl-1-(2,2-dimethylpropyl)butoxycarbonylmethoxy}-9,10-secopregna-5,7,10(19),16-tetraene The mixture containing 1α,3β-bis(tert-butyldimethylsilyloxy)-20(S)-{3,3-dimethyl-1-(2,2-dimethylpropyl)butoxycarbonylmethoxy}-9,10-secopregna-5,7,10(19),16-tetraene from Example 47 (1) (20 mg) was treated in tetrahydrofuran (0.52 ml) with a 1M tetrahydrofuran solution of tetra-n-butylammonium fluoride (0.26 ml) in the same manner as shown in Example 17(4) (at an external temperature of 60° C. for 2 hours) and then worked up. The resulting residue was purified by preparative thin layer chromatography (0.5 mm×2 plates, dichloromethane:ethanol=20:1, developed twice) to give the titled compound (12.122 mg, 45.6% for 2 steps) as a colorless oil.

IR(neat): 3390, 2952, 2869, 2852, 1747, 1727, 1367, 1191, 1126, 1051 cm$^{-1}$. $^1$H NMR δ: 0.76 (s, 3H), 0.91 (s, 6H), 0.92 (s, 6H), 1.37 (d, J=6.4 Hz, 3H), 2.17-2.47 (m, 3H), 2.55-2.66 (m, 1H), 2.76-2.88 (m, 1H), 3.84 (d, J=16.7 Hz, 1H), 3.96 (d, J=16.5 Hz, 1H), 4.09 (q, J=6.4 Hz, 1H), 4.18-4.30 (m, 1H), 4.41-4.49 (m, 1H), 5.01 (brs, 1H), 5.16-5.27 (m, 1H), 5.34 (brs, 1H), 5.58 (brs, 1H), 6.10 (d, J=11.4 Hz, 1H), 6.37 (d, J=11.2 Hz, 1H). MS m/z: 527 (M$^+$-Me), 57 (100%). UV λ$_{max}$nm: 264.

Example 48

(1) Preparation of 1α,3β-bis(tert-butyldimethylsilyloxy)-20(S)-(1,1,3,3-tetramethylbutoxycarbonylmethoxy)-9,10-secopregna-5,7,10(19),16-tetraene

[{1α,3β-Bis(tert-butyldimethylsilyloxy)-9,10-secopregna-5,7,10(19),16-tetraen-20(S)-yl}oxy]acetic acid (63.1 mg, 0.102 mmol) was treated with 2,4,4-trimethylpentan-2-ol (21.5 mg, 0.165 mmol), N,N'-dicyclohexylcarbodiimide (34.0 mg, 0.165 mmol) and 4-(dimethylamino)pyridine (12.5 mg, 0.102 mmol) in dichloromethane (1.5 ml) in the same manner as shown in Example 17(3) (at room temperature for 15 hours), followed by work up and purification using preparative thin layer chromatography (0.5 mm×4 plates, hexane:ethyl acetate=15:1, developed twice) to give a mixture (7.7 mg) containing the titled compound.

(2) Preparation of 1α,3β-dihydroxy-20(S)-(1,1,3,3-tetramethylbutoxycarbonylmethoxy)-9,10-secopregna-5,7,10(19),16-tetraene The mixture containing 1α,3β-bis(tert-butyldimethylsilyloxy)-20(S)-(1,1,3,3-tetramethylbutoxycarbonylmethoxy)-9,10-secopregna-5,7,10(19),16-tetraene from Example 48 (1) (7.7 mg) was treated with a 1M tetrahydrofuran solution of tetra-n-butylammonium fluoride (0.1 ml) in the same manner as shown in Example 17(4) (at an external temperature of 43° C. for 30 minutes). The reaction mixture was purified by preparative thin layer chromatography (0.5 mm×1 plate, dichloromethane:ethanol=15:1, developed once) to give the titled compound (2.0 mg, 4% for 2 steps) as a colorless oil.

IR(neat): 3400, 2932, 1744, 1444, 1368, 1220, 1112, 1054 cm$^{-1}$. $^1$H NMR δ: 0.77 (s, 3H), 0.99 (s, 9H), 1.36 (d, J=6.6 Hz, 3H), 1.52 (s, 6H), 1.80 (s, 2H), 2.55-2.66 (m, 1H), 2.77-2.88 (m, 1H), 3.79 (d, J=16.3 Hz, 1H), 3.91 (d, J=16.3 Hz, 1H), 4.07 (q, J=6.6 Hz, 1H), 4.19-4.30 (m, 1H), 4.39-4.50 (m, 1H), 5.01 (brs, 1H), 5.34 (brs, 1H), 5.59 (brs, 1H), 6.10 (d, J=11.1 Hz, 1H), 6.37 (d, J=11.1 Hz, 1H). MS m/z: 482 (M$^+$-H$_2$O), 57 (100%). UV λ$_{max}$nm: 263.

Example 49

(1) Preparation of 1α,3β-bis(tert-butyldimethylsilyloxy)-20(S)-(1-tert-butyl-2,2-dimethylpropoxycarbonylmethoxy)-9,10-secopregna-5,7,10(19),16-tetraene

[{1α,3β-Bis(tert-butyldimethylsilyloxy)-9,10-secopregna-5,7,10(19),16-tetraen-20(S)-yl}oxy]acetic acid (18.7 mg, 0.030 mmol) was treated with a 0.1 M dichloromethane solution of 2,2,4,4-tetramethylpentan-3-ol (0.5 ml), N,N'-dicyclohexylcarbodiimide (10.0 mg, 0.048 mmol) and 4-(dimethylamino)pyridine (4.0 mg, 0.033 mmol) in the same manner as shown in Example 17(3) (at room temperature for 17 hours). The reaction mixture was purified by preparative thin layer chromatography (0.5 mm×2 plates, hexane:ethyl acetate=15:1, developed twice) to give a mixture (23.4 mg) containing the titled compound.

(2) Preparation of 1α,3β-dihydroxy-20(S)-(1-tertbutyl-2,2-dimethylpropoxycarbonylmethoxy)-9,10-secopregna-5,7,10(19),16-tetraene The mixture containing 1α,3β-bis(tert-butyldimethylsilyloxy)-20(S)-(1-tert-butyl-2,2-dimethylpropoxycarbonylmethoxy)-9,10-secopregna-5,7,10(19),16-tetraene from Example 49 (1) (23.0 mg) was treated with a 1M tetrahydrofuran solution of tetra-n-butylammonium fluoride (0.3 ml) in the same manner as shown in Example 17(4) (at an external temperature of 42° C. for 30 minutes). The reaction mixture was purified by preparative thin layer chromatography (0.5 mm×1 plate, dichloromethane:ethanol=15:1, developed twice) to give the titled compound (7.1 mg, 46% for 2 steps) as a colorless oil.

IR(neat): 3384, 2932, 1750, 1478, 1444, 1370, 1226, 1124, 1054 cm$^{-1}$. $^1$H NMR δ: 0.78 (s, 3H), 0.99 (s, 9H), 1.00 (s, 9H), 1.38 (d, J=6.3 Hz, 3H), 2.54-2.65 (m, 1H), 2.75-2.88 (m, 1H), 3.98 (d, J=16.8 Hz, 1H), 4.09 (d, J=16.8 Hz, 1H), 4.07-4.16 (m, 1H), 4.16-4.30 (m, 1H), 4.39-4.50 (m, 1H), 4.66 (s, 1H), 5.01 (brs, 1H), 5.34 (brs, 1H), 5.61 (brs, 1H), 6.11 (d, J=11.3 Hz, 1H), 6.37 (d, J=11.3 Hz, 1H). MS m/z: 496 (M$^+$-H$_2$O), 57 (100%). UV λ$_{max}$nm: 264.

Example 50

(1) Preparation of 1α,3β-bis(tert-butyldimethylsilyloxy)-20(S)-(1,1-diethyl-2-methylpropoxycarbonylmethoxy)-9,10-secopregna-5,7,10(19),16-tetraene

[{1α,3β-Bis(tert-butyldimethylsilyloxy)-9,10-secopregna-5,7,10(19),16-tetraen-20(S)-yl}oxy]acetic acid (600 mg, 0.97 mmol) was treated with 3-ethyl-2-methyl-3-pentanol (380 mg, 2.92 mmol), N,N'-dicyclohexylcarbodiimide (602 mg, 2.92 mmol) and 4-(dimethylamino)pyridine (357 mg, 2.92 mmol) in dichloromethane (9.7 ml) in the same manner as shown in Example 17(3) (at room temperature for 15 hours), followed by work up and purification using column chromatography (hexane:ethyl acetate=20:1) to give a crude product (460 mg), 100 mg of which was further purified by preparative thin layer chromatography (0.5 mm×1 plate, hexane:ethyl acetate=10:1, developed once) to give a mixture (6.0 mg) containing the titled compound.

(2) Preparation of 1α,3β-dihydroxy-20(S)-(1,1-diethyl-2-methylpropoxycarbonylmethoxy)-9,10-secopregna-5,7,10(19),16-tetraene The mixture containing 1α,3β-bis(tert-butyldimethylsilyloxy)-20(S)-(1,1-diethyl-2-methylpropoxycarbonylmethoxy)-9,10-secopregna-5,7,10(19),16-tetraene from Example 50 (1) (6 mg) was treated with a 1M tetrahydrofuran solution of tetra-n-butylammonium fluoride (1.0 ml) in the same manner as shown in Example 17(4) (at an external temperature of 50° C. for 1.5 hours) and then worked up. The resulting residue was purified by preparative thin layer chromatography (0.5 mm×2 plates, dichloromethane:ethanol=20:1, developed twice and then 0.25 mm×2 plates, dichloromethane:ethanol=20:1, developed twice) to give the titled compound (2.189 mg, 2.07% for 2 steps) as a colorless oil.

IR(neat): 3390, 2969, 2931, 2883, 2850, 1745, 1727, 1461, 1371, 1288, 1209, 1122, 1052 cm$^{-1}$. $^1$H NMR δ: 0.77 (s, 3H), 0.83-0.98 (m, 12H), 1.37 (d, J=6.6 Hz, 3H), 2.55-2.66 (m, 1H), 2.76-2.88 (m, 1H), 3.86 (d, J=16.5 Hz, 1H), 3.99 (d, J=16.5 Hz, 1H), 4.05-4.16 (m, 1H), 4.19-4.31 (m, 1H), 4.40-4.50 (m, 1H), 5.01 (brs, 1H), 5.34 (brs, 1H), 5.59 (brs, 1H), 6.11 (d, J=11.4 Hz, 1H), 6.37 (d, J=11.0 Hz, 1H). MS m/z: 387 (M$^+$-C(Et)$_2$(i-Pr)), 57 (100%). UV λ$_{max}$nm: 264.

Example 51

(1) Preparation of [{1α,3β-bis(tert-butyldimethylsilyloxy)-9,10-secopregna-5,7,10(19),16-tetraen-20 (S)-yl}oxy]-N-(2,2-dimethylpropyl)acetamide

[{1α,3β-Bis(tert-butyldimethylsilyloxy)-9,10-secopregna-5,7,10(19),16-tetraen-20(S)-yl}oxy]acetic acid (15 mg, 0.0243 mmol) was treated with 2,2-dimethylpropylamine (11 mg, 0.126 mmol), 1-ethyl-3-(3-dimethylaminopropyl)carbodiimide hydrochloride (23 mg, 0.120 mmol) and 1-hydroxybenzotriazole monohydrate (3 mg, 0.024 mmol) in dichloromethane (1.5 ml) in the same manner as shown in Example 22(1) (at room temperature for 13 hours), followed by work up and separation using preparative thin layer chromatography (0.5 mm×2 plates, hexane:ethyl acetate=2:1, developed once) to give a mixture (14 mg) containing the desired product as a colorless oil.

(2) Preparation of [{1α,3β-dihydroxy-9,10-secopregna-5,7,10(19),16-tetraen-20(S)-yl}oxy]-N-(2,2-dimethylpropyl)acetamide The mixture containing [{1α,3β-bis(tert-butyldimethylsilyloxy)-9,10-secopregna-5,7,10(19),16-tetraen-20(S)-yl}oxy]-N-(2,2-dimethylpropyl)acetamide from Example 51 (1) (13 mg) was treated in tetrahydrofuran (0.2 ml) with a 1M tetrahydrofuran solution of tetra-n-butylammonium fluoride (0.2 ml) in the same manner as shown in Example 17(4) (at an external temperature of 55° C. for 1 hour) and then worked up. The resulting residue was purified by preparative thin layer chromatography (0.5 mm×2 plates, dichloromethane:ethanol=10:1, developed once) to give the titled compound (4.174 mg, 40% for 2 steps) as a colorless glass.

IR(neat): 3421, 2931, 2852, 1670, 1541, 1367, 1055 cm$^{-1}$. $^1$H NMR δ: 0.80 (s, 3H), 0.93 (s, 9H), 1.36 (d, J=6.3 Hz, 3H), 2.20-2.45 (m, 3H), 2.55-2.64 (m, 1H), 2.78-2.90 (m, 1H), 3.05-3.15 (m, 2H), 3.79-4.08 (m, 3H), 4.20-4.30 (br, 1H), 4.39-4.49 (br, 1H), 5.01 (brs, 1H), 5.35 (s, 1H), 5.61 (brs, 1H), 6.10 (d, J=11.2 Hz, 1H), 6.37 (d, J=11.2 Hz, 1H), 6.70 (brs, 1H). MS m/z: 312 (M$^+$-HOCH$_2$CONHCH$_2$C(CH$_3$)$_3$), 57 (100%). UV λ$_{max}$nm: 264.

Example 52

(1) Preparation of [{1α,3β-bis(tert-butyldimethylsilyloxy)-9,10-secopregna-5,7,10(19),16-tetraen-20 (S)-yl}oxy]-N-(1-ethylpropyl)acetamide

[{1α,3β-Bis(tert-butyldimethylsilyloxy)-9,10-secopregna-5,7,10(19),16-tetraen-20(S)-yl}oxy]acetic acid (15 mg, 0.0243 mmol) was treated with 1-ethylpropylamine (11 mg, 0.126 mmol), 1-ethyl-3-(3-dimethylaminopropyl)carbodiimide hydrochloride (23 mg, 0.120 mmol) and 1-hydroxybenzotriazole monohydrate (3 mg, 0.024 mmol) in dichloromethane (1.5 ml) in the same manner as shown in Example 22(1) (at room temperature for 13 hours), followed by work up and separation using preparative thin layer chromatography (0.5 mm×2 plates, hexane:ethyl acetate=2:1, developed once) to give a mixture (15 mg) containing the desired product as a colorless oil.

(2) Preparation of {(1α,3β-dihydroxy-9,10-secopregna-5,7,10(19),16-tetraen-20(S)-yl)oxy}-N-(1-ethylpropyl)acetamide The mixture containing [{1α,3β-bis(tert-butyldimethylsilyloxy)-9,10-secopregna-5,7,10(19),16-tetraen-20(S)-yl}oxy]-N-(1-ethylpropyl)acetamide from Example 52 (1) (14 mg) was treated in tetrahydrofuran (0.2 ml) with a 1M tetrahydrofuran solution of tetra-n-butylammonium fluoride (0.2 ml) in the same manner as shown in Example 17(4) (at an external temperature of 55° C. for 1 hour) and then worked up. The resulting residue was purified by preparative thin layer chromatography (0.5 mm×2 plates, dichloromethane:ethanol=10:1, developed once) to give the titled compound (5.136 mg, 50% for 2 steps) as a colorless glass.

IR(neat): 3401, 2964, 2931, 2875, 2850, 1662, 1533, 1458, 1107, 1057 cm$^{-1}$. $^1$H NMR δ: 0.80 (s, 3H), 0.90 (t, J=7.3 Hz, 3H), 1.35 (d, J=6.3 Hz, 3H), 2.18-2.47 (m, 3H), 2.58-2.62 (m, 1H), 2.79-2.84 (m, 1H), 3.80-4.08 (m, 4H), 4.24 (brs, 1H), 4.39-4.49 (br, 1H), 5.01 (brs, 1H), 5.35 (s, 1H), 5.60 (brs, 1H), 6.10 (d, J=11.2 Hz, 1H), 6.37-6.38 (m, 2H). MS m/z: 312 (M$^+$-HOCH$_2$CONHCH(C$_2$H$_5$)CH$_2$CH$_3$), 58 (100%). UV λ$_{max}$nm: 264.

Example 53

(1) Preparation of [{1α,3β-bis(tert-butyldimethylsilyloxy)-9,10-secopregna-5,7,10(19),16-tetraen-20 (S)-yl}oxy]-N-isopropyl-N-methylacetamide

[{1α,3β-Bis(tert-butyldimethylsilyloxy)-9,10-secopregna-5,7,10(19),16-tetraen-20(S)-yl}oxy]acetic acid (14.2 mg, 0.023 mmol) was treated with isopropylmethylamine (8.4 mg, 0.115 mmol), 1-ethyl-3-(3-dimethylaminopropyl)carbodiimide hydrochloride (22 mg, 0.115 mmol) and 1-hydroxybenzotriazole monohydrate (3.5 mg, 0.023 mmol) in dichloromethane (0.4 ml) in the same manner as shown in Example 22(1) (at room temperature for 13 hours), followed by work up and separation using preparative thin layer chromatography (0.5 mm×2 plates, hexane:ethyl acetate=2:1, developed once) to give a mixture (7 mg) containing the desired product as a colorless oil.

(2) Preparation of {(1α,3β-dihydroxy-9,10-secopregna-5,7,10(19),16-tetraen-20(S)-yl)oxy}-N-isopropyl-N-methylacetamide The mixture containing [{1α,3β-bis(tert-butyldimethylsilyloxy)-9,10-secopregna-5,7,10(19),16-tetraen-20(S)-yl}oxy]-N-isopropyl-N-methylacetamide from Example 53(1) (6 mg) was treated in tetrahydrofuran (0.18 ml) with a 1M tetrahydrofuran solution of tetra-n-butylammonium fluoride (0.09 ml) in the same manner as shown in Example 17(4) (at an external temperature of 55° C. for 2 hours) and then worked up. The resulting residue was purified by preparative thin layer chromatography (0.5 mm×2 plates, dichloromethane:ethanol=10:1, developed once) to give the titled compound (2.330 mg, 27% for 2 steps) as a colorless glass.

IR(neat): 3408, 2970, 2931, 2875, 2850, 1628, 1367, 1101, 1054 $cm^{-1}$. $^1$H NMR δ: 0.77 (s, 3H), 1.09 (d, J=6.6 Hz, 3H), 1.13-1.38 (m, 6H), 2.79 (d, J=6.6 Hz, 3H), 3.90-4.30 (m, 5H), 4.39-4.49 (br, 1H), 5.01 (brs, 1H), 5.34 (s, 1H), 5.61 (brs, 1H), 6.10 (d, J=11.3 Hz, 1H), 6.37 (d, J=11.3 Hz, 1H). MS m/z: 312 ($M^+$-HOCH$_2$CON(CH$_3$)(i-Pr)), 58 (100%). UV $\lambda_{max}$nm: 264.

Example 54

(1) Preparation of [{1α,3β-bis(tert-butyldimethylsilyloxy)-9,10-secopregna-5,7,10(19),16-tetraen-20(S)-yl}oxy]-N-(1-propylbutyl)acetamide

[{1α,3β-Bis(tert-butyldimethylsilyloxy)-9,10-secopregna-5,7,10(19),16-tetraen-20(S)-yl}oxy]acetic acid (20.0 mg, 0.03 mmol) was treated with 4-heptylamine (14 mg, 0.12 mmol), 1-ethyl-3-(3-dimethylaminopropyl)carbodiimide hydrochloride (23 mg, 0.12 mmol) and 1-hydroxybenzotriazole monohydrate (3 mg, 0.024 mmol) in dichloromethane (0.3 ml) in the same manner as shown in Example 22(1) (at room temperature for 13 hours), followed by work up and separation using preparative thin layer chromatography (0.5 mm×2 plates, hexane:ethyl acetate=2:1, developed twice) to give a mixture (18 mg) containing the desired product as a colorless oil.

(2) Preparation of {(1α,3β-dihydroxy-9,10-secopregna-5,7,10(19),16-tetraen-20(S)-yl)oxy}-N-(1-propylbutyl)acetamide The mixture containing [{1α,3β-bis(tert-butyldimethylsilyloxy)-9,10-secopregna-5,7,10(19),16-tetraen-20(S)-yl}oxy]-N-(1-propylbutyl)acetamide from Example 54(1) (18 mg) was treated in tetrahydrofuran (0.5 ml) with a 1M tetrahydrofuran solution of tetra-n-butylammonium fluoride (0.25 ml) in the same manner as shown in Example 17(4) (at an external temperature of 50° C. for 1.5 hours) and then worked up. The resulting residue was purified by preparative thin layer chromatography (0.5 mm×2 plates, dichloromethane:ethanol=10:1, developed three times; 0.5 mm×1 plate, hexane:ethyl acetate:ethanol=10:5:1, developed four times; and then 0.5 mm×1 plate, dichloromethane:ethanol=20:1, developed twice) to give the titled compound (7.089 mg, 48.7% for 2 steps) as a colorless oil.

IR(neat): 3401, 2956, 2931, 2871, 1666, 1533, 1440, 1106, 1054 $cm^{-1}$. $^1$H NMR δ: 0.80 (s, 3H), 0.91 (t, J=6.8 Hz, 6H), 2.18-2.48 (m, 3H), 2.54-2.67 (m, 1H), 2.77-2.89 (m, 1H), 3.80 (d, J=15.2 Hz, 1H), 3.92 (d, J=15.2 Hz, 1H), 3.95-4.07 (m, 2H), 4.19-4.29 (m, 1H), 4.41-4.50 (m, 1H), 5.01 (brs, 1H), 5.35 (brs, 1H), 5.59 (brs, 1H), 6.11 (d, J=11.2 Hz, 1H), 6.30 (d, J=9.4 Hz, 1H), 6.36 (d, J=11.2 Hz, 1H). MS m/z: 485 ($M^+$), 294 (100%). UV $\lambda_{max}$nm: 264.

Example 55

(1) Preparation of [{1α,3β-bis(tert-butyldimethylsilyloxy)-9,10-secopregna-5,7,10(19),16-tetraen-20(S)-yl}oxy]-N-(2-ethylbutyl)acetamide

[{1α,3β-Bis(tert-butyldimethylsilyloxy)-9,10-secopregna-5,7,10(19),16-tetraen-20(S)-yl}oxy]acetic acid (21.9 mg, 0.035 mmol) was treated with 2-ethylbutylamine (18 mg, 0.178 mmol), 1-ethyl-3-(3-dimethylaminopropyl)carbodiimide hydrochloride (13 mg, 0.068 mmol) and 1-hydroxybenzotriazole monohydrate (5 mg, 0.033 mmol) in dichloromethane (0.4 ml) in the same manner as shown in Example 22(1) (at room temperature for 5 hours), followed by work up and separation using preparative thin layer chromatography (0.5 mm×2 plates, hexane:ethyl acetate=3:1, developed once) to give a mixture (20 mg) containing the desired product as a colorless oil.

(2) Preparation of {(1α,3β-dihydroxy-9,10-secopregna-5,7,10(19),16-tetraen-20(S)-yl)oxy}-N-(2-ethylbutyl)acetamide The mixture containing [{1α,3β-bis(tert-butyldimethylsilyloxy)-9,10-secopregna-5,7,10(19),16-tetraen-20(S)-yl}oxy]-N-(2-ethylbutyl)acetamide from Example 55 (1) (15 mg) was treated in tetrahydrofuran (0.42 ml) with a 1M tetrahydrofuran solution of tetra-n-butylammonium fluoride (0.21 ml) in the same manner as shown in Example 17(4) (at an external temperature of 60° C. for 2 hours) and then worked up. The resulting residue was purified by preparative thin layer chromatography (0.5 mm×2 plates, hexane:ethyl acetate:ethanol=10:10:1, developed once) to give the titled compound (6.954 mg, 55% for 2 steps) as a colorless foam.

IR(neat): 3419, 2962, 2929, 2875, 1668, 1540, 1446, 1106, 1055 $cm^{-1}$. $^1$H NMR δ: 0.79 (s, 3H), 0.90 (t, J=7.3 Hz, 6H), 2.20-2.47 (m, 3H), 2.57-2.62 (m, 1H), 2.79-2.84 (m, 1H), 3.19-3.27 (m, 2H), 3.77-4.02 (m, 3H), 4.20-4.30 (br, 1H), 4.39-4.49 (br, 1H), 5.01 (brs, 1H), 5.34 (s, 1H), 5.59 (brs, 1H), 6.10 (d, J=11.2 Hz, 1H), 6.36 (d, J=11.2 Hz, 1H), 6.58 (brs, 1H). MS m/z: 471 ($M^+$), 160 (100%). UV $\lambda_{max}$nm: 263.

Example 56

(1) Preparation of 1α,3β-bis(tert-butyldimethylsilyloxy)-20(R)-hydroxy-9,10-secopregna-5,7,10(19),16-tetraene 1α,3β-Bis(tert-butyldimethylsilyloxy)-20(R)-hydroxypregna-5,7,16-triene (5.24 g, 9.37 mmol) was treated in tetrahydrofuran (500 ml) in the same manner as shown in Example 25(4) (irradiated with light for 7 hours and 45 minutes, thermally isomerized at 25° C. for 10 days) and evaporated under reduced pressure to remove the solvent. The resulting residue was purified by column chromatography (hexane:ethyl acetate=10:1) to give a colorless foamy fraction containing the titled compound (1.95 g).

(2) Preparation of 1α,3β-bis(tert-butyldimethylsilyloxy)-20(R)-(tert-butoxycarbonylmethoxy)-9,10-secopregna-5,7,10(19),16-tetraene The fraction containing 1α,3β-bis(tert-butyldimethylsilyloxy)-20(R)-hydroxy-9,10-secopregna-5,7,10(19),16-tetraene from Example 56 (1) (572 mg) was treated in tetrahydrofuran (10 ml) with sodium hydride (60% in oil, 246 mg, 6.138 mmol), 15-crown-5 (225 mg, 1.023 mmol) and tert-butyl bromoacetate (1.20 g, 6.14 mmol) in the same manner as shown in Example 17(1) (heated at reflux for 5.5 hours), followed by work up and purification using column chromatography (hexane:ethyl acetate=15:1) to give a colorless oily fraction containing the titled compound (0.90 g).

(3) Preparation of [{1α,3β-bis(tert-butyldimethylsilyloxy)-9,10-secopregna-5,7,10(19),16-tetraen-20(R)-yl}oxy]acetic Acid The fraction containing 1α,3β-bis(tert-butyldimethylsilyloxy)-20(R)-(tert-butoxycarbonylmethoxy)-9,10-secopregna-5,7,10(19),16-tetraene from Example 56 (2) (0.90 g) was treated in tetrahydrofuran (10.2 ml) with a 1M methanol solution of sodium methoxide (10.2 ml) and water (0.26 ml) in the same manner as shown in Example 17(2) (at room temperature for 30 minutes and then at room temperature for 10 minutes), followed by work up and purification using column chromatography (dichloromethane:methanol=15:1) to give the titled compound (482 mg, 18% for 3 steps) as a colorless foam.

$^1$H NMR δ: 0.07 (s, 6H), 0.74 (s, 3H), 0.88 (s, 9H), 0.88 (s, 9H), 1.39 (d, J=6.6 Hz, 3H), 2.40-2.51 (m, 2H), 2.76-2.87 (m, 1H), 3.96-4.42 (m, 5H), 4.87 (brs, 1H), 5.19 (brs, 1H), 5.68 (brs, 1H), 6.10 (d, J=11.2 Hz, 1H), 6.23 (d, J=11.2 Hz, 1H), 6.60-7.80 (br, 1H).

(4) Preparation of 1α,3β-bis(tert-butyldimethylsilyloxy)-20(R)-(1-ethylpropoxycarbonylmethoxy)-9,10-secopregna-5,7,10(19),16-tetraene

[{1α,3β-Bis(tert-butyldimethylsilyloxy)-9,10-secopregna-5,7,10(19),16-tetraen-20(R)-yl}oxy]acetic acid (35.3 mg) was treated with 3-pentanol (15 mg, 0.170 mmol), 1-ethyl-3-(3-dimethylaminopropyl)carbodiimide hydrochloride (22 mg, 0.115 mmol) and 4-(dimethylamino)pyridine (21 mg, 0.172 mmol) in dichloromethane (0.6 ml) in the same manner as shown in Example 21(1) (at room temperature for 5 hours), followed by work up and purification using preparative thin layer chromatography (0.5 mm×2 plates, hexane:ethyl acetate=10:1, developed once) to give a mixture (28 mg) containing the titled compound.

(5) Preparation of 1α,3β-dihydroxy-20(R)-(1-ethylpropoxycarbonylmethoxy)-9,10-secopregna-5,7,10(19),16-tetraene The mixture containing 1α,3β-bis(tert-butyldimethylsilyloxy)-20(R)-(1-ethylpropoxycarbonylmethoxy)-9,10-secopregna-5,7,10(19),16-tetraene from Example 56(4) (20 mg) was treated in tetrahydrofuran (0.58 ml) with a 1M tetrahydrofuran solution of tetra-n-butylammonium fluoride (0.29 ml) in the same manner as shown in Example 17(4) (at an external temperature of 60° C. for 2 hours) and then worked up. The resulting residue was purified by preparative thin layer chromatography (0.5 mm×2 plates, hexane:ethyl acetate:ethanol=10:10:1, developed once and then 0.5 mm×2 plates, hexane:ethyl acetate:ethanol=8:8:1, developed once) to give the titled compound (4.302 mg, 23% for 2 steps) as a colorless glass.

IR(neat): 3392, 2968, 2933, 2879, 2850, 1749, 1371, 1286, 1203, 1126, 1055 cm$^{-1}$. $^1$H NMR δ: 0.76 (s, 3H), 0.88 (t, J=7.1 Hz, 6H), 1.37 (d, J=6.6 Hz, 3H), 2.21-2.50 (m, 3H), 2.57-2.62 (m, 1H), 2.78-2.84 (m, 1H), 3.96 (d, J=16.3 Hz, 1H), 4.05 (d, J=16.3 Hz, 1H), 4.09-4.20 (m, 1H), 4.20-4.30 (m, 1H), 4.40-4.49 (m, 1H), 5.01 (brs, 1H), 5.34 (s, 1H), 5.65 (brs, 1H), 6.10 (d, J=11.2 Hz, 1H), 6.37 (d, J=11.2 Hz, 1H). MS m/z: 458 (M$^+$), 133 (100%). UV λ$_{max}$nm: 264.

Example 57

(1) Preparation of [{1α,3β-bis(tert-butyldimethylsilyloxy)-9,10-secopregna-5,7,10(19),16-tetraen-20(S)-yl}oxy]-N-(2,2,2-trifluoroethyl)acetamide

[{1α,3β-Bis(tert-butyldimethylsilyloxy)-9,10-secopregna-5,7,10(19),16-tetraen-20(S)-yl}oxy]acetic acid (36 mg, 0.058 mmol) was treated with 2,2,2-trifluoroethylamine (29 mg, 0.293 mmol), 1-ethyl-3-(3-dimethylaminopropyl)carbodiimide hydrochloride (22 mg, 0.115 mmol) and 1-hydroxybenzotriazole monohydrate (9 mg, 0.047 mmol) in dichloromethane (0.58 ml) in the same manner as shown in Example 22(1) (at room temperature for 10 minutes), followed by work up and separation using preparative thin layer chromatography (0.5 mm×1 plate, hexane:ethyl acetate=2:1, developed once) to give a mixture (38 mg) containing the desired product as a colorless oil.

(2) Preparation of {(1α,3β-dihydroxy-9,10-secopregna-5,7,10(19),16-tetraen-20(S)-yl)oxy}-N-(2,2,2-trifluoroethyl)acetamide The mixture containing [{1α,3β-bis(tert-butyldimethylsilyloxy)-9,10-secopregna-5,7,10(19),16-tetraen-20(S)-yl}oxy]-N-(2,2,2-trifluoroethyl)acetamide from Example 57 (1) (33 mg) was treated in tetrahydrofuran (0.94 ml) with a 1M tetrahydrofuran solution of tetra-n-butylammonium fluoride (0.47 ml) in the same manner as shown in Example 17(4) (at an external temperature of 65° C. for 1.5 hours) and then worked up. The resulting residue was purified by preparative thin layer chromatography (0.5 mm×2 plates, hexane:ethyl acetate:ethanol=10:10:1, developed once) to give the titled compound (17.305 mg, 73% for 2 steps) as a colorless glass.

IR(neat): 3415, 2933, 2850, 1682, 1533, 1279, 1163, 1115, 1055 cm$^{-1}$. $^1$H NMR δ: 0.79 (s, 3H), 1.36 (d, J=6.6 Hz, 3H), 2.21-2.41 (m, 3H), 2.57-2.62 (m, 1H), 2.79-2.83 (m, 1H), 3.82-4.05 (m, 5H), 4.20-4.29 (m, 1H), 4.39-4.50 (m, 1H), 5.01 (brs, 1H), 5.34 (s, 1H), 5.61 (brs, 1H), 6.10 (d, J=11.2 Hz, 1H), 6.36 (d, J=11.2 Hz, 1H), 6.93 (brs, 1H). MS m/z: 312 (M$^+$-HOCH$_2$CONHCH$_2$CF$_3$), 91 (100%). UV λ$_{max}$nm: 263.

Example 58

(1) Preparation of 1α,3β-bis(tert-butyldimethylsilyloxy)-20(S)-(cyclobutoxycarbonylmethoxy)-9,10-secopregna-5,7,10(19),16-tetraene

[{1α,3β-Bis(tert-butyldimethylsilyloxy)-9,10-secopregna-5,7,10(19),16-tetraen-20(S)-yl}oxy]acetic acid (50 mg, 0.081 mmol) was treated with cyclobutanol (18 mg, 0.250 mmol), 1-ethyl-3-(3-dimethylaminopropyl)carbodiimide hydrochloride (31 mg, 0.162 mmol) and 4-(dimethylamino)pyridine (30 mg, 0.246 mmol) in dichloromethane (0.8 ml) in the same manner as shown in Example 21(1) (at room temperature for 2 hours), followed by work up and purification using preparative thin layer chromatography (0.5 mm×2 plates, hexane:ethyl acetate=5:1, developed once) to give a mixture (53 mg) containing the titled compound.

(2) Preparation of 1α,3β-dihydroxy-20(S)-(cyclobutoxycarbonylmethoxy)-9,10-secopregna-5,7,10(19),16-tetraene The mixture containing 1α,3β-bis(tert-butyldimethylsilyloxy)-20(S)-(cyclobutoxycarbonylmethoxy)-9,10-secopregna-5,7,10(19),16-tetraene from Example 58 (1) (53 mg) was treated with a 1M tetrahydrofuran solution of tetra-n-butylammonium fluoride (0.79 ml) in the same manner as shown in Example 17(4) (at an external temperature of 50° C. for 2.5 hours) and then worked up. The resulting residue was purified by preparative thin layer chromatography (0.5 mm×2 plates, dichloromethane:ethanol=10:1, developed twice; 0.5 mm×1 plate, dichloromethane:ethanol=10:1, developed twice; and then 0.5 mm×1 plate, hexane:ethyl acetate:ethanol=10:10:1, developed once) to give the titled compound (1.718 mg, 5% for 2 steps) as a colorless glass.

IR(neat): 3400, 2929, 2850, 1751, 1597, 1200, 1124, 1053 cm$^{-1}$. $^1$H NMR δ: 0.78 (s, 3H), 1.36 (d, J=6.4 Hz, 3H), 2.21-2.43 (m, 3H), 2.57-2.62 (m, 1H), 2.78-2.84 (m, 1H), 3.87-4.19 (m, 3H), 4.20-4.30 (br, 1H), 4.40-4.49 (br, 1H), 5.01-5.07 (m, 2H), 5.34 (s, 1H), 5.61 (brs, 1H), 6.10 (d, J=11.4 Hz, 1H), 6.37 (d, J=11.4 Hz, 1H). MS m/z: 312 (M$^+$-HOCH$_2$CO$_2$C$_4$H$_7$), 55 (100%). UV λ$_{max}$nm: 264.

Example 59

(1) Preparation of 1α,3β-bis(tert-butyldimethylsilyloxy)-20(S)-(1-ethylpropoxycarbonylmethoxy)-9,10-secopregna-5,7,10(19),16-tetraene

[{1α,3β-Bis(tert-butyldimethylsilyloxy)-9,10-secopregna-5,7,10(19),16-tetraen-20(S)-yl}oxy]acetic acid (53 mg, 0.086 mmol) was treated with 3-pentanol (23 mg, 0.258 mmol), 1-ethyl-3-(3-dimethylaminopropyl)carbodiimide hydrochloride (33 mg, 0.172 mmol) and 4-(dimethylamino)pyridine (32 mg, 0.258 mmol) in dichloromethane (0.9 ml) in the same manner as shown in Example 21(1) (at room temperature for 2 hours), followed by work up and purification using preparative thin layer chromatography (0.5 mm×2 plates, hexane:ethyl acetate=5:1, developed once) to give a mixture (51 mg) containing the titled compound.

(2) Preparation of 1α,3β-dihydroxy-20(S)-(1-ethylpropoxycarbonylmethoxy)-9,10-secopregna-5,7,10(19),16-tetraene The mixture containing 1α,3β-bis(tert-butyldimethylsilyloxy)-20(S)-(1-ethylpropoxycarbonylmethoxy)-9,10-secopregna-5,7,10(19),16-tetraene from Example 59(1) (45 mg) was treated with a 1M tetrahydrofuran solution of tetra-n-butylammonium fluoride (0.7 ml) in the same manner as shown in Example 17(4) (at an external temperature of 50° C. for 2.5 hours) and then worked up. The resulting residue was purified by preparative thin layer chromatography (0.5 mm×2 plates, hexane:ethyl acetate:ethanol=10:10:1, developed once) to give the titled compound (12.126 mg, 35% for 2 steps) as a colorless glass.

IR(neat): 3390, 2970, 2931, 2879, 2850, 1749, 1458, 1205, 1124, 1053 cm$^{-1}$. $^1$H NMR δ: 0.77 (s, 3H), 0.88 (dt, J=7.4, 2.1 Hz, 6H), 1.37 (d, J=6.4 Hz, 3H), 2.21-2.45 (m, 3H), 2.57-2.62 (m, 1H), 2.79-2.84 (m, 1H), 3.91-4.13 (m, 3H), 4.20-4.30 (br, 1H), 4.40-4.50 (br, 1H), 5.01 (brs, 1H), 5.34 (s, 1H), 5.61 (brs, 1H), 6.11 (d, J=11.2 Hz, 1H), 6.37 (d, J=11.2 Hz, 1H). MS m/z: 312 (M$^+$-HOCH$_2$CO$_2$CH(C$_2$H$_5$)$_2$), 71 (100%). UV λ$_{max}$nm: 263.

Example 60

(1) Preparation of 1α,3β-bis(tert-butyldimethylsilyloxy)-20(S)-(cyclopentyloxycarbonylmethoxy)-9,10-secopregna-5,7,10(19),16-tetraene

[{1α,3β-Bis(tert-butyldimethylsilyloxy)-9,10-secopregna-5,7,10(19),16-tetraen-20(S)-yl}oxy]acetic acid (65.1 mg, 0.106 mmol) was treated with cyclopentanol (30.0 mg, 0.348 mmol), 1-ethyl-3-(3-dimethylaminopropyl)carbodiimide hydrochloride (40.0 mg, 0.209 mmol) and 4-(dimethylamino)pyridine (40.0 mg, 0.327 mmol) in dichloromethane (0.8 ml) in the same manner as shown in Example 21(1) (at room temperature for 1 hour and 30 minutes), followed by purification using preparative thin layer chromatography (0.5 mm×2 plates, hexane:ethyl acetate=20:1, developed three times) to give a mixture (50.4 mg) containing the titled compound.

(2) Preparation of 1α,3β-dihydroxy-20(S)-(cyclopentyloxycarbonylmethoxy)-9,10-secopregna-5,7,10(19),16-tetraene The mixture containing 1α,3β-bis(tert-butyldimethylsilyloxy)-20(S)-(cyclopentyloxycarbonylmethoxy)-9,10-secopregna-5,7,10(19),16-tetraene from Example 60(1) (23.7 mg) was treated with a 1M tetrahydrofuran solution of tetra-n-butylammonium fluoride (0.35 ml) in the same manner as shown in Example 17(4) (at an external temperature of 47° C. for 50 minutes). The reaction mixture was purified by preparative thin layer chromatography (0.5 mm×1 plate, dichloromethane:ethanol=20:1, developed three times and then 0.25 mm×1 plate, hexane:ethyl acetate:ethanol=10:5:1, developed three times) to give the titled compound (4.1 mg, 23% for 2 steps) as a colorless oil.

IR(neat): 3392, 2932, 2872, 1746, 1440, 1370, 1208, 1122, 1052 cm$^{-1}$. $^1$H NMR δ: 0.77 (s, 3H), 1.36 (d, J=6.6 Hz, 3H), 2.54-2.65 (m, 1H), 2.76-2.86 (m, 1H), 3.89 (d, J=16.2 Hz, 1H), 4.00 (d, J=16.2 Hz, 1H), 4.06 (q, J=6.6 Hz, 1H), 4.20-4.30 (m, 1H), 4.40-4.50 (m, 1H), 5.01 (brs, 1H), 5.19-5.29 (m, 1H), 5.34 (brs, 1H), 5.61 (brs, 1H), 6.10 (d, J=10.6 Hz, 1H), 6.37 (d, J=10.6 Hz, 1H). MS m/z: 438 (M$^+$-H$_2$O), 69 (100%). UV λ$_{max}$nm: 264.

Example 61

(1) Preparation of 1α,3β-bis(tert-butyldimethylsilyloxy)-20(S)-(cyclopropylmethoxycarbonylmethoxy)-9,10-secopregna-5,7,10(19),16-tetraene

[{1α,3β-Bis(tert-butyldimethylsilyloxy)-9,10-secopregna-5,7,10(19),16-tetraen-20(S)-yl}oxy]acetic acid (31.3 mg, 0.051 mmol) was treated with cyclopropylmethanol (11.0 mg, 0.153 mmol), 1-ethyl-3-(3-dimethylaminopropyl)carbodiimide hydrochloride (20.0 mg, 0.104 mmol) and 4-(dimethylamino)pyridine (20.0 mg, 0.164 mmol) in dichloromethane (0.4 ml) in the same manner as shown in Example 21(1) (at room temperature for 16 hours), followed by purification using preparative thin layer chromatography (0.5 mm×2 plates, hexane:ethyl acetate=20:1, developed once, hexane:ethyl acetate=10:1, developed once) to give a mixture (25.6 mg) containing the titled compound.

(2) Preparation of 1α,3β-dihydroxy-20(S)-(cyclopropylmethoxycarbonylmethoxy)-9,10-secopregna-5,7,10(19),16-tetraene The mixture containing 1α,3β-bis(tert-butyldimethylsilyloxy)-20(S)-(cyclopropylmethoxycarbonylmethoxy)-9,10- secopregna-5,7,10(19),16-tetraene from Example 61(1) (24.0 mg) was treated with a 1M tetrahydrofuran solution of tetra-n-butylammonium fluoride (0.4 ml) in the same manner as shown in Example 17(4) (at an external temperature of 47° C. for 50 minutes). The reaction mixture was purified by preparative thin layer chromatography (0.5 mm×1 plate, dichloromethane:ethanol=20:1, developed twice and then 0.25 mm×1 plate, hexane:ethyl acetate:ethanol=10:5:1, developed three times) to give the titled compound (2.1 mg, 10% for 2 steps) as a colorless oil.

IR(neat): 3388, 2928, 2852, 1750, 1446, 1370, 1204, 1122, 1054 cm$^{-1}$. $^1$H NMR δ: 0.25-0.33 (m, 2H), 0.52-0.61 (m, 2H), 0.78 (s, 3H), 1.38 (d, J=6.7 Hz, 3H), 2.54-2.65 (m, 1H), 2.76-2.88 (m, 1H), 3.96 (d, J=16.3 Hz, 1H), 4.08 (d, J=16.3 Hz, 1H), 4.08 (q, J=6.7 Hz, 1H), 4.18-4.28 (m, 1H), 4.41-4.48 (m, 1H), 5.01 (brs, 1H), 5.34 (brs, 1H), 5.62 (brs, 1H), 6.10 (d, J=10.3 Hz, 1H), 6.37 (d, J=10.3 Hz, 1H). MS m/z: 442 (M$^+$), 55 (100%). UV λ$_{max}$nm: 264.

Example 62

(1) Preparation of 1α,3β-bis(tert-butyldimethylsilyloxy)-20(S)-(cyclohexyloxycarbonylmethoxy)-9,10-secopregna-5,7,10(19),16-tetraene

[{1α,3β-Bis(tert-butyldimethylsilyloxy)-9,10-secopregna-5,7,10(19),16-tetraen-20(S)-yl}oxy]acetic acid (31 mg, 0.050 mmol) was treated with cyclohexanol (15 mg, 0.150 mmol), 1-ethyl-3-(3-dimethylaminopropyl)carbodiimide hydrochloride (19 mg, 0.099 mmol) and 4-(dimethylamino)pyridine (18 mg, 0.148 mmol) in dichloromethane (2 ml) in the same manner as shown in Example 21(1) (at room temperature for 3 days), followed by work up and purification using preparative thin layer chromatography (0.5 mm×2 plates, hexane:ethyl acetate=5:1, developed once) to give a mixture (27 mg) containing the titled compound.

(2) Preparation of 1α,3β-dihydroxy-20(S)-(cyclohexyloxycarbonylmethoxy)-9,10-secopregna-5,7,10(19),16-tetraene The mixture containing 1α,3β-bis(tert-butyldimethylsilyloxy)-20(S)-(cyclohexyloxycarbonylmethoxy)-9,10-secopregna-5,7,10(19),16-tetraene from Example 62 (1) (26 mg) was treated with a 1M tetrahydrofuran solution of tetra-n-butylammonium fluoride (0.37 ml) in the same manner as shown in Example 17(4) (at an external temperature of 50° C. for 1 hour) and then worked up. The resulting residue was purified by preparative thin layer chromatography (0.5 mm×2 plates, hexane:ethyl acetate:ethanol=10:10:1, developed once) to give the titled compound (5.218 mg, 24% for 2 steps) as a colorless foam.

IR(neat): 3390, 2933, 2856, 1747, 1448, 1203, 1120, 1053 cm$^{-1}$. $^1$H NMR δ: 0.78 (s, 3H), 1.37 (d, J=6.6 Hz, 3H), 2.21-2.45 (m, 3H), 2.57-2.62 (m, 1H), 2.79-2.84 (m, 1H), 3.88-4.12 (m, 3H), 4.20-4.30 (br, 1H), 4.40-4.50 (br, 1H), 4.79-4.90 (m, 1H), 5.01 (brs, 2H), 5.34 (s, 1H), 5.61 (brs, 1H), 6.10 (d, J=11.4 Hz, 1H), 6.37 (d, J=11.4 Hz, 1H). MS m/z: 470 (M$^+$), 55 (100%). UV λ$_{max}$nm: 264.

Example 63

(1) Preparation of 1-[[{1α,3β-bis(tert-butyldimethylsilyloxy)-9,10-secopregna-5,7,10(19),16-tetraen-20(S)-yl}oxy]acetyl]piperidine

[{1α,3β-Bis(tert-butyldimethylsilyloxy)-9,10-secopregna-5,7,10(19),16-tetraen-20(S)-yl}oxy]acetic acid (31 mg, 0.050 mmol) was treated with piperidine (13 mg, 0.150 mmol), 1-ethyl-3-(3-dimethylaminopropyl)carbodiimide hydrochloride (19 mg, 0.099 mmol) and 4-(dimethylamino)pyridine (18 mg, 0.148 mmol) in dichloromethane (2 ml) in the same manner as shown in Example 21(1) (at room temperature for 3 days), followed by work up and purification using preparative thin layer chromatography (0.5 mm×2 plates, hexane:ethyl acetate=1:1, developed once) to give a mixture (23 mg) containing the titled compound.

(2) Preparation of 1-[{(1α,3β-dihydroxy-9,10-secopregna-5,7,10(19),16-tetraen-20(S)-yl)oxy}acetyl]piperidine The mixture containing 1-[[{1α,3β-bis(tert-butyldimethylsilyloxy)-9,10-secopregna-5,7,10(19),16-tetraen-20(S)-yl}oxy]acetyl]piperidine from Example 63 (1) (22 mg) was treated with a 1M tetrahydrofuran solution of tetra-n-butylammonium fluoride (0.32 ml) in the same manner as shown in Example 17(4) (at an external temperature of 50° C. for 2 hours) and then worked up. The resulting residue was purified by preparative thin layer chromatography (0.5 mm×2 plates, dichloromethane:ethanol=10:1, developed once) to give the titled compound (7.499 mg, 34% for 2 steps) as a colorless foam.

IR(neat): 3384, 2933, 2854, 1630, 1446, 1254, 1053 cm$^{-1}$. $^1$H NMR δ: 0.78 (s, 3H), 1.35 (d, J=6.4 Hz, 3H), 2.20-2.44 (m, 3H), 2.57-2.62 (m, 1H), 2.79-2.84 (m, 1H), 3.35-3.61 (m, 4H), 3.93-4.14 (m, 3H), 4.20-4.30 (br, 1H), 4.40-4.49 (br, 1H), 5.01 (brs, 2H), 5.34 (s, 1H), 5.60 (brs, 1H), 6.11 (d, J=11.4 Hz, 1H), 6.37 (d, J=11.4 Hz, 1H). MS m/z: 312 (M$^+$-HOCH$_2$COC$_5$H$_{10}$N), 144 (100%). UV λ$_{max}$nm: 264.

Example 64

(1) Preparation of 1α,3β-bis(tert-butyldimethylsilyloxy)-20(S)-(adamantan-1-yloxycarbonylmethoxy)-9,10-secopregna-5,7,10(19),16-tetraene

[{1α,3β-Bis(tert-butyldimethylsilyloxy)-9,10-secopregna-5,7,10(19),16-tetraen-20(S)-yl}oxy]acetic acid (40 mg, 0.065 mmol) was treated with 1-adamantanol (30 mg, 0.197 mmol), 1-ethyl-3-(3-dimethylaminopropyl)carbodiimide hydrochloride (25 mg, 0.130 mmol) and 4-(dimethylamino)pyridine (24 mg, 0.196 mmol) in dichloromethane (0.65 ml) in the same manner as shown in Example 21(1) (at room temperature for 15 hours), followed by work up and purification using preparative thin layer chromatography (0.5 mm×2 plates, hexane:ethyl acetate=5:1, developed once) to give a mixture (18 mg) containing the titled compound.

(2) preparation of 1α,3β-dihydroxy-20(S)-(adamantan-1-yloxycarbonylmethoxy)-9,10-secopregna-5,7,10(19),16-tetraene The mixture containing 1α,3β-bis(tert-butyldimethylsilyloxy)-20(S)-(adamantan-1-yloxycarbonylmethoxy)-9,10-secopregna-5,7,10(19),16-tetraene from Example 64 (1) (17 mg) in tetrahydrofuran (0.46 ml) was treated with a 1M tetrahydrofuran solution of tetra-n-butylammonium fluoride (0.23 ml) in the same manner as shown in Example 17(4) (at an external temperature of 60° C. for 2 hours) and then worked up. The resulting residue was purified by preparative thin layer chromatography (0.5 mm×2 plates, hexane:ethyl acetate:ethanol=10:10:1, developed once) to give the titled compound (7.471 mg, 23% for 2 steps) as a colorless glass.

IR(neat): 3380, 2916, 2852, 1745, 1456, 1209, 1122, 1053 cm$^{-1}$. $^1$H NMR δ: 0.77 (s, 3H), 1.36 (d, J=6.3 Hz, 3H), 2.57-2.62 (m, 1H), 2.79-2.84 (m, 1H), 3.82 (d, J=16.3 Hz, 1H), 3.92 (d, J=16.3 Hz, 1H), 4.04-4.16 (m, 1H), 4.20-4.30 (m, 1H), 4.41-4.49 (m, 1H), 5.01 (brs, 1H), 5.34 (s, 1H), 5.59 (brs, 1H), 6.10 (d, J=11.0 Hz, 1H), 6.37 (d, J=11.0 Hz, 1H). MS m/z: 522 (M$^+$), 135 (100%). UV $\lambda_{max}$nm: 264.

Example 65

(1) Preparation of 1α,3β-bis(tert-butyldimethylsilyloxy) -20(R)-(1-ethyl-1-methylpropoxycarbonyl)methoxy-9,10-secopregna-5,7,10(19),16-tetraene

[{1α,3β-Bis(tert-butyldimethylsilyloxy)-9,10-secopregna-5,7,10(19),16-tetraen-20(R)-yl}oxy]acetic acid (34 mg, 0.055 mmol) was treated with 3-methyl-3-pentanol (28 mg, 0.275 mmol), 1-ethyl-3-(3-dimethylaminopropyl)carbodiimide hydrochloride (21 mg, 0.110 mmol) and 4-(dimethylamino)pyridine (20 mg, 0.164 mmol) in dichloromethane (0.55 ml) in the same manner as shown in Example 21(1) (at room temperature for 5 hours), followed by work up and purification using preparative thin layer chromatography (0.5 mm×2 plates, hexane:ethyl acetate=10:1, developed once) to give a mixture (10 mg) containing the titled compound.

(2) Preparation of 1α,3β-dihydroxy-20(R)-(1-ethyl-1-methylpropoxycarbonylmethoxy)-9,10-secopregna-5,7,10(19),16-tetraene The mixture containing 1α,3β-bis(tert-butyldimethylsilyloxy)-20(R)-(1-ethyl-1-methylpropoxycarbonylmethoxy)-9,10-secopregna-5,7,10(19),16-tetraene from Example 65 (1) (9 mg) was treated in tetrahydrofuran (0.1 ml) with a 1M tetrahydrofuran solution of tetra-n-butylammonium fluoride (0.2 ml) in the same manner as shown in Example 17(4) (at an external temperature of 55° C. for 2 hours) and then worked up. The resulting residue was purified by preparative thin layer chromatography (0.5 mm×2 plates, hexane:ethyl acetate:ethanol=10:10:1, developed once) to give the titled compound (3.102 mg, 13% for 2 steps) as a colorless glass.

IR(neat): 3380, 2971, 2929, 2850, 1747, 1460, 1373, 1213, 1124, 1055 cm$^{-1}$. $^1$H NMR δ: 0.76 (s, 3H), 0.85 (t, J=7.4 Hz, 6H), 1.25 (s, 3H), 1.36 (d, J=6.6 Hz, 3H), 1.39 (s, 3H), 2.20-2.49 (m, 3H), 2.57-2.62 (m, 1H), 2.79-2.84 (m, 1H), 3.87 (d, J=16.3 Hz, 1H), 3.95 (d, J=16.3 Hz, 1H), 4.08-4.16 (m, 1H), 4.20-4.30 (m, 1H), 4.40-4.49 (m, 1H), 5.01 (brs, 1H), 5.34 (s, 1H), 5.63 (brs, 1H), 6.10 (d, J=11.2 Hz, 1H), 6.37 (d, J=11.2 Hz, 1H). MS m/z: 312 (M$^+$-HOCH$_2$CO$_2$C(C$_2$H$_5$)$_2$CH$_3$), 85 (100%). UV $\lambda_{max}$nm: 265.

Example 66

(1) Preparation of [{1α,3β-bis(tert-butyldimethylsilyloxy)-9,10-secopregna-5,7,10(19),16-tetraen-20(S)-yl}oxy]-N-methoxy-N-methylacetamide

[{1α,3β-Bis(tert-butyldimethylsilyloxy)-9,10-secopregna-5,7,10(19),16-tetraen-20(S)-yl}oxy]acetic acid (13.5 mg, 0.0219 mmol), N-methoxy-N-methylamine hydrochloride (11 mg, 0.109 mmol), 1-ethyl-3-(3-dimethylaminopropyl)carbodiimide hydrochloride (21 mg, 0.110 mmol), 1-hydroxybenzotriazole monohydrate (3 mg, 0.024 mmol), triethylamine (22 mg, 0.217 mmol) and dichloromethane (0.4 ml) were mixed and stirred at room temperature for 15 hours. The reaction mixture was partitioned between aqueous citric acid and dichloromethane. The resulting organic layer was washed sequentially with saturated aqueous sodium bicarbonate and saturated aqueous sodium chloride, dried over anhydrous sodium sulfate, filtered and evaporated under reduced pressure. The resulting residue was separated by preparative thin layer chromatography (0.5 mm×2 plates, hexane:ethyl acetate=2:1, developed once) to give a mixture (13 mg) containing the desired product as a colorless oil.

(2) Preparation of {(1α,3β-dihydroxy-9,10-secopregna-5,7,10(19),16-tetraen-20(S)-yl)oxy}-N-methoxy-N-methylacetamide The mixture containing [{1α,3β-bis(tert-butyldimethylsilyloxy)-9,10-secopregna-5,7,10(19),16-tetraen-20(S)-yl}oxy]-N-methoxy-N-methylacetamide from Example 66 (1) (12 mg) was treated in tetrahydrofuran (0.36 ml) with a 1M tetrahydrofuran solution of tetra-n-butylammonium fluoride (0.18 ml) in the same manner as shown in Example 17(4) (at an external temperature of 55° C. for 2 hours) and then worked up. The resulting residue was purified by preparative thin layer chromatography (0.5 mm×2 plates, dichloromethane:ethanol=10:1, developed once) to give the titled compound (3.800 mg, 44% for 2 steps) as a colorless glass.

IR(neat): 3399, 2933, 2850, 1668, 1436, 1052 cm$^{-1}$. $^1$H NMR δ: 0.78 (s, 3H), 1.38 (d, J=6.6 Hz, 3H), 2.18-2.47 (m, 3H), 2.57-2.62 (m, 1H), 2.79-2.84 (m, 1H), 3.18 (s, 3H), 3.66 (s, 3H), 4.07-4.27 (m, 4H), 4.39-4.49 (m, 1H), 5.01 (brs, 1H), 5.34 (s, 1H), 5.63 (brs, 1H), 6.10 (d, J=11.2 Hz, 1H), 6.37 (d, J=11.2 Hz, 1H). MS m/z: 312 (M$^+$-HOCH$_2$CON(OCH$_3$)CH$_3$), 91(100%). UV $\lambda_{max}$nm: 264.

Example 67

(1) Preparation of [{1α,3β-bis(tert-butyldimethylsilyloxy)-9,10-secopregna-5,7,10(19),16-tetraen-20(S)-yl}oxy]-N-methoxyacetamide

[{1α,3β-Bis(tert-butyldimethylsilyloxy)-9,10-secopregna-5,7,10(19),16-tetraen-20(S)-yl}oxy]acetic acid (13.6 mg, 0.0220 mmol) was treated with N-methoxyamine hydrochloride (9 mg, 0.108 mmol), 1-ethyl-3-(3-dimethylaminopropyl)carbodiimide hydrochloride (21 mg, 0.110 mmol), 1-hydroxybenzotriazole monohydrate (3 mg, 0.024 mmol) and triethylamine (22 mg, 0.217 mmol) in dichloromethane (0.88 ml) in the same manner as shown in Example 66(1) (at room temperature for 15 hours), followed by work up and separation using preparative thin layer chromatography (0.5 mm×2 plates, hexane:ethyl acetate=2:1, developed once) to give a mixture (12 mg) containing the desired product as a colorless oil.

(2) Preparation of {(1α,3β-dihydroxy-9,10-secopregna-5,7,10(19),16-tetraen-20(S)-yl)oxy}-N-methoxyacetamide The mixture containing [{1α,3β-bis(tert-butyldimethylsilyloxy)-9,10-secopregna-5,7,10(19),16-tetraen-20(S)-yl}oxy]-N-methoxyacetamide from Example 67 (1) (11 mg) was treated in tetrahydrofuran (0.34 ml) with a 1M tetrahydrofuran solution of tetra-n-butylammonium fluoride (0.17 ml) in the same manner as shown in Example 17(4) (at an external temperature of 55° C. for 2 hours) and then worked up. The resulting residue was purified by preparative thin layer chromatography (0.5 mm×2 plates, dichloromethane:ethanol=10:1, developed once) to give the titled compound (3.189 mg, 38% for 2 steps) as a colorless glass.

IR(neat): 3384, 2929, 2850, 1674, 1441, 1117, 1053 cm$^{-1}$.
$^1$H NMR δ: 0.78 (s, 3H), 1.34 (d, J=6.6 Hz, 3H), 2.18-2.46 (m, 3H), 2.57-2.62 (m, 1H), 2.79-2.83 (m, 1H), 3.81 (s, 3H), 3.81-4.07 (m, 3H), 4.20-4.30 (m, 1H), 4.41-4.48 (m, 1H), 5.01 (brs, 1H), 5.34 (s, 1H), 5.59 (brs, 1H), 6.10 (d, J=11.2 Hz, 1H), 6.36 (d, J=11.2 Hz, 1H), 8.92 (brs, 1H). MS m/z: 312 (M$^+$- HOCH$_2$CONHOMe), 91 (100%). UV λ$_{max}$nm: 264.

Example 68

(1) Preparation of 1α,3β-bis(tert-butyldimethylsilyloxy)-20(S)-(ethoxycarbonylmethoxy)-9,10-secopregna-5,7,10(19),16-tetraene To a solution of [{1α,3β-bis(tert-butyldimethylsilyloxy)-9,10-secopregna-5,7,10(19),16-tetraen-20(S)-yl}oxy]acetic acid (43.0 mg, 0.07 mmol) in dichloromethane (0.8 ml), ethanol (5 mg, 0.1 mmol), 2-chloro-1,3-dimethylimidazolinium chloride (17 mg, 0.1 mmol) and pyridine (17 mg, 0.21 mmol) were added at room temperature under a nitrogen atmosphere and then stirred for 15 hours. The reaction mixture was poured into water, extracted with ethyl acetate, washed sequentially with saturated aqueous sodium bicarbonate, aqueous sodium chloride and water, dried over anhydrous magnesium sulfate, and then evaporated under reduced pressure to remove the solvent. The resulting residue was purified by preparative thin layer chromatography (0.5 mm×2 plates, hexane:ethyl acetate=10:1, developed once) to give a mixture (28.0 mg) containing the titled compound.

(2) Preparation of 1α,3β-dihydroxy-20(S)-(ethoxycarbonylmethoxy)-9,10-secopregna-5,7,10(19),16-tetraene The mixture containing 1α,3β-bis(tert-butyldimethylsilyloxy)-20(S)-(ethoxycarbonylmethoxy)-9,10-secopregna-5,7,10(19),16-tetraene from Example 68 (1) (28 mg) was treated in tetrahydrofuran (2.0 ml) with a 1M tetrahydrofuran solution of tetra-n-butylammonium fluoride (0.65 ml) in the same manner as shown in Example 17(4) (at an external temperature of 50° C. for 2 hours) and then worked up. The resulting residue was purified by preparative thin layer chromatography (0.5 mm×2 plates, dichloromethane:ethanol=20:1, developed twice and then 0.5 mm×1 plate, hexane:ethyl acetate:ethanol=10:5:1, developed three times) to give the titled compound (3.167 mg, 10.9% for 2 steps) as a colorless oil.

IR(neat): 3347, 2975, 2931, 2848, 1751, 1442, 1369, 1288, 1203, 1124, 1052 cm$^{-1}$. $^1$H NMR δ: 0.78 (s, 3H), 1.27 (t, J=7.3 Hz, 3H), 1.37 (d, J=6.3 Hz, 3H), 2.19-2.48 (m, 3H), 2.55-2.66 (m, 1H), 2.78-2.87 (m, 1H), 3.93 (d, J=16.2 Hz, 1H), 4.05 (d, J=16.2 Hz, 1H), 4.03-4.12 (m, 1H), 4.15-4.30 (m, 3H), 4.39-4.50 (m, 1H), 5.01 (brs, 1H), 5.34 (brs, 1H), 5.62 (brs, 1H), 6.11 (d, J=11.5 Hz, 1H), 6.37 (d, J=11.2 Hz, 1H). MS m/z: 416 (M$^+$), 133 (100%). UV λ$_{max}$nm: 264.

Example 69

(1) Preparation of 1α,3β-bis(tert-butyldimethylsilyloxy)-20(S)-(isopropoxycarbonylmethoxy)-9,10-secopregna-5,7,10(19),16-tetraene

[{1α,3β-Bis(tert-butyldimethylsilyloxy)-9,10-secopregna-5,7,10(19),16-tetraen-20(S)-yl}oxy]acetic acid (641 mg, 1.039 mmol) was treated with isopropanol (0.641 ml, 9.350 mmol), 2-chloro-1,3-dimethylimidazolinium chloride (263 mg, 1.558 mmol) and pyridine (260 μl, 3.117 mmol) in dichloromethane (10 ml) in the same manner as shown in Example 68(1) (at room temperature for 2 hours), followed by work up and purification using column chromatography (hexane:ethyl acetate=10:1) to give a mixture (669 mg) containing the titled compound.

(2) Preparation of 1α,3β-dihydroxy-20(S)-(isopropoxycarbonylmethoxy)-9,10-secopregna-5,7,10(19), 16-tetraene The mixture containing 1α,3β-bis(tert-butyldimethylsilyloxy)-20(S)-(isopropoxycarbonylmethoxy)-9,10-secopregna-5,7,10(19),16-tetraene from Example 69(1) (669 mg) was treated with a 1M tetrahydrofuran solution of tetra-n-butylammonium fluoride (5.0 ml) in the same manner as shown in Example 17(4) (at an external temperature of 50° C. for 3 hours) and then worked up. The resulting residue was purified by column chromatography (dichloromethane:methanol=10:1) to give a mixture containing 1α,3β-dihydroxy-20(S)-(isopropoxycarbonylmethoxy)-9,10-secopregna-5,7,10(19),16-tetraene (246 mg) and [{1α,3β-dihydroxy-9,10-secopregna-5,7,10(19),16-tetraen-20(S)-yl}oxy]acetic acid (137 mg, 33% for 2 steps) as a colorless oil. Next, the mixture containing 1α,3β-dihydroxy-20(S)-(isopropoxycarbonylmethoxy)-9,10-secopregna-5,7,10(19), 16-tetraene was purified by preparative thin layer chromatography (0.5 mm×8 plates, hexane:ethyl acetate:ethanol=5:5:1, developed once) to give 1α,3β-dihydroxy-20(S)-(isopropoxycarbonylmethoxy)-9,10-secopregna-5,7,10(19),16-tetraene (169 mg, 37% for 2 steps) as a colorless oil. This compound had the same IR, MASS, $^1$H NMR and UV spectra as the compound prepared in Example 15.

For [{1α,3β-dihydroxy-9,10-secopregna-5,7,10(19),16-tetraen-20(S)-yl}oxy]acetic acid:

$^1$H NMR δ: 0.79 (s, 3H), 1.39 (d, J=6.8 Hz, 3H), 2.53-2.65 (m, 1H), 2.75-2.87 (m, 1H), 3.92 (d, J=16.5 Hz, 1H), 4.03-4.16 (m, 2H), 4.21-4.29 (m, 1H), 4.41-4.50 (m, 1H), 5.01 (s, 1H), 5.34 (s, 1H), 5.64 (brs, 1H), 6.11 (d, J=11.3 Hz, 1H), 6.36 (d, J=11.3 Hz, 1H). MS m/z: 388 (M$^+$), 91 (100%). UV λ$_{max}$nm: 264.

Example 70

(1) Preparation of [{1α,3β-bis(tert-butyldimethylsilyloxy)9,10-secopregna-5,7,10(19),16-tetraen-20(S)-yl}oxy]-N-(2-methylpropyl)acetamide

[{1α,3β-Bis(tert-butyldimethylsilyloxy)-9,10-secopregna-5,7,10(19),16-tetraen-20(S)-yl}oxy]acetic acid (60 mg, 0.097 mmol) was treated with 2-methylpropylamine (0.1 ml, 0.970 mmol), 2-chloro-1,3-dimethylimidazolinium chloride (25 mg, 0.146 mmol) and pyridine (80 μl, 0.970 mmol) in dichloromethane (1.0 ml) in the same manner as shown in Example 68(1) (at room temperature for 2 hours), followed by work up and purification using preparative thin layer chromatography (0.5 mm×2 plates, hexane:ethyl acetate:ethanol=5:1, developed once) to give a mixture (10.0 mg) containing the titled compound.

(2) Preparation of [{1α,3β-dihydroxy-9,10-secopregna-5,7,10(19),16-tetraen-20(S)-yl}oxy]-N-(2-methylpropyl)acetamide The mixture containing [{1α,3β-bis(tert-butyldimethylsilyloxy)9,10-secopregna-5,7,10(19),16-tetraen-20(S)-yl}oxy]-N-(2-methylpropyl)acetamide from Example 70(1) (10 mg) was treated with a 1M tetrahydrofuran solution of tetra-n-butylammonium fluoride (1.0 ml) in the same manner as shown in Example 17(4) (at an external temperature of 40° C. for 2 hours) and then worked up. The resulting residue was purified by preparative thin layer chromatography (0.5 mm×2 plates, hexane:ethyl acetate:ethanol=5:5:1, developed once) to give the titled compound (0.859 mg, 2% for 2 steps) as a colorless oil.

IR(neat): 3421, 2956, 2850, 1668, 1541, 1437, 1369, 1107, 1055 cm$^{-1}$. $^1$H NMR δ: 0.79 (s, 3H), 0.93 (d, J=6.8 Hz, 6H), 1.35 (d, J=6.8 Hz, 3H), 2.50-2.66 (m, 1H), 2.74-2.88 (m, 1H), 3.02-3.20 (m, 2H), 3.64-4.06 (m, 3H), 4.13-4.30 (m, 1H), 4.34-4.49 (m, 1H), 5.01 (s, 1H), 5.35 (s, 1H), 5.60 (brs, 1H), 6.10 (d, J=10.8 Hz, 1H), 6.36 (d, J=10.8 Hz, 1H), 6.58-6.71 (m, 1H). MS m/z: 425 (M$^+$-H$_2$O), 57 (100%). UV λ$_{max}$nm: 263.

Example 71

(1) Preparation of [{1α,3β-bis(tert-butyldimethylsilyloxy)9,10-secopregna-5,7,10(19),16-tetraen-20(S)-yl}oxy]-N-isopropylacetamide

[{1α,3β-Bis(tert-butyldimethylsilyloxy)-9,10-secopregna-5,7,10(19),16-tetraen-20(S)-yl}oxy]acetic acid (60 mg, 0.097 mmol) was treated with isopropylamine (0.1 ml, 0.970 mmol), 2-chloro-1,3-dimethylimidazolinium chloride (25 mg, 0.146 mmol) and pyridine (80 μl, 0.970 mmol) in dichloromethane (1.0 ml) in the same manner as shown in Example 68 (1) (at room temperature for 2 hours), followed by work up and purification using preparative thin layer chromatography (0.5 mm×2 plates, hexane:ethyl acetate:ethanol=5:1, developed once) to give a mixture (44.0 mg) containing the titled compound.

(2) Preparation of [{1α,3β-dihydroxy-9,10-secopregna-5,7,10(19),16-tetraen-20(S)-yl}oxy]-N-isopropylacetamide The mixture containing [{1α,3β-bis(tert-butyldimethylsilyloxy)9,10-secopregna-5,7,10(19),16-tetraen-20(S)-yl}oxy]-N-isopropylacetamide from Example 71(1) (44 mg) was treated with a 1M tetrahydrofuran solution of tetra-n-butylammonium fluoride (1.0 ml) in the same manner as shown in Example 17(4) (at an external temperature of 40° C. for 2 hours) and then worked up. The resulting residue was purified by preparative thin layer chromatography (0.5 mm×2 plates, hexane:ethyl acetate:ethanol=5:5:1, developed once) to give the titled compound (13.17 mg, 31% for 2 steps) as a colorless oil.

IR(neat): 3406, 2972, 2931, 2850, 1662, 1531, 1446, 1367, 1109, 1055 cm$^{-1}$. $^1$H NMR δ: 0.79 (s, 3H), 1.17 (d, J=6.8 Hz, 6H), 1.35 (d, J=6.5 Hz, 3H), 2.48-2.66 (m, 1H), 2.74-2.87 (m, 1H), 3.58-4.29 (m, 4H), 4.38-4.50 (m, 1H), 5.01 (s, 1H), 5.34 (s, 1H), 5.59 (brs, 1H), 6.10 (d, J=11.1 Hz, 1H), 6.25-6.49 (m, 2H). MS m/z: 429 (M$^+$), 118 (100%). UV λ$_{max}$nm: 264.

Example 72

(1) Preparation of {1α,3β-bis(tert-butyldimethylsilyloxy)-9,10-secopregna-5,7,10(19),16-tetraen-20(S)-yl}oxyacetamide A solution of [{1α,3β-bis(tert-butyldimethylsilyloxy)-9,10-secopregna-5,7,10(19),16-tetraen-20(S)-yl}oxy]acetic acid (15.0 mg, 0.024 mmol) in tetrahydrofuran (0.6 ml) was cooled to 0° C. under a nitrogen atmosphere. After addition of triethylamine (18.3 mg, 0.18 mmol) and ethyl chloroformate (15.6 mg, 0.14 mmol), the reaction mixture was stirred for 30 minutes and further stirred for 20 minutes while bubbling an ammonia gas. The reaction mixture was filtered and evaporated under reduced pressure to remove the solvent, followed by separation using preparative thin layer chromatography (0.5 mm×1 plate, dichloromethane:methanol=10:1, developed once) to give a mixture (14.5 mg) containing the desired product as a colorless oil.

(2) Preparation of {1α,3β-dihydroxy-9,10-secopregna-5,7,10(19),16-tetraen-20(S)-yl}oxyacetamide The mixture containing {1α,3β-bis(tert-butyldimethylsilyloxy)-9,10-secopregna-5,7,10(19),16-tetraen-20(S)-yl}oxyacetamide from Example 72(1) (14.5 mg) was treated in tetrahydrofuran (0.5 ml) with a 1M tetrahydrofuran solution of tetra-n-butylammonium fluoride (0.24 ml) in the same manner as shown in Example 17(4) (at an external temperature of 50° C. for 2 hours) and then worked up. The resulting residue was purified by preparative thin layer chromatography (0.25 mm×2 plates, dichloromethane:methanol=10:1, developed three times and then 0.5 mm×1 plate, hexane:ethyl acetate:ethanol=10:5:2, developed twice) to give the titled compound (5.249 mg, 56.4% for 2 steps) as a colorless oil.

IR(neat): 3353, 2960, 2931, 2873, 1727, 1681, 1457, 1288, 1118, 1056 cm$^{-1}$. $^1$H NMR δ: 0.79 (s, 3H), 1.35 (d, J=6.4 Hz, 3H), 2.18-2.47 (m, 3H), 2.55-2.66 (m, 1H), 2.76-2.88 (m, 1H), 3.78 (d, J=15.5 Hz, 1H), 3.96 (d, J=15.6 Hz, 1H), 3.96-4.06 (m, 1H), 4.19-4.30 (m, 1H), 4.40-4.49 (m, 1H), 5.01 (brs, 1H), 5.34 (brs, 1H), 5.52 (brs, 1H), 5.61 (brs, 1H), 6.11 (d, J=11.2 Hz, 1H), 6.36 (d, J=11.2 Hz, 1H), 6.56 (brs, 1H). MS m/z: 387 (M$^+$), 312 (100%). UV λ$_{max}$nm: 264.

Example 73

(1) Preparation of 1α,3β-dihydroxy-20(S)-(1-trifluoromethyl-2,2,2-trifluoroethoxycarbonylmethoxy)-9,10-secopregna-5,7,10(19),16-tetraene

[{1α,3β-Dihydroxy-9,10-secopregna-5,7,10(19),16-tetraen-20(S)-yl}oxy]acetic acid (9.6 mg, 0.025 mmol) was treated with 1,1,1,3,3,3-hexafluoro-2-propanol (420 mg, 2.5 mmol), 1-ethyl-3-(3-dimethylaminopropyl)carbodiimide hydrochloride (19 mg, 0.10 mmol) and 4-(dimethylamino)pyridine (12 mg, 0.10 mmol) in dichloromethane (0.25 ml) in the same manner as shown in Example 21(1) (at room temperature for 4 hours), followed by work up and purification using preparative thin layer chromatography (0.5 mm×2 plates, hexane:ethyl acetate=1:3, developed twice) to give the titled compound (2.867 mg, 22%) as a colorless glass.

IR(neat): 3360, 2931, 2850, 1803, 1386, 1290, 1234, 1203, 1113 cm$^{-1}$. $^1$H NMR δ: 0.77 (s, 3H), 1.38 (d, J=6.6 Hz, 3H), 2.20-2.41 (m, 3H), 2.57-2.62 (m, 1H), 2.79-2.84 (m, 1H), 4.05-4.30 (m, 4H), 4.39-4.49 (br, 1H), 5.01 (brs, 1H), 5.34 (s, 1H), 5.63 (brs, 1H), 5.75-5.84 (m, 1H), 6.11 (d, J=11.4 Hz, 1H), 6.37 (d, J=11.4 Hz, 1H). MS m/z: 312 (M$^+$-HOCH$_2$CO$_2$CH(CF$_3$)$_2$), 83 (100%). UV λ$_{max}$nm: 264.

Example 74

Preparation of 1α,3β-dihydroxy-20(S)-(isopropylthiocarbonylmethoxy)-9,10-secopregna-5,7,10(19),16-tetraene

[{1α,3β-Dihydroxy-9,10-secopregna-5,7,10(19),16-tetraen-20(S)-yl}oxy]acetic acid (15 mg, 0.0386 mmol) was treated with 2-propanethiol (36 μl, 0.386 mmol), 1-ethyl-3-

(3-dimethylaminopropyl)carbodiimide hydrochloride (74 mg, 0.386 mmol) and 4-(dimethylamino)pyridine (47 mg, 0.386 mmol) in dichloromethane (0.5 ml) in the same manner as shown in Example 21(1) (at room temperature for 2 hours), followed by work up and purification using preparative thin layer chromatography (0.5 mm×1 plate, hexane:ethyl acetate: ethanol=5:5:1, developed once) to give the titled compound (1.157 mg, 7%) as a colorless oil.

IR(neat): 3356, 2927, 2850, 1682, 1442, 1367, 1254, 1128, 1051 cm$^{-1}$. $^1$H NMR δ: 0.79 (s, 3H), 1.40 (d, J=6.5 Hz, 3H), 2.54-2.65 (m, 1H), 2.72-2.88 (m, 1H), 3.55-3.72 (m, 1H), 3.84-4.13 (m, 3H), 4.17-4.30 (m, 1H), 4.37-4.50 (m, 1H), 5.01 (s, 1H), 5.34 (s, 1H), 5.63 (brs, 1H), 6.10 (d, J=11.1 Hz, 1H), 6.37 (d, J=11.1 Hz, 1H). MS m/z: 428 (M$^+$-H$_2$O), 55 (100%). UV λ$_{max}$nm: 263.

Example 75

Preparation of 1α,3β-dihydroxy-20(S)-(tert-butylthiocarbonylmethoxy)-9,10-secopregna-5,7,10(19),16-tetraene

[{1α,3β-Dihydroxy-9,10-secopregna-5,7,10(19),16-tetraen-20(S)-yl}oxy]acetic acid (15 mg, 0.0386 mmol) was treated with 2-methyl-2-propanethiol (44 µl, 0.386 mmol), 1-ethyl-3-(3-dimethylaminopropyl)carbodiimide hydrochloride (74 mg, 0.386 mmol) and 4-(dimethylamino)pyridine (47 mg, 0.386 mmol) in dichloromethane (0.5 ml) in the same manner as shown in Example 21(1) (at room temperature for 2 hours), followed by work up and purification using preparative thin layer chromatography (0.5 mm×1 plate, hexane: ethyl acetate:ethanol=5:5:1, developed once) and then another run of preparative thin layer chromatography (0.5 mm×1 plate, toluene:ethyl acetate=1:1, developed once) to give the titled compound (0.236 mg, 1%) as a colorless oil.

IR(neat): 2927, 2852, 1676, 1456, 1363, 1126, 1051 cm$^{-1}$. $^1$H NMR δ: 0.78 (s, 3H), 1.39 (d, J=6.5 Hz, 3H), 2.52-2.66 (m, 1H), 2.74-2.88 (m, 1H), 3.84 (d, J=15.9 Hz, 1H), 3.93-4.08 (m, 2H), 4.19-4.29 (m, 1H), 4.37-4.49 (m, 1H), 5.01 (s, 1H), 5.34 (s, 1H), 5.62 (brs, 1H), 6.11 (d, J=11.6 Hz, 1H), 6.37 (d, J=11.6 Hz, 1H). MS m/z: 442 (M$^+$-H$_2$O), 57 (100%). UV λ$_{max}$nm: 263.

Example 76

(1) Preparation of tert-butyl [{1α,3β-bis(tert-butyldimethylsilyloxy)pregna-5,7-dien-20(S)-yl}oxy]acetate 1α,3β-Bis(tert-butyldimethylsilyloxy)-20(S)-hydroxypregna-5,7-diene (150 mg, 0.267 mmol) was treated in tetrahydrofuran (2.7 ml) with sodium hydride (60% in oil, 65 mg, 1.625 mmol), 15-crown-5 (16 mg, 0.268 mmol) and tert-butyl bromoacetate (316 mg, 1.62 mmol) in the same manner as shown in Example 17(1) (heated at reflux for 17 hours), followed by work up and separation using preparative thin layer chromatography (0.5 mm×5 plates, hexane:ethyl acetate=5:1, developed once and then 0.5 mm×2 plates, hexane:ethyl acetate=7:1, developed twice) to give the titled compound (30 mg, 17%) as a colorless foam.

$^1$H NMR δ: 0.05 (s, 3H), 0.06 (s, 6H), 0.11 (s, 3H), 0.61 (s, 3H), 0.89 (s, 18H), 1.20 (d, J=5.9 Hz, 3H), 1.48 (s, 9H), 2.73-2.85 (m, 1H), 3.32-3.46 (m, 1H), 3.64-4.13 (m, 4H), 5.29-5.38 (br, 1H), 5.55-5.61 (br, 1H).

(2) Preparation of 1α,3β-dihydroxy-20(S)-(tert-butyloxycarbonylmethoxy)-9,10-secopregna-5,7,10(19)-triene tert-Butyl [{1α,3β-bis(tert-butyldimethylsilyloxy)pregna-5,7-dien-20(S)-yl}oxy]acetate (110 mg, 0.267 mmol) was treated in tetrahydrofuran (200 ml) in the same manner as shown in Example 4(3) (irradiated with light for 6 minutes and 15 seconds, heated at reflux for 2 hours) and then evaporated to remove the solvent. Tetrahydrofuran (5 ml) and hydrogen fluoride/pyridine (70%, 2.31 g) were added to the resulting residue, which was then treated in the same manner as shown in Example 8(3) (at room temperature for 30 minutes), followed by work up and separation using preparative thin layer chromatography (0.5 mm×3 plates, dichloromethane:ethanol=10:1, developed once and then 0.5 mm×2 plates, hexane:ethyl acetate:ethanol=10:10:1, developed twice) to give the titled compound (6.252 mg, 9%) as a colorless foam.

IR(neat): 3380, 2929, 2875, 1749, 1369, 1223, 1128, 1055 cm$^{-1}$. $^1$H NMR δ: 0.54 (s, 3H), 1.18 (d, J=6.1 Hz, 3H), 1.47 (s, 9H), 2.31 (dd, J=13.4, 6.4 Hz, 1H), 2.57-2.63 (m, 1H), 2.80-2.86 (m, 1H), 3.31-3.41 (m, 1H), 3.90 (d, J=16.0 Hz, 1H), 3.98 (d, J=16.0 Hz, 1H), 4.21-4.30 (br, 1H), 4.40-4.49 (br, 1H), 4.99 (brs, 1H), 5.33 (s, 1H), 6.03 (d, J=11.4 Hz, 1H), 6.36 (d, J=11.4 Hz, 1H). MS m/z: 446 (M$^+$), 57 (100%). UV λ$_{max}$nm: 264.

Example 77

(1) Preparation of [{1α,3β-bis(tert-butyldimethylsilyloxy)pregna-5,7-dien-20(S)-yl}oxy]acetic acid To a solution of tert-butyl [{1α,3β-bis(tert-butyldimethylsilyloxy)pregna-5,7-dien-20(S)-yl}oxy]acetate (9 mg, 0.013 mmol) in tetrahydrofuran (0.13 ml), a 1M methanol solution of sodium methoxide (0.13 ml) was added and stirred at room temperature for 20 minutes. Water (0.26 ml) was further added and stirred at room temperature for 30 minutes. The reaction mixture was diluted with ethyl acetate, washed with saturated aqueous sodium dihydrogenphosphate, and then dried over anhydrous sodium sulfate. The solvent was removed under reduced pressure to give the titled compound (6 mg, 73%) as a colorless solid.

$^1$H NMR δ: 0.05 (s, 3H), 0.07 (s, 6H), 0.11 (s, 3H), 0.61 (s, 3H), 0.88 (s, 9H), 0.89 (s, 9H), 2.26-2.42 (m, 2H), 2.74-2.85 (m, 1H), 3.40-3.55 (m, 1H), 3.65-3.73 (br, 1H), 3.91-4.21 (m, 3H), 5.31-5.37 (br, 1H), 5.54-5.61 (m, 1H).

(2) Preparation of 1-ethylpropyl [{1α,3β-bis(tert-butyldimethylsilyloxy)pregna-5,7-dien-20(S)-yl}oxy]acetate

[{1α,3β-Bis(tert-butyldimethylsilyloxy)pregna-5,7-dien-20(S)-yl}oxy]acetic acid (91 mg, 0.147 mmol) was treated with 3-pentanol (39 mg, 0.443 mmol), N,N'-dicyclohexylcarbodiimide (61 mg, 0.296 mmol) and 4-(dimethylamino)pyridine (54 mg, 0.443 mmol) in dichloromethane (1.5 ml) in the same manner as shown in Example 17(3) (at room temperature for 15 hours), followed by work up and purification using preparative thin layer chromatography (0.5 mm×3 plates, hexane:ethyl acetate=5:1, developed once) to give the titled compound (37 mg, 37%) as a colorless oil.

$^1$H NMR δ: 0.05 (s, 3H), 0.06 (s, 6H), 0.11 (s, 3H), 0.61 (s, 3H), 0.89 (s, 18H), 1.21 (d, J=5.9 Hz, 3H), 2.29-2.41 (m, 2H), 2.73-2.85 (m, 1H), 3.35-3.48 (m, 1H), 3.66-3.73 (br, 1H), 3.94-4.16 (m, 3H), 4.78-4.91 (m, 1H), 5.30-5.37 (br, 1H), 5.54-5.63 (m, 1H).

(3) Preparation of 1α,3β-dihydroxy-20(S)-(1-ethyl-propyloxycarbonylmethoxy)-9,10-secopregna-5,7,10(19)-triene 1-Ethylpropyl [{1α,3β-bis(tert-butyldimethylsilyloxy)pregna-5,7-dien-20(S)-yl}oxy]acetate (35 mg, 0.051 mmol) was treated in tetrahydrofuran (200 ml) in the same manner as shown in Example 4(3) (irradiated with light for 4 minutes and 45 seconds, heated at reflux for 2 hours) and then evaporated to remove the solvent. Tetrahydrofuran (2 ml) and hydrogen fluoride/pyridine (70%, 0.51 g) were added to the resulting residue, which was then treated in the same manner as shown in Example 8(3) (at room temperature for 1 hour), followed by work up and purification using preparative thin layer chromatography (0.5 mm×2 plates, dichloromethane:ethanol=10:1, developed once and then 0.5 mm×1 plate, hexane:ethyl acetate:ethanol=10:10:1, developed once) to give the titled compound (2.506 mg, 11%) as a colorless glass.

IR(neat): 3390, 2931, 2877, 1751, 1458, 1375, 1286, 1203, 1055 cm$^{-1}$. $^1$H NMR δ: 0.54 (s, 3H), 0.88 (t, J=7.4 Hz, 6H), 1.20 (d, J=6.1 Hz, 3H), 2.31 (dd, J=13.4, 6.4 Hz, 1H), 2.57-2.63 (m, 1H), 2.80-2.86 (m, 1H), 3.35-3.43 (m, 1H), 4.02 (d, J=16.2 Hz, 1H), 4.10 (d, J=16.2 Hz, 1H), 4.21-4.30 (br, 1H), 4.40-4.49 (br, 1H), 4.79-4.88 (m, 1H), 4.99 (brs, 1H), 5.33 (s, 1H), 6.03 (d, J=11.4 Hz, 1H), 6.36 (d, J=11.4 Hz, 1H). MS m/z: 460 (M$^+$), 55 (100%). UV λ$_{max}$nm: 265.

Example 78

(1) Preparation of [{1α,3β-bis(tert-butyldimethylsilyloxy)-9,10-secopregna-5,7,10(19),16-tetraen-20(R)-yl}oxy]-N-(tert-butyl)acetamide 1α,3β-Bis(tert-butyldimethylsilyloxy)-20(S)-hydroxy-9,10-secopregna-5,7,10(19),16-tetraene (41 mg, 0.073 mmol) was treated in tetrahydrofuran (0.7 ml) with sodium hydride (60% in oil, 18 mg, 0.44 mmol), 15-crown-5 (16 mg, 0.073 mmol) and 2-bromo-N-(tert-butyl)acetamide (85 mg, 0.44 mmol) in the same manner as shown in Example 17(1) (heated at reflux for 6 hours), followed by work up and separation using preparative thin layer chromatography (0.5 mm×3 plates, dichloromethane alone, developed once) to give a mixture (33 mg) containing the desired product as a pale yellow oil.

(2) Preparation of {(1α,3β-dihydroxy-9,10-secopregna-5,7,10(19),16-tetraen-20(R)-yl)oxy}-N-(tert-butyl)acetamide The mixture containing [{1α,3β-bis(tert-butyldimethylsilyloxy)-9,10-secopregna-5,7,10(19),16-tetraen-20(R)-yl}oxy]-N-(tert-butyl)acetamide from Example 78 (1) (31 mg) was treated with a 1M tetrahydrofuran solution of tetra-n-butylammonium fluoride (0.5 ml) in the same manner as shown in Example 17(4) (at an external temperature of 60° C. for 1 hour) and then worked up. The resulting residue was purified by preparative thin layer chromatography (0.5 mm×2 plates, dichloromethane:ethanol=10:1, developed once) to give the titled compound (10.028 mg, 33% for 2 steps) as a colorless glass.

IR(neat): 3400, 2968, 2931, 1662, 1533, 1365, 1103, 1057 cm$^{-1}$. $^1$H NMR δ: 0.75 (s, 3H), 1.37 (s, 9H), 2.20-2.44 (m, 3H), 2.57-2.62 (m, 1H), 2.79-2.84 (m, 1H), 3.79 (s, 2H), 4.02-4.15 (m, 1H), 4.21-4.45 (m, 1H), 4.40-4.49 (m, 1H), 5.00 (brs, 1H), 5.34 (s, 1H), 5.64 (brs, 1H), 6.11 (d, J=11.4 Hz, 1H), 6.36 (d, J=11.4 Hz, 1H), 6.46 (brs, 1H). MS m/z: 443 (M$^+$), 57 (100%). UV λ$_{max}$nm: 263.

Example 79

(1) Preparation of 1α,3β-bis(tert-butyldimethylsilyloxy)-20(S)-(methoxycarbonylpropoxy)-9,10-secopregna-5,7,10(19),16-tetraene 1α,3β-Bis(tert-butyldimethylsilyloxy)-20(S)-hydroxy-9,10-secopregna-5,7,10(19),16-tetraene (147.4 mg, 0.264 mmol) was treated with sodium hydride (60% in oil, 112.0 mg, 2.800 mmol), 15-crown-5 (580.0 mg, 2.633 mmol) and 4-bromo-1,1,1-trimethoxybutane (346.0 mg, 1.523 mmol) in tetrahydrofuran (0.5 ml) in the same manner as shown in Example 17(1) (at an external temperature of 68° C. for 17 hours and 30 minutes) and then worked up. The resulting residue was purified by preparative thin layer chromatography (0.5 mm×2 plates, hexane:ethyl acetate=15:1, developed once and then 0.5 mm×1 plate, hexane:ethyl acetate=20:1, developed once) to give a mixture (43.1 mg) containing the titled compound.

(2) Preparation of 4-[{1α,3β-bis(tert-butyldimethylsilyloxy)-9,10-secopregna-5,7,10(19),16-tetraen-20(S)-yl}oxy]butyric Acid The mixture containing 1α,3β-bis(tert-butyldimethylsilyloxy)-20(S)-(methoxycarbonylpropoxy)-9,10-secopregna-5,7,10(19),16-tetraene (21.8 mg, 0.033 mmol) was treated with 2M aqueous sodium hydroxide (0.2 ml) in methanol (0.2 ml) and tetrahydrofuran (0.5 ml) in the same manner as shown in Example 17(2) (at room temperature for 16 hours) and then worked up. The resulting residue was purified by preparative thin layer chromatography (0.25 mm×1 plate, dichloromethane:ethanol=30:1, developed twice) to give the titled compound (6.9 mg, 49%) as a colorless oil.

IR(neat): 2936, 1712, 1462, 1362, 1252, 1214, 1166, 1080 cm$^{-1}$. $^1$H NMR δ: 0.06 (s, 6H), 0.07 (s, 3H), 0.76 (s, 3H), 0.88 (s, 18H), 1.30 (d, J=6.3 Hz, 3H), 2.16-2.28 (m, 2H), 2.34-2.55 (m, 2H), 2.75-2.87 (m, 1H), 3.25-3.39 (m, 1H), 3.44-3.56 (m, 1H), 3.87-3.98 (m, 1H), 4.14-4.25 (m, 1H), 4.35-4.40 (m, 1H), 4.88 (brs, 1H), 5.20 (brs, 1H), 5.57 (brs, 1H), 6.10 (d, J=11.0 Hz, 1H), 6.23 (d, J=11.0 Hz, 1H). UV λ$_{max}$nm: 263.

(3) Preparation of 1α,3β-bis(tert-butyldimethylsilyloxy)-20(S)-(tert-butoxycarbonylpropoxy)-9,10-secopregna-5,7,10(19),16-tetraene 4-[{1α,3β-Bis(tert-butyldimethylsilyloxy)-9,10-secopregna-5,7,10(19),16-tetraen-20(S)-yl}oxy]butyric acid (7.5 mg, 0.012 mmol) was treated with tert-butanol (288.0 mg, 3.886 mmol), 1-ethyl-3-(3-dimethylaminopropyl)carbodiimide hydrochloride (70.0 mg, 0.365 mmol) and 4-(dimethylamino)pyridine (71.0 mg, 0.581 mmol) in dichloromethane (0.05 ml) in the same manner as shown in Example 21(1) (at room temperature for 30 minutes). The reaction mixture was purified by preparative thin layer chromatography (0.5 mm×1 plate, hexane:ethyl acetate=15:1, developed twice, dichloromethane:ethanol=10:1, developed twice) to give the titled compound (3.5 mg, 43%) as a colorless oil and recover the starting material (2.1 mg, 28%).

IR(neat): 2952, 2932, 2856, 1732, 1462, 1366, 1254, 1156, 1088 cm$^{-1}$. $^1$H NMR δ: 0.06 (s, 6H), 0.07 (s, 6H), 0.76 (s, 3H), 0.87 (s, 9H), 0.88 (s, 9H), 1.28 (d, J=6.6 Hz, 3H), 1.44 (s, 9H), 2.76-2.86 (m, 1H), 3.20-3.34 (m, 1H), 3.34-3.48 (m, 1H), 3.86 (q, J=6.6 Hz, 1H), 4.15-4.26 (m, 1H), 4.34-4.42 (m, 1H), 4.88 (brs, 1H), 5.18 (brs, 1H), 5.55 (brs, 1H), 6.10 (d, J=11.2 Hz, 1H), 6.35 (d, J=11.2 Hz, 1H). MS m/z: 700 (M$^+$), 73 (100%). UV $\lambda_{max}$nm: 263.

(4) Preparation of 1α,3β-dihydroxy-20(S)-(tert-butoxycarbonylpropoxy)-9,10-secopregna-5,7,10(19), 16-tetraene The mixture containing 1α,3β-bis(tert-butyldimethylsilyloxy)-20(S)-(tert-butoxycarbonylpropoxy)-9,10-secopregna-5,7,10(19),16-tetraene from Example 79(3) (5.8 mg) was treated with a 1M tetrahydrofuran solution of tetra-n-butylammonium fluoride (0.1 ml) in the same manner as shown in Example 17(4) (at an external temperature of 43° C. for 20 minutes). The reaction mixture was purified by preparative thin layer chromatography (0.25 mm×1 plate, dichloromethane:ethanol=15:1, developed twice) to give the titled compound (1.1 mg, 10% for 2 steps) as a colorless oil.

IR(neat): 3388, 2928, 2852, 1728, 1446, 1368, 1252, 1156, 1106, 1058 cm$^{-1}$. $^1$H NMR δ: 0.77 (s, 3H), 1.28 (d, J=6.6 Hz, 3H), 1.44 (s, 9H), 2.30 (t, J=7.3 Hz, 2H), 2.56-2.65 (m, 1H), 2.78-2.88 (m, 1H), 3.22-3.33 (m, 1H), 3.35-3.48 (m, 1H), 4.19-4.30 (m, 1H), 4.40-4.50 (m, 1H), 5.01 (brs, 1H), 5.34 (brs, 1H), 5.55 (brs, 1H), 6.10 (d, J=11.3 Hz, 1H), 6.37 (d, J=11.3 Hz, 1H). MS m/z: 472 (M$^+$), 57 (100%). UV $\lambda_{max}$nm: 263.

Example 80

(1) Preparation of 1α,3β-bis(tert-butyldimethylsilyloxy)-17-methylandrosta-5,7,17-trien 4-phenyl-1,2, 4-triazolin-3,5-dione Adduct To a solution of 1α,3β-bis(tert-butyldimethylsilyloxy)-17-oxoandrosta-5,7-diene 4-phenyl-1,2,4-triazolin-3,5-dione adduct (70.0 g, 99 mmol) in tetrahydrofuran (300 ml), potassium tert-butoxide (14.50 g, 129 mmol) and then methyltriphenylphosphonium bromide (46.05 g, 129 mmol) were added, followed by heating at reflux for 2 hours. After cooling to room temperature, the reaction mixture was partitioned between ethyl acetate and aqueous sodium chloride. The organic layer was dried over anhydrous magnesium sulfate and evaporated under reduced pressure to remove the solvent. The resulting residue was stirred in acetonitrile (250 ml) at room temperature for 30 minutes and filtered. The resulting solid was washed again with acetonitrile and dried to give the titled compound (61.78 g, 89%) as a colorless solid.

$^1$H NMR δ: 0.06 (s, 3H), 0.08 (s, 3H), 0.09 (s, 3H), 0.13 (s, 3H), 0.87 (s, 9H), 0.89 (s, 9H), 2.35-2.72 (m, 5H), 3.23-3.30 (m, 1H), 3.85 (brs, 1H), 4.70 (s, 2H), 4.70-4.83 (m, 1H), 6.23 (d, J=7.9 Hz, 1H), 6.39 (d, J=7.9 Hz, 1H), 7.23-7.46 (m, 5H).

(2) Preparation of 1α,3β-bis(tert-butyldimethylsilyloxy)-16β-hydroxy-17-methylandrosta-5,7,17-triene To a suspension of selenium dioxide (4.87 g, 43.9 mmol) in dichloromethane (300 ml), tert-butyl hydroperoxide (70% aq., 25 ml) was added and stirred at room temperature for 20 minutes. A solution of 1α,3β-bis(tert-butyldimethylsilyloxy)-17-methylandrosta-5,7,17-triene 4-phenyl-1,2,4-triazolin-3,5-dione adduct (61.75 g, 87.7 mmol) in dichloromethane (300 ml) was further added and stirred at 30° C. for 15 hours. The reaction mixture was washed with 2M aqueous sodium hydroxide and aqueous sodium chloride, dried over anhydrous magnesium sulfate, and then evaporated under reduced pressure to remove the solvent. The resulting residue was purified by column chromatography (hexane:dichloromethane:acetone=5:5:1) to give 1α,3β-bis(tert-butyldimethylsilyloxy)-16-hydroxy-17-methylandrosta-5,7,17-triene 4-phenyl-1,2,4-triazolin-3,5-dione adduct (41.73 g) as a colorless solid. 1,3-Dimethyl-2-imidazolidinone (810 ml) was added to this solid and stirred at 160° C. for 50 minutes. After cooling to room temperature, the reaction mixture was partitioned between ethyl acetate and aqueous sodium chloride. The organic layer was washed twice with saturated aqueous sodium chloride, dried over anhydrous sodium sulfate, and then evaporated under reduced pressure to remove the solvent. The resulting residue was purified by column chromatography (hexane:ethyl acetate=9:1) to give the titled compound (12.30 g, 39% for 2 steps) as a slightly yellow solid and 1α,3β-bis(tert-butyldimethylsilyloxy)-16α-hydroxy-17-methylandrosta-5,7,17-triene (14.35 g, 45% for 2 steps) as a slightly yellow foam.

For 1α,3β-bis(tert-butyldimethylsilyloxy)-16β-hydroxy-17-methylandrosta-5,7,17-triene:

$^1$H NMR δ: 0.05 (s, 3H), 0.06 (s, 3H), 0.07 (s, 3H), 0.11 (s, 3H), 0.87 (s, 9H), 0.88 (s, 9H), 0.92 (s, 3H), 0.94 (s, 3H), 2.78-2.88 (m, 1H), 3.71 (brs, 1H), 4.00-4.15 (m, 1H), 4.60 (brs, 1H), 4.94 (d, J=1.7 Hz, 1H), 5.09 (d, J=1.3 Hz, 1H), 5.36-5.39 (m, 1H), 5.59 (d, J=5.6 Hz, 1H).

For 1α,3β-bis(tert-butyldimethylsilyloxy)-16α-hydroxy-17-methylandrosta-5,7,17-triene:

$^1$H NMR δ: 0.06 (s, 3H), 0.07 (s, 6H), 0.11 (s, 3H), 0.74 (s, 3H), 0.88 (s, 9H), 0.89 (s, 9H), 0.92 (s, 3H), 2.80-2.91 (m, 1H), 3.68-3.75 (br, 1H), 3.98-4.14 (m, 1H), 4.67-4.76 (m, 1H), 4.93 (brs, 1H), 5.11 (brs, 1H), 5.33-5.39 (m, 1H), 5.56-5.62 (m, 1H).

(3) Preparation of {1α,3β-bis(tert-butyldimethylsilyloxy)}-16β-hydroxy-17-methyl-9,10-secoandrosta-5, 7,10(19),17-tetraene 1α,3β-Bis(tert-butyldimethylsilyloxy)-16β-hydroxy-17-methylandrosta-5,7,17-triene (2.00 g, 3.67 mmol) was treated in ethanol (650 ml) in the same manner as shown in Example 4(3) (irradiated with light for 2.5 hours, heated at reflux for 2 hours), followed by work up and purification using column chromatography (hexane:dichloromethane=2:3 and then hexane:ethyl acetate=9:1) and preparative thin layer chromatography (0.5 mm×3 plates, hexane:ethyl acetate=9:1, developed three times) to give a colorless foamy fraction containing the titled compound (0.40 g).

(4) Preparation of 1α,3β-bis(tert-butyldimethylsilyloxy)-17-methyl-16-oxo-9,10-secoandrosta-5,7,10 (19),17-tetraene The fraction containing 1α,3β-bis(tert-butyldimethylsilyloxy)-16β-hydroxy-17-methyl-9,10-secoandrosta-5,7,10 (19),17-tetraene from Example 80(3) (400 mg) was dissolved in dichloromethane (20 ml). Molecular sieve 4A (2 g) was added to this solution, followed by ultrasonic irradiation for 1 minute. Manganese dioxide (2.40 g) was added to the reaction mixture and stirred at room temperature for 10 minutes. After insoluble products were filtered off, the solvent was removed under reduced pressure and the residue was purified by column chromatography (hexane:ethyl acetate=9:1) to give a fraction containing the titled compound (342 mg).

(5) 17β-Acetylthiomethyl-1α,3β-bis(tert-butyldimethylsilyloxy)-16-oxo-9,10-secoandrosta-5,7,10(19)-triene The fraction containing 1α,3β-bis(tert-butyldimethylsilyloxy)-17-methyl-16-oxo-9,10-secoandrosta-5,7,10(19),17-tetraene from Example 80 (4) (340 mg) was dissolved in dichloromethane (5 ml). Pyridine (0.6 ml) was added to this solution, which was then purged with argon. Thioacetic acid (480 mg, 6.3 mmol) was added to this solution and stirred at room temperature for 10 minutes. After evaporation under reduced pressure to remove the solvent, the resulting residue was purified by column chromatography (hexane:ethyl acetate=10:1) to give a fraction containing the titled compound (286 mg).

(6) 17β-Acetylthiomethyl-1α,3β-bis(tert-butyldimethylsilyloxy) -16β-hydroxy-9,10-secoandrosta-5,7,10(19)-triene The fraction containing 17β-acetylthiomethyl-1α,3β-bis (tert-butyldimethylsilyloxy)-16-oxo-9,10-secoandrosta-5,7,10(19)-triene from Example 80(5) (285 mg) was dissolved in tetrahydrofuran (15 ml), to which a 1M tetrahydrofuran solution of tri-tert-butoxyaluminum lithium hydride (0.92 ml) was then added and stirred at room temperature for 30 minutes. After addition of hexane (50 ml) and saturated aqueous ammonium chloride (0.5 ml), the reaction mixture was stirred for 30 minutes and filtered to remove insoluble products. The filtrate was concentrated under reduced pressure and purified by column chromatography (hexane:ethyl acetate=9:1) to give a fraction containing the titled compound (220 mg).

(7) 17β-Acetylthiomethyl-1α,3β,16β-trihydroxy-9,10-secoandrosta-5,7,10(19)-triene The fraction containing 17β-acetylthiomethyl-1α,3β-bis (tert-butyldimethylsilyloxy)-16β-hydroxy-9,10-secoandrosta-5,7,10(19)-triene from Example 80 (6) (220 mg) was treated with AMBERLYST 15 (1.5 g) in methanol (3 ml) and tetrahydrofuran (3 ml) in the same manner as shown in Example 6(3) (at room temperature for 2 hours) and then worked up. The resulting residue was purified by preparative thin layer chromatography (0.5 mm×1 plate, ethyl acetate alone, developed once) to give the titled compound (13 mg for 5 steps, 66%) as a colorless glass.
$^1$H NMR δ: 0.71 (s, 3H), 2.36 (s, 3H), 2.54-2.66 (m, 1H), 2.80-2.94 (m, 2H), 3.07-3.22 (m, 1H), 4.05-4.47 (m, 4H), 4.99 (brs, 1H), 5.32 (brs, 1H), 6.04 (d, J=11.5 Hz, 1H), 6.36 (d, J=11.5 Hz, 1H).

(8) Preparation of 17β-tert-butyloxycarbonylmethylthiomethyl-1α,3β,16β-trihydroxy-9,10-secoandrosta-5,7,10(19)-triene 17β-Acetylthiomethyl-1α,3β,16β-trihydroxy-9,10-secoandrosta-5,7,10(19)-triene (5 mg, 0.013 mmol) was treated with a 1M methanol solution of potassium hydroxide (0.13 ml) and tert-butyl bromoacetate (76 mg, 0.390 mmol) in tetrahydrofuran (2 ml) in the same manner as shown in Example 16(2) (at room temperature for 16 hours) and then worked up. The resulting residue was purified by preparative thin layer chromatography (0.5 mm×2 plates, dichloromethane:acetonitrile=3:2, developed once) to give the titled compound (3.056 mg, 52%) as a colorless glass.
IR(neat): 3400, 2933, 2838, 1716, 1296, 1257, 1053 cm$^{-1}$.
$^1$H NMR δ: 0.67 (s, 3H), 1.48 (s, 9H), 2.57-2.92 (m, 5H), 3.16 (d, J=15.5 Hz, 1H), 3.24 (d, J=15.5 Hz, 1H), 4.20-4.30 (m, 1H), 4.38-4.60 (m, 2H), 4.99 (brs, 1H), 5.31 (s, 1H), 6.05 (d, J=11.2 Hz, 1H), 6.36 (d, J=11.2 Hz, 1H). MS m/z: 464 (M$^+$), 57 (100%). UV λ$_{max}$nm: 263.

Example 81

(1) Preparation of 1α,3β-bis(tert-butyldimethylsilyloxy)-16-oxo-9,10-secopregna-5,7,10(19),(17E)-tetraene 1α,3β-Bis(tert-butyldimethylsilyloxy)-16β-hydroxy-9,10-secopregna-5,7,10(19),(17E)-tetraene (2.0 g, 3.578 mmol) was treated in dichloromethane (100 ml) with molecular sieve 4A (10 g) and manganese dioxide (12 g, 138.1 mmol) in the same manner as shown in Example 80(4) (at room temperature for 10 minutes), followed by work up and purification using column chromatography (hexane:ethyl acetate=30:1) to give the titled compound (1.56 g, 78%) as a white foam.
$^1$H NMR(C$_6$D$_6$) δ: 0.78 (s, 3H), 1.43 (d, J=7.6 Hz, 3H), 2.69-2.82 (m, 1H), 4.18-4.29 (m, 1H), 4.39-4.47 (m, 1H), 5.02 (brs, 1H), 5.28 (brs, 1H), 6.25 (d, J=11.6 Hz, 1H), 6.41 (d, J=11.6 Hz, 1H), 6.66 (q, J=7.6 Hz, 1H).

(2) Preparation of 20(S)-acetylthio-1α,3β-bis(tert-butyldimethylsilyloxy)-16-oxo-9,10-secopregna-5,7,10 (19-triene 1α,3β-Bis(tert-butyldimethylsilyloxy)-16-oxo-9,10-secopregna-5,7,10(19),(17E)-tetraene (1.56 g, 2.80 mmol) was treated in dichloromethane (50 ml) with pyridine (2.27 ml, 28.0 mmol) and thioacetic acid (2.01 ml, 28.0 mmol) in the same manner as shown in Example 80 (5) (at room temperature for 1.5 hours), followed by work up and purification using column chromatography (hexane:ethyl acetate=10:1, twice) to give a mixture (1.20 g) containing the titled compound.

(3) Preparation of 20(S)-acetylthio-1α,3β-bis(tert-butyldimethylsilyloxy)-16β-hydroxy-9,10-secopregna-5,7,10(19)-triene The mixture containing 20(S)-acetylthio-1α,3β-bis(tert-butyldimethylsilyloxy)-16-oxo-9,10-secopregna-5,7,10 (19)-triene from Example 81 (2) (1.20 g) was treated with a 1M tetrahydrofuran solution of tri-tert-butoxyaluminum lithium hydride (3.8 ml) in tetrahydrofuran (45 ml) in the same manner as shown in Example 80 (6) (at room temperature for 1 hour), followed by work up and purification using column chromatography (hexane:ethyl acetate=10:1) to give a mixture (1.02 g) containing the titled compound.

(4) Preparation of 1α,3β-bis(tert-butyldimethylsilyloxy)-16β-hydroxy-20(S)-(tert-butoxycarbonylmethylthio)-9,10-secopregna-5,7,10(19)-triene The mixture containing 20(S)-acetylthio-1α,3β-bis(tert-butyldimethylsilyloxy)-16β-hydroxy-9,10-secopregna-5,7, 10(19)-triene from Example 81 (3) (20 mg) was dissolved in tetrahydrofuran (0.2 ml), to which methanol (0.2 ml) and 2M aqueous sodium hydroxide (0.16 ml) were then added under an argon atmosphere. After stirring at room temperature for 30 minutes, tert-butyl bromoacetate (0.046 ml) was added to the reaction mixture and further stirred at room temperature for 1 hour. Ethyl acetate was added to the reaction mixture, which was then washed with water and saturated aqueous sodium chloride, dried over anhydrous sodium sulfate and filtered to remove solids. After evaporation under reduced pressure to remove the solvent, the resulting residue was purified by preparative thin layer chromatography (0.5 mm×1 plate, hexane:ethyl acetate=6:1, developed once) to give the titled compound (12 mg) as a colorless oil.

$^1$H NMR δ: 0.06 (s, 6H), 0.07 (s, 6H), 0.84 (s, 3H), 0.87 (s, 9H), 0.88 (s, 9H), 1.47 (s, 9H), 2.77-2.88 (m, 1H), 3.10 (d, J=14.6 Hz, 1H), 3.22-3.34 (m, 2H), 4.13-4.25 (m, 1H), 4.34-4.50 (m, 2H), 4.87 (s, 1H), 5.20 (s, 1H), 6.01 (d, J=11.3 Hz, 1H), 6.22 (d, J=11.3 Hz, 1H).

(5) Preparation of 1α,3β,16β-trihydroxy-20(S)-(tert-butoxycarbonylmethylthio)-9,10-secopregna-5,7,10(19)-triene To a solution of 1α,3β-bis(tert-butyldimethylsilyloxy)-16β-hydroxy-20(S)-(tert-butoxycarbonylmethylthio)-9,10-secopregna-5,7,10(19)-triene (16 mg, 0.0228 mmol) in tetrahydrofuran (0.5 ml), a 1M tetrahydrofuran solution of tetra-n-butylammonium fluoride (0.5 ml) was added under a nitrogen atmosphere and stirred at room temperature for 2 days. The reaction mixture was poured into water, extracted with ethyl acetate, and then washed sequentially with 0.5 M hydrochloric acid, saturated aqueous sodium bicarbonate and saturated aqueous sodium chloride. The organic layer was dried over anhydrous sodium sulfate and filtered to remove solids. After evaporation under reduced pressure to remove the solvent, the resulting residue was purified by preparative thin layer chromatography (0.5 mm×1 plate, hexane:ethyl acetate:ethanol=5:5:1, developed once) to give the titled compound (5.821 mg, 53%) as a colorless oil.

IR(neat): 2925, 2863, 2358, 2332, 1699, 1647, 1296, 1128, 1053 cm$^{-1}$. $^1$H NMR δ: 0.85 (s, 3H), 1.47 (s, 9H), 2.77-2.87 (m, 1H), 3.09 (d, J=14.0 Hz, 1H), 3.22-3.35 (m, 2H), 4.18-4.29 (m, 1H), 4.38-4.49 (m, 2H), 5.01 (s, 1H), 5.33 (s, 1H), 6.01 (d, J=11.3 Hz, 1H), 6.37 (d, J=11.3 Hz, 1H). MS m/z: 478 (M$^+$), 57 (100%). UV λ$_{max}$nm: 264.

Example 82

(1) Preparation of {1α,3β-bis(tert-butyldimethylsilyloxy)}-20(S)-(tert-butyloxycarbonylmethylthio)-9,10-secopregna-5,7,10(19),16-tetraene {1α,3β-Bis(tert-butyldimethylsilyloxy)}-20(S)-phenoxycarbonylthio-9,10-secopregna-5,7,10(19),16-tetraene (20 mg, 0.0220 mmol), tetrahydrofuran (0.34 ml) and methanol (0.34 ml) were mixed, to which 2M aqueous sodium hydroxide (0.17 ml) and then tert-butyl bromoacetate (56 mg, 0.288 mmol) were added under an argon atmosphere. After stirring at room temperature for 30 minutes, the reaction mixture was diluted with ethyl acetate and washed with aqueous sodium chloride. The organic layer was dried over anhydrous sodium sulfate, filtered and evaporated under reduced pressure to remove the solvent. The resulting residue was separated by preparative thin layer chromatography (0.5 mm×2 plates, hexane:ethyl acetate=100:9, developed once) to give a mixture (10 mg) containing the desired product as a colorless oil.

(2) Preparation of 1α,3β-dihydroxy-20(S)-(tert-butyloxycarbonylmethylthio)-9,10-secopregna-5,7,10(19),16-tetraene The mixture containing {1α,3β-bis(tert-butyldimethylsilyloxy)}-20(S)-(tert-butyloxycarbonylmethylthio)-9,10-secopregna-5,7,10(19),16-tetraene from Example 82 (1) (10 mg) was treated in tetrahydrofuran (0.5 ml) with a 1M tetrahydrofuran solution of tetra-n-butylammonium fluoride (1.0 ml) in the same manner as shown in Example 17(4) (at an external temperature of 50° C. for 1 hour) and then worked up. The resulting residue was purified by preparative thin layer chromatography (0.5 mm×2 plates, dichloromethane:acetonitrile=3:2, developed once; 0.5 mm×1 plate, toluene:ethyl acetate=9:11, developed twice; and then 0.5 mm×1 plate, hexane:ethyl acetate:ethanol=8:8:1, developed once) to give the titled compound (1.754 mg, 13% for 2 steps) as a colorless glass.

IR(neat): 3379, 2929, 2850, 1724, 1367, 1292, 1132, 1055 cm$^{-1}$. $^1$H NMR δ: 0.81 (s, 3H), 1.42 (d, J=7.3 Hz, 3H), 1.46 (s, 9H), 2.22-2.43 (m, 3H), 2.57-2.62 (m, 1H), 2.79-2.83 (m, 1H), 3.12 (s, 2H), 4.20-4.30 (br, 1H), 4.39-4.49 (br, 1H), 5.01 (brs, 1H), 5.34 (s, 1H), 5.64 (brs, 1H), 6.10 (d, J=11.2 Hz, 1H), 6.37 (d, J=11.2 Hz, 1H). MS m/z: 460 (M$^+$), 57 (100%). UV λ$_{max}$nm: 264.

Example 83

(1) Preparation of 1α,3β-dihydroxy-20(S)-phenoxycarbonylthio-9,10-secopregna-5,7,10(19),16-tetraene {1α,3β-Bis(tert-butyldimethylsilyloxy)}-20(S)-phenoxycarbonylthio-9,10-secopregna-5,7,10(19),16-tetraene (55 mg, 0.0791 mmol) was treated in tetrahydrofuran (5 ml) and methanol (5 ml) with AMBERLYST 15 (2 g) in the same manner as shown in Example 6(3) (at room temperature for 3 hours), followed by work up and purification using preparative thin layer chromatography (0.5 mm×3 plates, dichloromethane:ethanol=10:1, developed once) to give the titled compound (17 mg, 46%) as a colorless glass.

$^1$H NMR δ: 0.86 (s, 3H), 1.58 (d, J=6.9 Hz, 3H), 2.54-2.66 (m, 1H), 2.77-2.88 (m, 1H), 4.12 (q, J=7.3 Hz, 1H), 4.19-4.29 (m, 1H), 4.40-4.48 (m, 1H), 5.01 (brs, 1H), 5.34 (s, 1H), 5.74 (brs, 1H), 6.11 (d, J=10.9 Hz, 1H), 6.37 (d, J=10.9 Hz, 1H), 7.12-7.41 (m, 5H).

(2) Preparation of {(1α,3β-dihydroxy-9,10-secopregna-5,7,10(19),16-tetraen-20(S)-yl)thio}-N-(tert-butyl)acetamide 1α,3β-Dihydroxy-20(S)-phenoxycarbonylthio-9,10-secopregna-5,7,10(19),16-tetraene (6 mg, 0.0129 mmol) was treated with a 1M methanol solution of potassium hydroxide (0.5 ml) and 2-bromo-N-(tert-butyl)acetamide (10 mg, 0.0515 mmol) in the same manner as shown in Example 16(2) (at room temperature for 15 hours) and then worked up. The resulting residue was purified by preparative thin layer chromatography (0.5 mm×2 plates, dichloromethane:acetonitrile=3:2, developed once) to give the titled compound (3.874 mg, 66%) as a colorless glass.

IR(neat): 3340, 2964, 2931, 1653, 1525, 1454, 1223, 1057 cm$^{-1}$. $^1$H NMR δ: 0.83 (s, 3H), 1.36 (s, 9H), 2.22-2.42 (m, 3H), 2.57-2.62 (m, 1H), 2.79-2.83 (m, 1H), 3.07 (s, 2H), 3.33-3.48 (m, 1H), 4.20-4.30 (br, 1H), 4.39-4.49 (br, 1H), 5.01 (brs, 1H), 5.34 (s, 1H), 5.63 (brs, 1H), 6.10 (d, J=11.2 Hz, 1H), 6.36 (d, J=11.2 Hz, 1H), 6.72 (brs, 1H). MS m/z: 459 (M$^+$), 57 (100%). UV λ$_{max}$nm: 263.

Example 84

Preparation of {(1α,3β-dihydroxy-9,10-secopregna-5,7,10(19),16-tetraen-20(S)-yl)thio}-N-(tert-butyl)-N-methyl-acetamide 1α,3β-Dihydroxy-20(S)-phenoxycarbonylthio-9,10-secopregna-5,7,10(19),16-tetraene (5 mg, 0.0107 mmol) was treated with a 1M methanol solution of potassium hydroxide (0.5 ml) and 2-bromo-N-(tert-butyl)-N-methylacetamide (10 mg, 0.0481 mmol) in the same manner as shown in Example 16(2) (at room temperature for 15 hours) and then worked up. The resulting residue was purified by preparative thin layer chromatography (0.5 mm×2 plates, dichloromethane:acetonitrile=2:1, developed twice) to give the titled compound (3.102 mg, 61%) as a colorless glass.

IR(neat): 3380, 2927, 2850, 1630, 1367, 1211, 1093, 1057 cm$^{-1}$. $^1$H NMR δ: 0.82 (s, 3H), 1.41 (s, 9H), 1.46 (d, J=6.9 Hz, 3H), 2.21-2.42 (m, 3H), 2.57-2.62 (m, 1H), 2.79-2.83 (m, 1H), 2.94 (s, 3H), 3.19-3.29 (m, 2H), 3.58-3.66 (m, 1H), 4.20-4.30 (br, 1H), 4.39-4.49 (br, 1H), 5.01 (brs, 1H), 5.34 (s, 1H), 5.66 (brs, 1H), 6.10 (d, J=11.2 Hz, 1H), 6.37 (d, J=11.2 Hz, 1H). MS m/z: 473 (M$^+$), 57 (100%). UV $\lambda_{max}$nm: 263.

Example 85

Preparation of {(1α,3β-dihydroxy-9,10-secopregna-5,7,10(19),16-tetraen-20(S)-yl)thio}-N-methoxy-N-methylacetamide and {(1α,3β-dihydroxy-9,10-secopregna-5,7,10(19),16-tetraen-20(S)-yl)thio}-N-methylacetamide 1α,3β-Dihydroxy-20(S)-phenoxycarbonylthio-9,10-secopregna-5,7,10(19),16-tetraene (5 mg, 0.0107 mmol) was treated with a 1M methanol solution of potassium hydroxide (0.5 ml) and 2-bromo-N-methoxy-N-methylacetamide (10 mg, 0.0549 mmol) in the same manner as shown in Example 16(2) (at room temperature for 15 hours) and then worked up. The resulting residue was purified by preparative thin layer chromatography (0.5 mm×1 plate, hexane:ethyl acetate:ethanol=10:10:1, developed once and then 0.5 mm×1 plate, dichloromethane:acetonitrile=1:1, developed once) to give {(1α,3β-dihydroxy-9,10-secopregna-5,7,10(19),16-tetraen-20(S)-yl)thio}-N-methoxy-N-methylacetamide (0.847 mg, 18%) as a colorless glass and ((1α,3β-dihydroxy-9,10-secopregna-5,7,10(19),16-tetraen-20(S)-yl)thio)-N-methylacetamide (0.839 mg, 19%) as a colorless glass.

For {(1α,3β-dihydroxy-9,10-secopregna-5,7,10(19),16-tetraen-20(S)-yl)thio}-N-methoxy-N-methylacetamide:

IR(neat): 3401, 2922, 2850, 1647, 1446, 1055 cm$^{-1}$. $^1$H NMR δ: 0.83 (s, 3H), 1.44 (d, J=6.9 Hz, 3H), 2.22-2.39 (m, 3H), 2.57-2.62 (m, 1H), 2.79-2.83 (m, 1H), 3.20 (s, 3H), 3.24-3.38 (m, 2H), 3.66-3.73 (m, 1H), 3.73 (s, 3H), 4.20-4.30 (br, 1H), 4.39-4.49 (br, 1H), 5.01 (brs, 1H), 5.34 (s, 1H), 5.67 (brs, 1H), 6.10 (d, J=10.9 Hz, 1H), 6.37 (d, J=10.9 Hz, 1H). MS m/z: 429 (M$^+$-H$_2$O), 91 (100%). UV $\lambda_{max}$nm: 263.

For {(1α,3β-dihydroxy-9,10-secopregna-5,7,10(19),16-tetraen-20(S)-yl)thio}-N-methylacetamide:

IR(neat): 3326, 2924, 2850, 1653, 1417, 1122, 1055 cm$^{-1}$. $^1$H NMR δ: 0.81 (s, 3H), 1.41 (d, J=6.9 Hz, 3H), 2.20-2.36 (m, 3H), 2.57-2.62 (m, 1H), 2.79-2.86 (m, 1H), 2.85 (d, J=4.9 Hz, 3H), 3.16 (s, 2H), 3.42-3.49 (m, 1H), 4.20-4.30 (br, 1H), 4.39-4.49 (br, 1H), 5.01 (brs, 1H), 5.35 (s, 1H), 5.62 (brs, 1H), 6.10 (d, J=11.2 Hz, 1H), 6.36 (d, J=11.2 Hz, 1H). MS m/z: 399 (M$^+$-H$_2$O), 91 (100%). UV $\lambda_{max}$nm: 264.

Example 86

Preparation of 1α,3β-dihydroxy-20(S)-tert-butoxycarbonylethylthio-9,10-secopregna-5,7,10(19),16-tetraene 1α,3β-Dihydroxy-20(S)-phenoxycarbonylthio-9,10-secopregna-5,7,10(19),16-tetraene (8.7 mg, 0.0186 mmol) was treated with a 1M methanol solution of potassium hydroxide (0.04 ml) and tert-butyl acrylate (120.0 mg, 0.936 mmol) in the same manner as shown in Example 16(2) (at room temperature for 30 minutes) and then worked up. The resulting residue was purified by preparative thin layer chromatography (0.25 mm×1 plate, dichloromethane:ethanol=15:1, developed three times and then 0.25 mm×1 plate, hexane:ethyl acetate:ethanol=10:5:1, developed three times) to give the titled compound (3.6 mg, 40%) as a colorless glass.

IR(neat): 3400, 2928, 1728, 1450, 1368, 1252, 1152, 1056 cm$^{-1}$. $^1$H NMR δ: 0.82 (s, 3H), 1.41 (d, J=6.9 Hz, 3H), 1.45 (s, 9H), 2.75-2.88 (m, 1H), 3.46 (q, J=6.9 Hz, 1H), 4.20-4.30 (m, 1H), 4.40-4.50 (m, 1H), 5.01 (brs, 1H), 5.34 (brs, 1H), 5.61 (brs, 1H), 6.10 (d, J=11.4 Hz, 1H), 6.37 (d, J=11.4 Hz, 1H). MS m/z: 474 (M$^+$), 57 (100%). UV $\lambda_{max}$nm: 263.

Example 87

Preparation of 1α,3β-dihydroxy-20(S)-tert-butoxycarbonylpropylthio-9,10-secopregna-5,7,10(19),16-tetraene 1α,3β-Dihydroxy-20(S)-phenoxycarbonylthio-9,10-secopregna-5,7,10(19),16-tetraene (6.2 mg, 0.0133 mmol) was treated with a 2M aqueous sodium hydroxide (65 μl) and tert-butyl 4-bromobutyrate (155.0 mg, 0.695 mmol) in the same manner as shown in Example 16(2) (at room temperature for 30 minutes) and then worked up. The resulting residue was purified by preparative thin layer chromatography (0.25 mm×1 plate, dichloromethane:ethanol=20:1, developed once, dichloromethane:ethanol=10:1, developed once; 0.25 mm×1 plate, dichloromethane:ethyl acetate=3:1, developed once, dichloromethane:ethyl acetate=1:1, developed once; and then 0.25 mm×1 plate, hexane:ethyl acetate:ethanol=10:5:1, developed twice) to give the titled compound (2.9 mg, 45%) as a colorless oil.

IR(neat): 3384, 2968, 2928, 2848, 1728, 1448, 1368, 1240, 1160, 1056 cm$^{-1}$. $^1$H NMR δ: 0.82 (s, 3H), 1.41 (d, J=7.0 Hz, 3H), 1.44 (s, 9H), 1.84 (t, J=7.3 Hz, 2H), 2.32 (t, J=7.3 Hz, 2H), 2.45 (dt, J=3.3, 7.3 Hz, 2H), 2.55-2.65 (m, 1H), 2.75-2.86 (m, 1H), 3.44 (q, J=7.0 Hz, 1H), 4.19-4.30 (m, 1H), 4.40-4.50 (m, 1H), 5.01 (brs, 1H), 5.34 (brs, 1H), 5.58 (brs, 1H), 6.10 (d, J=11.2 Hz, 1H), 6.37 (d, J=11.2 Hz, 1H). MS m/z: 470 (M$^+$-H$_2$O), 57 (100%). UV $\lambda_{max}$nm: 263.

Test Example 1

Eight week old male Balb/c mice were percutaneously administered with active vitamin D$_3$ (1α,25 (OH)$_2$D$_3$, 125 μg/ml in ethanol) or Compounds 1 to 5 (vitamin D derivatives prepared in the above Examples, 500 μg/ml in ethanol) or ethanol alone (as a control). These samples were applied once to the dorsal skin (about 1.5×2.0 cm$^2$) of the mice in a volume of 2 ml/kg. Each of the mice was then fitted with a necklace harness in order to avoid oral ingestion. On the next day, the administered sites were cleaned and the necklace harnesses were removed. Two days after administration, blood was taken from each mouse and assayed for ionized calcium level by the ion selective electrode method. The assay was performed in groups of 3 mice. Table 45 shows the results obtained. Ionized calcium levels in the table are expressed as mean values.

Test Example 2

Keratinocytes from human neonatal foreskin (Clonetics) were seeded in 96-well plates (COSTAR 3595) at a cell density of 2×10$^3$/well. The wells were then supplemented with the given concentrations of active vitamin $D_3$ (1α,25 $(OH)_2D_3$) or Compounds 1 to 5, followed by incubation in KGM-2 medium at a cell density of $2 \times 10^3$ cells/200 µl/well for 3 days at 37° C. in 5% $CO_2$ and 95% air. [$^3$H]Thymidine was added to each well (7.4 kBq/well) and the plates were further incubated for 1 day. Each well was washed once with calcium- and magnesium-free phosphate buffer (Dulbecco's PBS(-), Nissui, code 05913, pH 7.3-7.65) and then treated with 0.25% trypsin to strip the cells. The [$^3$H]thymidine uptake of the cells was determined by a liquid scintillation counter (1450 MicroBeta, Wallac). Table 45 shows the results obtained. Growth inhibition against human keratinocytes in the table was expressed as a relative value of each compound compared to active vitamin $D_3$: Relative inhibition=($IC_{50}$ (mol/l) of active vitamin $D_3$)/($IC_{50}$ (mol/l) of each compound).

TABLE 45

|  | Dose (µg/kg) | Test Example 1 Blood ionized calcium level (mmol/l) | Test Example 2 Growth inhibition against human keratinocytes (relative value) |
| --- | --- | --- | --- |
| Control | — | 1.35 | — |
| 1α,25(OH)$_2$D$_3$ | 250 | 2.66 | 1.0 |
| Compound 1 | 1000 | 1.65 | 2.0 |
| Compound 2 | 1000 | 2.27 | 5.9 |
| Compound 3 | 1000 | 1.54 | 0.5 |
| Compound 4 | 1000 | 2.16 | 7.0 |
| Compound 5 | 1000 | 1.35 | 0.3 |

Compound 1 is 20(S)-(tert-butoxycarbonylmethoxy)-1α,3β-dihydroxy-9,10-secopregna-5,7,10(19),16-tetraene prepared in Example 8(3), Compound 2 is 1α,3β-dihydroxy-20(S)-(N-tert-butyl-N-methylaminocarbonylmethoxy)-9,10-secopregna-5,7,10(19),16-tetraene prepared in Example 13, Compound 3 is 1α,3β-dihydroxy-20(S)-(tert-butoxycarbonylethoxy)-9,10-secopregna-5,7,10(19),16-tetraene prepared in Example 11(2), Compound 4 is 1α,3β-dihydroxy-20(S)-(N-tert-butylaminocarbonylmethoxy)-9,10-secopregna-5,7,10(19),16-tetraene prepared in Example 14, and Compound 5 is 1α,3β-dihydroxy-20(S)-(isopropoxycarbonylmethoxy)-9,10-secopregna-5,7,10(19),16-tetraene prepared in Example 15.

Test Example 3

The same procedures as shown in Test Example 1 were repeated to assay blood ionized calcium levels in mice, except that Compounds 6 to 12 were used as vitamin D derivatives. Table 46 shows the results obtained. Ionized calcium levels in the table are expressed as mean values.

Test Example 4

Keratinocytes from adult human skin (Clonetics) were seeded in 96-well plates (COSTAR 3595) at a cell density of $1 \times 10^3$/well. The wells were then supplemented with the given concentrations of active vitamin $D_3$ (1α,25 $(OH)_2D_3$) or Compounds 6 to 12, followed by incubation in KGM-2 medium at a cell density of $1 \times 10^3$ cells/200 µl/well for 3 days at 37° C. in 5% $CO_2$ and 95% air. [$^3$H]Thymidine was added to each well (7.4 kBq/well) and the plates were further incubated for 1 day. After removal of the medium, each well was treated with 0.05% trypsin/0.53 mM EDTA to strip the cells. The amount of [$^3$H]thymidine incorporated into the cells was determined with a liquid scintillation counter (1450 MicroBeta, Wallac). Table 46 shows the results obtained. Growth inhibition against keratinocytes in the table was expressed as a relative value of each compound compared to active vitamin $D_3$: Relative inhibition=($IC_{50}$ (mol/l) of active vitamin $D_3$)/($IC_{50}$ (mol/l) of test compound).

TABLE 46

|  | Dose (µg/kg) | Test Example 3 Blood ionized calcium level (mmol/l) | Test Example 4 Growth inhibition against human keratinocytes (relative value) |
| --- | --- | --- | --- |
| Control | — | 1.35 | — |
| 1α,25(OH)$_2$D$_3$ | 250 | 2.66 | 1.0 |
| Compound 6 | 1000 | 1.57 | 12.0 |
| Compound 7 | 1000 | 1.28 | 0.4 |
| Compound 8 | 1000 | 1.39 | 2.5 |
| Compound 9 | 1000 | 1.55 | 0.7 |
| Compound 10 | 1000 | 1.43 | 1.6 |
| Compound 11 | 1000 | 1.42 | 0.4 |
| Compound 12 | 1000 | 1.58 | 8.3 |

Compound 6 is 1α,3β-dihydroxy-20(S)-(1-ethyl-1-methylpropoxycarbonylmethoxy)-9,10-secopregna-5,7,10(19),16-tetraene prepared in Example 17(4), Compound 7 is 1α,3β-dihydroxy-20(S)-(1-isopropyl-2-methylpropoxycarbonylmethoxy)-9,10-secopregna-5,7,10(19),16-tetraene prepared in Example 21(2), Compound 8 is 1α,3β-dihydroxy-20(S)-(1,1-dimethylbutoxycarbonylmethoxy)-9,10-secopregna-5,7,10(19),16-tetraene prepared in Example 18(2), Compound 9 is 1α,3β-dihydroxy-20(S)-(1-ethyl-1-methylpropoxycarbonylmethoxy)-9,10-secopregna-5,7,10(19)-triene prepared in Example 23(4), Compound 10 is 1α,3β-dihydroxy-20(S)-(1,1-dimethylhexyloxycarbonylmethoxy)-9,10-secopregna-5,7,10(19),16-tetraene prepared in Example 19(2), Compound 11 is 1α,3β-dihydroxy-20(S)-{2-(1-ethyl-1-methylpropoxycarbonyl)ethoxy}-9,10-secopregna-5,7,10(19),16-tetraene prepared in Example 20(3), and Compound 12 is {(1α,3β-dihydroxy-9,10-secopregna-5,7,10(19),16-tetraen-20(S)-yl)oxy}-N-(2,2,3,3,3-pentafluoropropyl)acetamide prepared in Example 22(2).

INDUSTRIAL APPLICABILITY

The vitamin D derivatives of the present invention not only have excellent physiological activities, but also have a reduced hypercalcemic effect when compared to conventional vitamin D derivatives. The vitamin D derivatives of the present invention are therefore effective in treating diseases which allow only limited administration of conventional vitamin D derivatives in order to avoid hypercalcemia and other problems.

The invention claimed is:
1. A compound of Formula (1):

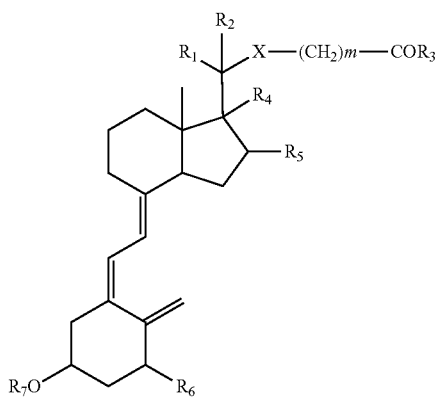

Formula (1)

wherein
X represents an oxygen atom;
m is 1
$R_1$ and $R_2$ each represent a hydrogen atom or a $C_1$-$C_6$ alkyl group,
provided that when one of $R_1$ and $R_2$ is hydrogen, one of $R_1$ and $R_2$ should represent a methyl group;
$R_4$ and $R_5$ together form a double bond between the 16- and 17-positions;
$R_3$ represents —$NR_9R_{10}$ (wherein $R_9$ represents a hydrogen atom, and $R_{10}$ represents a linear or branched $C_1$-$C_4$ alkyl group which is substituted with 3 to 12 fluorine atoms;
$R_6$ represents a hydroxyl group and
$R_7$ represents a hydrogen atom.

2. {(1α,3β-Dihydroxy-9,10-secopregna-5,7,10(19),16-tetraen-20(S)-yl)oxy}-N-(2,2,3,3,3-pentafluoropropyl)acetamide.

3. A pharmaceutical composition comprising a compound according to claim 1.

4. A method of treating psoriasis, which comprises the step of administering to a patient in need of such treatment a therapeutically effective amount of the compound according to claim 1.

5. The pharmaceutical composition according to claim 3 wherein said composition is used for treating psoriasis.

6. A method for inhibiting the growth of human keratinocytes comprising administering to a patient in need thereof an effective amount of a pharmaceutical composition according to claim 3 to inhibit the growth of human keratinocytes.

* * * * *